US009765078B2

(12) United States Patent
Claiborne et al.

(10) Patent No.: US 9,765,078 B2
(45) Date of Patent: Sep. 19, 2017

(54) COMPOUNDS AND METHODS FOR INHIBITING MITOTIC PROGRESSION

(71) Applicant: Millennium Pharmaceuticals, Inc., Cambridge, MA (US)

(72) Inventors: Christopher F. Claiborne, Cambridge, MA (US); Lloyd J. Payne, Cambridge (GB); Richard J. Boyce, Boxworth (GB); Todd B. Sells, Bellingham, MA (US); Stephen G. Stroud, Medford, MA (US); Stuart Travers, Meppershall (GB); Tricia J. Vos, Medford, MA (US); Gabriel S. Weatherhead, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/810,225

(22) Filed: Jul. 27, 2015

(65) Prior Publication Data

US 2016/0185782 A1 Jun. 30, 2016

Related U.S. Application Data

(63) Continuation of application No. 13/644,216, filed on Oct. 3, 2012, now Pat. No. 9,102,678, which is a continuation of application No. 12/472,583, filed on May 27, 2009, now Pat. No. 8,399,659, which is a continuation of application No. 11/127,855, filed on May 12, 2005, now Pat. No. 7,572,784.

(60) Provisional application No. 60/617,221, filed on Oct. 8, 2004, provisional application No. 60/571,653, filed on May 14, 2004.

(51) Int. Cl.
| | |
|---|---|
| *A61K 31/55* | (2006.01) |
| *C07D 471/12* | (2006.01) |
| *C07D 487/04* | (2006.01) |
| *C07D 487/12* | (2006.01) |
| *C07D 487/14* | (2006.01) |
| *C07D 491/14* | (2006.01) |
| *C07D 495/14* | (2006.01) |
| *C07D 513/14* | (2006.01) |

(52) U.S. Cl.
CPC ......... *C07D 487/04* (2013.01); *C07D 487/14* (2013.01); *C07D 491/14* (2013.01); *C07D 495/14* (2013.01); *C07D 513/14* (2013.01)

(58) Field of Classification Search
CPC .... A61K 31/55; C07D 471/12; C07D 487/04; C07D 487/12
USPC .......................................... 514/215; 540/578
See application file for complete search history.

(56) References Cited

U.S. PATENT DOCUMENTS

| | | | |
|---|---|---|---|
| 4,099,012 | A | 7/1978 | Gschwend |
| 4,469,633 | A | 9/1984 | Trybulski |
| 4,481,142 | A | 11/1984 | Fryer et al. |
| 5,166,151 | A | 11/1992 | Freidinger et al. |
| 5,210,082 | A | 5/1993 | Bock et al. |
| 5,747,487 | A | 5/1998 | Albright et al. |
| 6,057,329 | A | 5/2000 | Davis et al. |
| 6,277,844 | B1 | 8/2001 | Spector et al. |
| 7,572,784 | B2 | 8/2009 | Claiborne et al. |
| 8,399,659 | B2 | 3/2013 | Claiborne et al. |
| 9,102,678 | B2 | 8/2015 | Claiborne et al. |
| 2003/0022885 | A1 | 1/2003 | Bebbington et al. |
| 2003/0055068 | A1 | 3/2003 | Bebbington et al. |
| 2005/0256102 | A1 | 11/2005 | Claiborne et al. |
| 2007/0185087 | A1 | 8/2007 | Claiborne et al. |
| 2008/0167292 | A1 | 7/2008 | Claiborne et al. |
| 2009/0299060 | A1 | 12/2009 | Claiborne et al. |
| 2011/0312943 | A1 | 12/2011 | Claiborne et al. |
| 2014/0046055 | A1 | 2/2014 | Claiborne et al. |
| 2015/0166545 | A1 | 6/2015 | Claiborne et al. |

FOREIGN PATENT DOCUMENTS

| | | |
|---|---|---|
| EP | 0014470 A2 | 8/1980 |
| EP | 0273697 A2 | 7/1988 |
| WO | WO-98/28281 A1 | 7/1998 |
| WO | WO-00/67754 A1 | 11/2000 |
| WO | WO-02/22607 A1 | 3/2002 |
| WO | WO-02/066461 A1 | 8/2002 |
| WO | WO-03/013545 A1 | 2/2003 |
| WO | WO-2005/037843 A1 | 4/2005 |
| WO | WO-2005/111039 A2 | 11/2005 |
| WO | WO-2006/070198 A1 | 7/2006 |
| WO | WO-2008/063525 A1 | 5/2008 |
| WO | WO-2009/070652 A1 | 6/2009 |

OTHER PUBLICATIONS

Berdnik, D. et al., Drosophila aurora-A is required for centrosome maturation and actin-dependent asymmetirc protein localization during mitosis, Current Biology, 12:640-647 (2002).
Bischoff, J.R. et al., A homologue of Drosophila aurora kinase is oncogenic and amplified in human colorectal cancers, European Molecular Biology Organization, 17:3062-3065 (1998).
Cantor, E.H. et al., Interaction of calcium channel blockers with non-neuronal benzodiazepine binding sites, Proceedings of the National Academy of Sciences, 81:1549-1552 (1984).
Carmena, M. et. al., The Cellular Geography of Aurora Kinases, Nature, 4:842-854 (2003).
Carvajal, R. et al., Aurora kinases: new targets for cancer therapy, Clinical Cancer Research 12(23):6869-6875 (2006).
Ditchfield, C. et al., Aurora B couples chromosome alignment with anaphase by targeting BubR1, Mad2, and Cenp-E to kinetochores, The Journal of Cell Biology, 161(2):267-280 (2003).

(Continued)

*Primary Examiner* — Brenda Coleman
(74) *Attorney, Agent, or Firm* — Choate, Hall & Stewart LLP; Brenda Herschbach Jarrell; Kristen C. Buteau

(57) ABSTRACT

This invention relates to compounds and methods for the treatment of cancer. In particular, the invention provides compounds that inhibit Aurora kinase, pharmaceutical compositions comprising the compounds, and methods of using the compounds for the treatment of cancer.

18 Claims, No Drawings

(56) References Cited

OTHER PUBLICATIONS

Dutertre, D. et al., On the role of aurora-A in centrosome function, Oncogene, 21:6175-6183 (2002).

Finch, et al., An Efficient General Route to Furo-, Pyrido- and Thieno-[d][2]benzazepines via Pdo Catalysed Cross Coupling Reactions and Nitrile Ylide Cyclisations, Journal of the Chemical Society Perkin Transactions, 1:1193-1203 (1994).

Gautschi, O. et al., Aurora kinases as anticancer drug targets, Clinical Cancer Research, 14(6):1639-1648 (2008).

Harrington, E.A. et al., VX-680, a potent and selective small-molecular inhibitor of the Aurora kinases, suppresses tumor growth in vivo, Nature Medicine, 10(3):262-267 (2004).

Hauf, S. et al., The small molecule Hesperadin reveals a role for Aurora B in correcting kinetochore-microtubule attachment and in maintaining the spindle assembly checkpoint, The Journal of Cell Biology, 161(2):281-294 (2003).

Hoar, K. et al., MLN8054, a small-molecule inhibitor of aurora A, causes spindle pole and chromosome congression defects leading to aneuploidy, Molecular and Cellular Biology, 27(12):4513-4525 (2007).

International Search Report for PCT/US2005/016445, 4 pages (Dec. 21, 2011).

International Search Report for PCT/US2007/023948, 4 pages (Dec. 21, 2011).

Jones, S. et al., Phase I clinical trial of MLN8054, a selective inhibitor of Aurora A kinase, Journal of Clinical Oncology, 25(18S):3577 (2007).

Jones, S.F. et al., Phase I clinical trial of MLN8054, a selective inhibitor of aurora A kinase, Journal of Clinical Oncology, ASCO Annual Meeting Proceedings Part 1, 25(18S):3577 (2007).

Manfredi, M.G. et al., Antitumor activity in MLN8054, an orally active small-molecule inhibitor of aurora A kinase, Proceedings of the National Academy of Sciences USA, 104(10):4106-4111 (2007).

Meraldi, P. et al., Aurora-A overexpression reveals tetraploidization as a major route to centrosome amplification in $p53^{-/-}$ cells, The European Molecular Biology Organization Journal, 21(4):483-492 (2002).

Sausville, E.A., Aurora kinases dawn as cancer drug targets, Nature Medicine, 10(3):234-235 (2004).

Solowey, W.E. et al., Peripheral-Acting Benzodiazepines Inhibit the Growth of Human Melanoma Cells and Potentiate the Antiproliferative Activity of Recombinant Human Interferons, The Journal of Interferon Research, 10(3):269-280 (1990).

Vankayalapati, H. et al., Targeting Aurora2 Kinase in Oncogenesis: A Structural Bioinformatics Approach to Target Validation and Rational Drug Design, Molecular Cancer Therapeutics, 2:283-294 (2003).

Wang, J.K.T. et al., Benzodiazepines that bind at peripheral sites inhibit cell proliferation, Proceedings of the National Academy of Sciences, 81:753-756 (1984).

Warner, S.L. et al., Targeting aurora-2 kinase in cancer, Molecular Cancer Therapeutics, 2:589-595 (2003).

Written Opinion for PCT/US2005/016445, 4 pages (Dec. 21, 2011).
Written Opinion for PCT/US2007/023948, 4 pages (Dec. 21, 2011).

Xia, W. et al., Tumor selective G2/M cell cycle arrest and apoptosis of epithelial and hematological malignancies by BBL22, a benzazepine, Proceedings of the National Academy of Sciences, 97(13):7494-7499 (2000).

Zhou, H. et al., Tumor amplified kinase STK15/BTAK induces centrosome amplification, aneuploidy and transformation, Nature Genetics, 20:189-193 (1998).

COMPOUNDS AND METHODS FOR INHIBITING MITOTIC PROGRESSION

PRIORITY CLAIM

The present application is a continuation of U.S. patent application Ser. No. 11/127,855, filed May 12, 2005 (pending), which claims the benefit of U.S. Provisional Application Ser. No. 60/571,653, filed May 14, 2004, and U.S. Provisional Application Ser. No. 60/617,221, filed Oct. 8, 2004. The entire contents of each of the above-referenced patent applications are incorporated herein by this reference.

BACKGROUND OF THE INVENTION

Field of the Invention

This invention relates to compounds and methods for the treatment of cancer. In particular, the invention provides compounds that inhibit Aurora kinase enzymes, pharmaceutical compositions comprising the compounds, and methods of using the compounds for the treatment of cancer.

Background of the Invention

According to the American Cancer Society, an estimated 1.4 million Americans were newly-diagnosed with cancer in 2004 and about 560,000 victims died from the disease. While medical advance have improved cancer survival rates, there is a continuing need for new and more effective treatment.

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment, and cytokinesis (Dutertre et al., *Oncogene*, 21: 6175 (2002); Berdnik et al., *Curr. Biol.*, 12: 640 (2002)). Overexpression and/or amplification of Aurora kinases have been linked to oncogenesis in several tumor types including those of colon and breast (Warner et al., *Mol. Cancer Ther.*, 2: 589 (2003); Bischoff et al., *EMBO*, 17: 3062 (1998); Sen et al., *Cancer Res.*, 94: 1320 (2002)). Moreover, Aurora kinase inhibition in tumor cells results in mitotic arrest and apoptosis, suggesting that these kinases are important targets for cancer therapy (Ditchfield, *J. Cell Biol.*, 161: 267 (2003); Harrington et al., *Nature Med.*, 1 (2004)). Given the central role of mitosis in the progression of virtually all malignancies, inhibitors of the Aurora kinases are expected to have application across a broad range of human tumors. There is thus a need for new Aurora kinase inhibitors.

DESCRIPTION OF THE INVENTION

This invention provides compounds that inhibit Aurora kinase. These compounds are useful for inhibiting Aurora kinase in vitro or in vivo, and are especially useful for the treatment of cell proliferative disorders, including cancer. The Aurora kinase inhibitors of the invention have the formula (A):

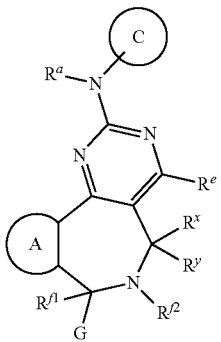

(A)

or a pharmaceutically acceptable salt thereof, wherein Ring A, Ring C, and each of the variables $R^a$, $R^e$, $R^{f1}$, $R^{f2}$, $R^x$, $R^y$ and G have the values described below.

$R^{f1}$ is hydrogen, or $R^{f1}$ and $R^{f2}$ together form a bond.

$R^{f2}$ is hydrogen, or $R^{f2}$ forms a bond with either $R^{f1}$ or $R^x$.

Each of $R^x$ and $R^y$ independently is hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring; or $R^x$ and $R^{f2}$ together form a bond.

G is hydrogen, an optionally substituted aliphatic, or Ring B when $R^{f1}$ is hydrogen; and G is hydrogen, —$OR^5$, —$N(R^4)_2$, —$SR^5$, an optionally substituted aliphatic, or Ring B when $R^{f1}$ and $R^{f2}$ together form a bond.

Ring A is a substituted or unsubstituted 5- or 6-membered aryl, heteroaryl, cycloaliphatic, or heterocyclyl ring.

Ring B is a substituted or unsubstituted aryl, heteroaryl, cycloaliphatic, or heterocyclyl ring.

Ring C is a substituted or unsubstituted aryl, heteroaryl, heterocyclyl, or cycloaliphatic ring.

$R^a$ is hydrogen, —$C(O)R^1$, —$CO_2R^1$, —$SO_2R^1$, or a $C_{1-3}$ aliphatic having 0-2 substituents independently selected from $R^3$ or $R^7$.

$R^e$ is hydrogen, —$OR^5$, —$N(R^4)_2$, —$SR^5$, —$NR^4C(O)R$, —$NR^4C(O)N(R^4)_2$, —$NR^4CO_2R^6$, —$N(R^4)SO_2R^6$, —$N(R^4)SO_2N(R^4)_2$, or a $C_{1-3}$ aliphatic optionally substituted with $R^3$ or $R^7$.

$R^1$ is $C_{1-6}$ aliphatic or an optionally substituted aryl, heteroaryl, or heterocyclyl group.

Each $R^3$ independently is selected from the group consisting of -halo, —OH, —O($C_{1-3}$ alkyl), —CN, —$N(R^4)_2$, —C(O)($C_{1-3}$ alkyl), —$CO_2H$, —$CO_2(C_{1-3}$ alkyl), —$C(O)NH_2$, and —$C(O)NH(C_{1-3}$alkyl).

Each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S.

Each $R^5$ independently is hydrogen or an optionally substituted aliphatic, aryl, heteroaryl, or heterocyclyl group.

Each $R^6$ independently is an optionally substituted aliphatic or aryl group.

Each $R^7$ independently is an optionally substituted aryl, heterocyclyl, or heteroaryl group.

The invention further provides pharmaceutical compositions comprising a compound of formula (A), as well as uses of the claimed compounds for inhibiting Aurora kinase activity and for treating Aurora kinase-mediated disorders.

Compounds of this invention include those described generally above, and are further illustrated by the classes, subclasses, and species disclosed herein. Terms used herein shall be accorded the following defined meanings, unless otherwise indicated.

As used herein, the term "Aurora kinase" refers to any one of a family of related serine/threonine kinases involved in mitotic progression. A variety of cellular proteins that play a role in cell division are substrates for phosphorylation by Aurora kinase enzymes, including, without limitation, histone H3, p 53, CENP-A, myosin II regulatory light chain, protein phosphatase-1, TPX-2, INCENP, survivin, topoisomerase II alpha, vimentin, MBD-3, MgcRacGAP, desmin, Ajuba, XIEg5 (in *Xenopus*), Ndc10p (in budding yeast), and D-TACC (in *Drosophila*). Aurora kinase enzymes also are themselves substrates for autophosphorylation, e.g., at Thr288. Unless otherwise indicated by context, the term "Aurora kinase" is meant to refer to any Aurora kinase protein from any species, including, without limitation, Aurora A, Aurora B, and Aurora C, preferably Aurora A or B. Preferably, the Aurora kinase is a human Aurora kinase.

The term "Aurora kinase inhibitor" or "inhibitor of Aurora kinase" is used to signify a compound having a structure as defined herein, which is capable of interacting with an Aurora kinase and inhibiting its enzymatic activity. Inhibiting Aurora kinase enzymatic activity means reducing the ability of an Aurora kinase to phosphorylate a substrate peptide or protein. In various embodiments, such reduction of Aurora kinase activity is at least about 50%, at least about 75%, at least about 90%, at least about 95%, or at least about 99%. In various embodiments, the concentration of Aurora kinase inhibitor required to reduce an Aurora kinase enzymatic activity is less than about 1 µM, less than about 500 nM, less than about 100 nM, or less than about 50 nM.

In some embodiments, such inhibition is selective, i.e., the Aurora kinase inhibitor reduces the ability of an Aurora kinase to phosphorylate a substrate peptide or protein at a concentration that is lower than the concentration of the inhibitor that is required to produce another, unrelated biological effect, e.g., reduction of the enzymatic activity of a different kinase. In some embodiments, the Aurora kinase inhibitor also reduces the enzymatic activity of another kinase, preferably one that is implicated in cancer.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

The term "aliphatic", as used herein, means straight-chain, branched or cyclic $C_{1-12}$ hydrocarbons which are completely saturated or which contain one or more units of unsaturation, but which are not aromatic. For example, suitable aliphatic groups include substituted or unsubstituted linear, branched or cyclic alkyl, alkenyl, or alkynyl groups and hybrids thereof, such as (cycloalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight and branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The terms "cycloaliphatic", "carbocycle", "carbocyclyl", "carbocyclo", or "carbocyclic", used alone or as part of a larger moiety, refer to a saturated or partially unsaturated cyclic aliphatic ring system having from 3 to about 14 members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3 to 6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl or tetrahydronaphthyl, where the radical or point of attachment is on the aliphatic ring.

The terms "haloaliphatic", "haloalkyl", "haloalkenyl" and "haloalkoxy" refer to an aliphatic, alkyl, alkenyl or alkoxy group, as the case may be, substituted with one or more halogen atoms. As used herein, the term "halogen" or "halo" means F, Cl, Br, or I.

The terms "aryl" and "ar-", used alone or as part of a larger moiety, e.g., "aralkyl", "aralkoxy", or "aryloxyalkyl", refer to a $C_6$ to $C_{14}$ aromatic moiety comprising one to three aromatic rings, which are optionally substituted. Preferably, the aryl group is a $C_{6-10}$ aryl group. Aryl groups include, without limitation, phenyl, naphthyl, and anthracenyl.

The term "aryl", as used herein, also includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to aromatic groups having 5 to 14 ring atoms, preferably 5, 6, 9, or 10 ring atoms; having 6, 10, or 14 π electrons shared in a cyclic array; and having, in addition to one or more carbon atoms, from one to four heteroatoms.

The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or +NR (as in N-substituted pyrrolidinyl).

A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R^)—, —C≡C—, —O—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)CO$_2$—, —C(O)N(R$^+$)—, —C(O)—, —C(O)—C(O)—, —CO$_2$—, —OC(O)—, —OC(O)O—, —OC(O)N(R$^+$)—, —C(NR$^+$)=N—, —C(OR*)=N—, —N(R$^+$)—N(R$^+$)—, or —N(R$^+$)S(O)$_2$—. Each R$^+$, independently, is hydrogen or an optionally substituted aliphatic, aryl, heteroaryl, or heterocyclyl group, or two R$^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group. Each R^ independently is hydrogen —CO$_2$R*, —C(O)N(R$^+$)$_2$, or an optionally substituted aliphatic, aryl, heteroaryl, or heterocyclyl group.

Examples of $C_{3-6}$ alkylene chains that have been "interrupted" with —O-include —CH$_2$OCH$_2$—, —CH$_2$O (CH$_2$)$_2$—, —CH$_2$O(CH$_2$)$_3$—, —CH$_2$O(CH$_2$)$_4$—, —(CH$_2$)$_2$ OCH$_2$—, —(CH$_2$)$_2$O(CH$_2$)$_2$—, —(CH$_2$)$_2$O(CH$_2$)$_3$—, —(CH$_2$)$_3$O(CH$_2$)—, —(CH$_2$)$_3$O(CH$_2$)$_2$—, and —(CH$_2$)$_4$O (CH$_2$)—. Other examples of alkylene chains that are "interrupted" with functional groups include —CH$_2$GCH$_2$—, —CH$_2$G(CH$_2$)$_2$—, —CH$_2$G(CH$_2$)$_3$—, —CH$_2$G(CH$_2$)$_4$—, —(CH$_2$)$_2$GCH$_2$—, —(CH$_2$)$_2$G(CH$_2$)$_2$—, —(CH$_2$)$_2$G (CH$_2$)$_3$—, —(CH$_2$)$_3$G(CH$_2$)—, —(CH$_2$)$_3$G(CH$_2$)$_2$—, and —(CH$_2$)$_4$G(CH$_2$)—, wherein G is one of the "interrupting" functional groups listed above.

The term "substituted", as used herein, means that one or more hydrogens of the designated moiety are replaced, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —NO$_2$, —CN, —R*, —C(R*)=C(R*)(Rˆ), —C≡C—Rˆ, —OR*, —SR°, —S(O)R°, —SO$_2$R°, —SO$_3$R*, —SO$_2$N(R$^+$)$_2$, —N(R$^+$)$_2$, —NR$^+$C(O)R*, —NR$^+$C(O)N(R$^+$)$_2$, —NR$^+$CO$_2$R°, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(O)N(R$^+$)C(=NR$^+$)—N(R$^+$)$_2$, —N(R$^+$)C(=NR$^+$)—N(R$^+$)—C(O)R*, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR+SO$_2$R°, —NR+SO$_2$N(R$^+$)$_2$, —P(O)(R*)$_2$, —P(O)(OR*)$_2$, —O—P(O)—OR*, and —P(O)(NR$^+$)—N(R$^+$)$_2$, or two adjacent substituents, taken together with their intervening atoms, form a 5-6 membered unsaturated or partially unsaturated ring having 0-3 ring atoms selected from the group consisting of N, O, and S. In such substituents, R° is an optionally substituted aliphatic or aryl group, and R$^+$, R*, and Rˆ are as defined above.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—NHR*, =N—N(R*)$_2$, =N—OR*, =N—NHC(O)R*, =N—NHCO$_2$R°, =N—NHSO$_2$R°, or =N—R*, where each R* and R° is as defined above.

Suitable substituents on the nitrogen atom of a non-aromatic heterocyclic ring include —R*, —N(R*)$_2$, —C(O)R*, —CO$_2$R*, —C(O)—C(O)R*—C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*; wherein each R* is as defined above.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. By way of example, the compounds of formula (A) wherein R$^{f1}$ is hydrogen can have R or S configuration at the carbon atom bearing Ring B. Both the R and the S stereochemical isomers, as well as all mixtures thereof, are included within the scope of the invention.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

Unless otherwise stated, structures depicted herein are also meant to include solvated and hydrated forms of the depicted compounds. Also included within the scope of the invention are pharmaceutically acceptable salts of compounds of formula (A), as well as solvated and hydrated forms of such salts.

Some embodiments of the invention relate to compounds of formula (A) where R$^e$ is hydrogen, —OR$^5$, —N(R$^4$)$_2$, —SR$^5$, —NR$^4$C(O)R$^5$, —NR$^4$C(O)N(R$^4$)$_2$, —NR$^4$CO$_2$R$^6$, —N(R$^4$)SO$_2$R$^6$, —N(R$^4$)SO$_2$N(R$^4$)$_2$, or a C$_{1-3}$ aliphatic optionally substituted with R$^3$ or R$^7$. In some embodiments, R$^e$ is hydrogen or a C$_{1-3}$ aliphatic optionally substituted with one R$^3$ or R$^7$. In certain embodiments, R$^e$ is hydrogen.

In some embodiments, R$^x$ and R$^y$ are each independently selected from hydrogen, fluoro, or a C$_{1-6}$ aliphatic optionally substituted with one or two R$^3$. In some other embodiments, R$^x$ and R$^y$, taken together with the carbon atom to which they are attached, form an optionally substituted 3- to 6-membered cycloaliphatic ring. In some other embodiments, R$^x$ and R$^{f2}$ together form a bond. In some embodiments, R$^x$ and R$^y$ are each hydrogen. In certain embodiments, R$^x$, R$^y$, and R$^e$ are each hydrogen.

Some embodiments of the invention relate to compounds of formula (A) where R$^{f1}$ is hydrogen, R$^{f2}$ is hydrogen or R$^{f2}$ and R$^x$ together form a bond, and G is hydrogen, an optionally substituted aliphatic, or Ring B.

Some other embodiments relate to compounds of formula (A), where R$^{f1}$ and R$^{f2}$ together form a bond, and G is hydrogen, —SR$^5$, —OR$^5$, —N(R$^4$)$_2$, or an optionally substituted aliphatic. In such embodiments, G preferably is hydrogen, —OR$^5$, —N(R$^4$)$_2$, or an optionally substituted aliphatic. More preferably, G is —H, —OH, —NH$_2$, —O(C$_{1-3}$ alkyl), —NH(C$_{1-3}$alkyl), —N(C$_{1-3}$ alkyl)$_2$, C$_{1-3}$ alkyl, C$_{1-3}$ fluoroalkyl, —O-L$^1$-R$^7$, —N(C$_{1-3}$alkyl)-L$^1$-R$^7$, or -L$^1$-R$^7$, where L$^1$ is a covalent bond or C$_{1-3}$alkylene.

Other embodiments of the invention relate to a subgenus of the compounds of formula (A) characterized by formula (A-1):

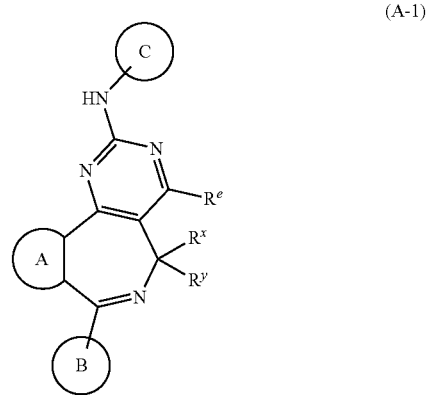

(A-1)

or a pharmaceutically acceptable salt thereof, where the variables R$^e$, R$^x$, and R$^y$ are as defined above for formula (A). Values and preferred values for Rings A, B, and C in formulae (A) and (A-1) are described below.

Ring A is a substituted or unsubstituted 5- or 6-membered aryl, heteroaryl, cycloaliphatic, or heterocyclyl ring. Examples of Ring A include furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridino, piperidino, dioxano, morpholino, dithiano, thiomorpholino, pyridazino, pyrimidino, pyrazino, piperazino, and triazino, any of which groups may be substituted or unsubstituted. Preferred values for Ring A include, without limitation, substituted or unsubstituted rings selected from the group consisting of furano, thieno, pyrrolo, oxazolo, thiazolo, imidazolo, pyrazolo, isoxazolo, isothiazolo, triazolo, benzo, pyridino, pyridazino, pyrimidino, and pyrazino.

Ring A may be substituted or unsubstituted. In some embodiments, each substitutable saturated ring carbon atom in Ring A is unsubstituted or is substituted with =O, =S, =C($R^5$)$_2$, =N—N($R^4$)$_2$, =N—O$R^5$, =N—NHC(O)$R^5$, =N—NHCO$_2R_6$, =N—NHSO$_2R_6$, =N—$R^5$ or —$R^b$, where $R^b$, $R^4$, $R^5$, and $R^6$ are as defined below. Each substitutable unsaturated ring carbon atom in Ring A is unsubstituted or substituted with —$R^b$. Each substitutable ring nitrogen atom in Ring A is unsubstituted or is substituted with —$R^{9b}$, and one ring nitrogen atom in Ring A optionally is oxidized. Each $R^{9b}$ independently is —C(O)$R^5$, —C(O)N($R^4$)$_2$, —CO$_2R^6$, —SO$_2R^6$, —SO$_2$N($R^4$)$_2$, or a $C_{1-4}$ aliphatic optionally substituted with $R^3$ or $R^7$.

Each $R^b$ independently is $R^{2b}$, an optionally substituted aliphatic, or an optionally substituted aryl, heterocyclyl, or heteroaryl group; or two adjacent $R^b$, taken together with the intervening ring atoms, form an optionally substituted fused 4- to 8-membered aromatic or non-aromatic ring having 0-3 ring heteroatoms selected from the group consisting of O, N, and S.

Each $R^{2b}$ independently is -halo, —NO$_2$, —CN, —C($R^5$)=C($R^5$)$_2$, —C($R^5$)=C($R^5$)($R^{10}$), —C≡C—$R^5$, —C≡C—$R^{10}$, —O$R^5$, —S$R^6$, —S(O)$R^6$, —SO$_2R^6$, —SO$_2$N($R^4$)$_2$, —N($R^4$)$_2$, —N$R^4$C(O)$R^5$, —N$R^4$C(O)N($R^4$)$_2$, —N$R^4$CO$_2R^6$, —O—CO$_2$R, —OC(O)N($R^4$)$_2$, —O—C(O)$R^5$, —CO$_2R^5$, —C(O)—C(O)$R^5$, —C(O)$R^5$, —C(O)N($R^4$)$_2$, —C(=N$R^4$)—N($R^4$)$_2$, —C(=N$R^4$)—O$R^5$, —N($R^4$)—N($R^4$)$_2$, N($R^4$)C(=N$R^4$)—N($R^4$)$_2$, —N($R^4$)SO$_2R^6$, —N($R^4$)SO$_2$N($R^4$)$_2$, —P(O)($R^5$)$_2$, or —P(O)(OR)$_2$.

Each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$alkyl).

Each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S.

Each $R^5$ independently is hydrogen or an optionally substituted aliphatic, aryl, heteroaryl, or heterocyclyl group;

Each $R^6$ independently is an optionally substituted aliphatic or aryl group;

Each $R^7$ independently is an optionally substituted aryl, heterocyclyl, or heteroaryl group;

Each $R^{10}$ independently is —CO$_2R^5$ or —C(O)N($R^4$)$_2$.

In some embodiments, each $R^b$ independently is selected from the group consisting of $C_{1-6}$ aliphatic, $C_{1-6}$ fluoroaliphatic, —$R^{2b}$, —$R^{7b}$, -$T^1$-$R^{2b}$, and -$T^1$-$R^{7b}$; or two adjacent $R^b$, taken together with the intervening ring atoms, form an optionally substituted fused 4- to 8-membered aromatic or non-aromatic ring having 0-3 ring heteroatoms selected from the group consisting of O, N, and S. The variable $R^{2b}$ is as described above, and $T^1$ and $R^{7b}$ are described below.

$T^1$ is a $C_{1-6}$ alkylene chain optionally substituted with $R^3$ or $R^{3b}$, wherein $T^1$ or a portion thereof optionally forms part of a 3- to 7-membered ring.

Each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$alkyl).

Each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring.

Each $R^{7b}$ independently is an optionally substituted aryl, heteroaryl, or heterocyclyl group.

In some embodiments, Ring A is substituted with 0-3, 0-2, or 0-1 substituents $R^b$, wherein the substituents $R^b$ may be the same or different. In some embodiments, each $R^b$ independently is selected from the group consisting of $C_{1-3}$ aliphatic, $R^{2b}$, $R^{7b}$, -$T^1$-$R^{2b}$, and -$T^1$-$R^{7b}$, where $T^1$ is a $C_{1-3}$ alkylene chain optionally substituted with fluoro. In some embodiments, two adjacent $R^b$, taken together with the intervening ring carbon atoms, form an optionally substituted fused 4- to 8-membered aromatic or non-aromatic ring having 0-3 ring heteroatoms selected from the group consisting of O, N, and S. In some embodiments, each $R^b$ independently is selected from the group consisting of $C_{1-3}$ aliphatic, $R^{2b}$, and -$T^1$-$R^{2b}$, where $T^1$ is a $C_{1-3}$ alkylene chain, optionally substituted with fluoro. In some such embodiments, each $R^{2b}$ independently is selected from the group consisting of -halo, —NO$_2$, —C($R^5$)=C($R^5$)$_2$, —C≡C—$R^5$, —O$R^5$, and —N($R^4$)$_2$.

In some embodiments, Ring A is substituted by 0-2 substituents $R^b$. In some such embodiments, each $R^b$ independently is $C_{1-3}$ aliphatic or $R^{2b}$, and each $R^{2b}$ independently is selected from the group consisting of -halo, —NO$_2$, —C($R^5$)=C($R^5$)$_2$, —C≡C—$R^5$, —OR$^5$, and —N($R^4$)$_2$. In some embodiments, each $R^b$ independently is selected from the group consisting of -halo, $C_{1-3}$ aliphatic, $C_{1-3}$ fluoroaliphatic, and —OR$^5$, where $R^5$ is hydrogen or $C_{1-3}$ aliphatic. In certain preferred embodiments, Ring A is substituted with 0, 1, or 2 substituents, preferably 0 or 1 substituents, independently selected from the group consisting of chloro, fluoro, bromo, methyl, trifluoromethyl, and methoxy.

Certain examples of Ring A moieties are shown in Table 1. For ease of viewing, the optional substituents $R^b$ on ring carbon atoms and $R^{9b}$ on ring nitrogen atoms are not shown.

TABLE 1

Examples of Ring A Moieties

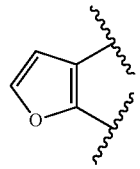 [SMILES: *c1ccoc1*]

A-1

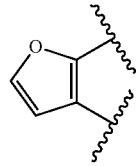 [SMILES: *c1ccoc1*]

A-2

TABLE 1-continued
| Examples of Ring A Moieties | | Examples of Ring A Moieties | |
|---|---|---|---|
| 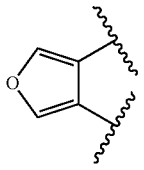 [SMILES: *c1cocc1*] | A-3 | 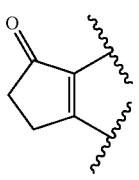 | A-11 |
| 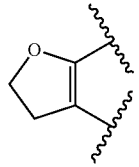 [SMILES: *C1=C(*)OCC1] | A-4 | 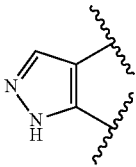 | A-12 |
| 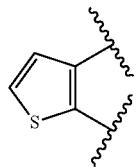 [SMILES: *c1ccsc1*] | A-5 | 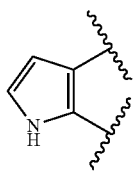 | A-13 |
| 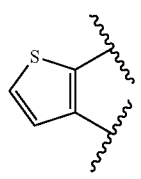 | A-6 | 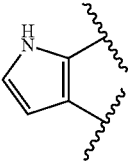 | A-14 |
| 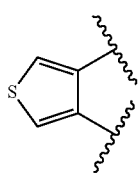 [SMILES: *c1cscc1*] | A-7 | 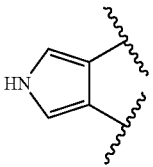 | A-15 |
| 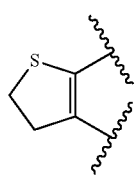 [SMILES: *C1=C(*)SCC1] | A-8 | 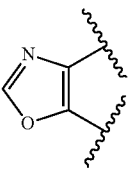 | A-16 |
| 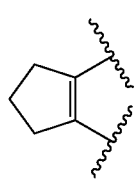 [SMILES: *C1=C(*)CCC1] | A-9 | 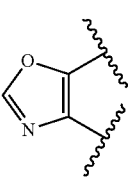 [SMILES: *c1ncoc1*] | A-17 |
| 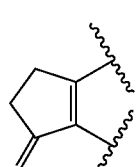 | A-10 | 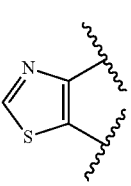 [SMILES: *c1ncsc1*] | A-18 |

TABLE 1-continued
Examples of Ring A Moieties
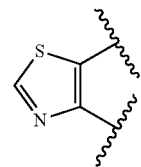 [SMILES: *c1ncsc1*] A-19
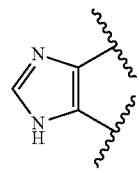 A-20
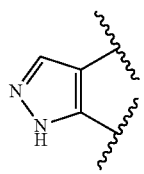 [SMILES: *c1cn[nH]c1*] A-21
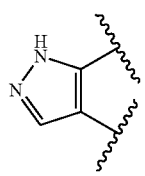 [SMILES: *c1cn[nH]c1*] A-22
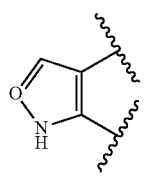 A-23
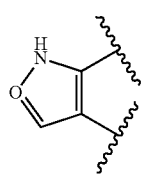 A-24
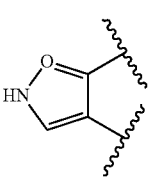 A-25
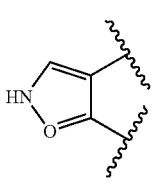 A-26
TABLE 1-continued
Examples of Ring A Moieties
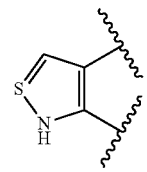 A-27
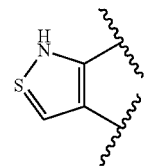 A-28
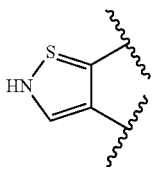 A-29
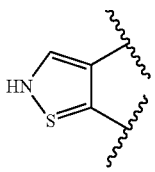 A-30
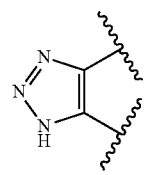 [SMILES: *c1nn[nH]c1*] A-31
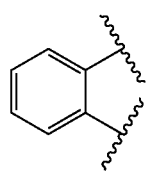 [SMILES: *c1ccccc1*] A-32
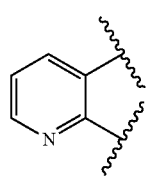 [SMILES: *c1cccnc1*] A-33
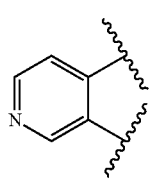 A-34

TABLE 1-continued

Examples of Ring A Moieties

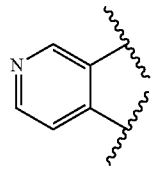 A-35

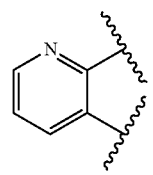 [SMILES: *c1cccnc1*] A-36

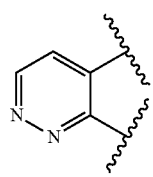 [SMILES: *c1ccnnc1*] A-37

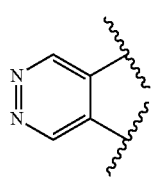 [SMILES: *c1cnncc1*] A-38

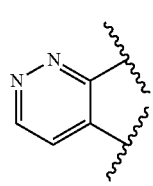 [SMILES: *c1ccnnc1*] A-39

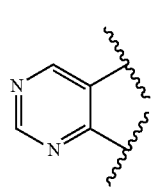 [SMILES: *c1cncnc1*] A-40

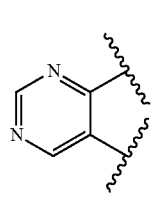 [SMILES: *c1cncnc1*] A-41

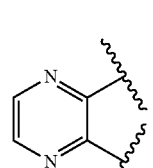 A-42

TABLE 1-continued

Examples of Ring A Moieties

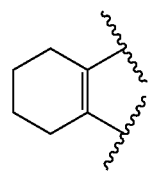 [SMILES: *C1=C(*)CCCC1] A-43

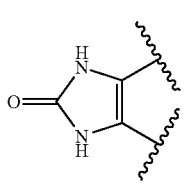 [SMILES: *c1[nH]c(=O)[nH]c1*] A-44

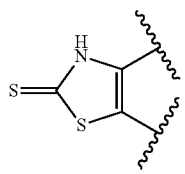 A-45

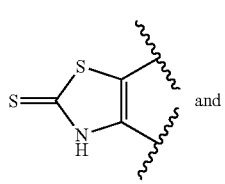 [SMILES: *c1[nH]c(=S)sc1*] A-46 and

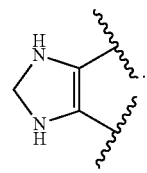 A-47

In some embodiments, two adjacent $R^b$ on one of the above Ring A moieties, taken together with the intervening ring atoms, form an optionally substituted fused 4- to 8-membered aromatic or nonaromatic fused ring, so that Ring A is a bicyclic moiety. Certain examples of such bicyclic moieties are shown in Table 2, any of which moieties optionally is substituted on any substitutable ring carbon atom and any substitutable ring nitrogen atom.

TABLE 2

Examples of Bicyclic Ring A Moieties

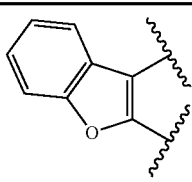 A-48

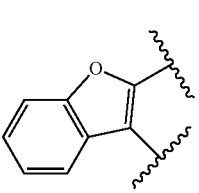 [SMILES: *c1oc2ccccc2c1*] A-49

TABLE 2-continued
Examples of Bicyclic Ring A Moieties
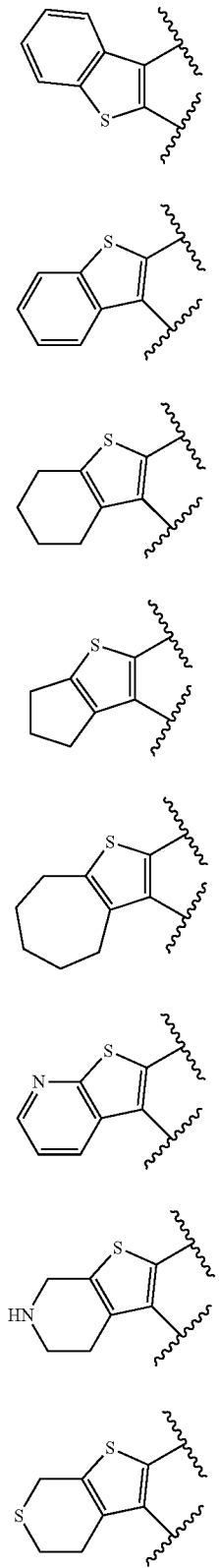
A-50
A-51
A-52
A-53
A-54
A-55
A-56
A-57
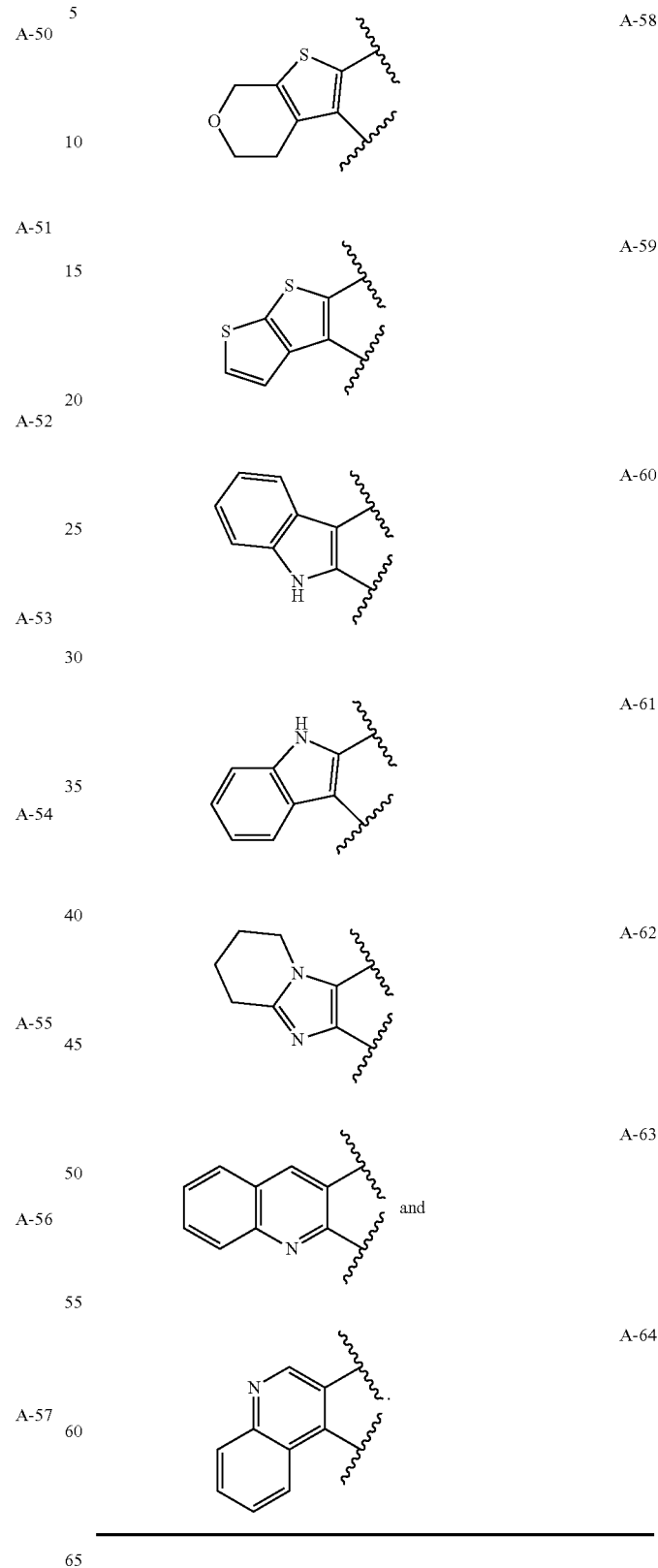
A-58
A-59
A-60
A-61
A-62
A-63 and
A-64
In some embodiments, the invention relates to a compound of formula (B):

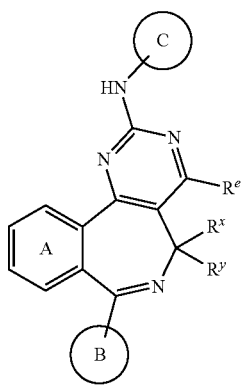

(B)

or a pharmaceutically acceptable salt thereof, wherein Ring A is substituted with 0-3 $R^b$. Rings B and C, and the variables $R^e$, $R^x$, and $R^y$ are as defined above for formula (A).

In certain such embodiments, Ring A has the formula A-i:

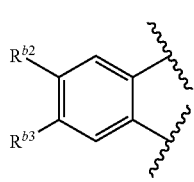

A-i wherein each of $R^{b2}$ and $R^{b3}$ independently is hydrogen or $R^b$. In some embodiments, each of $R^{b2}$ and $R^{b3}$ independently is selected from the group consisting of hydrogen, -halo, $C_{1-3}$ aliphatic, $C_{1-3}$ fluoroaliphatic, and —$OR^5$, where $R^5$ is hydrogen or $C_{1-3}$ aliphatic. In certain embodiments, each of $R^{b2}$ and $R^{b3}$ independently is selected from the group consisting of hydrogen, chloro, fluoro, bromo, methyl, trifluoromethyl, and methoxy. In some other embodiments, $R^{b2}$ and $R^{b3}$, taken together with the intervening ring carbon atoms, form an optionally substituted fused 4- to 8-membered aromatic or non-aromatic ring having 0-3 ring heteroatoms selected from the group consisting of O, N, and S.

In the compounds of formulae (A), (A-1), and (B) above, Ring B is a mono-, bi-, or tricyclic ring system. In some embodiments, the point of attachment for Ring B to the rest of the formula is on an aryl or heteroaryl ring of the Ring B moiety. In other embodiments, the point of attachment is on an heterocyclyl or cycloaliphatic ring. Preferably, Ring B is mono- or bicyclic.

Each substitutable saturated ring carbon atom in Ring B is unsubstituted or is substituted with =O, =S, =C($R^5$)$_2$, =N—N($R^4$)$_2$, =N—$OR^5$, =N—NHC(O)$R^5$, =N—NHCO$_2R^6$, =N—NHSO$_2R^6$, =N—$R^5$ or —$R^c$. Each substitutable unsaturated ring carbon atom in Ring B is unsubstituted or substituted with —$R^c$. Each substitutable ring nitrogen atom in Ring B is unsubstituted or is substituted with —$R^{9c}$, and one ring nitrogen atom in Ring B optionally is oxidized. Each $R^{9c}$ independently is —C(O)$R^5$, —C(O)N($R^4$)$_2$, —CO$_2R^6$, —SO$_2R^6$, —SO$_2$N($R^4$)$_2$, or a $C_{1-4}$ aliphatic optionally substituted with $R^3$ or $R^7$. Ring B may be unsubstituted or may be substituted on any one or more of its component rings, wherein the substituents may be the same or different. In some embodiments, Ring B is substituted with 0-2 independently selected $R^c$ and 0-3 independently selected $R^{2c}$ or $C_{1-6}$ aliphatic groups. The variables $R^3$, $R^4$, $R^5$, $R^6$, and $R^7$ are as defined above for Ring A, and $R^c$ and $R^{2c}$ are defined below.

Each $R^c$ independently is $R^{2c}$, an optionally substituted $C_{1-6}$ aliphatic, or an optionally substituted aryl, heteroaryl, or heterocyclyl group.

Each $R^{2c}$ independently is -halo, —NO$_2$, —CN, —C($R^5$)=C($R^5$)$_2$, —C($R^5$)=C($R^5$)($R^{10}$), —C≡C—R, —C≡C—$R^{10}$, —$OR^5$, —$SR^6$, —S(O)$R^6$, —SO$_2R^6$, —SO$_2$N($R^4$)$_2$, —N($R^4$)$_2$, —$NR^4$C(O)$R^5$, —$NR^4$C(O)N($R^4$)$_2$, —$NR^4$CO$_2R^6$, —O—CO$_2R^5$, —OC(O)N($R^4$)$_2$, —O—C(O) $R^5$, —CO$_2R^5$, —C(O)—C(O)$R^5$, —C(O)$R^5$, —C(O)N ($R^4$)$_2$, —C(=N$R^4$)—N($R^4$)$_2$, —C(=N$R^4$)—$OR^5$, —N($R^4$)—N($R^4$)$_2$, —N($R^4$)C(=N$R^4$)—N($R^4$)$_2$, —N($R^4$) SO$_2R^6$, —N($R^4$)SO$_2$N($R^4$)$_2$, —P(O)($R^5$)$_2$, or —P(O)($OR^5$)$_2$.

In some embodiments, each $R^c$ independently is selected from the group consisting of $C_{1-6}$ aliphatic, $R^{2c}$, $R^{7c}$, -$T^1$-$R^{2c}$, and -$T^1$-$R^{7c}$, where $R^{2c}$ is as described above and $T^1$ and $R^{7c}$ are described below.

$T^1$ is a $C_{1-6}$ alkylene chain optionally substituted with $R^3$ or $R^{3b}$, wherein $T^1$ or a portion thereof optionally forms part of a 3- to 7-membered ring.

Each $R^3$ independently is selected from the group consisting of -halo, —OH, —O($C_{1-3}$ alkyl), —CN, —N($R^4$)$_2$, —C(O)($C_{1-3}$ alkyl), —CO$_{2H}$, —CO$_2$($C_{1-3}$ alkyl), —C(O)NH$_2$, and —C(O)NH($C_{1-3}$alkyl).

Each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring.

Each $R^{7c}$ independently is an optionally substituted aryl, heterocyclyl, or heteroaryl group.

In some embodiments, each $R^c$ independently is selected from the group consisting of $C_{1-3}$ aliphatic, $R^{2c}$, $R^{7c}$, -$T^1$-$R^{2c}$, and -$T^1$-$R^{7c}$, where $T^1$ is a $C_{1-3}$ alkylene chain optionally substituted with fluoro. In some embodiments, each $R^c$ independently is selected from the group consisting of $C_{1-3}$ aliphatic, $R^{2c}$, and -$T^1$-$R^{2c}$, where $T^1$ is a $C_{1-3}$ alkylene chain optionally substituted with fluoro. In some such embodiments, each $R^{2c}$ independently is selected from the group consisting of -halo, —NO$_2$, —C($R^5$)=C($R^5$)$_2$, —C≡C—$R^5$, —$OR^5$, and —N($R^4$)$_2$.

In some embodiments, Ring B is a substituted or unsubstituted mono- or bicyclic aryl or heteroaryl ring selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, triazinyl, indolizinyl, indolyl, isoindolyl, indazolyl, benzo[b]furanyl, benzo[b]thienyl, benzimidazolyl, benzthiazolyl, benzoxazolyl, purinyl, quinolyl, isoquinolyl, cinnolinyl, phthalazinyl, quinazolinyl, quinoxalinyl, naphthyridinyl, and pteridinyl.

In some embodiments, Ring B is a monocyclic 5- or 6-membered aryl or heteroaryl ring, substituted with 0-2 independently selected $R^c$ and 0-2 independently selected $R^{2c}$ or $C_{1-6}$ aliphatic groups. In certain such embodiments, Ring B is a substituted or unsubstituted phenyl or pyridyl ring.

In some embodiments, Ring B is substituted with 0-2 substituents $R^c$. In some such embodiments, each $R^c$ independently is $C_{1-3}$ aliphatic or $R^{2c}$, and each $R^{2c}$ independently is selected from the group consisting of -halo, —NO$_2$, —C($R^5$)=C($R^5$)$_2$, —C≡C—$R^5$, —$OR^5$, and —N($R^4$)$_2$. In some embodiments, each $R^c$ independently is selected from the group consisting of -halo, $C_{1-3}$ aliphatic, $C_{1-3}$ haloaliphatic, and —$OR^5$, where $R^5$ is hydrogen or $C_{1-3}$ aliphatic. In certain preferred embodiments, Ring B is substituted with 0, 1, or 2 substituents, independently selected from the group consisting of chloro, fluoro, bromo, methyl, trifluoromethyl, and methoxy.

In some embodiments, Ring B has the formula B-i:

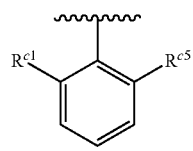

wherein each of $R^{c1}$ and $R^{c5}$ independently is hydrogen or $R^c$. In some embodiments, each of $R^{c1}$ and $R^{c5}$ independently is selected from the group consisting of hydrogen, -halo, $C_{1-3}$ aliphatic, $C_{1-3}$ fluoroaliphatic, and —$OR^5$, where $R^5$ is hydrogen or $C_{1-3}$ aliphatic. In certain embodiments, each of $R^{c1}$ and $R^{c5}$ independently is selected from the group consisting of hydrogen, chloro, fluoro, bromo, methyl, trifluoromethyl, and methoxy.

In the compounds of formulae (A), (A-1), and (B) above, Ring C is a substituted or unsubstituted mono-, bi-, or tricyclic ring system. In some embodiments, the point of attachment for Ring C to the rest of the formula is on an aryl or heteroaryl ring of the Ring C moiety. In other embodiments, the point of attachment is on a heterocyclyl or cycloaliphatic ring. Preferably, Ring C is mono-, or bicyclic.

Each substitutable saturated ring carbon atom in Ring C is unsubstituted or is substituted with =O, =S, =$C(R^5)_2$, =N—$N(R^4)_2$, =N—$OR^5$, =N—$NHC(O)R^5$, =N—$NHCO_2R^6$, =N—$NHSO_2R^6$, =N—$R^5$ or —$R^d$. Each substitutable unsaturated ring carbon atom in Ring C is unsubstituted or substituted with —$R^d$. Each substitutable ring nitrogen atom in Ring C is unsubstituted or is substituted with —$R^{9d}$, and one ring nitrogen atom in Ring C optionally is oxidized. Each $R^{9d}$ independently is —$C(O)R^5$, —$C(O)N(R^4)_2$, —$CO_2R^6$, —$SO_2R^6$, —$SO_2N(R^4)_2$, or a $C_{1-4}$ aliphatic optionally substituted with $R^3$ or $R^7$. Ring C may be unsubstituted or may be substituted on any one or more of its component rings, wherein the substituents may be the same or different. In some embodiments, Ring C is substituted with 0-2 independently selected $R^d$ and 0-3 independently selected $R^{2d}$ or $C_{1-6}$ aliphatic groups. The variables $R^3$, $R^4$, $R^5$, $R^6$, and $R^7$ are as described above for Rings A and B. The variables $R^d$ and $R^{2d}$ are described below.

Each $R^d$ independently is $R^{2d}$, an optionally substituted aliphatic, or an optionally substituted aryl, heteroaryl, or heterocyclyl group.

Each $R^{2d}$ independently is -halo, —$NO_2$, —CN, —$C(R^5)$=$C(R^5)_2$, —$C(R^5)$=$C(R^5)_2(R^{10})$, —C≡C—$R^5$, —C≡C—$R^{10}$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$NR^4CO_2R^6$, —O—$CO_2R^5$, —$OC(O)N(R^4)_2$, —O—$C(O)R^5$, —$CO_2R^5$, —$C(O)$—$C(O)R^5$, —$C(O)R^5$, —$C(O)N(R^4)_2$, —$C(=NR^4)$—$N(R^4)_2$, —$C(=NR^4)$—$OR^5$, —$N(R^4)$—$N(R^4)_2$, —$N(R^4)C(=NR^4)$—$N(R^4)_2$, —$N(R^4)SO_2R^6$, —$N(R^4)SO_2N(R^4)_2$, —$P(O)(R^5)_2$, or —$P(O)(OR^5)_2$. Additionally, $R^{2d}$ can be —$SO_3R^5$, —$C(O)N(R^4)C(=NR^4)$—$N(R^4)_2$ or —$N(R^4)C(=NR^4)$—$N(R^4)$—$N(R^4)$—$C(O)R^5$.

In some embodiments, each $R^d$ independently is selected from the group consisting of $C_{1-6}$ aliphatic, $R^{2d}$, $R^{7d}$, -$T^2$-$R^{2d}$, -$T^2$-$R^{7d}$, —V-$T^3$-$R^{2d}$, and —V-$T^3$-$R^{7d}$, wherein $R^{2d}$ is as described above, and $T^2$, $T^3$, V, and $R^{7d}$ are described below.

$T^2$ is a $C_{1-6}$ alkylene chain optionally substituted with $R^3$ or $R^{3b}$, wherein the alkylene chain optionally is interrupted by —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC(O)O—, —$OC(O)N(R^4)$—, —$N(R^4)$—$N(R^4)$—, —$N(R^4)SO_2$—, or —$SO_2N(R^4)$—, and wherein $T^2$ or a portion thereof optionally forms part of a 3-7 membered ring.

$T^3$ is a $C_{1-6}$ alkylene chain optionally substituted with $R^3$ or $R^{3b}$, wherein the alkylene chain optionally is interrupted by —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC(O)O—, —$OC(O)N(R^4)$—, —$N(R^4)$—$N(R^4)$—, —$N(R^4)SO_2$—, or —$SO_2N(R^4)$—, and wherein $T^3$ or a portion thereof optionally forms part of a 3-7 membered ring.

V is —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC(O)O—, —$OC(O)N(R^4)$—, —$C(NR^4)$=N—, —$C(OR^5)$=N—, —$N(R^4)$—$N(R^4)$—, —$N(R^4)SO_2$—, —$N(R^4)SO_2N(R^4)$—, —$P(O)(R^5)$—, —$P(O)(OR^5)$—O—, —P(O)—O—, or —$P(O)(NR^5)$—$N(R^5)$—.

Each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring.

Each $R^{7d}$ independently is an optionally substituted aryl, heterocyclyl, or heteroaryl group.

In some embodiments, each $R^{2d}$ independently is selected from the group consisting of -halo, —$OR^5$, —$N(R^4)_2$, —$N(R^4)C(O)$—, —$CO_2R^5$, —$C(O)N(R^4)_2$, and —$SO_2N(R_4)_2$. In some other embodiments, each $R^{2d}$ independently is -halo, —$OR^5$, —$N(R^4)_2$, —$N(R^4)C(O)$—, —$CO_2R^5$, —$C(O)N(R^4)_2$, and —$SO_2N(R_4)_2$, —$C(O)N(R^4)C(=NR^4)$—$N(R^4)_2$ or —$N(R^4)C(=NR^4)$—$N(R^4)$—$N(R^4)$—$C(O)R^5$.

In some embodiments, $T^2$ is a $C_{1-6}$ alkylene chain, which optionally is substituted with one or two substituents $R^{3b}$ independently selected from the group consisting of -halo, —$C_{1-3}$ aliphatic, —OH, and —$O(C_{1-3}$ aliphatic), or two substituents $R^{3b}$ on the same carbon atom, taken together with the carbon atom to which they are attached, form a 3- to 6-membered carbocyclic ring. In some embodiments, $T^2$ optionally is interrupted by —$C(R^5)$=$C(R^5)$—, —C≡C—, —O—, —C(O)—, —$C(O)N(R^4)$—, —$N(R^4)C(O)$— or —$N(R^4)$—.

In some embodiments, V is —$C(R^5)$=$C(R^5)$—, —C≡C—, —O—, —$N(R^4)$—, —C(O)—, —$N(R^4)C(O)$—, or —$C(O)N(R^4)$—. In some embodiments, $T^3$ is a $C_{1-4}$ alkylene chain, which optionally is substituted with one or two $R^{3b}$ independently selected from the group consisting of -halo, —$C_{1-3}$ aliphatic, —OH, and —$O(C_{1-3}$ aliphatic), or two substituents $R^{3b}$ on the same carbon atom, taken together with the carbon atom to which they are attached, form a 3- to 6-membered carbocyclic ring. In some embodiments, $T^3$ is a $C_{1-4}$alkylene chain, which optionally is interrupted by —C($R^5$)=C($R^5$)—, —C≡C—, —O—, —C(O)—, —C(O)N($R^4$)—, —N($R^4$)C(O)— or —N($R^4$)—.

In some embodiments, each $R^d$ independently is selected from the group consisting of $C_{1-3}$ aliphatic, $R^{2d}$, $R^{7d}$, -$T^2$-$R^{2d}$, -$T^2$-$R^{7d}$, —V-$T^3$-$R^{2d}$, and —V-$T^3$-$R^{7d}$, where $R^{2d}$ is selected from the group consisting of -halo, —$OR^5$, —N($R^4$)$_2$, —N($R^4$)C(O)—, —$CO_2R^5$, —C(O)N($R^4$)$_2$, and —$SO_2N(R_4)_2$. Additionally, $R^{2d}$ can be —$SO_3R^5$, —C(O)N($R^4$)C(=N$R^4$)—N($R^4$)$_2$ or —N($R^4$)C(=N$R^4$)—N($R^4$)—C(O)$R^5$.

In some embodiments, Ring C is substituted with at least one $R^{7d}$ selected from the group consisting of:

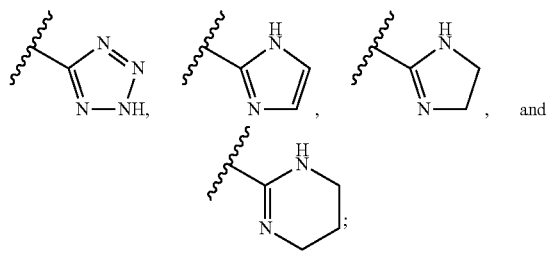

any of which groups optionally is substituted on any substitutable ring carbon or ring nitrogen atom.

In some embodiments, Ring C is substituted with at least one -$T^2$-$R^{2d}$ or -$T^2$-$R^{7d}$, where:

$T^2$ is a $C_{1-6}$ alkylene chain, wherein $T^2$ optionally is substituted with one or two substituents $R^{3b}$ independently selected from the group consisting of -halo, —$C_{1-3}$ aliphatic, —OH, and —O($C_{1-3}$ aliphatic), or two substituents $R^{3b}$ on the same carbon atom, taken together with the carbon atom to which they are attached, form a 3- to 6-membered carbocyclic ring, and wherein $T^2$ optionally is interrupted by —C($R^5$)=C($R^5$)—, —C≡C—, —O—, —C(O)—, —$NR^4C(O)R^5$, —N($R^4$)C(O)— or —N($R^4$)—; and $R^{2d}$ is selected from the group consisting of -halo, —$OR^5$, —N($R^4$)$_2$, —N($R^4$)C(O)—, —$CO_2R^5$, —C(O)N($R^4$)$_2$, —$SO_2N(R_4)_2$, —C(O)N($R^4$)C(=N$R^4$)—N($R^4$)$_2$, and —N($R^4$)C(=N$R^4$)—N($R^4$)—C(O)$R^5$.

In certain such embodiments, Ring C is substituted with one -$T^2$-$R^{2d}$ or -$T^2$-$R^{7d}$, and optionally one other substituent selected from the group consisting of hydrogen, -halo, $C_{1-3}$ aliphatic, and —$OR^5$, where $R^5$ is hydrogen or $C_{1-3}$ aliphatic. In some embodiments, $T^2$ is a $C_{1-6}$ alkylene chain, which optionally is interrupted by —C(O)N($R^4$)— or —N($R^4$)C(O)—.

In some embodiments, Ring C is substituted with at least one —V-$T^3$-$R^{2d}$ or —V-$T^3$-$R^{7d}$, where:

V is —N($R^4$)—, —O—, —C(O)N($R^4$)—, —C(O)—, or —C≡C—;

$T^3$ is a $C_{1-4}$ alkylene chain, which is optionally substituted by one or two substituents $R^{3b}$ independently selected from the group consisting of -halo, —$C_{1-3}$ aliphatic, —OH, and —O($C_{1-3}$ aliphatic), or two substituents $R^{3b}$ on the same carbon atom, taken together with the carbon atom to which they are attached, form a 3- to 6-membered carbocyclic ring; and $R^{2d}$ is selected from the group consisting of -halo, —$OR^5$, —N($R^4$)$_2$, —$NR^4C(O)R^5$, —$CO_2R^5$, —C(O)N($R^4$)$_2$, and —$SO_2N(R_4)_2$.

In certain such embodiments, Ring C is substituted with one —V-$T^3$-$R^{2d}$ or —V-$T^3$-$R^{7d}$, and optionally one other substituent selected from the group consisting of hydrogen, -halo, $C_{1-3}$ aliphatic, and —$OR^5$, where $R^5$ is hydrogen or $C_{1-3}$ aliphatic.

In some embodiments, Ring C is substituted with —V-$T^3$-$R^{2d}$, where V is —C(O)N($R^4$)—, $T^3$ is a $C_{2-4}$ alkylene chain, and $R^{2d}$ is —N($R^4$)$_2$. Each $R^4$ independently is hydrogen or $C_{1-3}$ aliphatic, or —N($R^4$)$_2$ is an optionally substituted 5- to 6-membered heteroaryl or 4- to 8-membered heterocyclyl ring having, in addition to the nitrogen, 0-2 ring heteroatoms selected from N, O, and S. In certain such embodiments, —N($R^4$)$_2$ is an optionally substituted heterocyclyl selected from the group consisting of piperidinyl, piperazinyl, and morpholinyl. In certain other such embodiments, —N($R^4$)$_2$ is an optionally substituted heterocyclyl selected from pyrrolidinyl and azetidinyl.

In other embodiments, Ring C is substituted with —V-$T^3$-$R^{7d}$, where V is —C(O)N($R^4$)—, $T^3$ is a $C_{2-4}$ alkylene chain, and $R^{7d}$ is an optionally substituted 4- to 8-membered heterocyclyl or an optionally substituted 5- to 6-membered heteroaryl. In certain such embodiments, $R^{7d}$ is selected from the group consisting of pyridyl, pyridazinyl, pyrimidinyl, pyrazinyl, pyrrolyl, oxazolyl, imidazolyl, and pyrazolyl. In certain other such embodiments, $R^{7d}$ is a 6- to 8-membered bicyclic heterocyclyl.

In some embodiments, Ring C is substituted with one or two substituents independently selected from the group consisting of $C_{1-3}$ aliphatic, -halo, —$OR^5$, —$CO_2R^5$, —C(O)N($R^4$)$_2$, and —$SO_2N(R^4)_2$. Additional selections possible for Ring C substituents in these embodiments include —C(=N$R^4$)N($R^4$)$_2$, —$NR^4C(O)R^5$, —C(O)N($R^4$)C(=N$R^4$)—N($R^4$)$_2$ and —N($R^4$)C(=N$R^4$)—N($R^4$)—C(O)$R^5$. In some embodiments, Ring C is substituted with at least one substituent selected from the group consisting of —$CO_2R^5$, —C(O)N($R^4$)$_2$, —C(=N$R^4$)N($R^4$)$_2$, —C(O)N($R^4$)C(=N$R^4$)—N($R^4$)$_2$, —N($R^4$)C(=N$R^4$)—N($R^4$)—C(O)$R^5$, and —$NR^4C(O)R^5$. In certain embodiments, Ring C is substituted with at least one —$CO_2R^5$, where $R^5$ is hydrogen or $C_{1-6}$ aliphatic.

In some embodiments, Ring C is substituted with at least one —C(O)—N($R^4$)$_2$, —C(=N$R^4$)N($R^4$)$_2$, or —$NR^4C(O)R^5$, where —N($R^4$)$_2$ is an optionally substituted 4- to 8-membered heterocyclyl ring having, in addition to the nitrogen atom, 0-2 ring heteroatoms selected from N, O, and S, and $R^5$ is an optionally substituted 4- to 8-membered nitrogen-containing heterocyclyl ring. In some such embodiments, —N($R^4$)$_2$ is an optionally substituted heterocyclyl selected from the group consisting of piperidinyl, piperazinyl, morpholinyl, pyrrolidinyl, and azetidinyl. In some other such embodiments, —N($R^4$)$_2$ is a bridged or spiro bicyclic heterocyclyl.

In certain embodiments, Ring C is substituted with at least one substituent having the formula D-i:

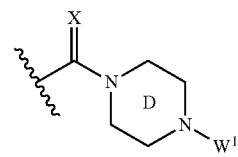

D-i wherein:
Ring D optionally is substituted on one or two ring carbon atoms;
X is O or NH;

$W^1$ is hydrogen, —C(O)$R^5$, —C(O)N($R^4$)$_2$, —CO$_2$$R^6$, —SO$_2$$R^6$, —SO$_2$N($R^4$)$_2$, or an optionally substituted aliphatic, aryl, heteroaryl, or heterocyclyl group.

In some embodiments, Ring D in formula D-i is substituted with one or two substituents selected from the group consisting of C$_{1-3}$ aliphatic, —CO$_2$$R^5$, —C(O)N($R^4$)$_2$, and -T$^5$-R$^m$, where T$^5$ is a C$_{1-3}$ alkylene chain and R$^m$ is —OR$^5$, —N($R^4$)$_2$, —CO$_2$$R^5$, or —C(O)N($R^4$)$_2$. In some such embodiments, Ring D in formula D-1 is substituted with one or two substituents selected from the group consisting of C$_{1-3}$ aliphatic, —CO$_2$H, —CO$_2$(C$_{1-3}$ alkyl), —C(O)N(C$_{1-3}$ alkyl)$_2$, —C(O)NH(C$_{1-3}$alkyl), —C(O)NH$_2$, —(C$_{1-3}$ alkyl)-OH, —(C$_{1-3}$ alkylene)-O(C$_{1-3}$alkyl), —(C$_{1-3}$alkylene)-NH$_2$, —(C$_{1-3}$alkylene)-NH(C$_{1-3}$alkyl), —(C$_{1-3}$alkylene)-N(C$_{1-3}$ alkyl)$_2$, —(C$_{1-3}$ alkylene)-CO$_2$H, —(C$_{1-3}$alkylene)-CO$_2$(C$_{1-3}$alkyl), —(C$_{1-3}$ alkylene)-C(O)NH$_2$, —(C$_{1-3}$ alkylene)-C(O)NH(C$_{1-3}$ alkyl), and —(C$_{1-3}$alkylene)-C(O)N(C$_{1-3}$ alkyl)$_2$.

In certain other embodiments, Ring C is substituted with at least one substituent having one of the formulae D-ii to D-v below:

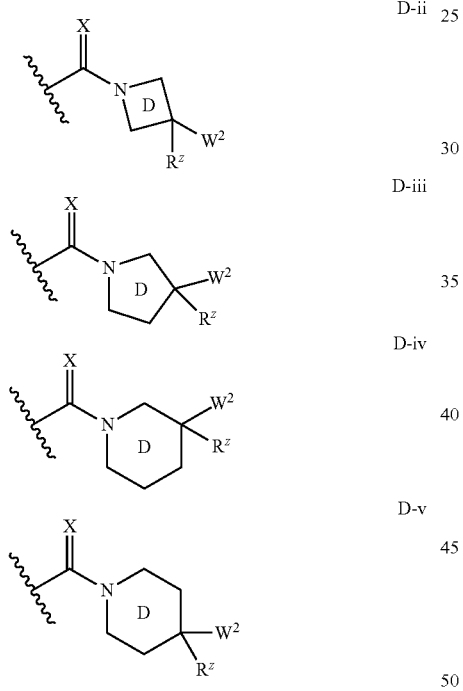

wherein:
Ring D optionally is substituted on one or two substitutable ring carbon atoms;
X is O or NH;
$W^2$ is R" or -T$^6$-R";
T$^6$ is a C$_{1-3}$ alkylene chain optionally substituted with R$^3$ or R$^{3b}$; and
R" is —N($R^4$)$_2$ or —C(O)N($R^4$)$_2$; and
R$^z$ is hydrogen, —CO$_2$$R^5$, C(O)N($R^4$)$_2$, —C(O)$R^5$, or a C$_{1-3}$ aliphatic optionally substituted with R$^3$ or R$^7$; or R$^z$ and $W^2$, taken together with the carbon atom to which they are attached, form a 4- to 7-membered cycloaliphatic or heterocyclyl ring.

In some embodiments, Ring D in formulae D-ii to D-v is substituted with one or two substituents selected from the group consisting of C$_{1-3}$ aliphatic, —CO$_2$$R^5$, —C(O)N($R^4$)$_2$, —OR$^5$, —N($R^4$)$_2$, and -T$^5$-R$^m$, where T$^5$ is a C$_{1-3}$alkylene chain and R$^m$ is —OR$^5$, —N($R^4$)$_2$, —CO$_2$$R^5$, or —C(O)N($R^4$)$_2$.

In certain embodiments, at least one substituent on Ring C is selected from the group consisting of:

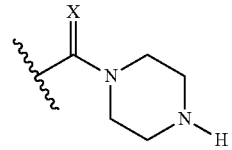

D-1

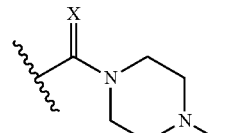

D-2

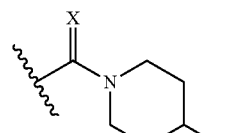

D-3

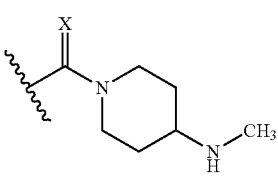

D-4

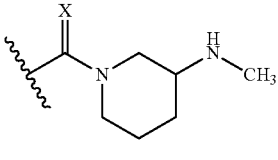

D-5

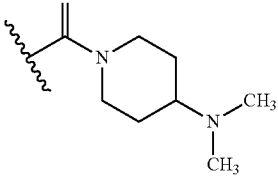

D-6

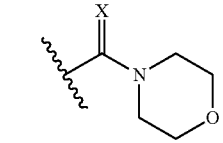

D-7

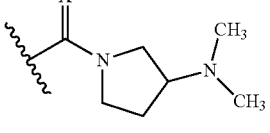

D-8

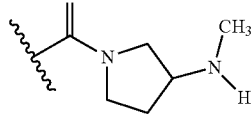

D-9

-continued
D-10
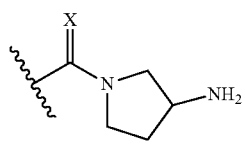
D-11
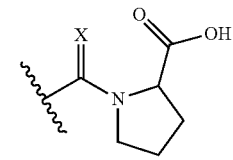
D-12
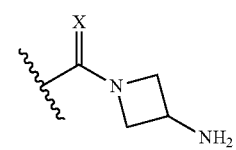
D-13
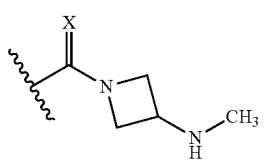
D-14
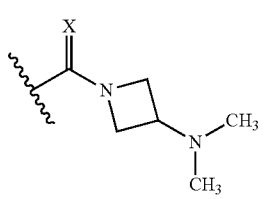
D-15
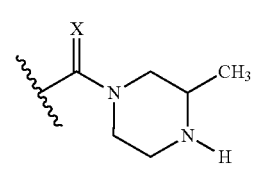
D-16
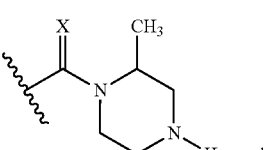
D-17
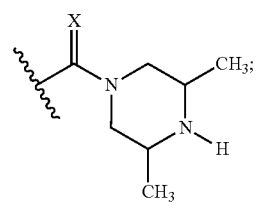
where X is O or NH.
In certain other embodiments, at least one substituent on Ring C is selected from the group consisting of:
D-18
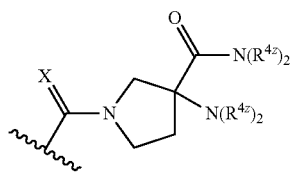
D-19
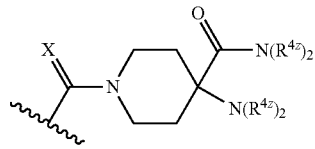
D-20
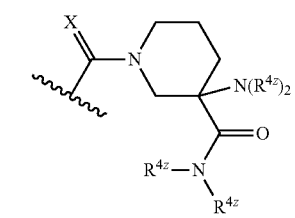
D-21
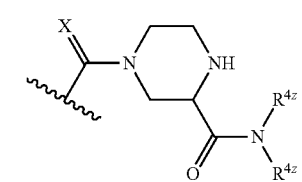
D-22
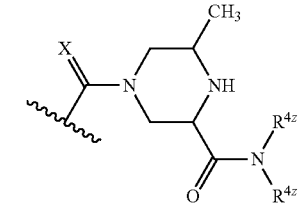
D-23
D-24
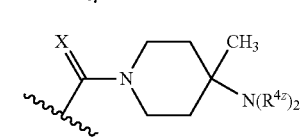
D-25
D-26
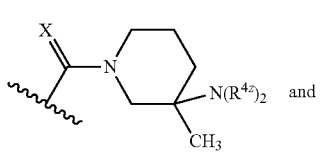
where X is O or NH, and each $R^{4z}$ independently is hydrogen or —CH$_3$.

In certain other embodiments, at least one substituent on Ring C is selected from the group consisting of:

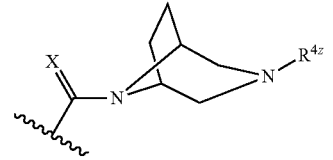
D-27

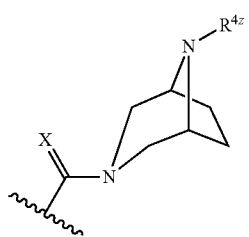
D-28

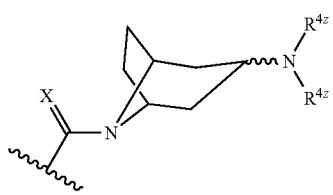
D-29

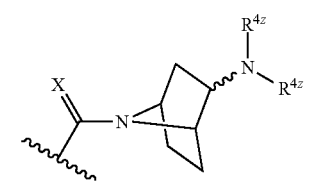
D-30

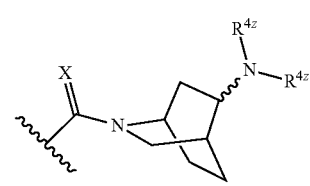
D-31

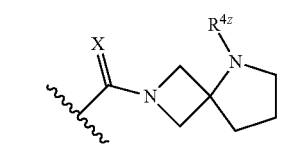
D-32

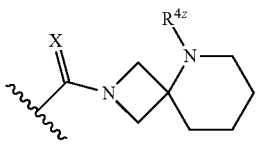
D-33

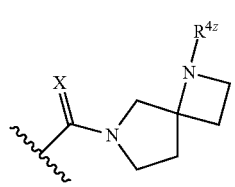
D-34

-continued

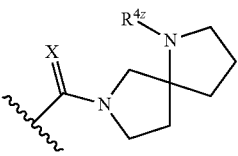
D-35

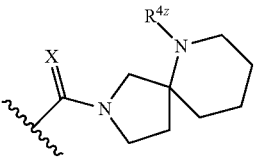
D-36

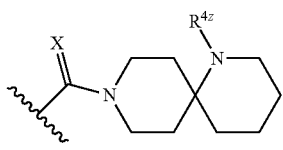
D-37

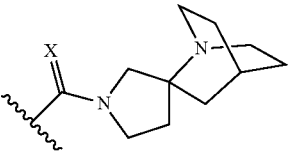
D-38

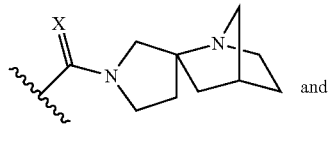
D-39 and

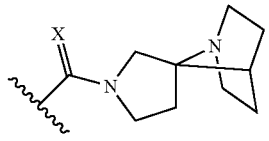
D-40 where X is O or NH, and each $R^{4z}$ independently is hydrogen or —CH$_3$.

In some embodiments, Ring C is substituted with at least one —C(O)N(R$^4$)$_2$ or —C(=NH)N(R$^4$)$_2$, where one R$^4$ is hydrogen or C$_{1-3}$alkyl, and the other R$^4$ is an optionally substituted heterocyclyl or heterocyclylalkyl. In some such embodiments, Ring C is substituted with at least one substituent selected from the group consisting of:

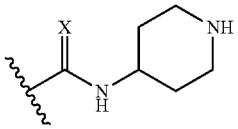
D-41

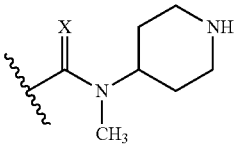
D-42

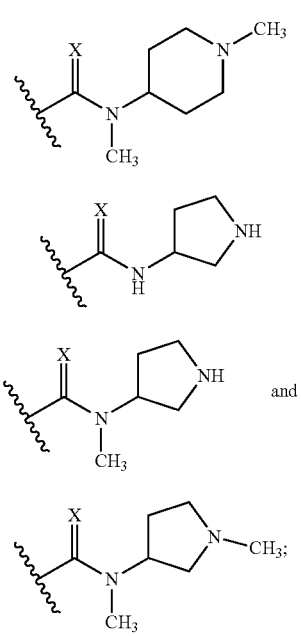

where X is O or NH.

In some other such embodiments, Ring C is substituted with at least one substituent selected from the group consisting of:

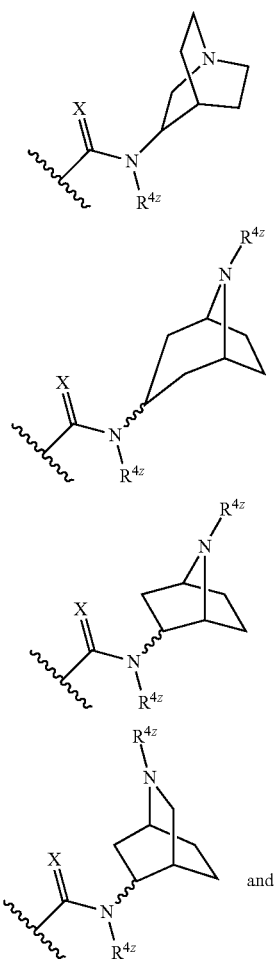

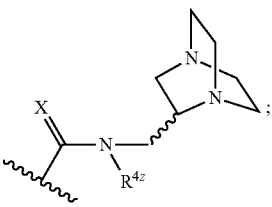

where X is O or NH, and each $R^{4z}$ independently is H or $CH_3$.

In some embodiments, Ring C is a bicyclic aryl group, which is substituted with 0-2 independently selected $R^d$ and 0-3 independently selected $R^{2d}$ or $C_{1-6}$ aliphatic groups. In some such embodiments, Ring C is a phenyl ring fused to a 5- or 6-membered carbocyclic, heteroaryl, or heterocyclyl ring, wherein each ring independently is substituted or unsubstituted. In certain such embodiments, Ring C is an optionally substituted benzodioxanyl or benzodioxolyl ring. In certain other such embodiments, Ring C is an optionally substituted benzimidazolyl, benzthiazolyl, benzoxazolyl, or phthalimidyl ring, wherein Ring C is attached to the rest of formula (A), (A-1), or (B) at the benzo ring of the bicyclic Ring C moiety.

In some other embodiments, Ring C is a monocyclic 5- or 6-membered aryl or heteroaryl ring, which is substituted with 0-2 independently selected substituents $R^d$ and 0-2 independently selected $R^{2d}$ or $C_{1-6}$ aliphatic groups. In some such embodiments, Ring C is an optionally substituted heteroaryl ring selected from the group consisting of pyridyl, pyrimidinyl, pyrazinyl, pyridazinyl, imidazolyl, pyrazolyl, and oxazolyl. In some other embodiments, Ring C is a substituted or unsubstituted phenyl ring. In some embodiments, Ring C is a monocyclic 5- or 6-membered aryl or heteroaryl ring, which is substituted with 0, 1, or 2 substituents $R^d$, as defined above.

In yet other embodiments, Ring C is a monocyclic 5- or 6-membered heterocyclyl or cycloaliphatic ring, which is substituted with 0-2 independently selected substituents $R^d$ and 0-2 independently selected $R^{2d}$ or $C_{1-6}$ aliphatic groups.

Some embodiments of the invention relate to a subgenus of formula (A) defined by formula (I):

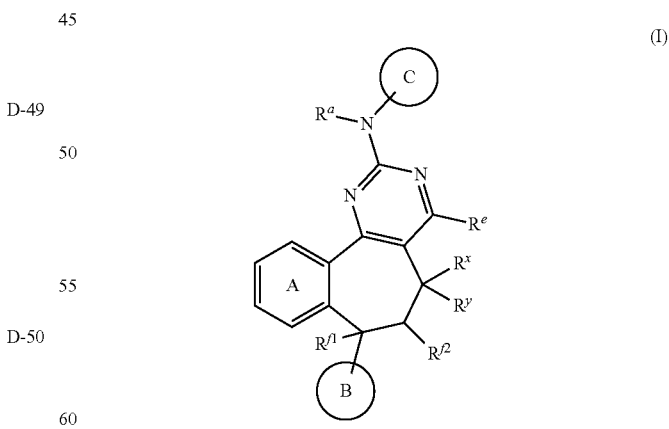

or a pharmaceutically acceptable salt thereof, wherein Ring A, Ring B, Ring C, and each of the variables $R^a$, $R^b$, $R^e$, $R^{f1}$, and $R^{f2}$ have the values described below.

Ring A is substituted with 0-3 $R^b$.

Ring B is a substituted or unsubstituted aryl or heteroaryl ring.

Ring C is a substituted or unsubstituted aryl or heteroaryl ring. Additionally, Ring C can be a heterocyclyl, or cycloaliphatic ring.

$R^a$ is hydrogen, —C(O)$R^1$, —CO$_2R^1$, —SO$_2R^1$, or a $C_{1-3}$ aliphatic having 0-2 substituents independently selected from $R^3$ or $R^7$.

$R^1$ is an optionally substituted $C_{1-6}$ aliphatic or an optionally substituted aryl, heteroaryl, or heterocyclyl group.

Each $R^b$ independently is $R^{2b}$, an optionally substituted aliphatic, or an optionally substituted aryl, heteroaryl, or heterocyclyl group. In some embodiments each $R^b$ independently is selected from the group consisting of $C_{1-6}$ aliphatic, $R^{2b}$, $R^{7b}$, -$T^1$-$R^{2b}$, and -$T^1$-$R^{7b}$. In some embodiments, two adjacent $R^b$, taken together with the intervening carbon atoms, form an optionally substituted fused 4- to 8-membered aromatic or non-aromatic ring having 0-3 ring heteroatoms selected from the group consisting of O, N, and S.

$T^1$ is a $C_{1-6}$ alkylene chain optionally substituted with $R^3$ or $R^{3b}$, wherein $T^1$ or a portion thereof optionally forms part of a 3- to 7-membered ring.

Each $R^{2b}$ independently is -halo, —NO$_2$, —CN, —C($R^5$)=C($R^5$)$_2$, —C($R^5$)=C($R^5$)($R^{10}$), —C≡C—$R^5$, —C≡C—$R^{10}$, —O$R^5$, —S$R^6$, —S(O)$R^6$, —SO$_2R^6$, —SO$_2$N($R^4$)$_2$, —N($R^4$)$_2$, —NR$^4$C(O)$R^5$, —NR$^4$C(O)N($R^4$)$_2$, —NR$^4$CO$_2R^6$, —O—CO$_2R^5$, —OC(O)N($R^4$)$_2$, —O—C(O)$R^5$, —CO$_2R^5$, —C(O)—C(O)$R^5$, —C(O)$R^5$, —C(O)N($R^4$)$_2$, —C(=N$R^4$)—N($R^4$)$_2$, —C(=N$R^4$)—O$R^5$, —N($R^4$)—N($R^4$)$_2$, —N($R^4$)C(=N$R^4$)—N($R^4$)$_2$, —N($R^4$)SO$_2R^6$, —N($R^4$)SO$_2$N($R^4$)$_2$, —P(O)($R^5$)$_2$, or —P(O)(O$R^5$)$_2$.

Each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring.

Each $R^{7b}$ independently is an optionally substituted aryl, heterocyclyl, or heteroaryl group.

$R^e$ is hydrogen or a $C_{1-3}$ aliphatic optionally substituted with $R^3$ or $R^7$.

$R^{f1}$ and $R^{f2}$ each are hydrogen, or $R^{f1}$ and $R^{f2}$ together form a bond.

Each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$alkyl).

Each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered or 5- to 8-membered heteroaryl or heterocyclyl ring having, in addition to the nitrogen atom, 0-2 ring heteroatoms selected from N, O, and S.

Each $R^5$ independently is hydrogen or an optionally substituted aliphatic, aryl, heteroaryl, or heterocyclyl group.

Each $R^6$ independently is an optionally substituted aliphatic or aryl group.

Each $R^7$ independently is an optionally substituted aryl, heterocyclyl, or heteroaryl group.

Each $R^{10}$ independently is —CO$_2R^5$ or —C(O)N($R^4$)$_2$.

In some embodiments, the compound of formula (I) is characterized by at least one, two, or three of the following features (a)-(f):

(a) $R^a$ is hydrogen or $C_{1-3}$ alkyl;
(b) $R^{f1}$ and $R^{f2}$ together form a bond;
(c) Ring A is substituted with 0-2 $R^b$, where each $R^b$ independently is selected from the group consisting of $C_{1-3}$ aliphatic, $R^{2b}$, $R^{7b}$, -$T^1$-$R^{2b}$, and -$T^1$-$R^b$, where $T^1$ is a $C_{1-3}$ alkylene chain;
(d) Ring B is a monocyclic 5- or 6-membered aryl or heteroaryl ring, which is substituted with 0-2 $R^c$, where each $R^c$ independently is selected from the group consisting of $C_{1-3}$ aliphatic, $R^{2c}$, $R^{7c}$, -$T^1$-$R^{2c}$, and -$T^1$-$R^{7c}$, where $T^1$ is a $C_{1-3}$ alkylene chain;
(e) Ring C is a mono- or bicyclic aryl or heteroaryl ring, which is substituted with 0-2 independently selected $R^d$ and 0-2 independently selected $R^{2d}$ or $C_{1-6}$ aliphatic groups; and
(f) $R^e$ is hydrogen.

In some embodiments, the compound of formula (I) is characterized by all six of the features (a)-(f) above.

Some embodiments of the invention relate to a subgenus of formula (A) defined by formula (B) or (II):

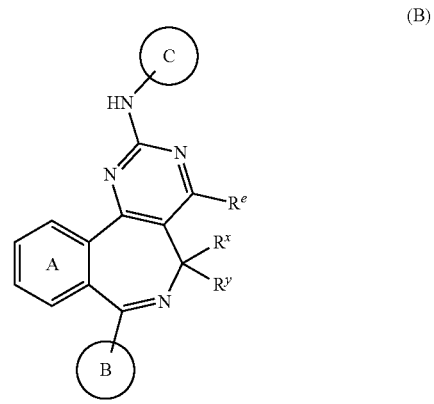

(B)

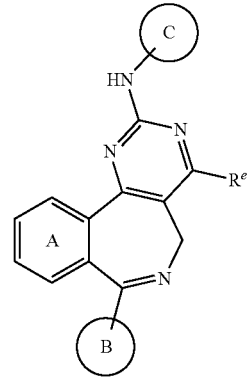

(II)

wherein each of $R^e$, $R^x$, $R^y$, and Rings A, B, and C have the values and preferred values described above for formulae (B) and (I). In some such embodiments, Ring B is a mono- or bicyclic aryl or heteroaryl ring, which is substituted with 0-2 independently selected $R^c$ and 0-2 independently selected $R^{2c}$ or $C_{1-6}$ aliphatic groups, and Ring C as a mono- or bicyclic aryl, heteroaryl, heterocyclyl or cycloaliphatic ring, which is substituted with 0-2 independently selected $R^d$ and 0-2 independently selected $R^{2d}$ or $C_{1-6}$ aliphatic groups.

In some embodiments, the compound of formula (II) is defined by formula (IIa):

(IIa)

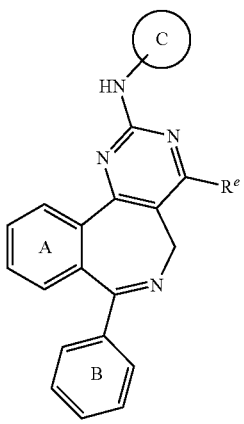

wherein Ring A is substituted with 0-2 independently selected $R^b$, and Ring B is substituted with 0-2 independently selected $R^c$. In some embodiments, the compound of formula (IIa) is characterized by at least one of the following features (a)-(c):

(a) each $R^b$ independently is selected from the group consisting of $C_{1-3}$ aliphatic, $R^{2b}$, $R^{7b}$, $-T^1-R^{2b}$, and $-T^1-R^{7b}$, where $T^1$ is a $C_{1-3}$ alkylene chain optionally substituted with fluoro, and each $R^{2b}$ independently is selected from the group consisting of -halo, $-NO_2$, $-C(R^5)=C(R^5)_2$, $-C\equiv C-R^5$, $-OR^5$, and $-N(R^4)_2$;

(b) each $R^c$ independently is selected from the group consisting of $C_{1-3}$ aliphatic, $R^{2c}$, $R^{7c}$, $-T^1-R^{2c}$, and $-T^1-R^{7c}$, where T is a $C_{1-3}$alkylene chain optionally substituted with fluoro, and each $R^{2c}$ independently is selected from the group consisting of -halo, $-NO_2$, $-C(R^5)=C(R^5)_2$, $-C\equiv C-R^5$, $-OR^5$, and $-N(R^4)_2$; and (c) $R^e$ is hydrogen.

Some embodiments of the invention relate to a subgenus of the compounds of formula (IIa) defined by formula (III):

(III)

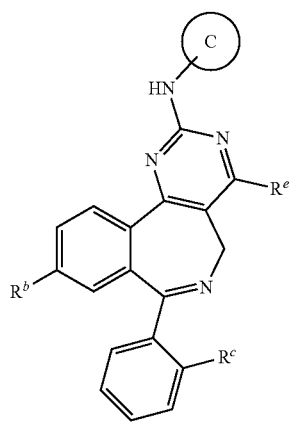

wherein each of $R^b$, $R^c$, $R^e$, and Ring C have the values or preferred values described above for any preceding formula.

Some embodiment of the invention relate to a subgenus of the compounds of formula (IIa) defined by formula (IIIa):

(IIIa)

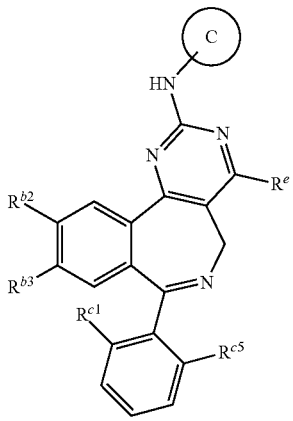

wherein: each of $R^{b2}$ and $R^{b3}$ independently is hydrogen or $R^b$; each of $R^{c1}$ and $R^{c5}$ independently is hydrogen or $R^c$; and each of Ring C, $R^b$, $R^c$, and $R^e$ have the values and preferred values described above for any preceding formula.

In some embodiments, each $R^b$ in formula (III) or (IIIa) is selected from the group consisting of $C_{1-3}$ aliphatic, $C_{1-3}$ fluoroaliphatic, and $R^{2b}$; and each $R^c$ is selected from the group consisting of $C_{1-3}$ aliphatic, $C_{1-3}$ fluoroaliphatic, and $R^{2c}$. In certain such embodiments, each of $R^{2b}$ and $R^{2c}$ independently is selected from the group consisting of -halo, $-NO_2$, $-C(R^5)=C(R^5)_2$, $-C\equiv C-R^5$, $-OR^5$, and $-N(R^4)_2$.

In some embodiments, the invention relates to a compound of formula (IIIa), wherein $R^e$ is hydrogen; each of $R^{b2}$ and $R^{b3}$ independently is selected from the group consisting of hydrogen, -halo, $C_{1-3}$ aliphatic, $C_{1-3}$ fluoroaliphatic, and $-OR^5$, where $R^5$ is hydrogen or $C_{1-3}$ aliphatic; and each of $R^{c1}$ and $R^{c5}$ independently is selected from the group consisting of hydrogen, -halo, $C_{1-3}$ aliphatic, $C_{1-3}$ fluoroaliphatic, and $-OR^5$, where $R^5$ is hydrogen or $C_{1-3}$ aliphatic. In some embodiments, each of $R^{b3}$ and $R^{c1}$ independently is selected from the group consisting of -halo, $C_{1-3}$ aliphatic, $C_{1-3}$ fluoroaliphatic, and $-OR^5$, where $R^5$ hydrogen or $C_{1-3}$ aliphatic. In certain such embodiments, $R^{b2}$ is hydrogen, $R^{c5}$ is selected from the group consisting of hydrogen, -halo, $C_{1-3}$ aliphatic, $C_{1-3}$ fluoroaliphatic, and $-OR^5$, and each of $R^{b3}$ and $R^{c1}$ independently is selected from the group consisting of -halo, $C_{1-3}$ aliphatic, $C_{1-3}$ fluoroaliphatic, and $-OR^5$, where $R^5$ hydrogen or $C_{1-3}$ aliphatic. In certain embodiments, $R^{b2}$ is hydrogen, $R^{c2}$ is hydrogen, chloro, fluoro, bromo, methyl, trifluoromethyl, or methoxy, and each of $R^{b3}$ and $R^{c1}$ independently is chloro, fluoro, bromo, methyl, trifluoromethyl, or methoxy.

Some embodiments of the invention relate to a subgenus of the compounds of formula (A) defined by formula (IV):

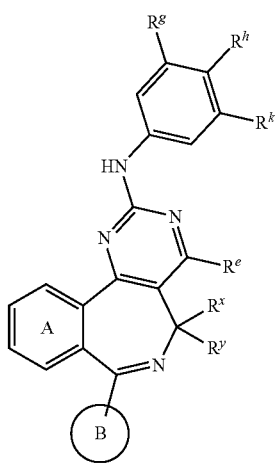

(IV)

wherein:
Ring A is substituted with 0-2 $R^b$;
Ring B is a mono- or bicyclic aryl or heteroaryl ring, which optionally is substituted with 0-2 independently selected $R^c$ and 0-3 independently selected $R^{2c}$ or $C_{1-6}$ aliphatic groups;
$R^e$ is hydrogen or a $C_{1-3}$ aliphatic optionally substituted with $R^3$ or $R^7$;
$R^g$ is selected from the group consisting of hydrogen, $C_{1-6}$ aliphatic, and $R^{2d}$; and each of $R^h$ and $R^k$ independently is hydrogen or $R^d$.

In some such embodiments, the invention relates to a compound of formula (IV), wherein:
each $R^4$ in $R^d$ or $R^{2d}$ is hydrogen, $C_{1-3}$alkyl, or a 5- or 6-membered aryl or heteroaryl ring; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S; and
each $R^5$ in $R^d$ or $R^{2d}$ is hydrogen, $C_{1-3}$ alkyl, or a 5- or 6-membered aryl or heteroaryl ring.

In some such embodiments, two $R^4$ on the same nitrogen atom in $R^d$ or $R^{2d}$ taken together with the nitrogen atom, form an optionally substituted piperidinyl, piperazinyl, or morpholinyl ring.

In some embodiments, the invention relates to a compound of formula (IV) wherein:
Ring A is substituted with 0-2 $R^b$, where each $R^b$ independently is selected from the group consisting of $C_{1-3}$ aliphatic, $R^{2b}$, $R^b$, -$T^1$-$R^{2b}$, and -$T^1$-$R^{7b}$, where $T^1$ is a $C_{1-3}$ alkylene chain;
Ring B is a monocyclic 5- or 6-membered aryl or heteroaryl ring, which is substituted with 0-2 independently selected $R^c$, where each $R^c$ independently is selected from the group consisting of $C_{1-3}$ aliphatic, $R^{2c}$, $R^{7c}$, -$T^1$-$R^{2c}$, and -$T^1$-$R^{7c}$, where $T^1$ is a $C_{1-3}$ alkylene chain; and $R^e$ is hydrogen.

In some such embodiments, each $R^b$ independently is selected from the group consisting of $C_{1-3}$ aliphatic, $R^{2b}$, and -$T^1$-$R^{2b}$, and each $R^c$ independently is selected from the group consisting of $C_{1-3}$ aliphatic, $R^{2c}$, and -$T^1$-$R^{2c}$. In some embodiments, each $R^{2b}$ independently is selected from the group consisting of -halo, —$NO_2$, —$C(R^5)$=$C(R^5)_2$, —C≡C—$R^5$, —$OR^5$, and —$N(R^4)_2$, and each $R^{2c}$ independently is selected from the group consisting of -halo, —$NO_2$, —$C(R^5)$=$C(R^5)_2$, —C≡C—$R^5$, —$OR^5$, and —$N(R^4)_2$.

In some embodiments, the invention is directed to the compound of formula (IV), wherein one of $R^h$ and $R^k$ is $R^{7d}$. In some such embodiments, $R^g$ is hydrogen, and $R^{7d}$ is tetrazolyl.

In some embodiments, the invention relates to a compound of formula (IV), wherein $R^g$ is hydrogen, one of $R^h$ and $R^k$ has the formula -$T^2$-$R^{2d}$ or -$T^2$-$R^{7d}$, and the other of $R^h$ and $R^k$ is selected from the group consisting of hydrogen, -halo, $C_{1-3}$ aliphatic, and —$OR^5$, where $R^5$ is hydrogen or $C_{1-3}$ aliphatic. In some embodiments, $T^2$ is a $C_{1-6}$ alkylene chain, which optionally is interrupted by —C(O)N($R^4$)— or —N($R^4$)C(O)—.

In some embodiments, the invention is directed to a compound of formula (IV) wherein $R^g$ is hydrogen, one of $R^h$ and $R^k$ has the formula —V-$T^3$-$R^{2d}$, and the other of $R^h$ and $R^k$ is selected from the group consisting of hydrogen, -halo, $C_{1-3}$ aliphatic, and —$OR^5$, where $R^5$ is hydrogen or $C_{1-3}$ aliphatic. In some such embodiments, V is —C(O)N($R^4$)—, $T^3$ is a $C_{2-4}$ alkylene chain, and $R^{2d}$ is —$N(R^4)_2$, where each $R^4$ independently is hydrogen or $C_{1-3}$ aliphatic, or —$N(R^4)_2$ is an optionally substituted 5- to 6-membered heteroaryl or 4- to 8-membered heterocyclyl ring having, in addition to the nitrogen, 0-2 ring heteroatoms selected from N, O, and S. In certain such embodiments, —$N(R^4)_2$ is an optionally substituted heterocyclyl selected from the group consisting of piperidinyl, piperazinyl, and morpholinyl.

In certain other such embodiments, —$N(R^4)_2$ is an optionally substituted heterocyclyl selected from pyrrolidinyl and azetidinyl.

In some other embodiments, the invention relates to a compound of formula (IV), wherein $R^g$ is hydrogen, one of $R^h$ and $R^k$ has the formula —V-$T^3$-$R^{7d}$, and the other of $R^h$ and $R^k$ is selected from the group consisting of hydrogen, -halo, $C_{1-3}$ aliphatic, and —$OR^5$, where $R^5$ is hydrogen or $C_{1-3}$ aliphatic. In certain such embodiments, V is —C(O)N($R^4$)—, $T^3$ is a $C_{2-4}$ alkylene chain, and $R^{7d}$ is an optionally substituted 4- to 8-membered heterocyclyl or an optionally substituted 5- to 6-membered heteroaryl. In certain such embodiments, $R^{7d}$ is an optionally substituted heteroaryl selected from the group consisting of pyridyl, pyridazinyl, pyrimidinyl, pyrazinyl, pyrrolyl, oxazolyl, imidazolyl, and pyrazolyl. In certain other such embodiments, $R^{7d}$ is a 6- to 8-membered bridged bicyclic heterocyclyl.

In some embodiments, the invention is directed to a compound of formula (IV) wherein $R^g$ is hydrogen, and at least one of $R^h$ and $R^k$ is selected from the group consisting of —$CO_2R^5$, —$C(O)N(R^4)_2$, —$C(=NR^4)N(R^4)_2$, —$C(O)N(R^4)C(=NR^4)$—$N(R^4)_2$, —$N(R^4)C(=NR^4)$—$N(R^4)$—C(O)$R^5$, or —$NR^4C(O)R^5$. In some such embodiments, at least one of $R^h$ and $R^k$ is —$CO_2R^5$, where $R^5$ is hydrogen or $C_{1-6}$ aliphatic. In some embodiments, each of $R^g$ and $R^k$ is hydrogen, and $R^h$ is —$CO_2R^5$.

In some embodiments, $R^g$ is hydrogen, and one of $R^h$ and $R^k$ is —C(O)—$N(R^4)_2$ or —$C(=NR^4)N(R^4)_2$, where —$N(R^4)_2$ is an optionally substituted heterocyclyl selected from the group consisting of piperidinyl, piperazinyl, morpholinyl, pyrrolidinyl, and azetidinyl. In some such embodiments, one of $R^h$ and $R^k$ has one of the formulae D-i to D-v, as defined above. In certain such embodiments, one of $R^h$ or $R^k$ has one of the formulae D-1 to D-51, or has the formula embodied at the relevant position of any of the compounds depicted in Table 3 below.

Some embodiment of the invention relate to a subgenus of the compounds of formula (A) defined by formula (C):

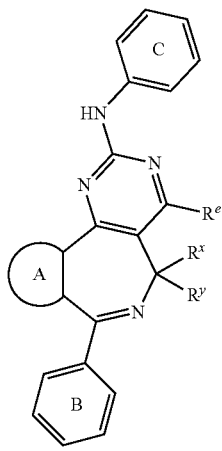

(C)

wherein:
Ring A is a substituted or unsubstituted 5- or 6-membered aryl, heteroaryl, cycloaliphatic, or heterocyclyl ring;
Ring B is substituted with 0-2 independently selected $R^c$ and 0-3 independently selected $R^{2c}$ or $C_{1-6}$ aliphatic groups;
Ring C is substituted 0-2 independently selected $R^d$ and 0-3 independently selected $R^{2d}$ or $C_{1-6}$ aliphatic groups; and
each of $R^e$, $R^x$, and $R^y$ has the values and preferred values described above.

In some embodiments, the invention relates to a subgenus of formula (C) defined by formula (V):

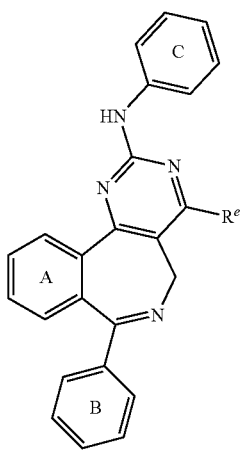

(V)

wherein:
$R^e$ is hydrogen or a $C_{1-3}$ aliphatic optionally substituted with $R^3$ or $R^7$;
Ring A is substituted with 0-3 $R^b$;
Ring B is substituted with 0-2 independently selected $R^c$ and 0-2 independently selected $R^{2c}$ or $C_{1-6}$ aliphatic groups; and
Ring C is substituted or unsubstituted.

In some embodiments, the compound of formula (V) is defined by formula (Va):

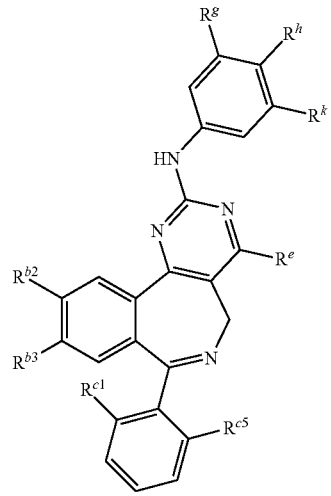

(Va)

wherein:
$R^e$ is hydrogen;
each of $R^{b2}$ and $R^{b3}$ independently is selected from the group consisting of hydrogen, -halo, $C_{1-3}$ aliphatic, $C_{1-3}$ fluoroaliphatic, and —$OR^5$, where $R^5$ is hydrogen or $C_{1-3}$ aliphatic;
each of $R^{c1}$ and $R^{c5}$ independently is selected from the group consisting of hydrogen, -halo, $C_{1-3}$ aliphatic, $C_{1-3}$ fluoroaliphatic, and —$OR^5$, where $R^5$ is hydrogen or $C_{1-3}$ aliphatic;
$R^g$ is selected from the group consisting of hydrogen, $C_{1-6}$ aliphatic, and $R^{2d}$; and each of $R^h$ and $R^k$ independently is hydrogen or $R^d$.

In some embodiments, the invention relates to a compound of formula (Va) wherein at least one of $R^h$ and $R^k$ has the formula —V-$T^3$-$R^{2d}$ or —V-$T^3$-$R^d$, where:
V is —C(O)N($R^4$)—;
$T^3$ is a $C_{2-4}$ alkylene chain;
$R^{2d}$ is —N($R^4$)$_2$, where $R^4$ is hydrogen or $C_{1-3}$ aliphatic, or two $R^4$ on the same nitrogen atom, taken together with the nitrogen atom, form an optionally substituted 4- to 8-membered heterocyclyl or an optionally substituted 5- to 6-membered heteroaryl ring having, in addition to the nitrogen, 0-2 ring heteroatoms selected from N, O, and S; and
$R^{7d}$ is an optionally substituted 4- to 8-membered heterocyclyl or an optionally substituted 5- to 6-membered heteroaryl.

In some other embodiments, the invention relates to a compound of formula (Va), wherein $R^g$ is hydrogen, and at least one of $R^h$ and $R^k$ is selected from the group consisting of —$CO_2R^5$, —$C(O)N(R^4)_2$, —$C(=NR^4)N(R^4)_2$, —$C(O)N(R^4)C(=NR^4)$—$N(R^4)_2$, —$N(R^4)C(=NR^4)$—$N(R^4)$—$C(O)R^5$, or —$NR^4C(O)R^5$.

In a particular embodiment, the invention relates to a compound of formula (Va), wherein:
$R^e$, $R^{b2}$, $R^g$, and $R^k$ are each hydrogen;
$R^{b3}$ and $R^{c1}$ are each independently selected from the group consisting of -halo, $C_{1-3}$ aliphatic, $C_{1-3}$ fluoroaliphatic, and —$OR^5$, where $R^5$ is hydrogen or $C_{1-3}$ aliphatic;
$R^{c5}$ is selected from the group consisting of hydrogen, -halo, $C_{1-3}$ aliphatic, $C_{1-3}$ fluoroaliphatic, and —$OR^5$, where $R^5$ is hydrogen or $C_{1-3}$ aliphatic; and $R^h$ is —CO$_2$H, —C(O)N(R$^4$)$_2$, —C(=NR$^4$)N(R$^4$)$_2$, —C(O)N(R$^4$)C(=NR$^4$)—N(R$^4$)$_2$, or —N(R$^4$)C(=NR$^4$)—N(R$^4$)—C(O)R$^5$, where R$^5$ is an optionally substituted 4- to 8-membered nitrogen-containing heterocyclyl ring, and —N(R$^4$)$_2$ is an optionally substituted 4- to 8-membered heterocyclyl ring having in addition to the nitrogen atom 0-2 heteroatoms selected from N, O, and S.

Compounds embodying any combination of the preferred values for the variables described herein are considered to be within the scope of the present invention.

Table 3 shows specific examples of compounds of formula (V).

TABLE 3

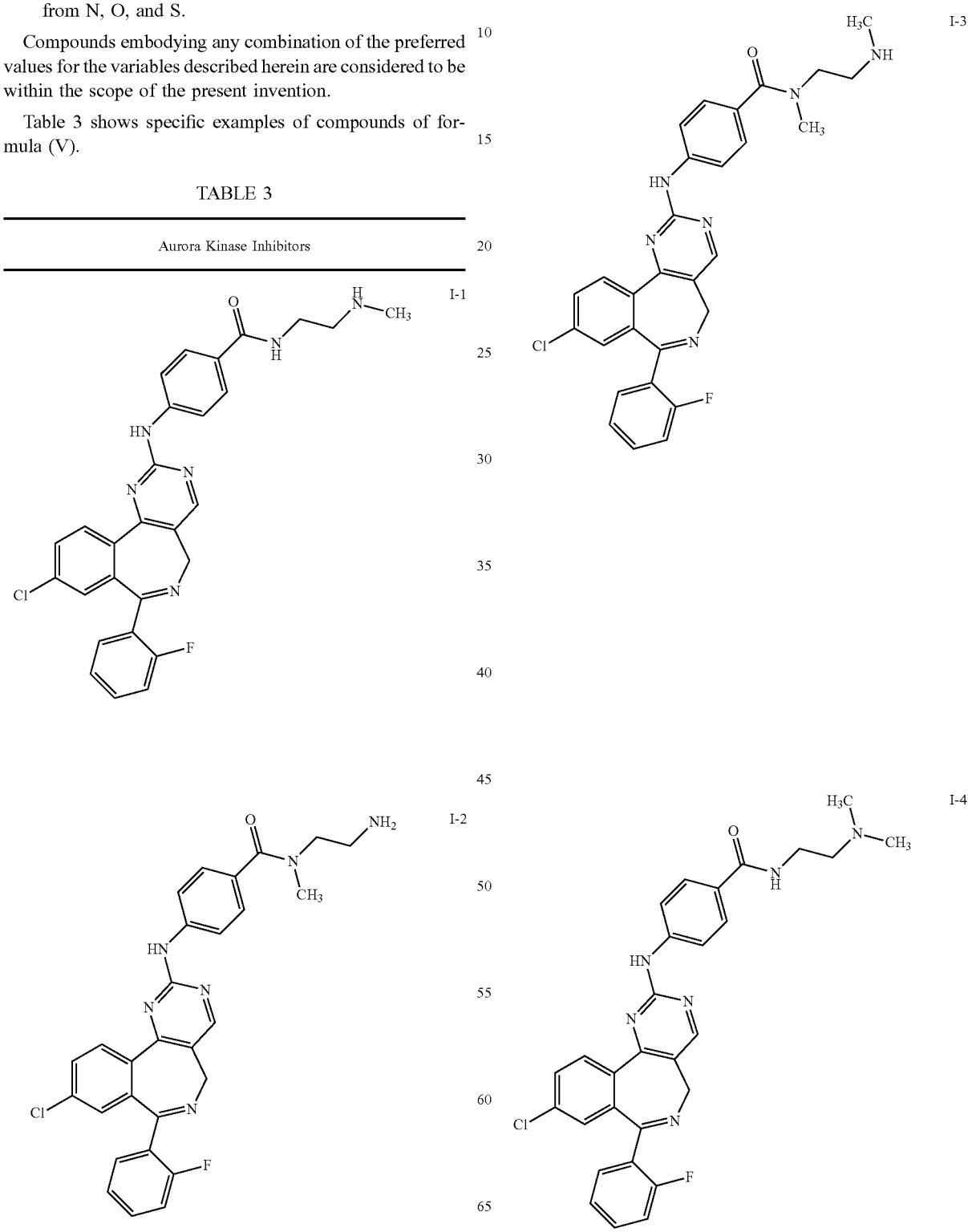

TABLE 3-continued
Aurora Kinase Inhibitors
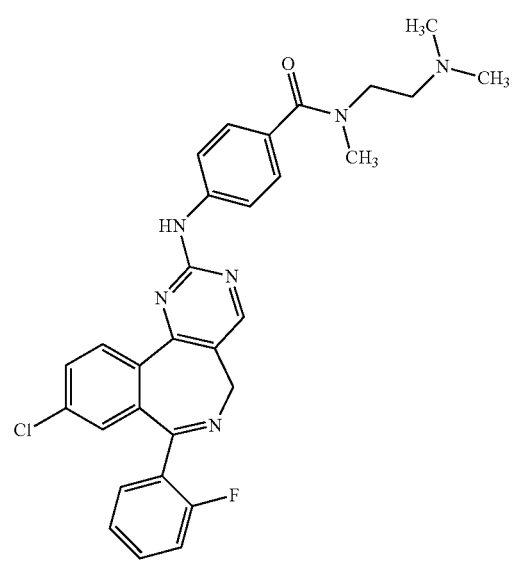 [SMILES: CN(C)CCN(C)C(=O)c1ccc(Nc2ncc3c(n2)-c2ccc(Cl)cc2C(c2ccccc2F)=NC3)cc1]
I-5
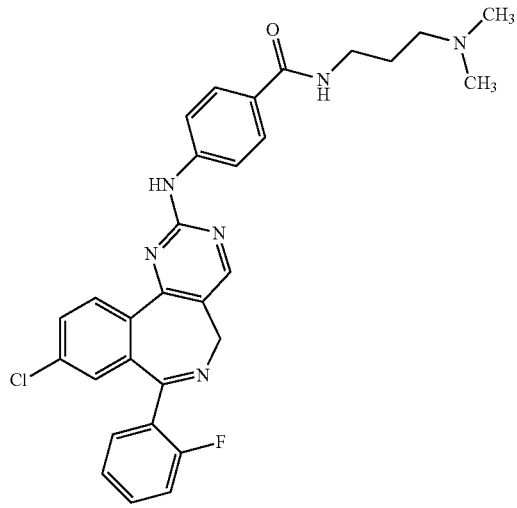 [SMILES: CN(C)CCCNC(=O)c1ccc(Nc2ncc3c(n2)-c2ccc(Cl)cc2C(c2ccccc2F)=NC3)cc1]
I-6
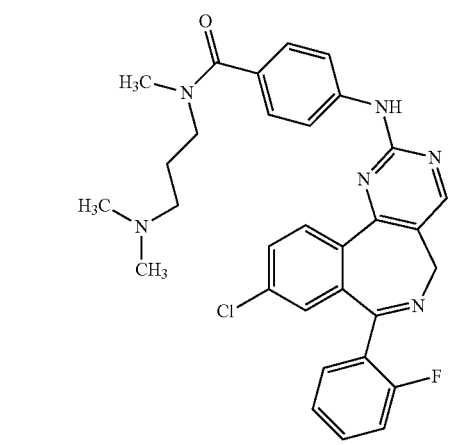 [SMILES: CN(C)CCCN(C)C(=O)c1ccc(Nc2ncc3c(n2)-c2ccc(Cl)cc2C(c2ccccc2F)=NC3)cc1]
I-7
TABLE 3-continued
Aurora Kinase Inhibitors
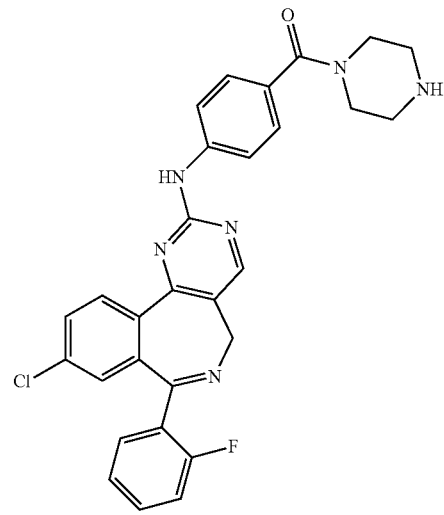 [SMILES: O=C(c1ccc(Nc2ncc3c(n2)-c2ccc(Cl)cc2C(c2ccccc2F)=NC3)cc1)N1CCNCC1]
I-8
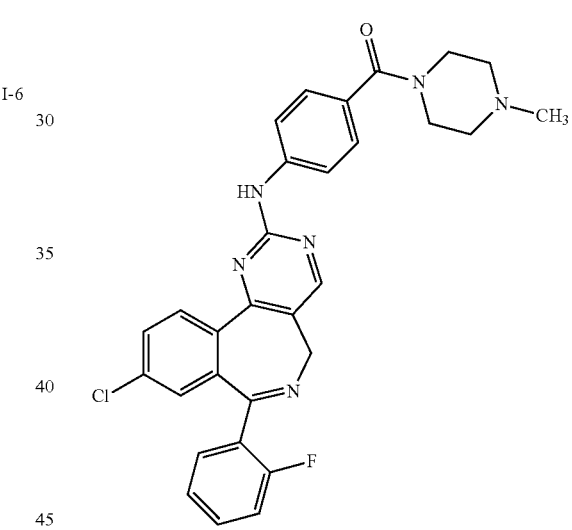
I-9
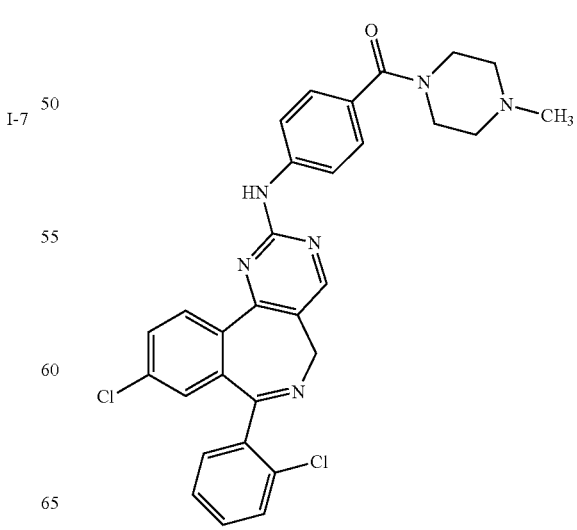
I-10

TABLE 3-continued
Aurora Kinase Inhibitors
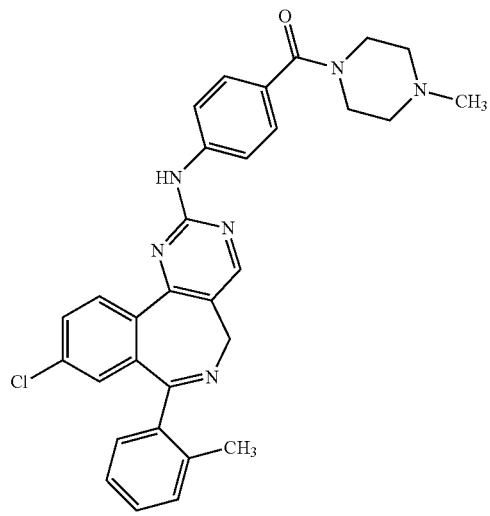 [SMILES: Cc1ccccc1C1=NCc2cnc(Nc3ccc(C(=O)N4CCN(C)CC4)cc3)nc2-c2ccc(Cl)cc21]
I-11
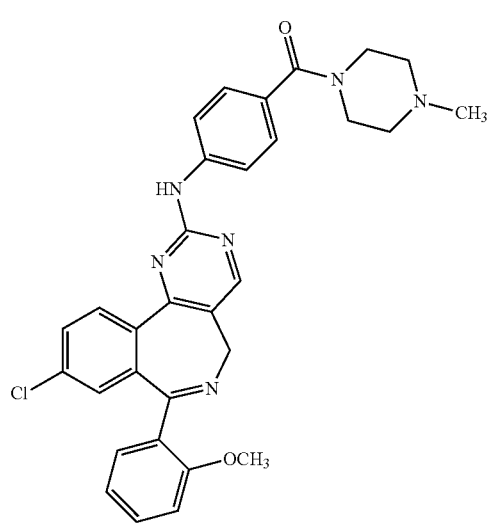 [SMILES: COc1ccccc1C1=NCc2cnc(Nc3ccc(C(=O)N4CCN(C)CC4)cc3)nc2-c2ccc(Cl)cc21]
I-12
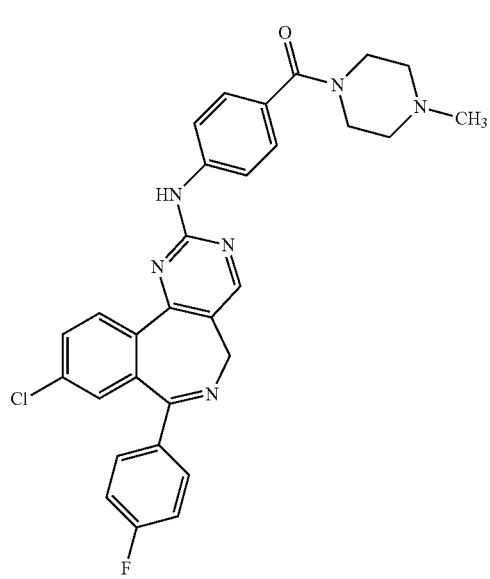 [SMILES: CN1CCN(C(=O)c2ccc(Nc3ncc4c(n3)-c3ccc(Cl)cc3C(c3ccc(F)cc3)=NC4)cc2)CC1]
I-13
TABLE 3-continued
Aurora Kinase Inhibitors
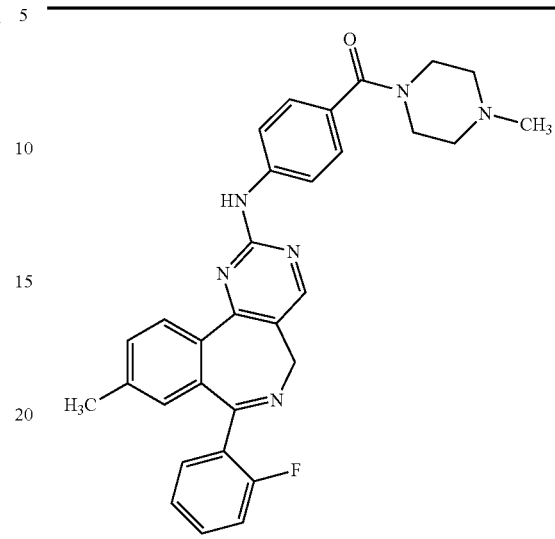
I-14
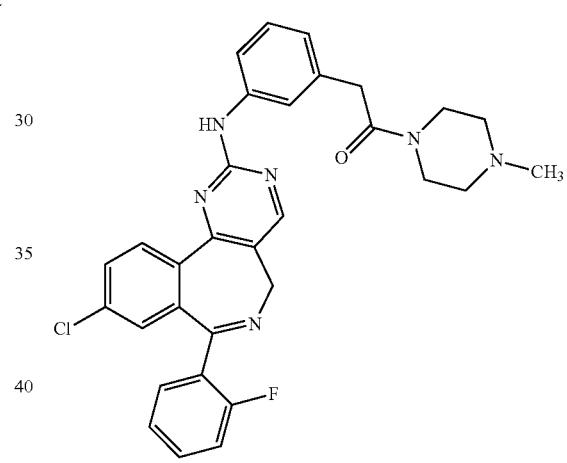
I-15
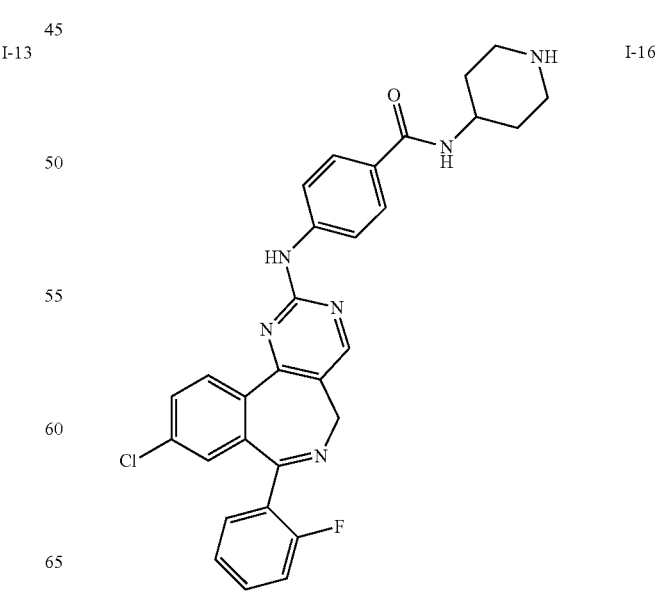
I-16

TABLE 3-continued
Aurora Kinase Inhibitors
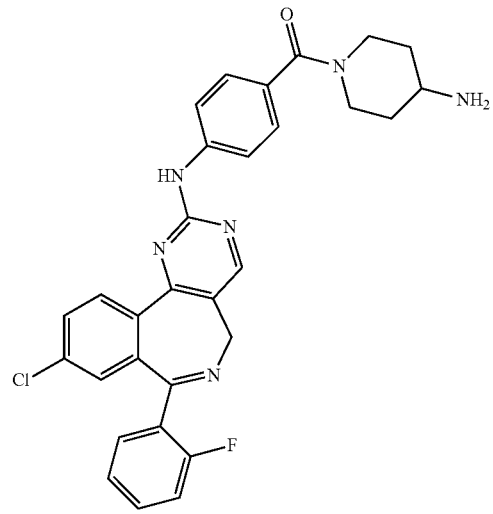 [SMILES: NC1CCN(C(=O)c2ccc(Nc3ncc4c(n3)-c3ccc(Cl)cc3C(c3ccccc3F)=NC4)cc2)CC1]
I-17
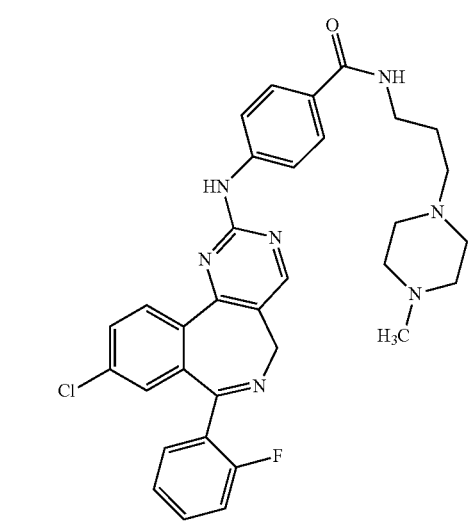 [SMILES: CN1CCN(CCCNC(=O)c2ccc(Nc3ncc4c(n3)-c3ccc(Cl)cc3C(c3ccccc3F)=NC4)cc2)CC1]
I-18
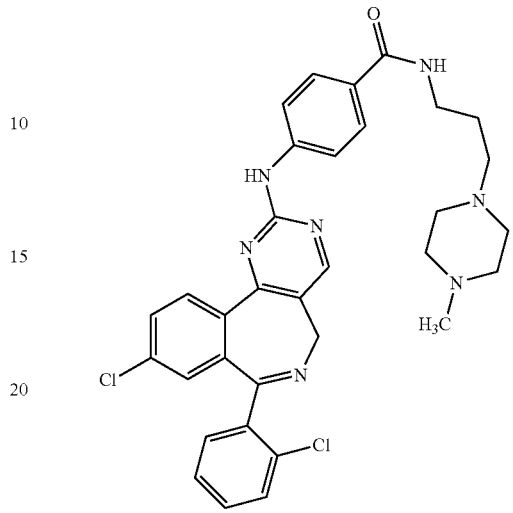
I-20
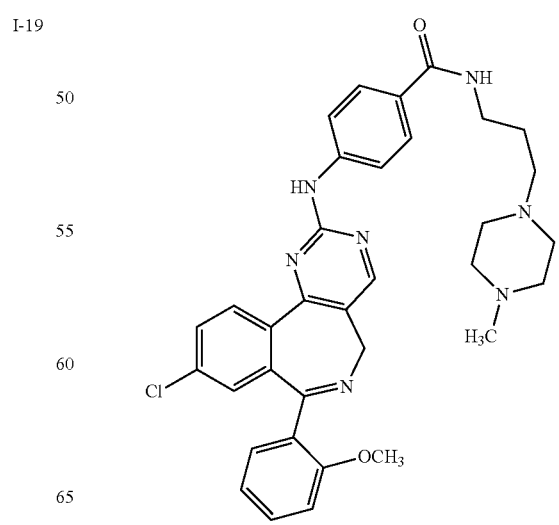
I-21
I-19
I-22

TABLE 3-continued
Aurora Kinase Inhibitors
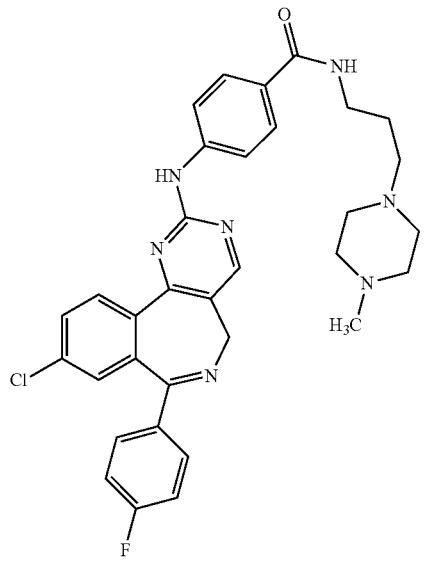 [SMILES: CN1CCN(CCCNC(=O)c2ccc(Nc3ncc4c(n3)-c3ccc(Cl)cc3C(c3ccc(F)cc3)=NC4)cc2)CC1]
I-23
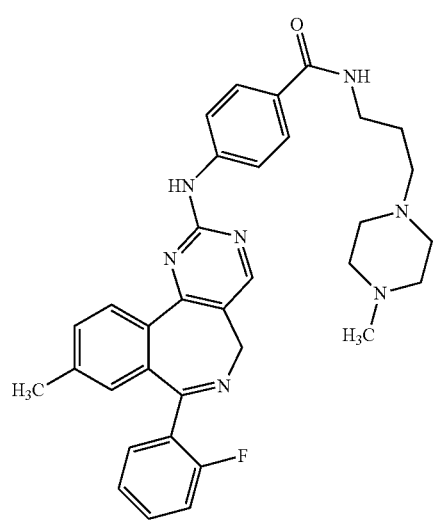 [SMILES: Cc1ccc2c(c1)C(c1ccccc1F)=NCc1cnc(Nc3ccc(C(=O)NCCCN4CCN(C)CC4)cc3)nc1-2]
I-24
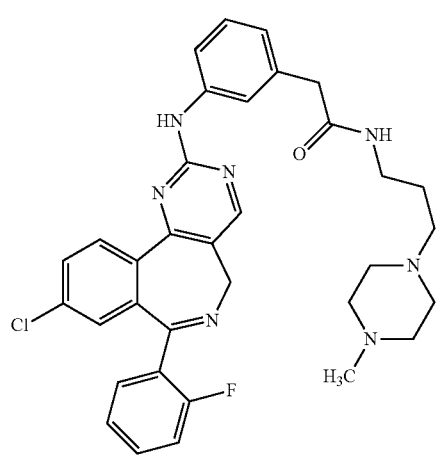 [SMILES: CN1CCN(CCCNC(=O)Cc2cccc(Nc3ncc4c(n3)-c3ccc(Cl)cc3C(c3ccccc3F)=NC4)c2)CC1]
I-25
TABLE 3-continued
Aurora Kinase Inhibitors
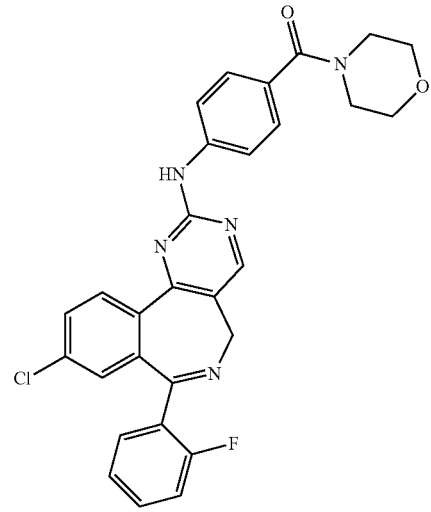 [SMILES: O=C(c1ccc(Nc2ncc3c(n2)-c2ccc(Cl)cc2C(c2ccccc2F)=NC3)cc1)N1CCOCC1]
I-26
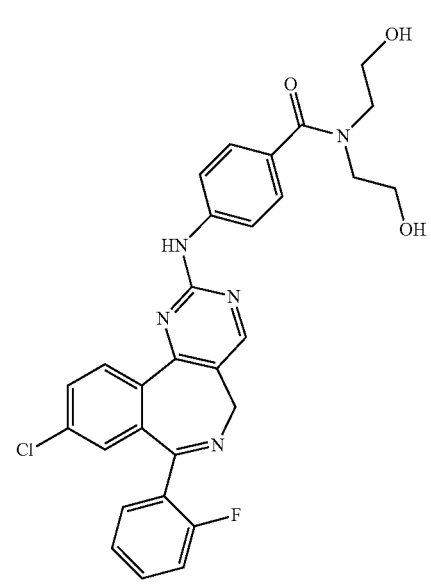 [SMILES: O=C(c1ccc(Nc2ncc3c(n2)-c2ccc(Cl)cc2C(c2ccccc2F)=NC3)cc1)N(CCO)CCO]
I-27
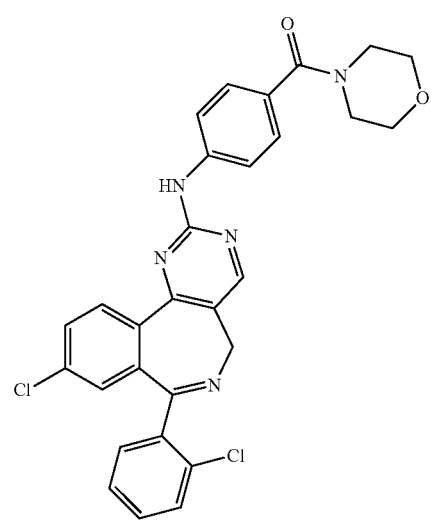 [SMILES: O=C(c1ccc(Nc2ncc3c(n2)-c2ccc(Cl)cc2C(c2ccccc2Cl)=NC3)cc1)N1CCOCC1]
I-28

TABLE 3-continued
Aurora Kinase Inhibitors
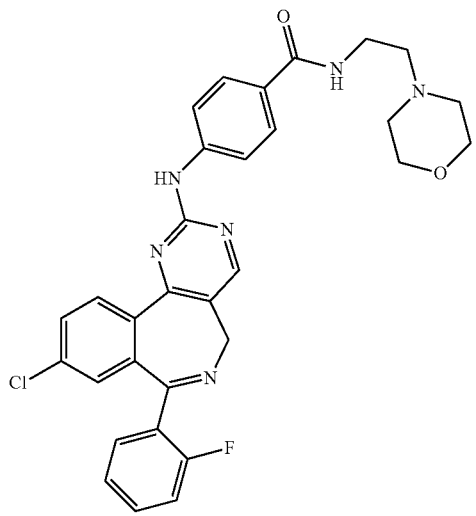 [SMILES: O=C(NCCN1CCOCC1)c1ccc(Nc2ncc3c(n2)-c2ccc(Cl)cc2C(c2ccccc2F)=NC3)cc1]
I-29
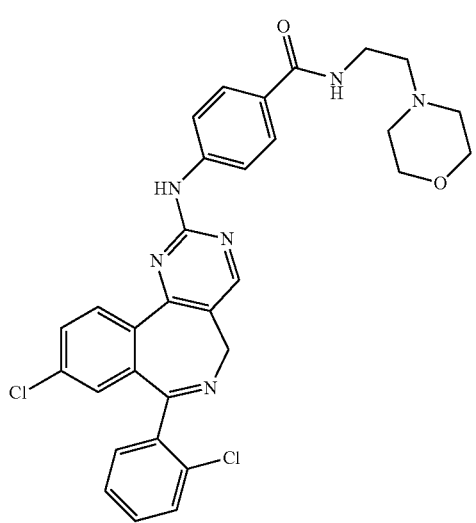
I-30
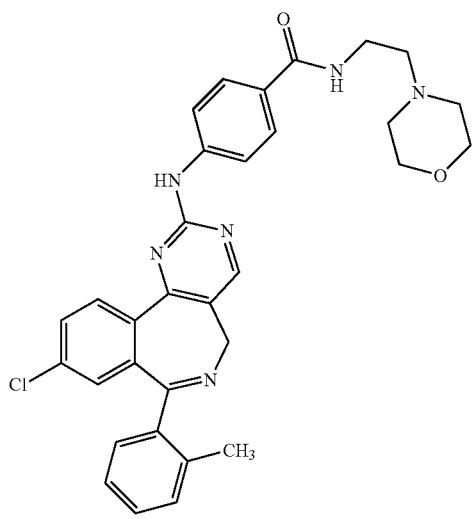 [SMILES: Cc1ccccc1C1=NCc2cnc(Nc3ccc(C(=O)NCCN4CCOCC4)cc3)nc2-c2ccc(Cl)cc21]
I-31
TABLE 3-continued
Aurora Kinase Inhibitors
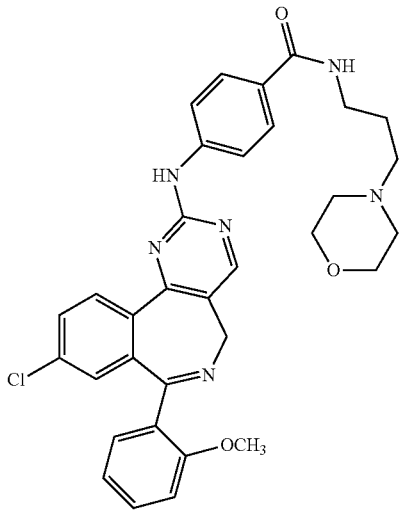 [SMILES: COc1ccccc1C1=NCc2cnc(Nc3ccc(C(=O)NCCCN4CCOCC4)cc3)nc2-c2ccc(Cl)cc21]
I-32
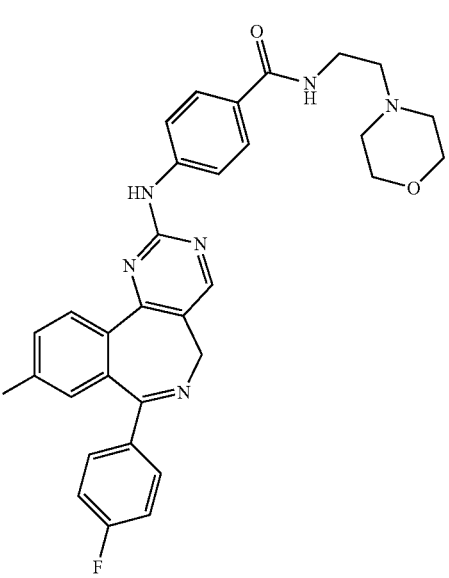
I-33
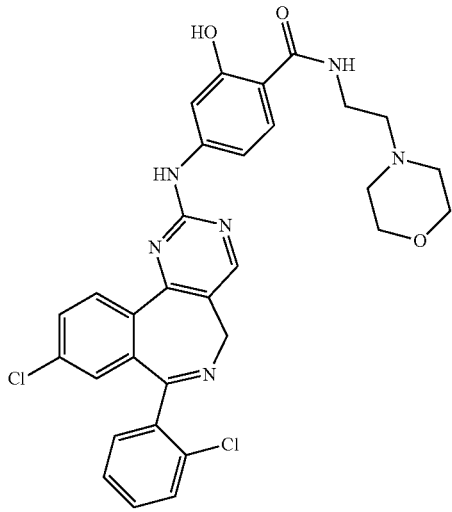 [SMILES: O=C(NCCN1CCOCC1)c1ccc(Nc2ncc3c(n2)-c2ccc(Cl)cc2C(c2ccccc2Cl)=NC3)cc1O]
I-34

TABLE 3-continued
Aurora Kinase Inhibitors
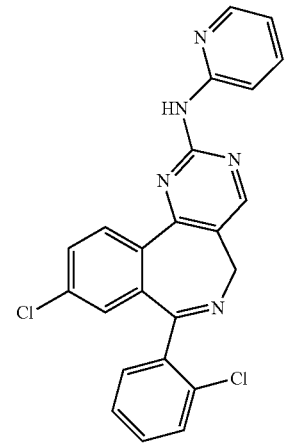 [SMILES: Clc1ccc2c(c1)C(c1ccccc1Cl)=NCc1cnc(Nc3ccccn3)nc1-2]
I-35
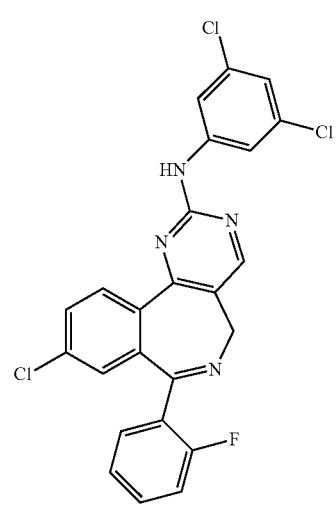 [SMILES: Fc1ccccc1C1=NCc2cnc(Nc3cc(Cl)cc(Cl)c3)nc2-c2ccc(Cl)cc21]
I-36
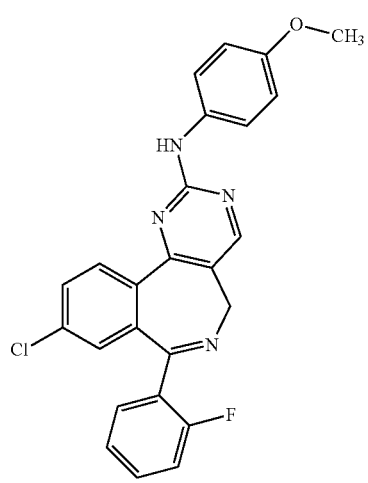 [SMILES: COc1ccc(Nc2ncc3c(n2)-c2ccc(Cl)cc2C(c2ccccc2F)=NC3)cc1]
I-37
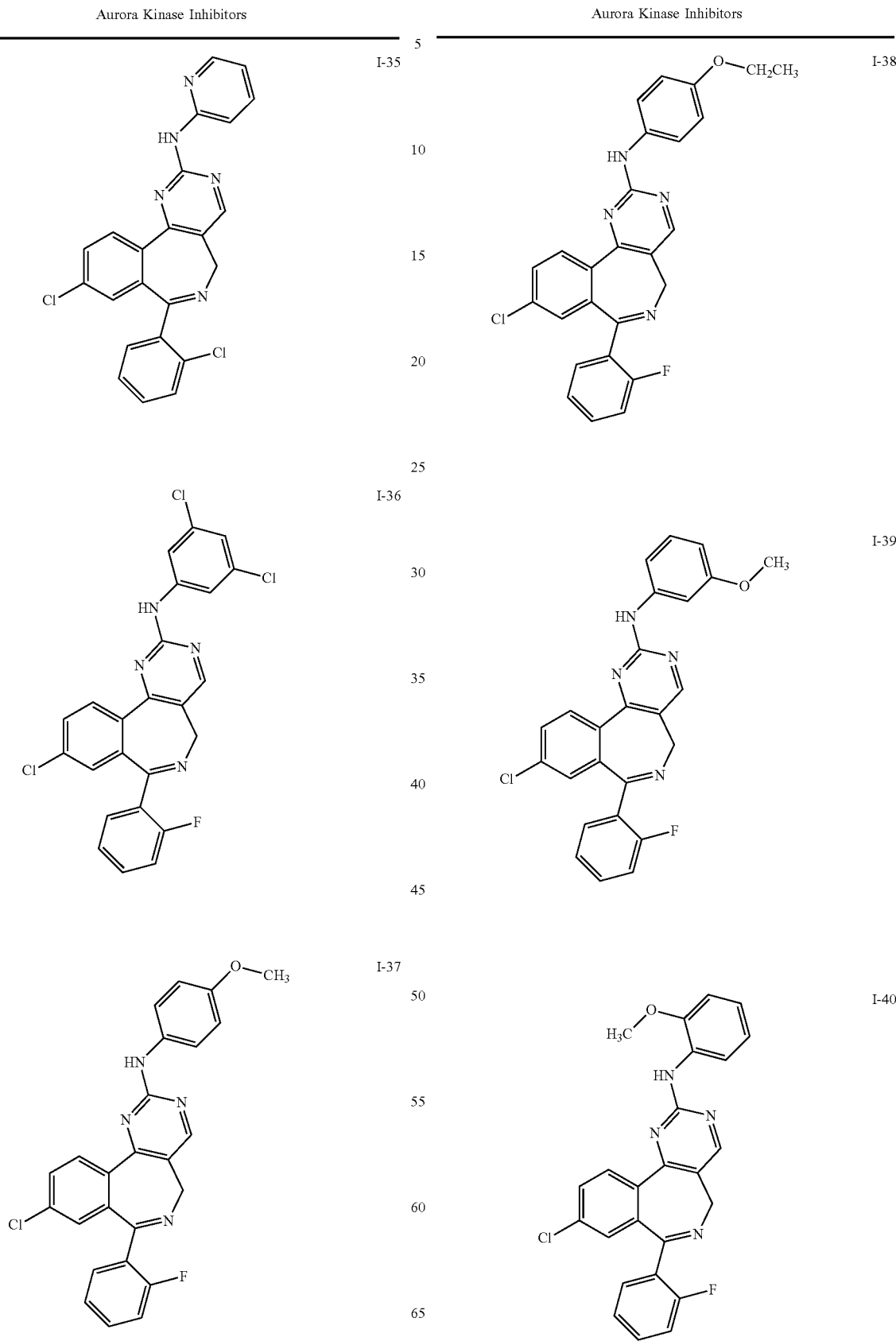

TABLE 3-continued
Aurora Kinase Inhibitors
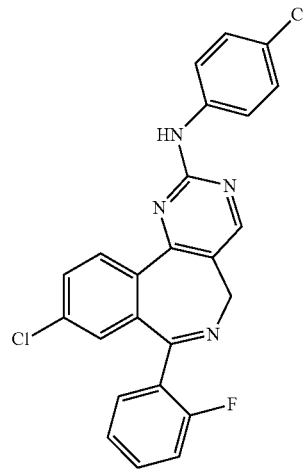
I-41
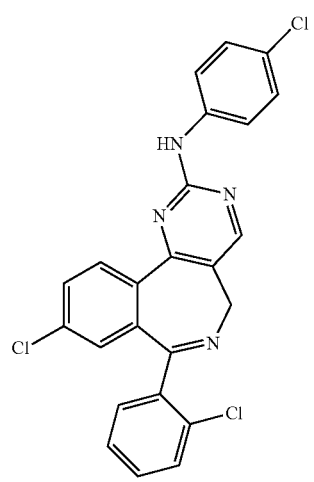 [SMILES: Clc1ccc(Nc2ncc3c(n2)-c2ccc(Cl)cc2C(c2ccccc2Cl)=NC3)cc1]
I-42
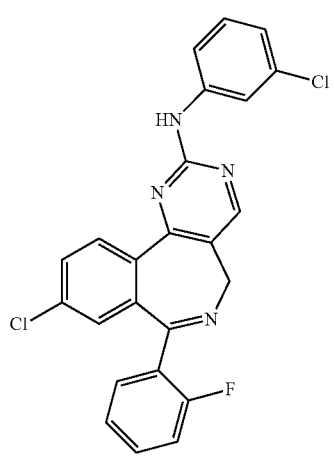 [SMILES: Fc1ccccc1C1=NCc2cnc(Nc3cccc(Cl)c3)nc2-c2ccc(Cl)cc21]
I-43
TABLE 3-continued
Aurora Kinase Inhibitors
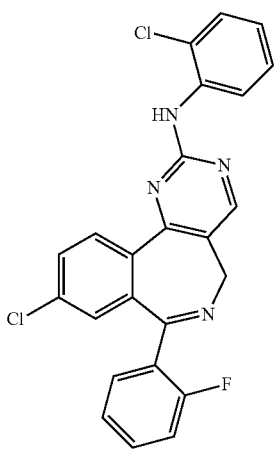 [SMILES: Fc1ccccc1C1=NCc2cnc(Nc3ccccc3Cl)nc2-c2ccc(Cl)cc21]
I-44
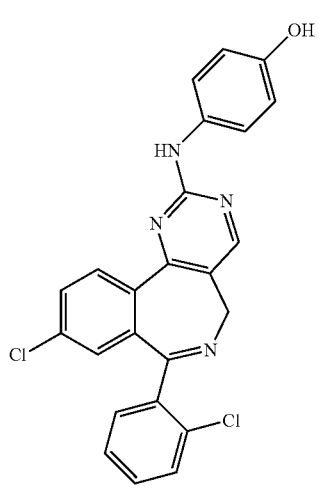 [SMILES: Oc1ccc(Nc2ncc3c(n2)-c2ccc(Cl)cc2C(c2ccccc2Cl)=NC3)cc1]
I-45
I-46

TABLE 3-continued
Aurora Kinase Inhibitors
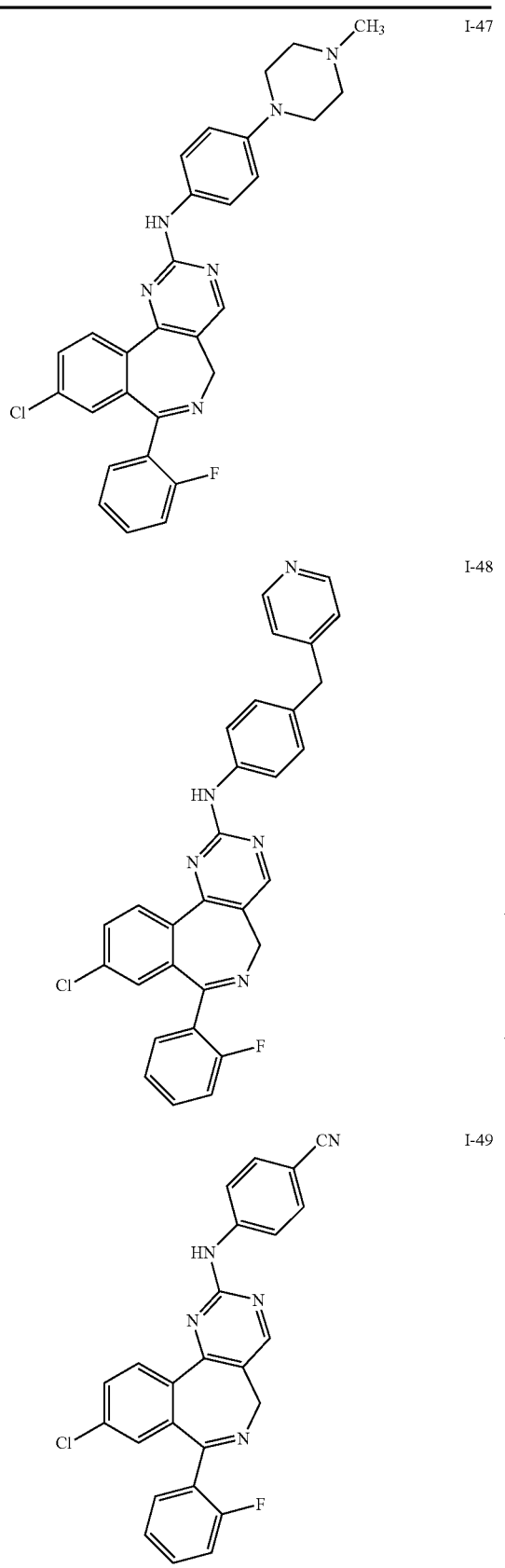
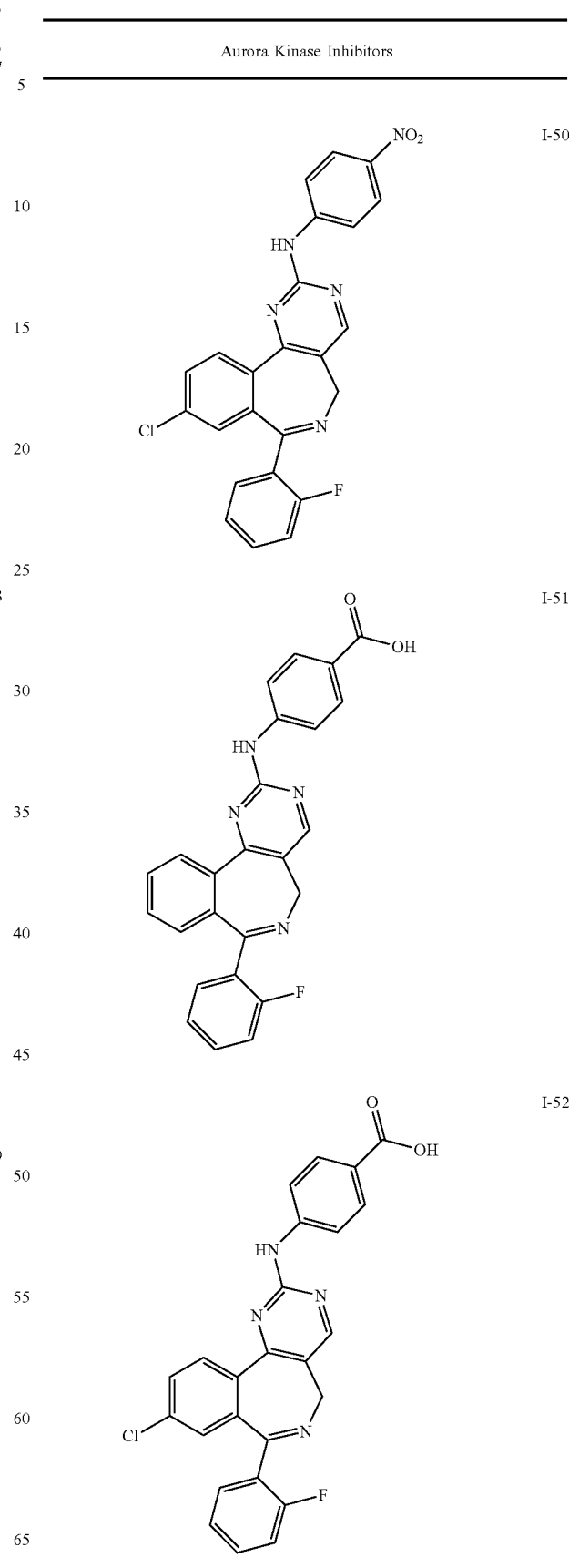

TABLE 3-continued
Aurora Kinase Inhibitors
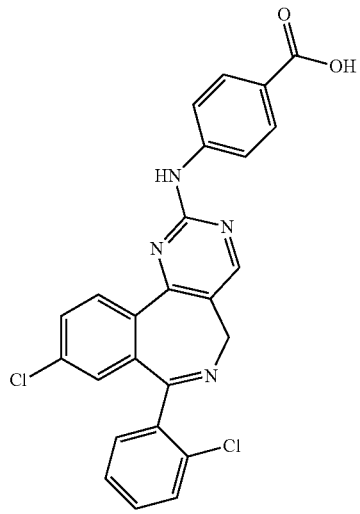 [SMILES: O=C(O)c1ccc(Nc2ncc3c(n2)-c2ccc(Cl)cc2C(c2ccccc2Cl)=NC3)cc1]
I-53
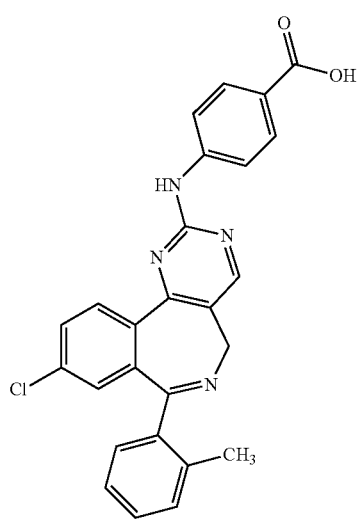
I-54
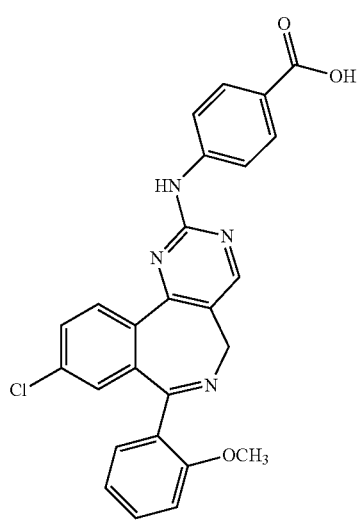 [SMILES: COc1ccccc1C1=NCc2cnc(Nc3ccc(C(=O)O)cc3)nc2-c2ccc(Cl)cc21]
I-55
TABLE 3-continued
Aurora Kinase Inhibitors
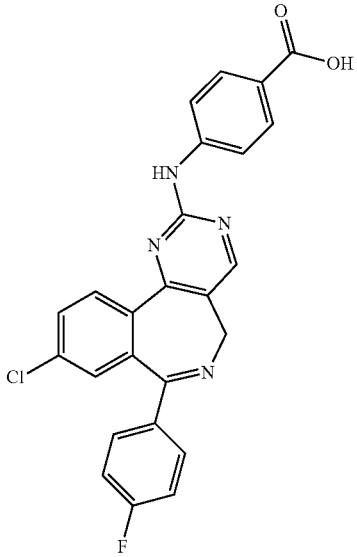 [SMILES: O=C(O)c1ccc(Nc2ncc3c(n2)-c2ccc(Cl)cc2C(c2ccc(F)cc2)=NC3)cc1]
I-56
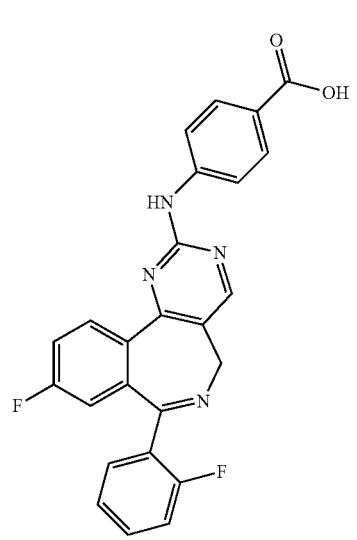 [SMILES: O=C(O)c1ccc(Nc2ncc3c(n2)-c2ccc(F)cc2C(c2ccccc2F)=NC3)cc1]
I-57
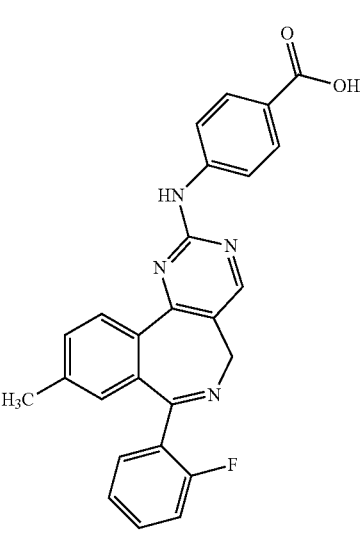 [SMILES: Cc1ccc2c(c1)C(c1ccccc1F)=NCc1cnc(Nc3ccc(C(=O)O)cc3)nc1-2]
I-58

TABLE 3-continued
Aurora Kinase Inhibitors
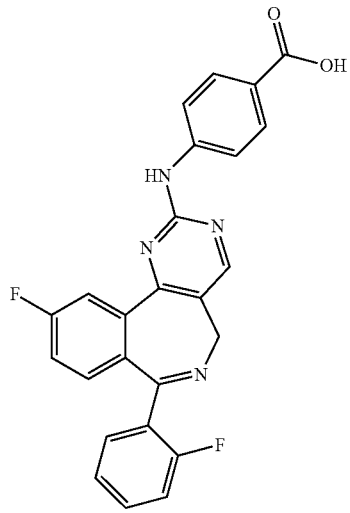 [SMILES: O=C(O)c1ccc(Nc2ncc3c(n2)-c2cc(F)ccc2C(c2ccccc2F)=NC3)cc1]
I-59
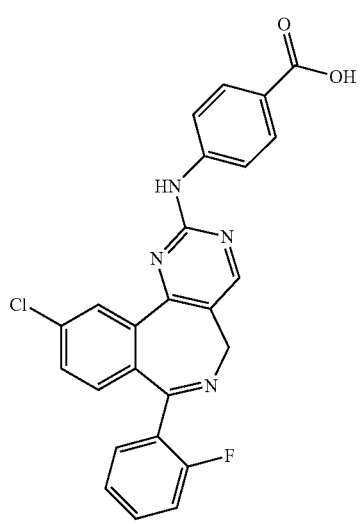
I-60
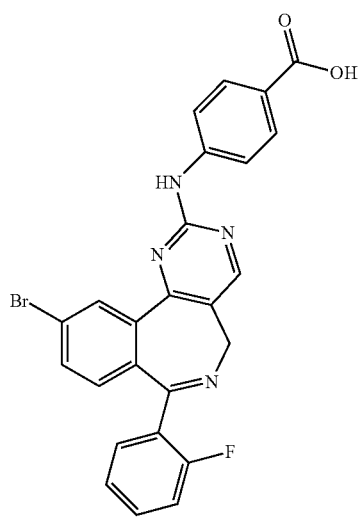 [SMILES: O=C(O)c1ccc(Nc2ncc3c(n2)-c2cc(Cl)ccc2C(c2ccccc2F)=NC3)cc1]
I-61
TABLE 3-continued
Aurora Kinase Inhibitors
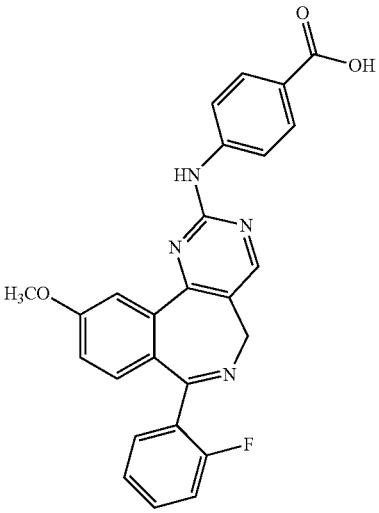 [SMILES: COc1ccc2c(c1)-c1nc(Nc3ccc(C(=O)O)cc3)ncc1CN=C2c1ccccc1F]
I-62
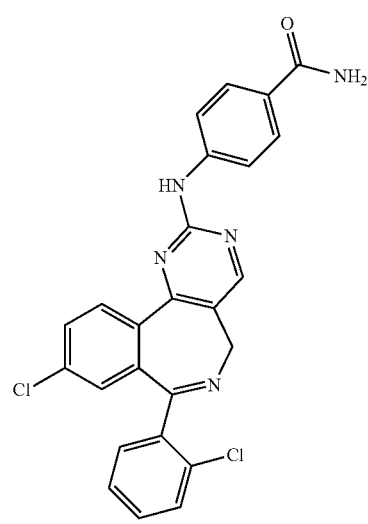 [SMILES: NC(=O)c1ccc(Nc2ncc3c(n2)-c2ccc(Cl)cc2C(c2ccccc2Cl)=NC3)cc1]
I-63
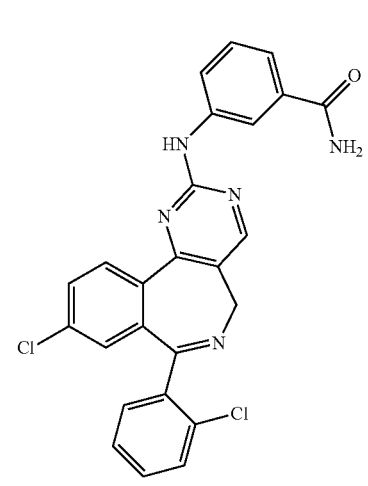 [SMILES: NC(=O)c1cccc(Nc2ncc3c(n2)-c2ccc(Cl)cc2C(c2ccccc2Cl)=NC3)c1]
I-64

TABLE 3-continued
Aurora Kinase Inhibitors
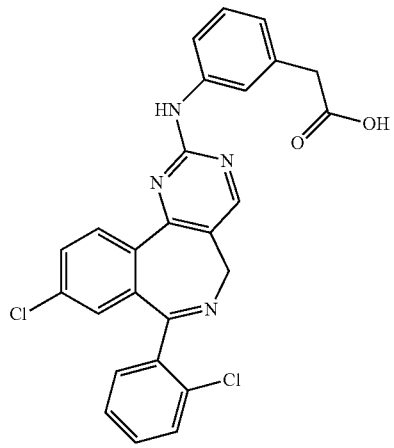 [SMILES: O=C(O)Cc1cccc(Nc2ncc3c(n2)-c2ccc(Cl)cc2C(c2ccccc2Cl)=NC3)c1]
I-65
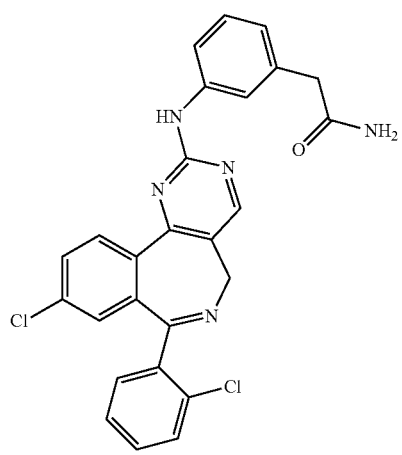 [SMILES: NC(=O)Cc1cccc(Nc2ncc3c(n2)-c2ccc(Cl)cc2C(c2ccccc2Cl)=NC3)c1]
I-66
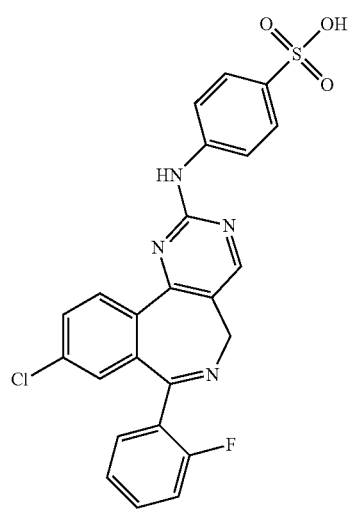
I-67
TABLE 3-continued
Aurora Kinase Inhibitors
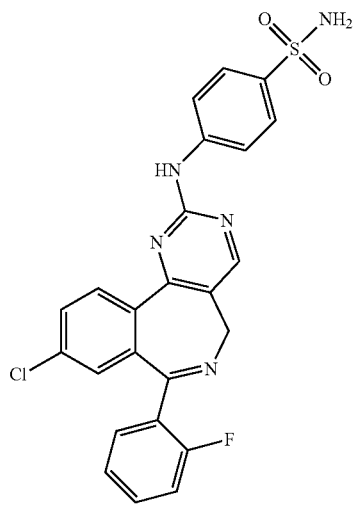 [SMILES: NS(=O)(=O)c1ccc(Nc2ncc3c(n2)-c2ccc(Cl)cc2C(c2ccccc2F)=NC3)cc1]
I-68
I-69
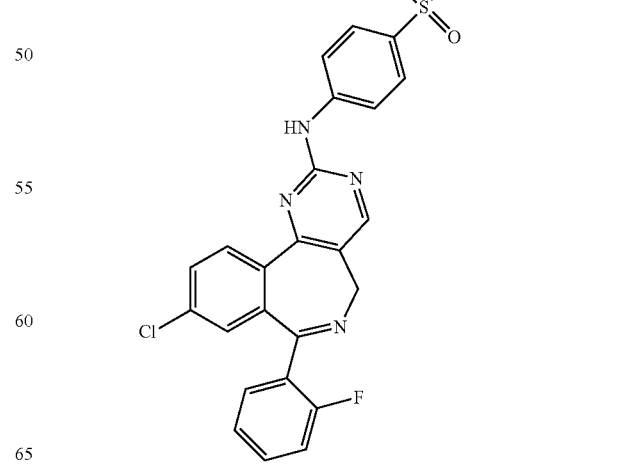
I-70

TABLE 3-continued
Aurora Kinase Inhibitors
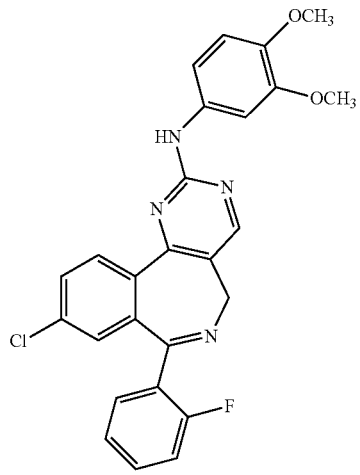 [SMILES: COc1ccc(Nc2ncc3c(n2)-c2ccc(Cl)cc2C(c2ccccc2F)=NC3)cc1OC]
I-71
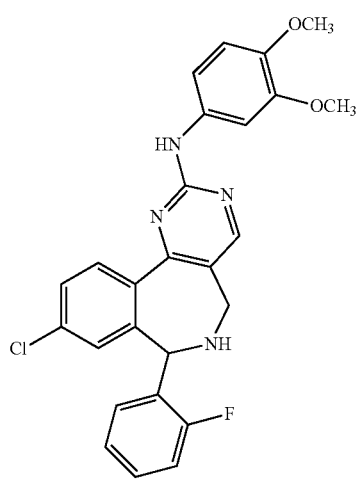 [SMILES: COc1ccc(Nc2ncc3c(n2)-c2ccc(Cl)cc2C(c2ccccc2F)NC3)cc1OC]
I-72
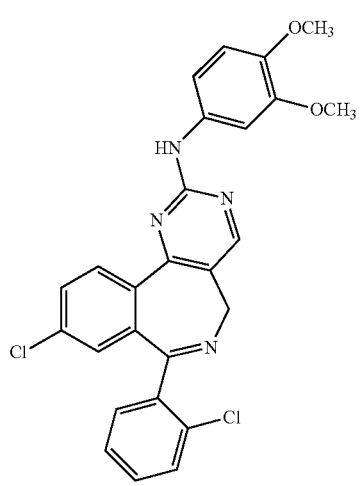
I-73
TABLE 3-continued
Aurora Kinase Inhibitors
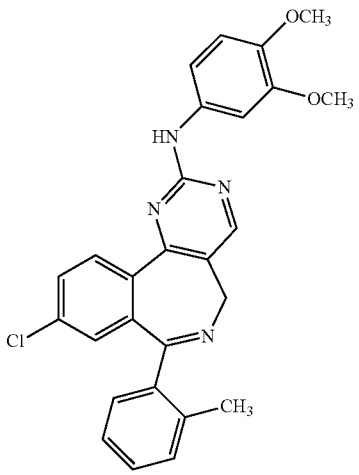 [SMILES: COc1ccc(Nc2ncc3c(n2)-c2ccc(Cl)cc2C(c2ccccc2C)=NC3)cc1OC]
I-74
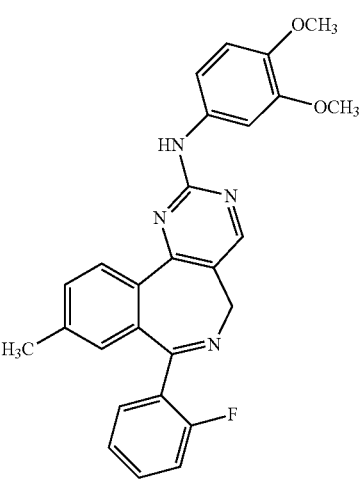 [SMILES: COc1ccc(Nc2ncc3c(n2)-c2ccc(C)cc2C(c2ccccc2F)=NC3)cc1OC]
I-75
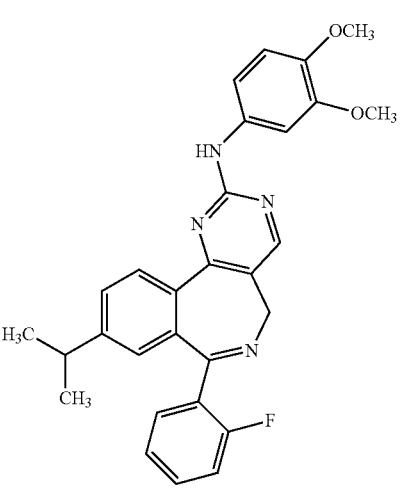 [SMILES: COc1ccc(Nc2ncc3c(n2)-c2ccc(C(C)C)cc2C(c2ccccc2F)=NC3)cc1OC]
I-76

TABLE 3-continued
Aurora Kinase Inhibitors
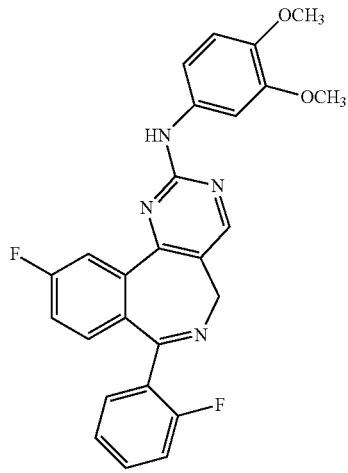 [SMILES: COc1ccc(Nc2ncc3c(n2)-c2cc(F)ccc2C(c2ccccc2F)=NC3)cc1OC]
I-77
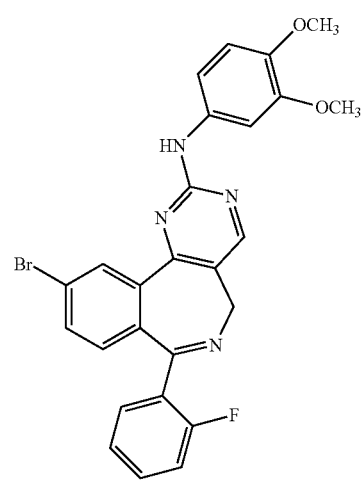 [SMILES: COc1ccc(Nc2ncc3c(n2)-c2cc(Br)ccc2C(c2ccccc2F)=NC3)cc1OC]
I-78
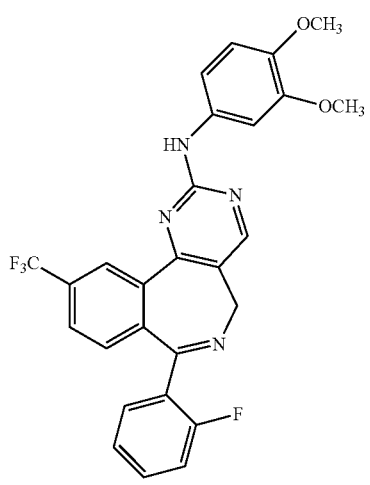 [SMILES: COc1ccc(Nc2ncc3c(n2)-c2cc(C(F)(F)F)ccc2C(c2ccccc2F)=NC3)cc1OC]
I-79
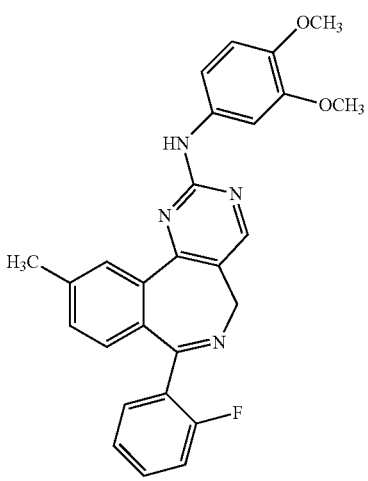 [SMILES: COc1ccc(Nc2ncc3c(n2)-c2cc(C)ccc2C(c2ccccc2F)=NC3)cc1OC]
I-80
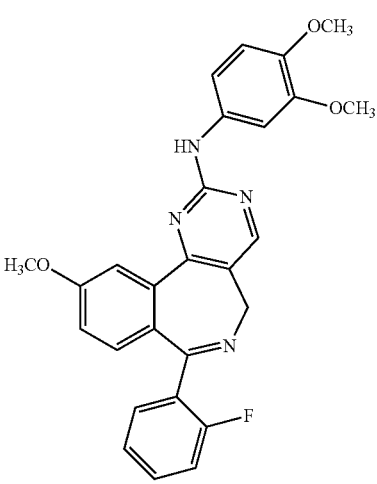 [SMILES: COc1ccc2c(c1)-c1nc(Nc3ccc(OC)c(OC)c3)ncc1CN=C2c1ccccc1F]
I-81
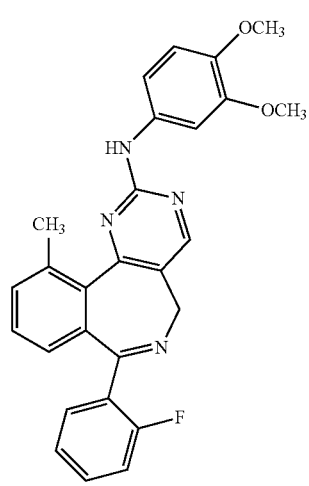 [SMILES: COc1ccc(Nc2ncc3c(n2)-c2c(C)cccc2C(c2ccccc2F)=NC3)cc1OC]
I-82

TABLE 3-continued
Aurora Kinase Inhibitors
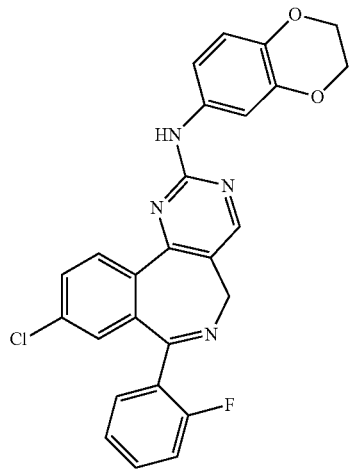 [SMILES: Fc1ccccc1C1=NCc2cnc(Nc3ccc4c(c3)OCCO4)nc2-c2ccc(Cl)cc21]
I-83
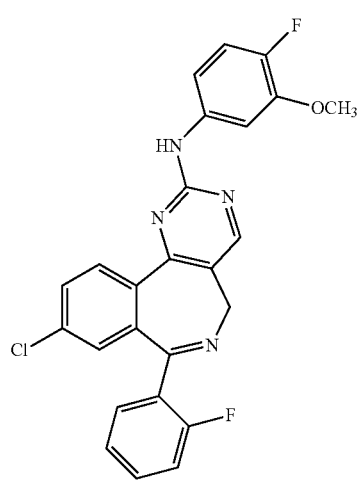 [SMILES: COc1cc(Nc2ncc3c(n2)-c2ccc(Cl)cc2C(c2ccccc2F)=NC3)ccc1F]
I-84
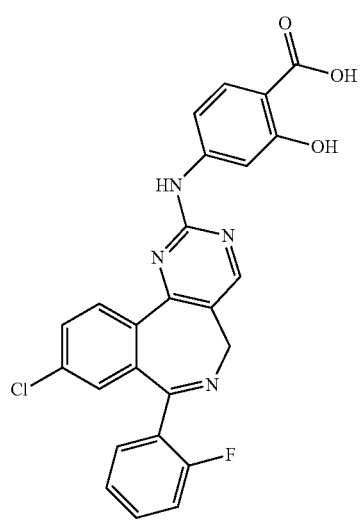 [SMILES: O=C(O)c1ccc(Nc2ncc3c(n2)-c2ccc(Cl)cc2C(c2ccccc2F)=NC3)cc1O]
I-85
TABLE 3-continued
Aurora Kinase Inhibitors
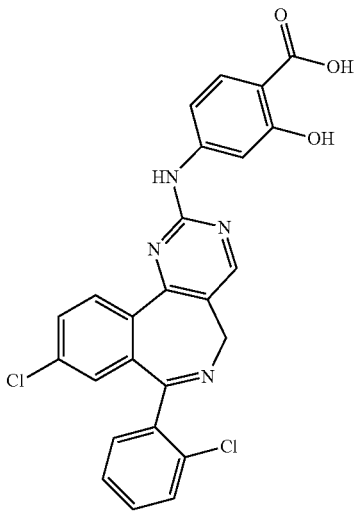 [SMILES: O=C(O)c1ccc(Nc2ncc3c(n2)-c2ccc(Cl)cc2C(c2ccccc2Cl)=NC3)cc1O]
I-86
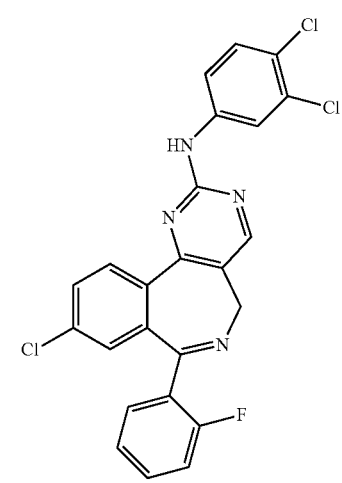 [SMILES: Fc1ccccc1C1=NCc2cnc(Nc3ccc(Cl)c(Cl)c3)nc2-c2ccc(Cl)cc21]
I-87
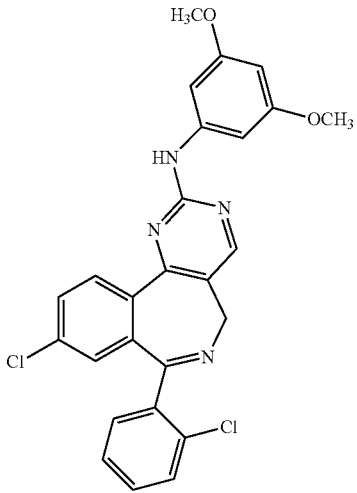 [SMILES: COc1cc(Nc2ncc3c(n2)-c2ccc(Cl)cc2C(c2ccccc2Cl)=NC3)cc(OC)c1]
I-88

TABLE 3-continued
Aurora Kinase Inhibitors
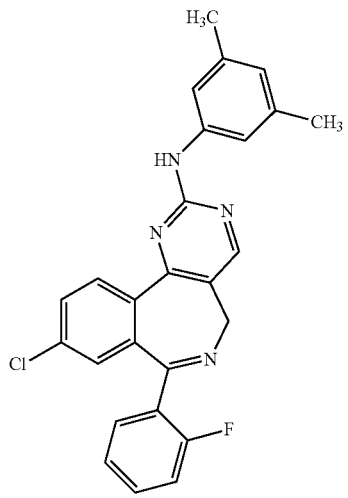 [SMILES: Cc1cc(C)cc(Nc2ncc3c(n2)-c2ccc(Cl)cc2C(c2ccccc2F)=NC3)c1]
I-89
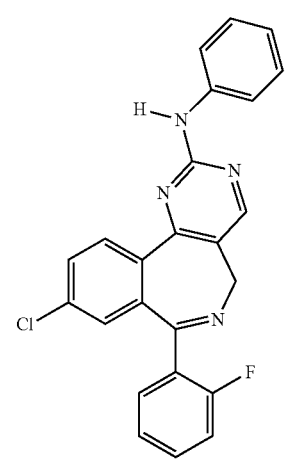 [SMILES: Fc1ccccc1C1=NCc2cnc(Nc3ccccc3)nc2-c2ccc(Cl)cc21]
I-90
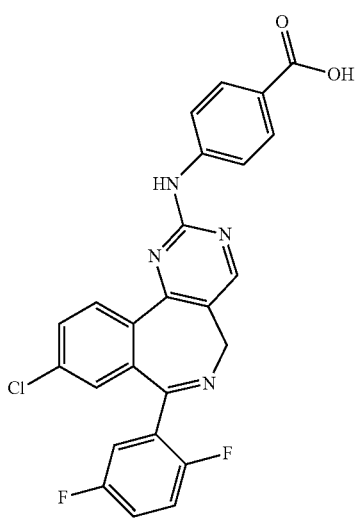 [SMILES: O=C(O)c1ccc(Nc2ncc3c(n2)-c2ccc(Cl)cc2C(c2cc(F)ccc2F)=NC3)cc1]
I-91
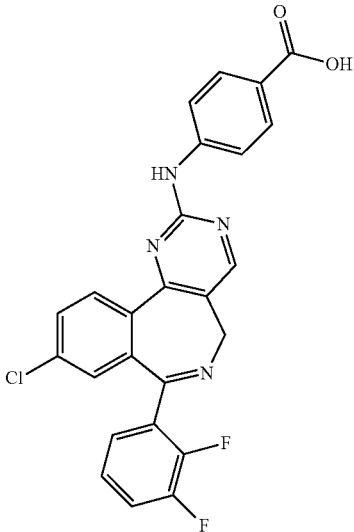 [SMILES: O=C(O)c1ccc(Nc2ncc3c(n2)-c2ccc(Cl)cc2C(c2cccc(F)c2F)=NC3)cc1]
I-92
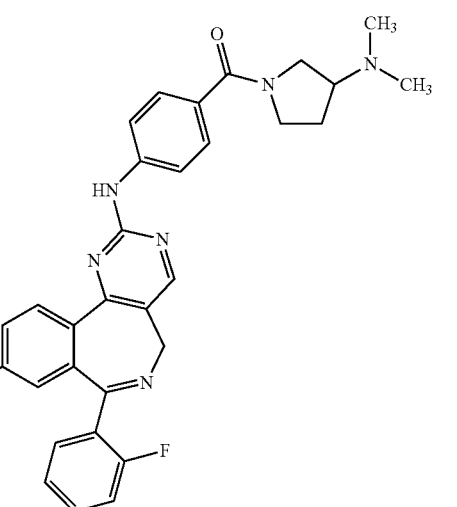
I-93
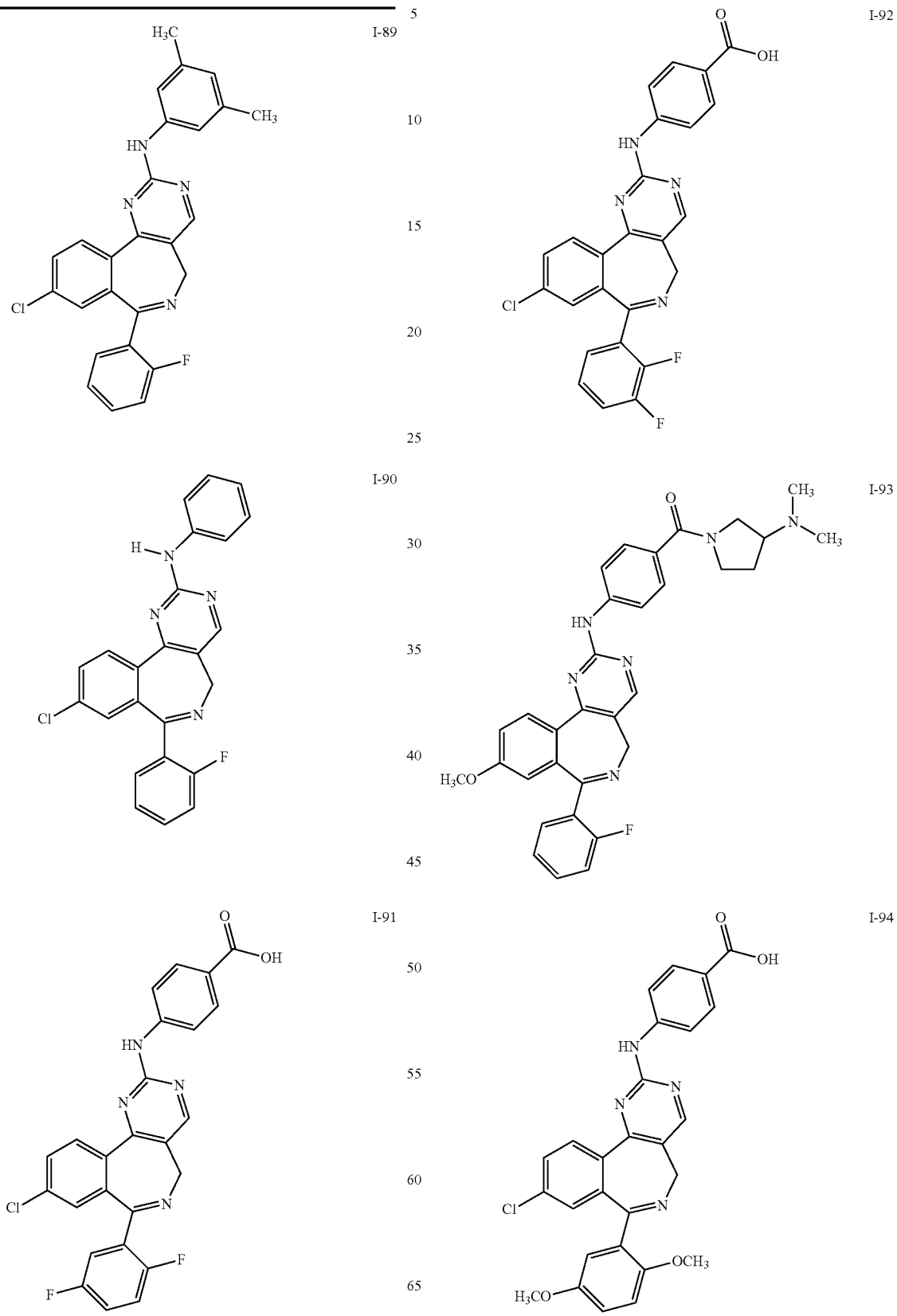
I-94

TABLE 3-continued
Aurora Kinase Inhibitors
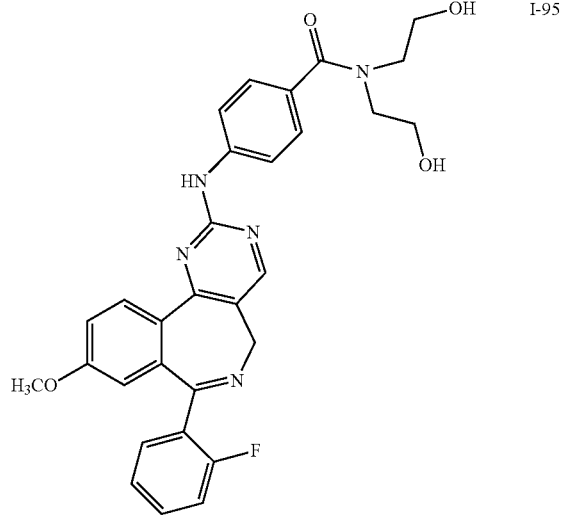
I-95
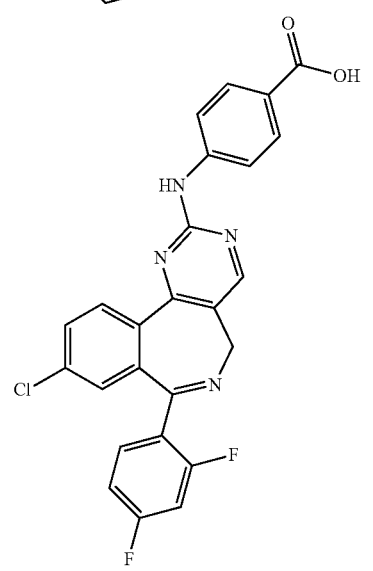
I-96
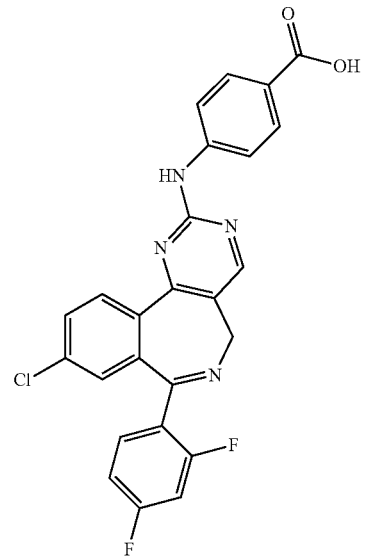 [SMILES: O=C(O)c1ccc(Nc2ncc3c(n2)-c2ccc(Cl)cc2C(c2ccc(F)cc2F)=NC3)cc1]
I-97
TABLE 3-continued
Aurora Kinase Inhibitors
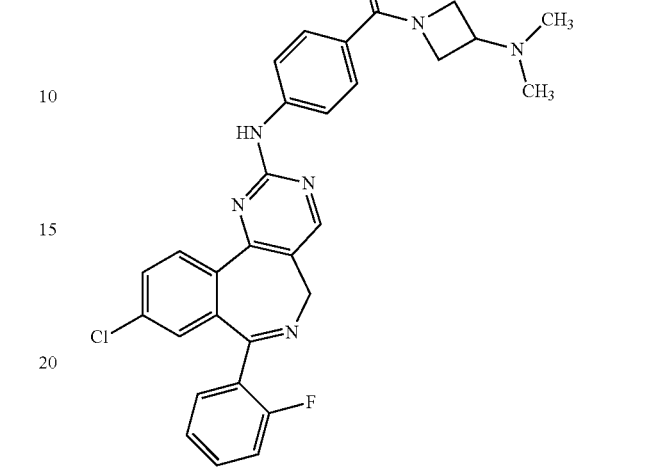
I-98
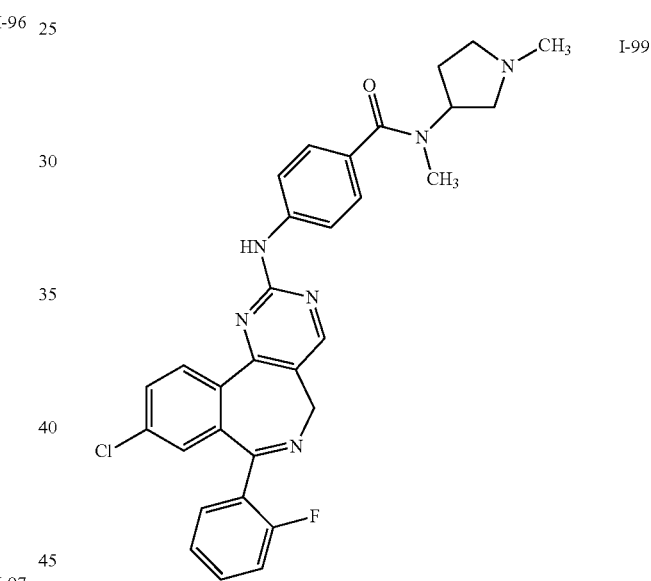
I-99
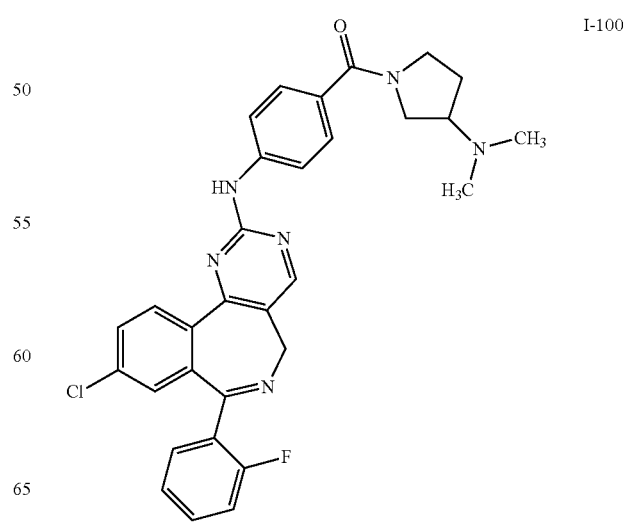
I-100

TABLE 3-continued
Aurora Kinase Inhibitors
I-101
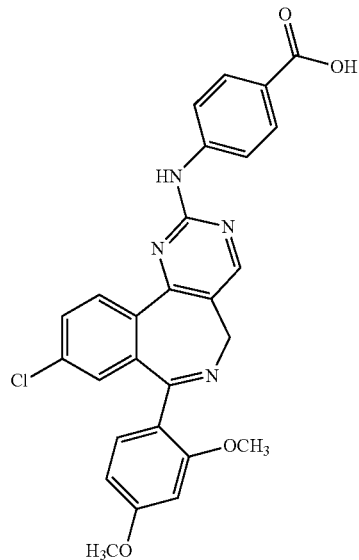 [SMILES: COc1ccc(C2=NCc3cnc(Nc4ccc(C(=O)O)cc4)nc3-c3ccc(Cl)cc32)c(OC)c1]
I-102
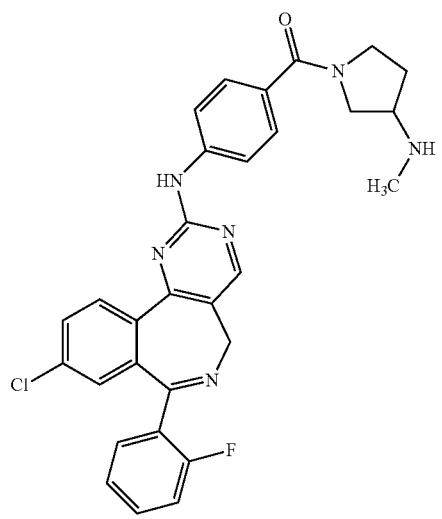 [SMILES: CNC1CCN(C(=O)c2ccc(Nc3ncc4c(n3)-c3ccc(Cl)cc3C(c3ccccc3F)=NC4)cc2)C1]
I-103
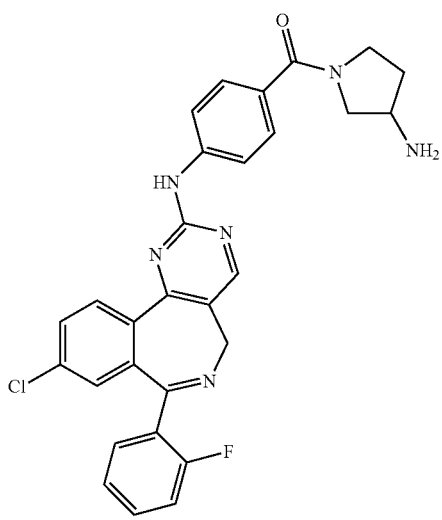 [SMILES: NC1CCN(C(=O)c2ccc(Nc3ncc4c(n3)-c3ccc(Cl)cc3C(c3ccccc3F)=NC4)cc2)C1]
TABLE 3-continued
Aurora Kinase Inhibitors
I-104
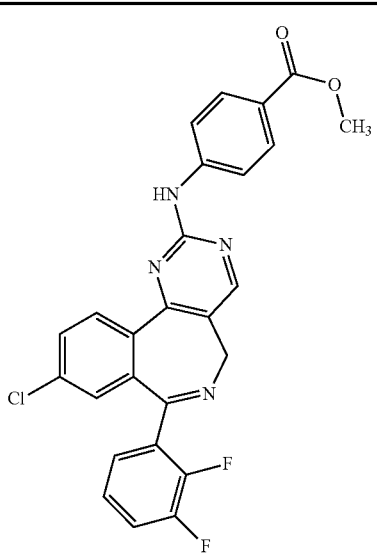
I-105
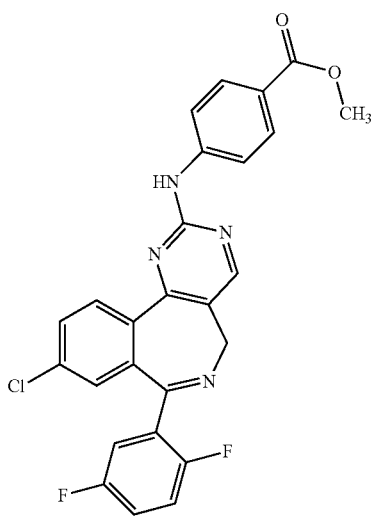 [SMILES: COC(=O)c1ccc(Nc2ncc3c(n2)-c2ccc(Cl)cc2C(c2cc(F)ccc2F)=NC3)cc1]
I-106
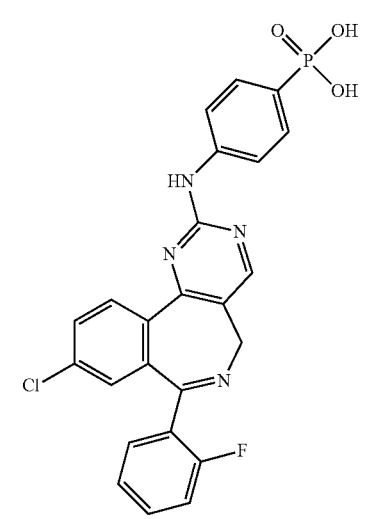 [SMILES: O=P(O)(O)c1ccc(Nc2ncc3c(n2)-c2ccc(Cl)cc2C(c2ccccc2F)=NC3)cc1]

TABLE 3-continued
Aurora Kinase Inhibitors
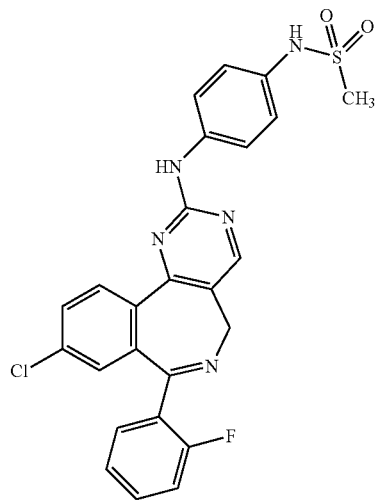 [SMILES: CS(=O)(=O)Nc1ccc(Nc2ncc3c(n2)-c2ccc(Cl)cc2C(c2ccccc2F)=NC3)cc1]
I-107
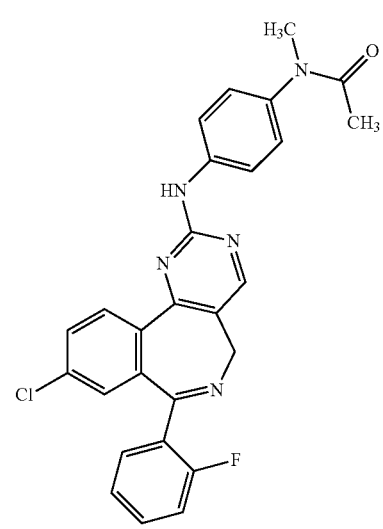 [SMILES: CC(=O)N(C)c1ccc(Nc2ncc3c(n2)-c2ccc(Cl)cc2C(c2ccccc2F)=NC3)cc1]
I-108
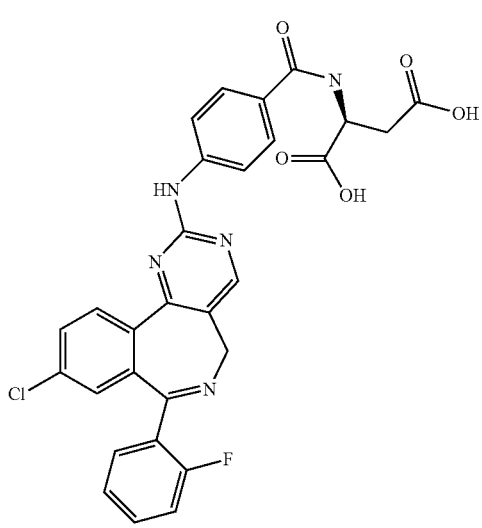 [SMILES: O=C(O)C[C@H](NC(=O)c1ccc(Nc2ncc3c(n2)-c2ccc(Cl)cc2C(c2ccccc2F)=NC3)cc1)C(=O)O]
I-109
TABLE 3-continued
Aurora Kinase Inhibitors
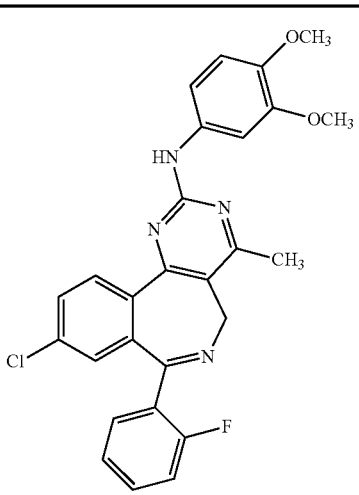
I-110
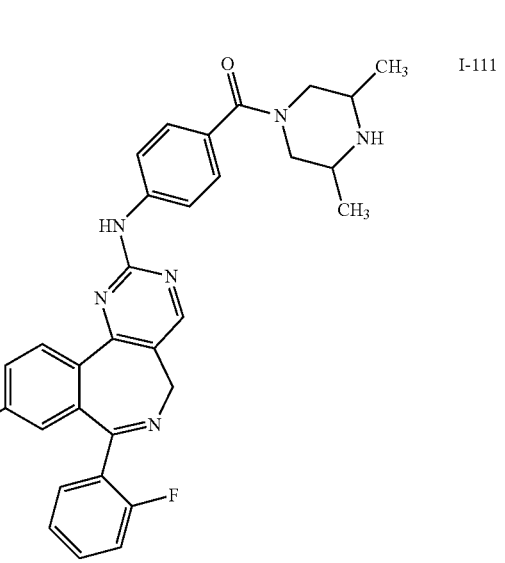
I-111
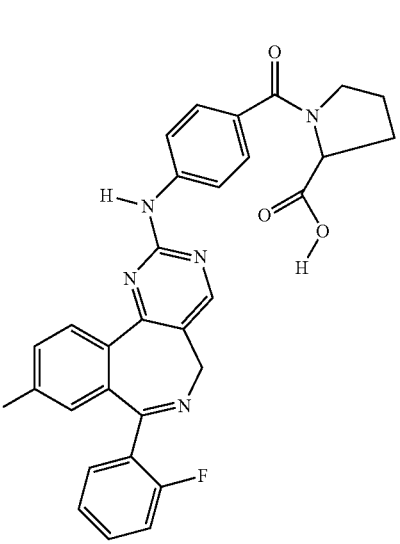
I-112

TABLE 3-continued
Aurora Kinase Inhibitors
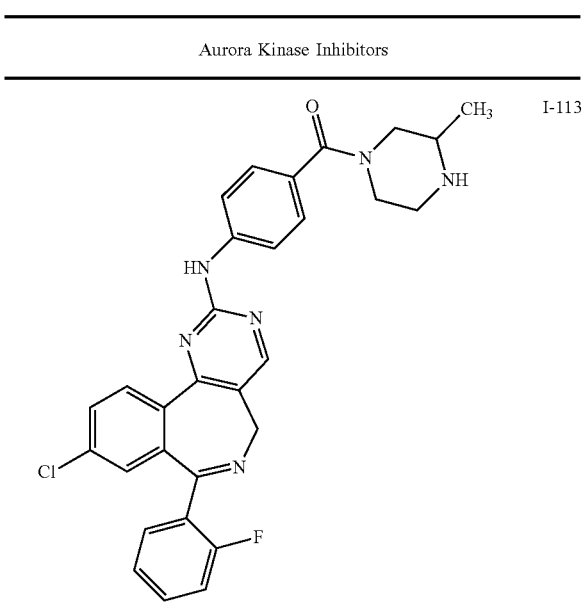
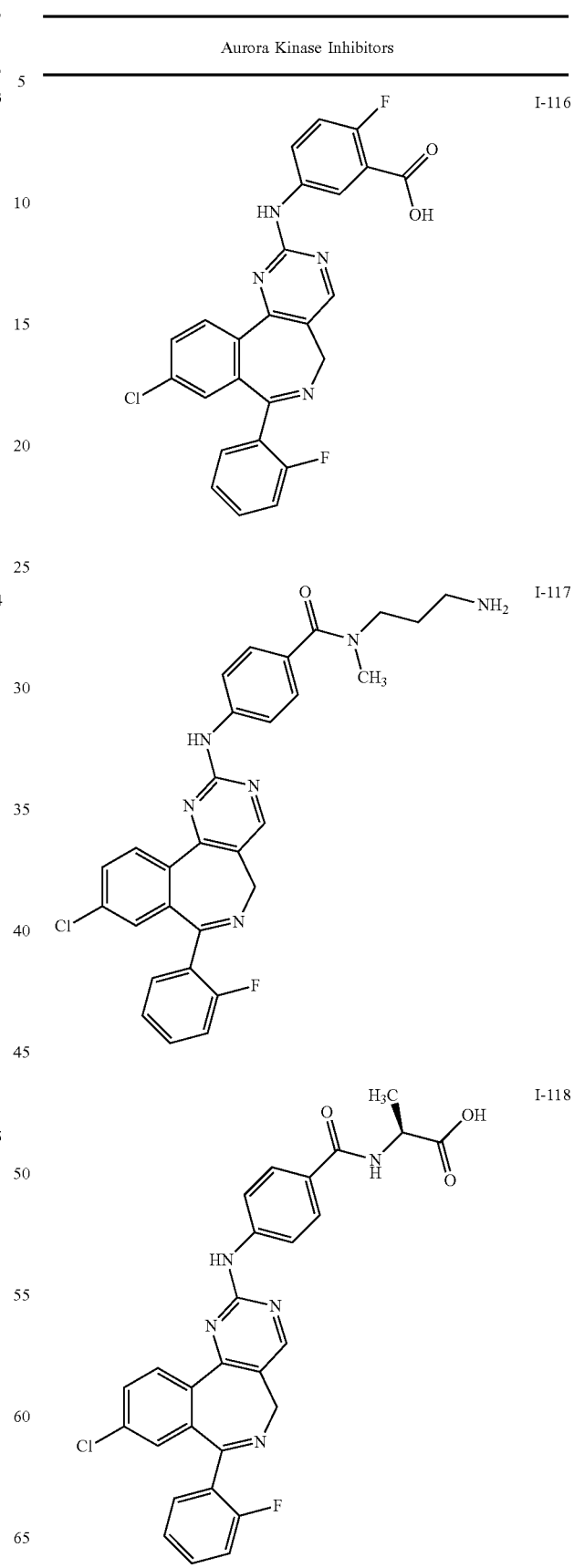

TABLE 3-continued
Aurora Kinase Inhibitors
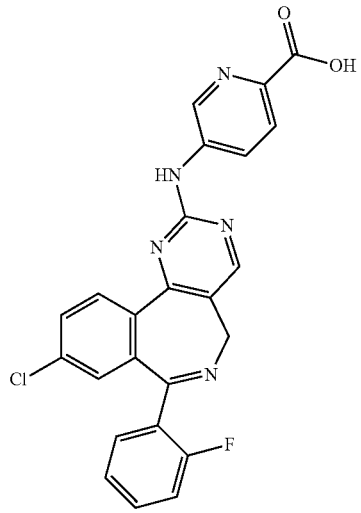 [SMILES: O=C(O)c1ccc(Nc2ncc3c(n2)-c2ccc(Cl)cc2C(c2ccccc2F)=NC3)cn1]
I-119
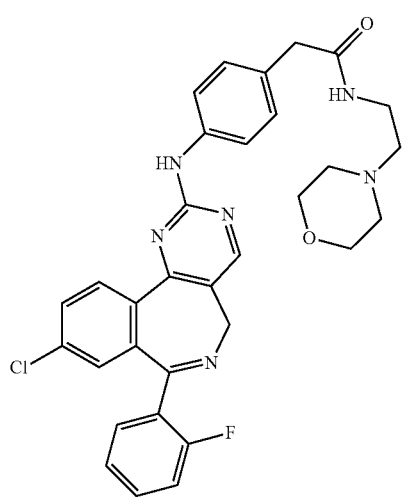 [SMILES: O=C(Cc1ccc(Nc2ncc3c(n2)-c2ccc(Cl)cc2C(c2ccccc2F)=NC3)cc1)NCCN1CCOCC1]
I-120
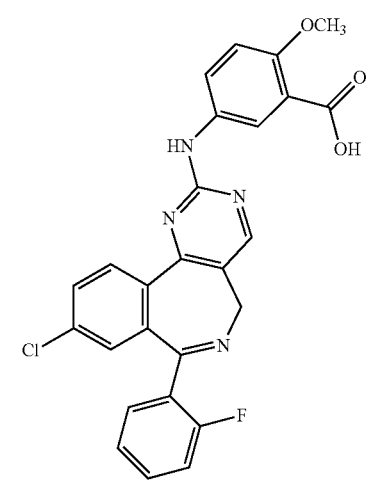 [SMILES: COc1ccc(Nc2ncc3c(n2)-c2ccc(Cl)cc2C(c2ccccc2F)=NC3)cc1C(=O)O]
I-121
TABLE 3-continued
Aurora Kinase Inhibitors
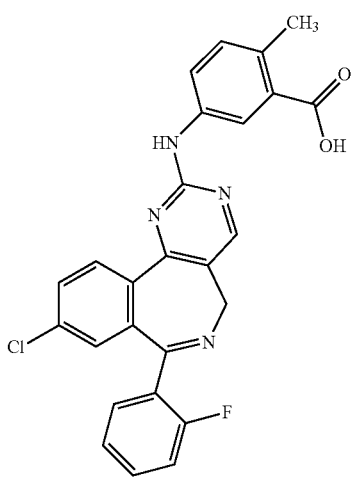 [SMILES: Cc1ccc(Nc2ncc3c(n2)-c2ccc(Cl)cc2C(c2ccccc2F)=NC3)cc1C(=O)O]
I-122
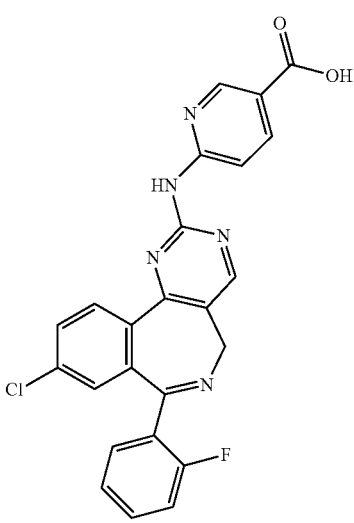 [SMILES: O=C(O)c1ccc(Nc2ncc3c(n2)-c2ccc(Cl)cc2C(c2ccccc2F)=NC3)nc1]
I-123
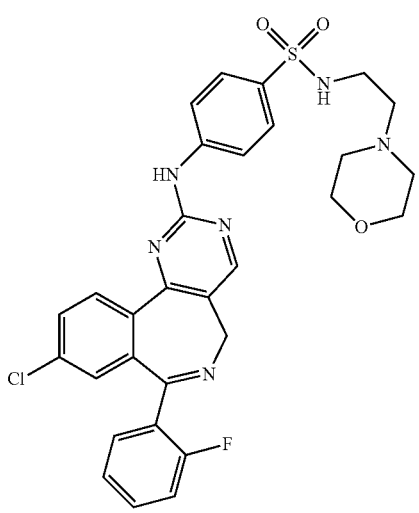 [SMILES: O=S(=O)(NCCN1CCOCC1)c1ccc(Nc2ncc3c(n2)-c2ccc(Cl)cc2C(c2ccccc2F)=NC3)cc1]
I-124

TABLE 3-continued
Aurora Kinase Inhibitors
I-125
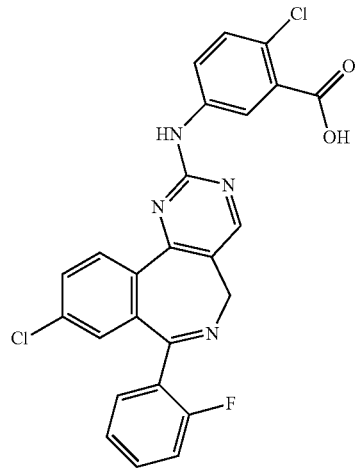 [SMILES: O=C(O)c1cc(Nc2ncc3c(n2)-c2ccc(Cl)cc2C(c2ccccc2F)=NC3)ccc1Cl]
I-126
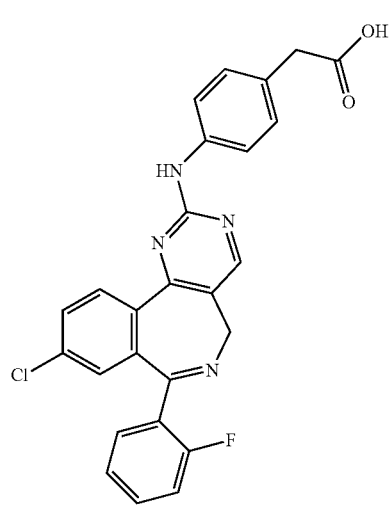 [SMILES: O=C(O)Cc1ccc(Nc2ncc3c(n2)-c2ccc(Cl)cc2C(c2ccccc2F)=NC3)cc1]
I-127
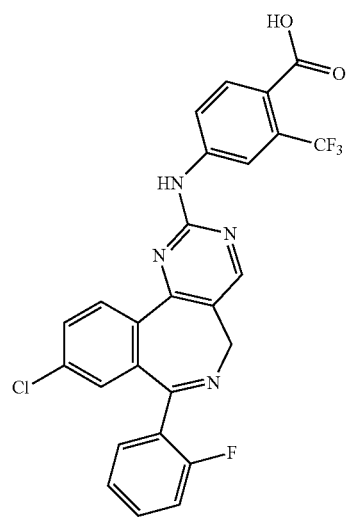 [SMILES: O=C(O)c1ccc(Nc2ncc3c(n2)-c2ccc(Cl)cc2C(c2ccccc2F)=NC3)cc1C(F)(F)F]
TABLE 3-continued
Aurora Kinase Inhibitors
I-128
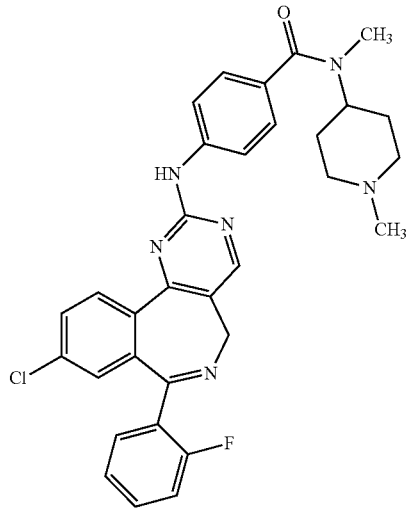 [SMILES: CN1CCC(N(C)C(=O)c2ccc(Nc3ncc4c(n3)-c3ccc(Cl)cc3C(c3ccccc3F)=NC4)cc2)CC1]
I-129
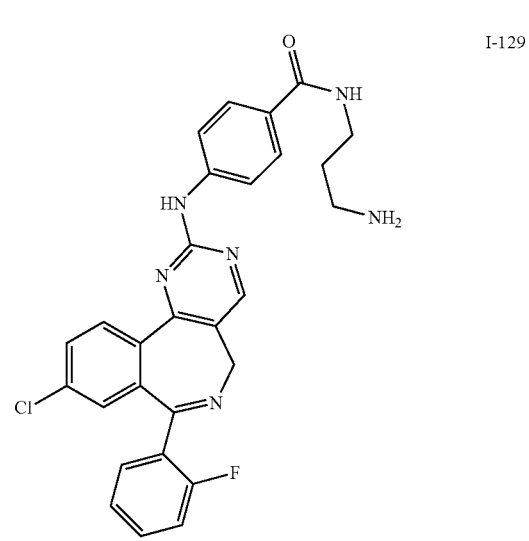
I-130
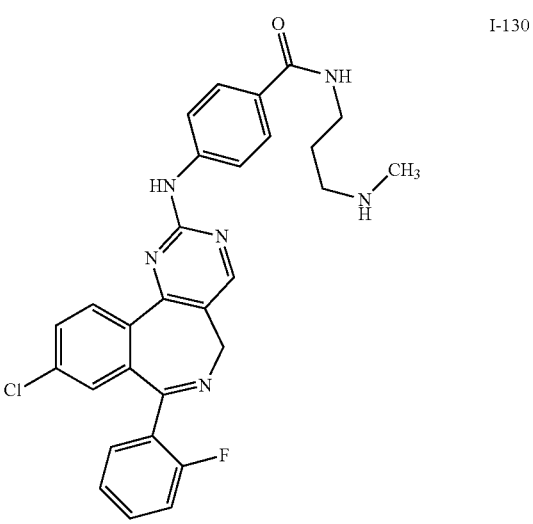

TABLE 3-continued
Aurora Kinase Inhibitors
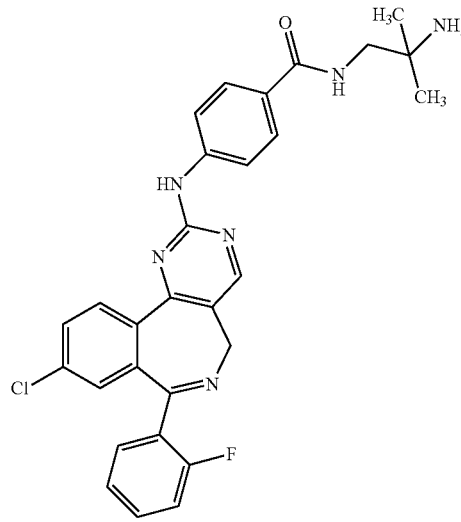
I-131
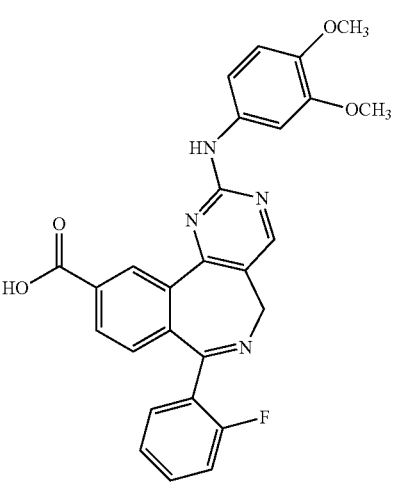 [SMILES: COc1ccc(Nc2ncc3c(n2)-c2cc(C(=O)O)ccc2C(c2ccccc2F)=NC3)cc1OC]
I-132
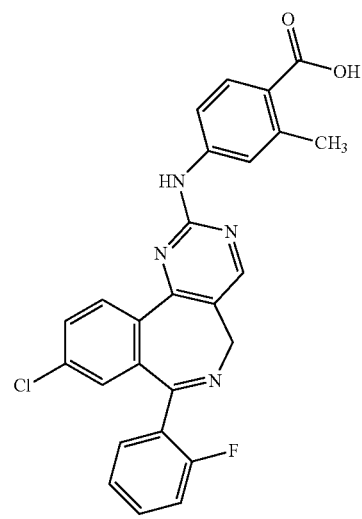 [SMILES: Cc1cc(Nc2ncc3c(n2)-c2ccc(Cl)cc2C(c2ccccc2F)=NC3)ccc1C(=O)O]
I-133
TABLE 3-continued
Aurora Kinase Inhibitors
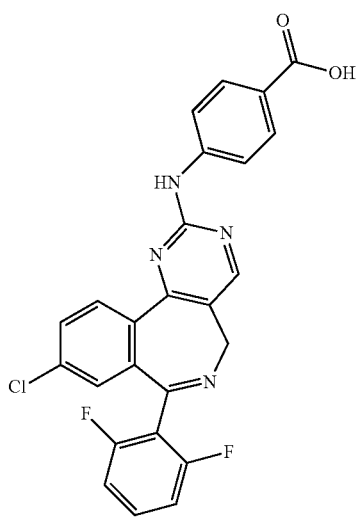
I-134
I-135
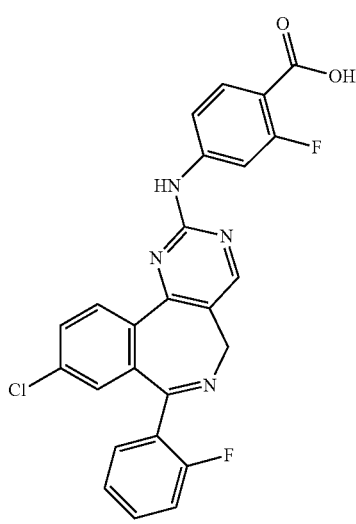 [SMILES: O=C(O)c1ccc(Nc2ncc3c(n2)-c2ccc(Cl)cc2C(c2ccccc2F)=NC3)cc1Cl]
I-136

TABLE 3-continued
Aurora Kinase Inhibitors
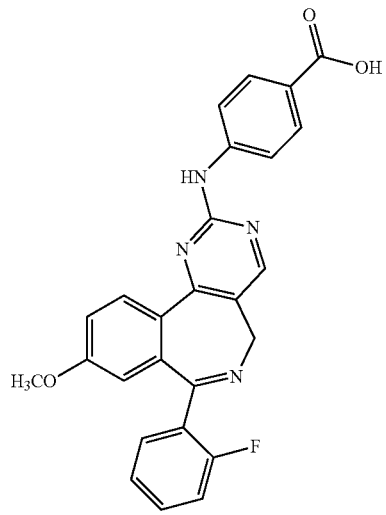 [SMILES: COc1ccc2c(c1)C(c1ccccc1F)=NCc1cnc(Nc3ccc(C(=O)O)cc3)nc1-2]
I-137
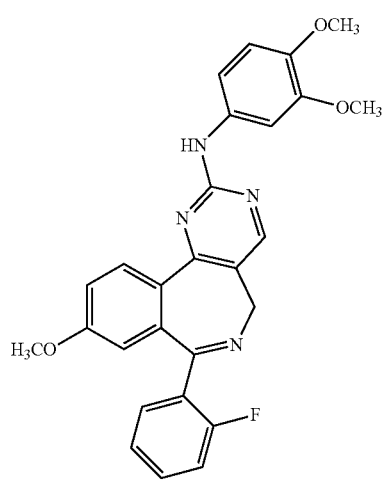 [SMILES: COc1ccc2c(c1)C(c1ccccc1F)=NCc1cnc(Nc3ccc(OC)c(OC)c3)nc1-2]
I-138
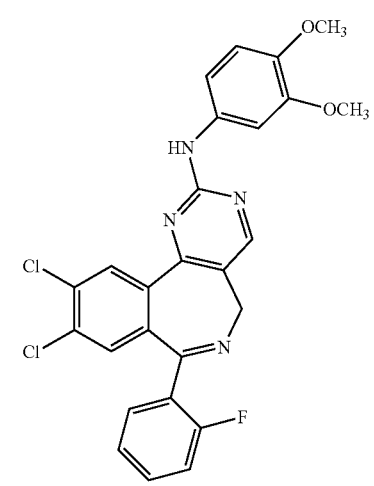 [SMILES: COc1ccc(Nc2ncc3c(n2)-c2cc(Cl)c(Cl)cc2C(c2ccccc2F)=NC3)cc1OC]
I-139
TABLE 3-continued
Aurora Kinase Inhibitors
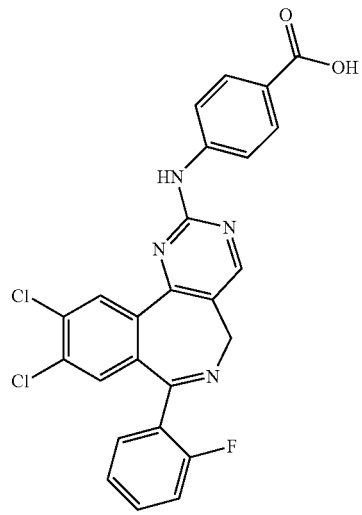 [SMILES: O=C(O)c1ccc(Nc2ncc3c(n2)-c2cc(Cl)c(Cl)cc2C(c2ccccc2F)=NC3)cc1]
I-140
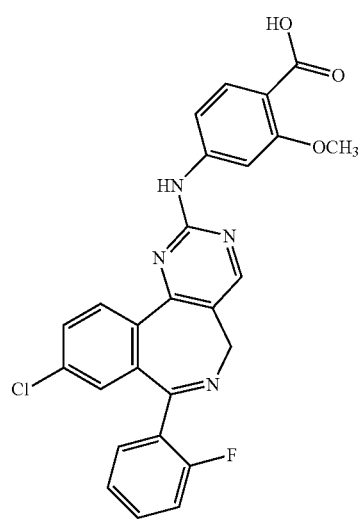 [SMILES: COc1cc(Nc2ncc3c(n2)-c2ccc(Cl)cc2C(c2ccccc2F)=NC3)ccc1C(=O)O]
I-141
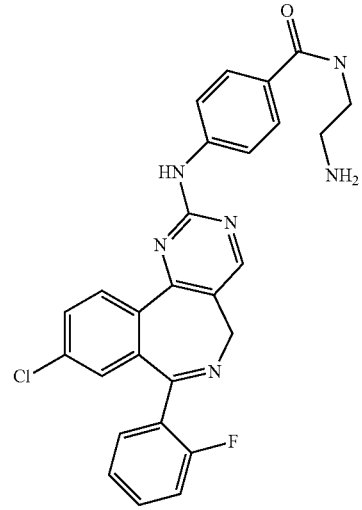 [SMILES: NCCNC(=O)c1ccc(Nc2ncc3c(n2)-c2ccc(Cl)cc2C(c2ccccc2F)=NC3)cc1]
I-142

TABLE 3-continued
Aurora Kinase Inhibitors
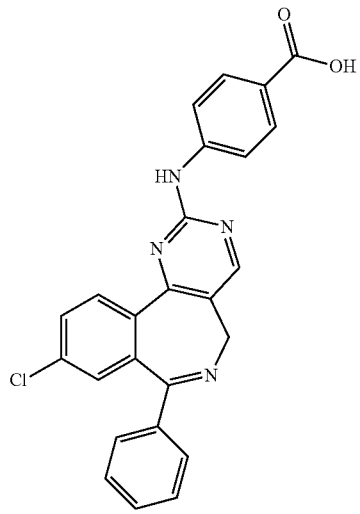 [SMILES: O=C(O)c1ccc(Nc2ncc3c(n2)-c2ccc(Cl)cc2C(c2ccccc2)=NC3)cc1]
I-143
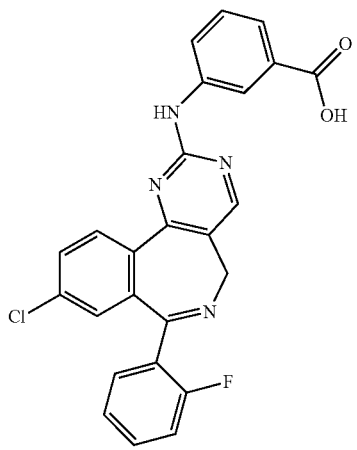
I-146
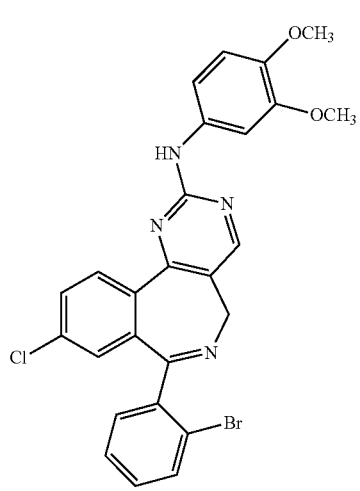 [SMILES: COc1ccc(Nc2ncc3c(n2)-c2ccc(Cl)cc2C(c2ccccc2Br)=NC3)cc1OC]
I-144
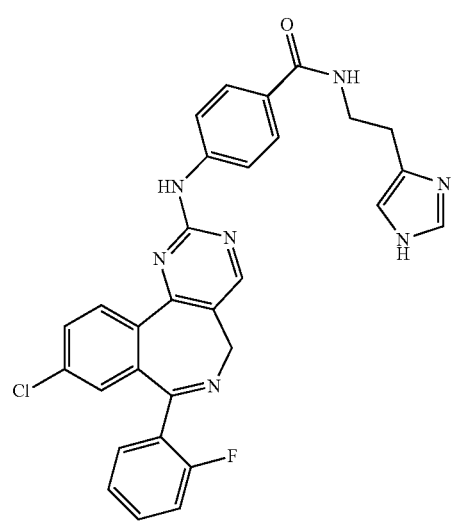
I-147
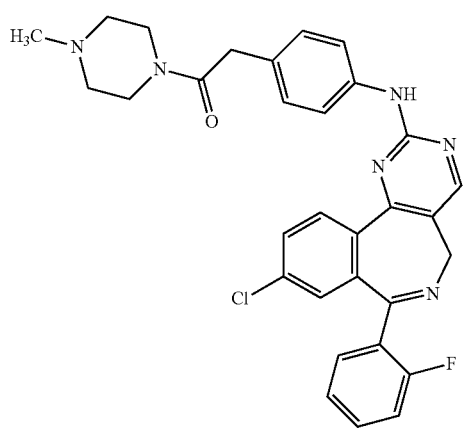 [SMILES: CN1CCN(C(=O)Cc2ccc(Nc3ncc4c(n3)-c3ccc(Cl)cc3C(c3ccccc3F)=NC4)cc2)CC1]
I-145
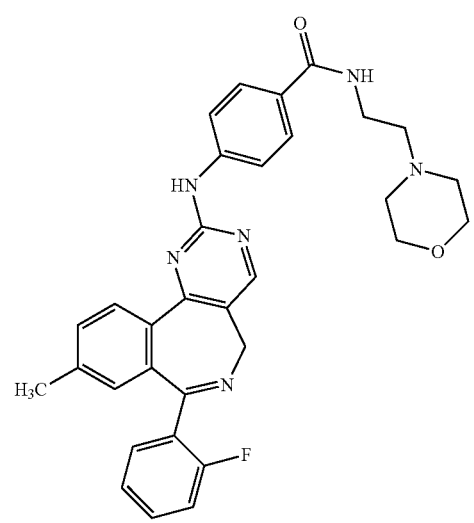 [SMILES: Cc1ccc2c(c1)C(c1ccccc1F)=NCc1cnc(Nc3ccc(C(=O)NCCN4CCOCC4)cc3)nc1-2]
I-148

TABLE 3-continued
Aurora Kinase Inhibitors
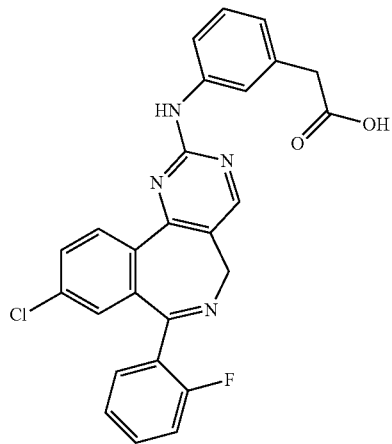 [SMILES: O=C(O)Cc1cccc(Nc2ncc3c(n2)-c2ccc(Cl)cc2C(c2ccccc2F)=NC3)c1]
I-149
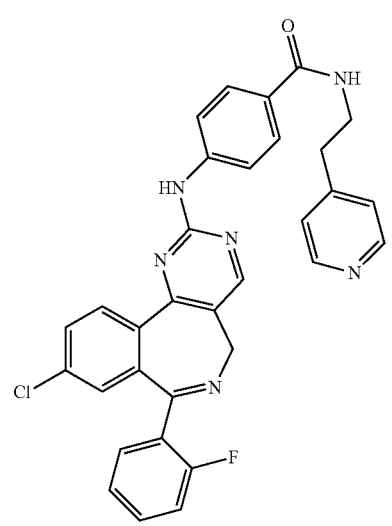 [SMILES: O=C(NCCc1ccncc1)c1ccc(Nc2ncc3c(n2)-c2ccc(Cl)cc2C(c2ccccc2F)=NC3)cc1]
I-150
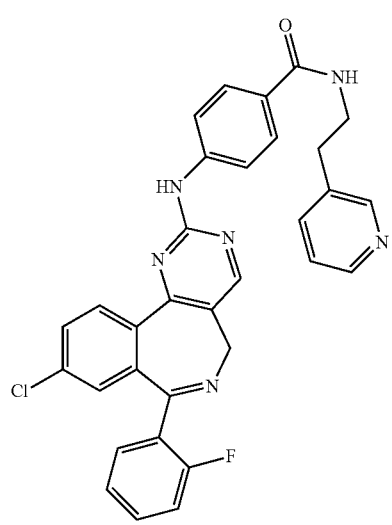 [SMILES: O=C(NCCc1cccnc1)c1ccc(Nc2ncc3c(n2)-c2ccc(Cl)cc2C(c2ccccc2F)=NC3)cc1]
I-151
TABLE 3-continued
Aurora Kinase Inhibitors
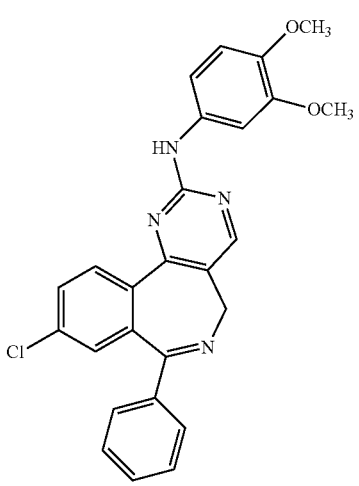 [SMILES: COc1ccc(Nc2ncc3c(n2)-c2ccc(Cl)cc2C(c2ccccc2)=NC3)cc1OC]
I-152
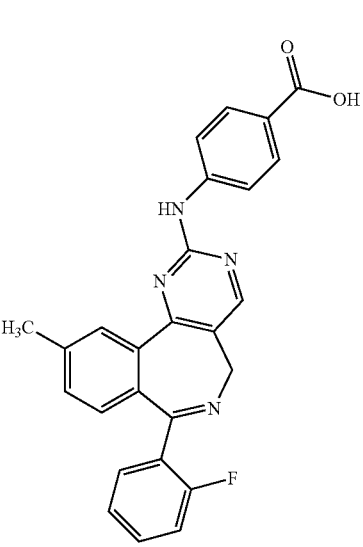 [SMILES: Cc1ccc2c(c1)-c1nc(Nc3ccc(C(=O)O)cc3)ncc1CN=C2c1ccccc1F]
I-153
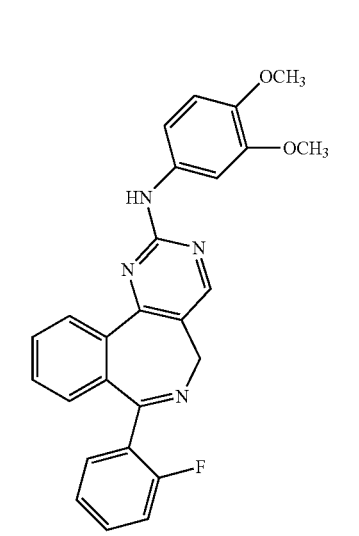 [SMILES: COc1ccc(Nc2ncc3c(n2)-c2ccccc2C(c2ccccc2F)=NC3)cc1OC]
I-154

TABLE 3-continued
Aurora Kinase Inhibitors
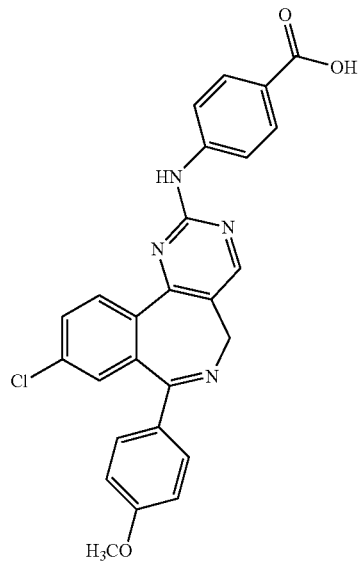 [SMILES: COc1ccc(C2=NCc3cnc(Nc4ccc(C(=O)O)cc4)nc3-c3ccc(Cl)cc32)cc1]
I-155
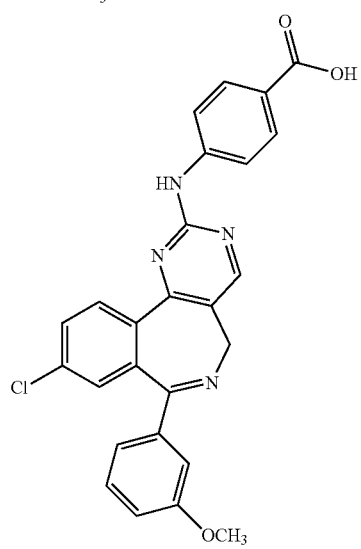
I-156
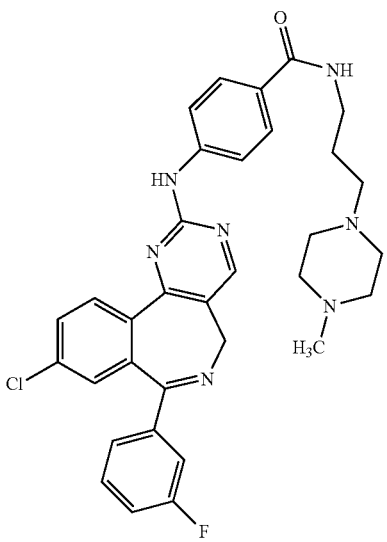 [SMILES: CN1CCN(CCCNC(=O)c2ccc(Nc3ncc4c(n3)-c3ccc(Cl)cc3C(c3cccc(F)c3)=NC4)cc2)CC1]
I-157
TABLE 3-continued
Aurora Kinase Inhibitors
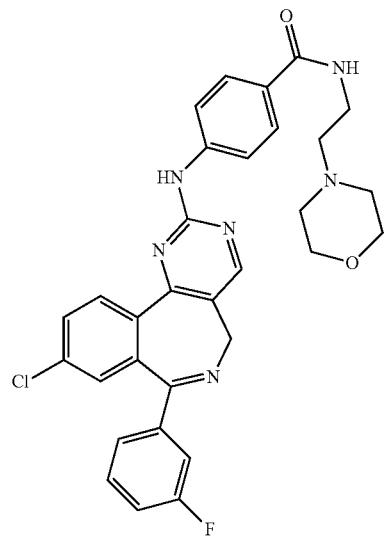 [SMILES: O=C(NCCN1CCOCC1)c1ccc(Nc2ncc3c(n2)-c2ccc(Cl)cc2C(c2cccc(F)c2)=NC3)cc1]
I-158
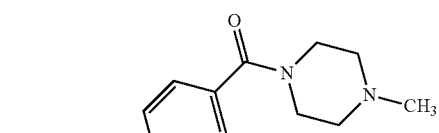
I-159
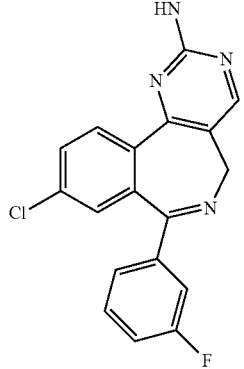
I-160

TABLE 3-continued
Aurora Kinase Inhibitors
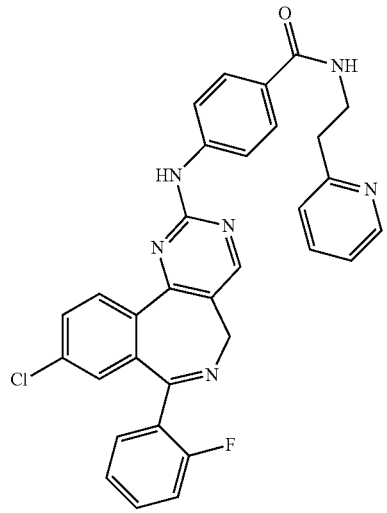 [SMILES: O=C(NCCc1ccccn1)c1ccc(Nc2ncc3c(n2)-c2ccc(Cl)cc2C(c2ccccc2F)=NC3)cc1]
I-161
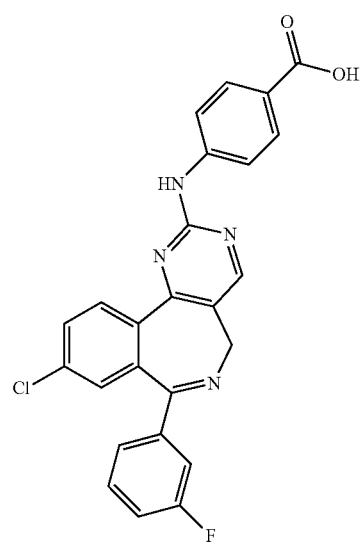 [SMILES: O=C(O)c1ccc(Nc2ncc3c(n2)-c2ccc(Cl)cc2C(c2cccc(F)c2)=NC3)cc1]
I-162
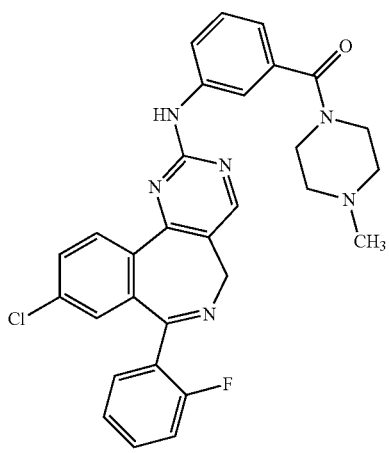 [SMILES: CN1CCN(C(=O)c2cccc(Nc3ncc4c(n3)-c3ccc(Cl)cc3C(c3ccccc3F)=NC4)c2)CC1]
I-163
TABLE 3-continued
Aurora Kinase Inhibitors
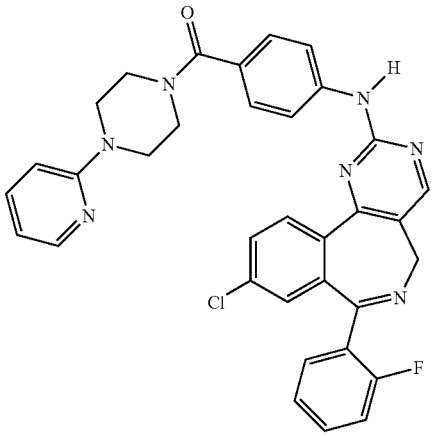 [SMILES: O=C(c1ccc(Nc2ncc3c(n2)-c2ccc(Cl)cc2C(c2ccccc2F)=NC3)cc1)N1CCN(c2ccccn2)CC1]
I-164
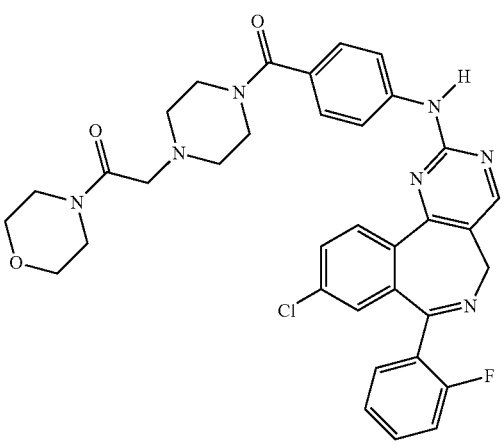 [SMILES: O=C(CN1CCN(C(=O)c2ccc(Nc3ncc4c(n3)-c3ccc(Cl)cc3C(c3ccccc3F)=NC4)cc2)CC1)N1CCOCC1]
I-165
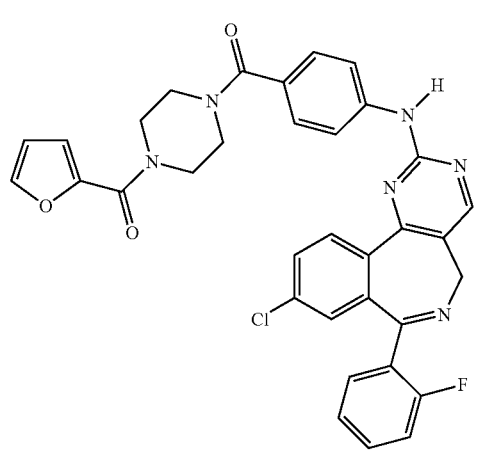 [SMILES: O=C(c1ccc(Nc2ncc3c(n2)-c2ccc(Cl)cc2C(c2ccccc2F)=NC3)cc1)N1CCN(C(=O)c2ccco2)CC1]
I-166

TABLE 3-continued
Aurora Kinase Inhibitors
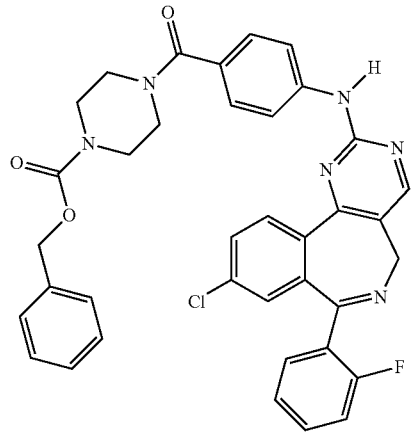 [SMILES: O=C(OCc1ccccc1)N1CCN(C(=O)c2ccc(Nc3ncc4c(n3)-c3ccc(Cl)cc3C(c3ccccc3F)=NC4)cc2)CC1]
I-167
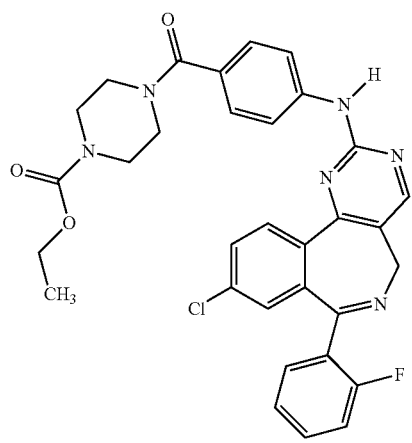 [SMILES: CCOC(=O)N1CCN(C(=O)c2ccc(Nc3ncc4c(n3)-c3ccc(Cl)cc3C(c3ccccc3F)=NC4)cc2)CC1]
I-168
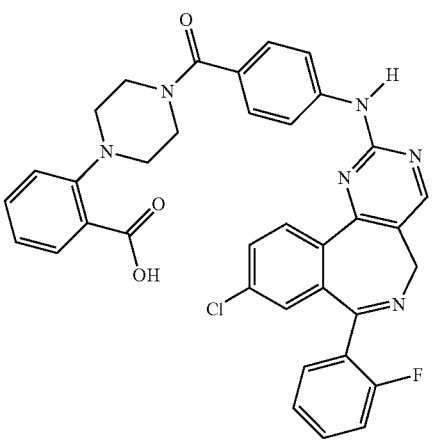 [SMILES: O=C(O)c1ccccc1N1CCN(C(=O)c2ccc(Nc3ncc4c(n3)-c3ccc(Cl)cc3C(c3ccccc3F)=NC4)cc2)CC1]
I-169
TABLE 3-continued
Aurora Kinase Inhibitors
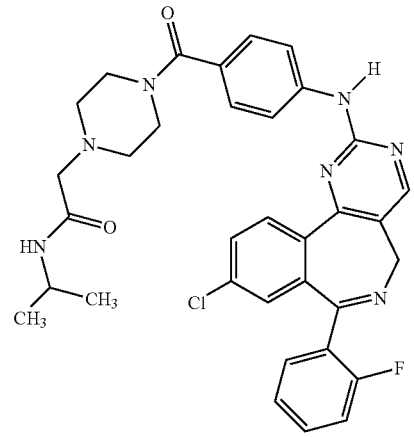 [SMILES: CC(C)NC(=O)CN1CCN(C(=O)c2ccc(Nc3ncc4c(n3)-c3ccc(Cl)cc3C(c3ccccc3F)=NC4)cc2)CC1]
I-170
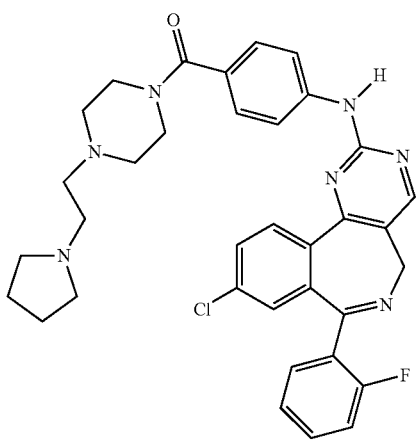 [SMILES: O=C(c1ccc(Nc2ncc3c(n2)-c2ccc(Cl)cc2C(c2ccccc2F)=NC3)cc1)N1CCN(CCN2CCCC2)CC1]
I-171
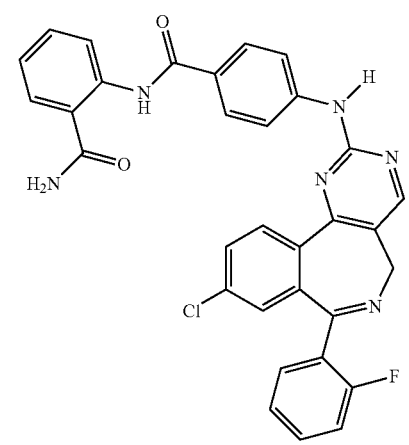 [SMILES: NC(=O)c1ccccc1NC(=O)c1ccc(Nc2ncc3c(n2)-c2ccc(Cl)cc2C(c2ccccc2F)=NC3)cc1]
I-172

TABLE 3-continued
Aurora Kinase Inhibitors
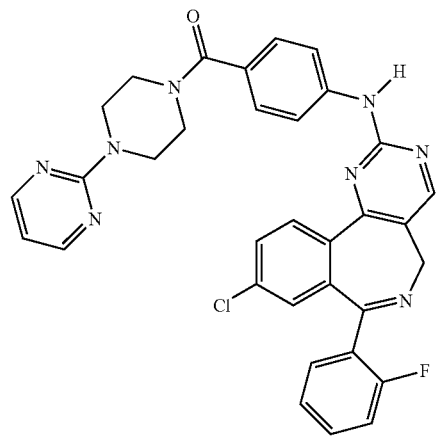 [SMILES: O=C(c1ccc(Nc2ncc3c(n2)-c2ccc(Cl)cc2C(c2ccccc2F)=NC3)cc1)N1CCN(c2ncccn2)CC1]
I-173
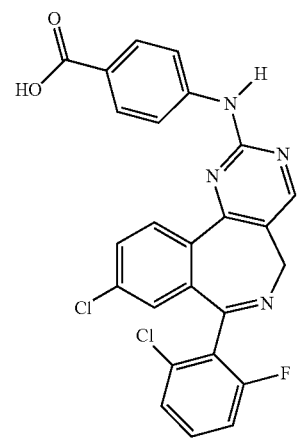 [SMILES: O=C(O)c1ccc(Nc2ncc3c(n2)-c2ccc(Cl)cc2C(c2c(F)cccc2Cl)=NC3)cc1]
I-174
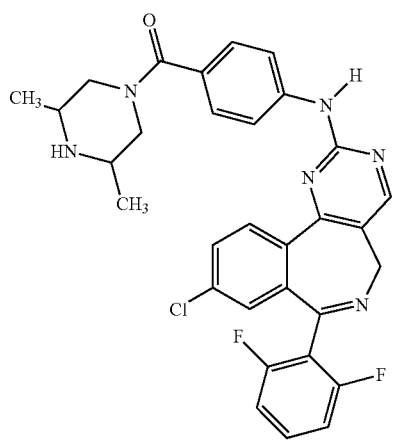 [SMILES: CC1CN(C(=O)c2ccc(Nc3ncc4c(n3)-c3ccc(Cl)cc3C(c3c(F)cccc3F)=NC4)cc2)CC(C)N1]
I-175
TABLE 3-continued
Aurora Kinase Inhibitors
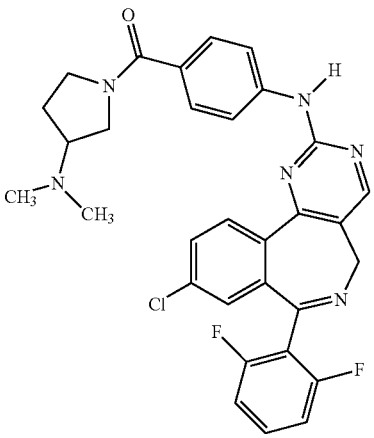 [SMILES: CN(C)C1CCN(C(=O)c2ccc(Nc3ncc4c(n3)-c3ccc(Cl)cc3C(c3c(F)cccc3F)=NC4)cc2)C1]
I-176
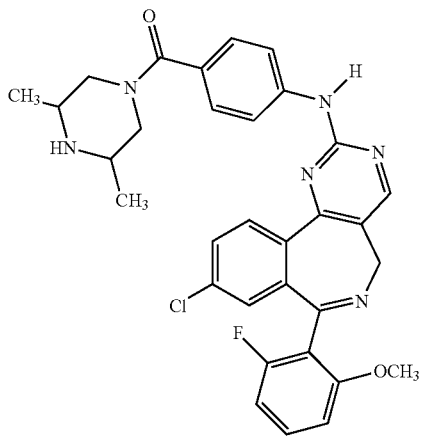 [SMILES: COc1cccc(F)c1C1=NCc2cnc(Nc3ccc(C(=O)N4CC(C)NC(C)C4)cc3)nc2-c2ccc(Cl)cc21]
I-177
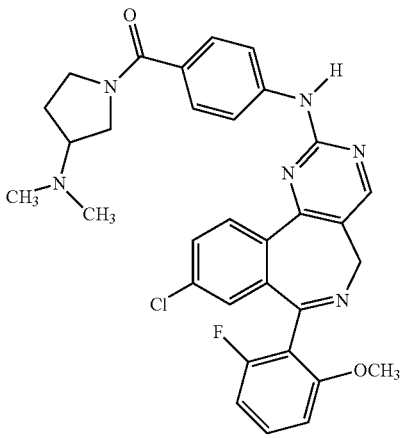 [SMILES: COc1cccc(F)c1C1=NCc2cnc(Nc3ccc(C(=O)N4CCC(N(C)C)C4)cc3)nc2-c2ccc(Cl)cc21]
I-178

TABLE 3-continued
Aurora Kinase Inhibitors
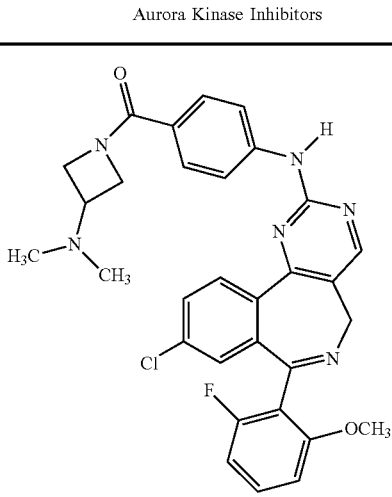
I-179
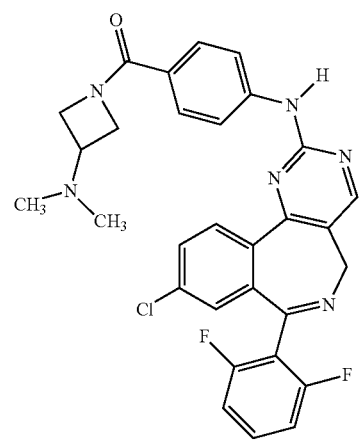 [SMILES: CN(C)C1CN(C(=O)c2ccc(Nc3ncc4c(n3)-c3ccc(Cl)cc3C(c3c(F)cccc3F)=NC4)cc2)C1]
I-180
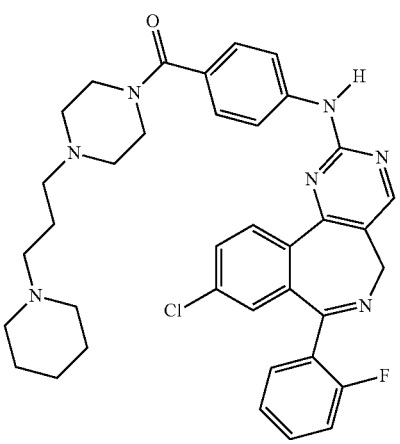 [SMILES: O=C(c1ccc(Nc2ncc3c(n2)-c2ccc(Cl)cc2C(c2ccccc2F)=NC3)cc1)N1CCN(CCCN2CCCCC2)CC1]
I-181
TABLE 3-continued
Aurora Kinase Inhibitors
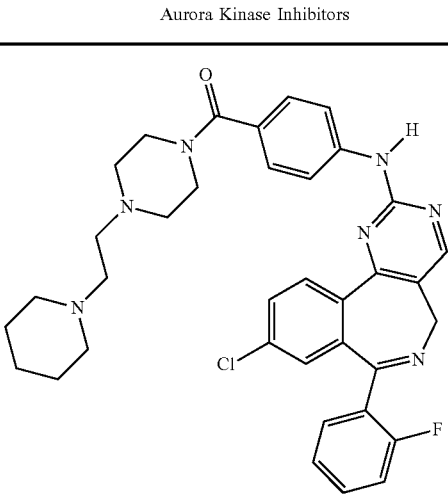
I-182
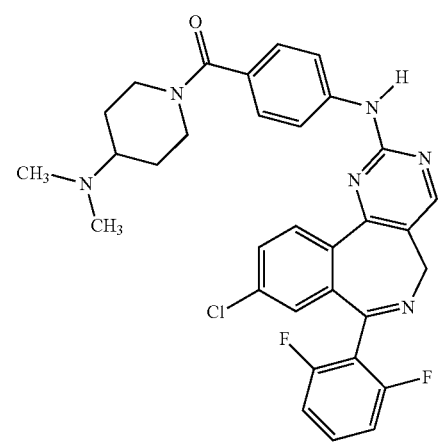 [SMILES: CN(C)C1CCN(C(=O)c2ccc(Nc3ncc4c(n3)-c3ccc(Cl)cc3C(c3c(F)cccc3F)=NC4)cc2)CC1]
I-183
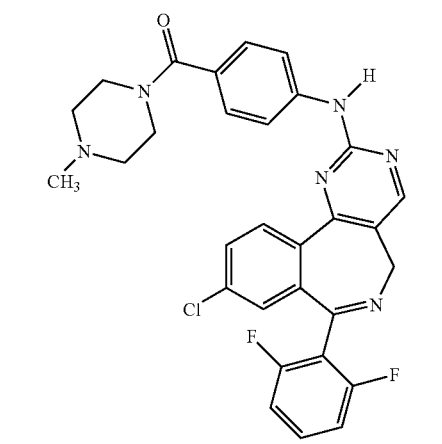 [SMILES: CN1CCN(C(=O)c2ccc(Nc3ncc4c(n3)-c3ccc(Cl)cc3C(c3c(F)cccc3F)=NC4)cc2)CC1]
I-184

TABLE 3-continued
Aurora Kinase Inhibitors
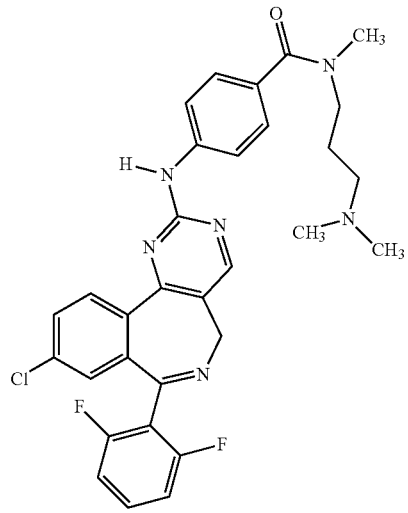 [SMILES: CN(C)CCCN(C)C(=O)c1ccc(Nc2ncc3c(n2)-c2ccc(Cl)cc2C(c2c(F)cccc2F)=NC3)cc1]
I-185
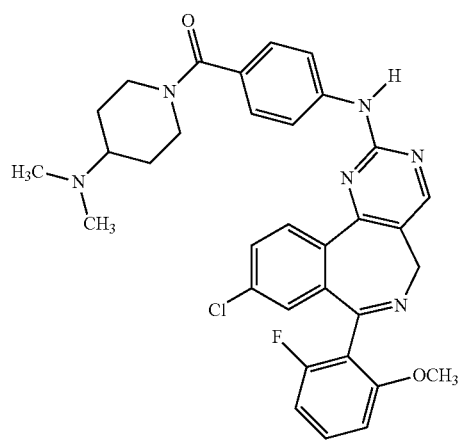 [SMILES: COc1cccc(F)c1C1=NCc2cnc(Nc3ccc(C(=O)N4CCC(N(C)C)CC4)cc3)nc2-c2ccc(Cl)cc21]
I-186
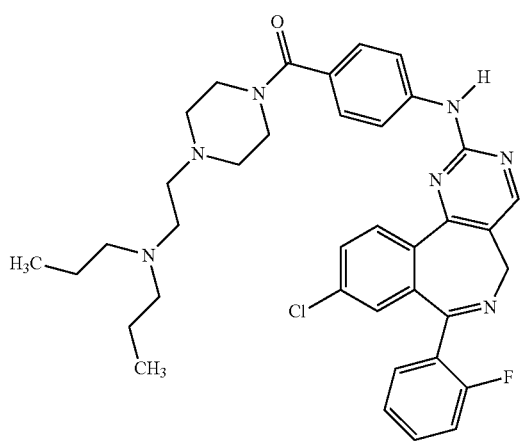 [SMILES: CCCN(CCC)CCN1CCN(C(=O)c2ccc(Nc3ncc4c(n3)-c3ccc(Cl)cc3C(c3ccccc3F)=NC4)cc2)CC1]
I-187
TABLE 3-continued
Aurora Kinase Inhibitors
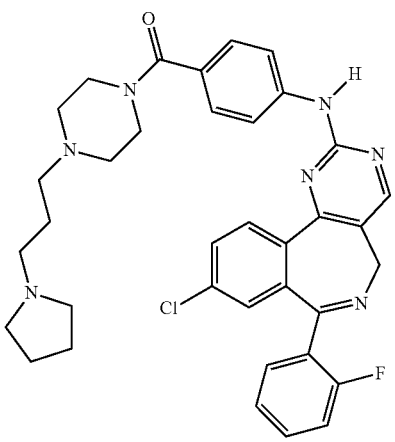 [SMILES: O=C(c1ccc(Nc2ncc3c(n2)-c2ccc(Cl)cc2C(c2ccccc2F)=NC3)cc1)N1CCN(CCCN2CCCC2)CC1]
I-188
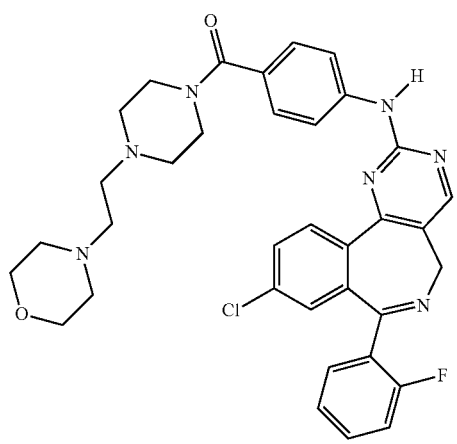 [SMILES: O=C(c1ccc(Nc2ncc3c(n2)-c2ccc(Cl)cc2C(c2ccccc2F)=NC3)cc1)N1CCN(CCN2CCOCC2)CC1]
I-189
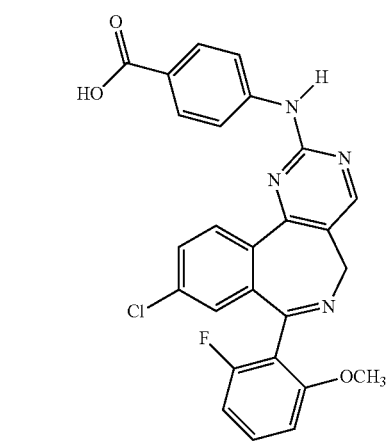 [SMILES: COc1cccc(F)c1C1=NCc2cnc(Nc3ccc(C(=O)O)cc3)nc2-c2ccc(Cl)cc21]
I-190

TABLE 3-continued
Aurora Kinase Inhibitors
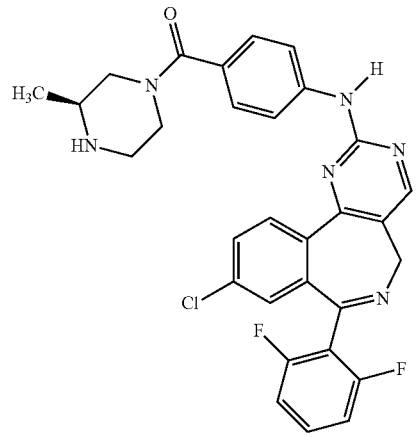 [SMILES: C[C@H]1CN(C(=O)c2ccc(Nc3ncc4c(n3)-c3ccc(Cl)cc3C(c3c(F)cccc3F)=NC4)cc2)CCN1]
I-191
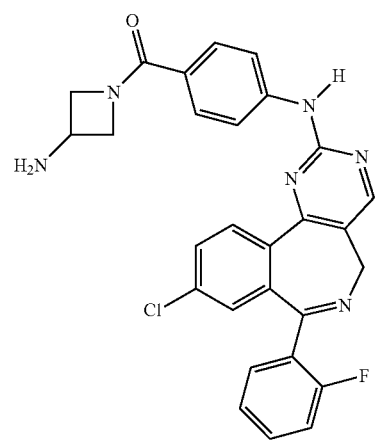 [SMILES: NC1CN(C(=O)c2ccc(Nc3ncc4c(n3)-c3ccc(Cl)cc3C(c3ccccc3F)=NC4)cc2)C1]
I-192
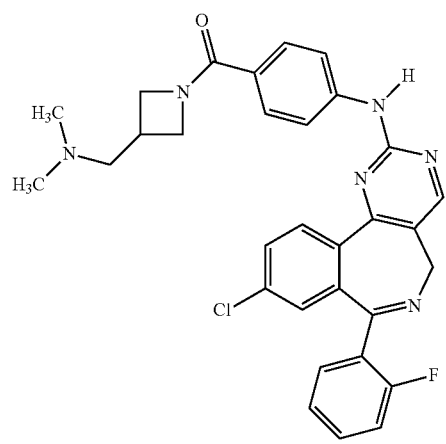 [SMILES: CN(C)CC1CN(C(=O)c2ccc(Nc3ncc4c(n3)-c3ccc(Cl)cc3C(c3ccccc3F)=NC4)cc2)C1]
I-193
TABLE 3-continued
Aurora Kinase Inhibitors
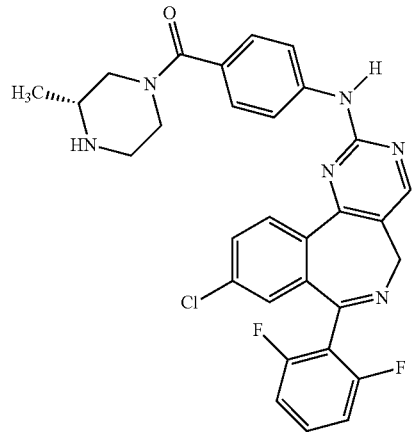 [SMILES: C[C@@H]1CN(C(=O)c2ccc(Nc3ncc4c(n3)-c3ccc(Cl)cc3C(c3c(F)cccc3F)=NC4)cc2)CCN1]
I-194
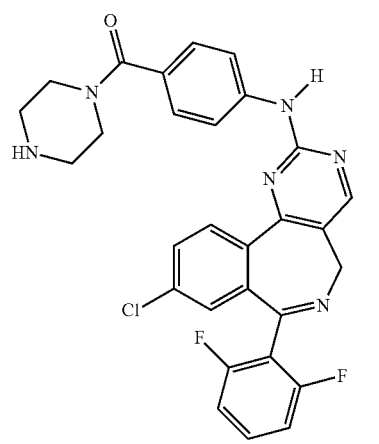 [SMILES: O=C(c1ccc(Nc2ncc3c(n2)-c2ccc(Cl)cc2C(c2c(F)cccc2F)=NC3)cc1)N1CCNCC1]
I-195
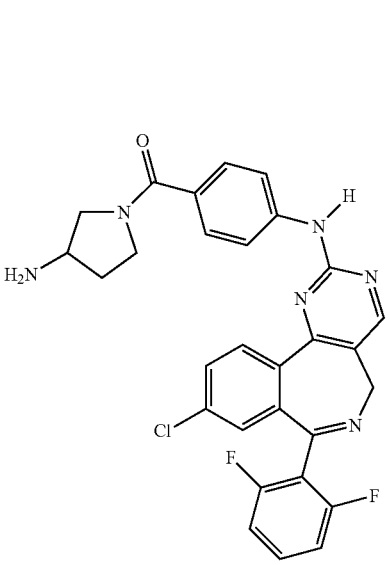 [SMILES: NC1CCN(C(=O)c2ccc(Nc3ncc4c(n3)-c3ccc(Cl)cc3C(c3c(F)cccc3F)=NC4)cc2)C1]
I-196

TABLE 3-continued
Aurora Kinase Inhibitors
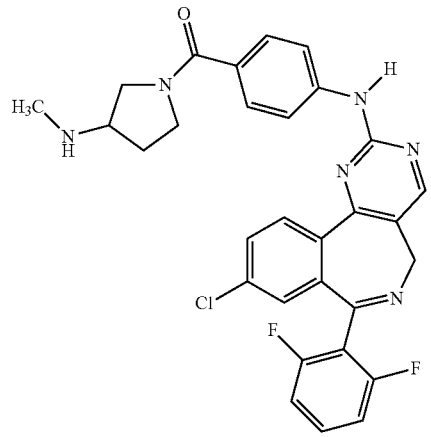 [SMILES: CNC1CCN(C(=O)c2ccc(Nc3ncc4c(n3)-c3ccc(Cl)cc3C(c3c(F)cccc3F)=NC4)cc2)C1]
I-197
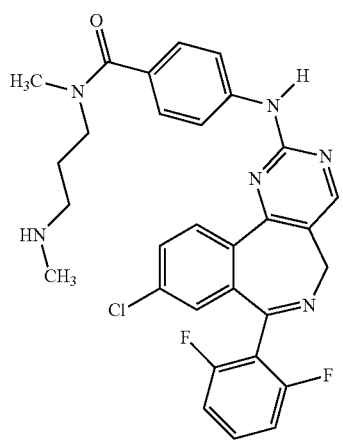 [SMILES: CNCCCN(C)C(=O)c1ccc(Nc2ncc3c(n2)-c2ccc(Cl)cc2C(c2c(F)cccc2F)=NC3)cc1]
I-198
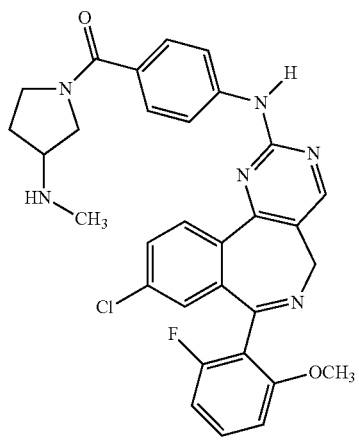 [SMILES: CNC1CCN(C(=O)c2ccc(Nc3ncc4c(n3)-c3ccc(Cl)cc3C(c3c(F)cccc3OC)=NC4)cc2)C1]
I-199
TABLE 3-continued
Aurora Kinase Inhibitors
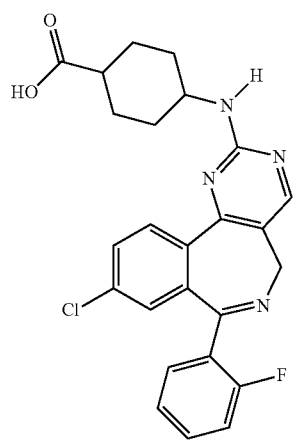 [SMILES: O=C(O)C1CCC(Nc2ncc3c(n2)-c2ccc(Cl)cc2C(c2ccccc2F)=NC3)CC1]
I-200
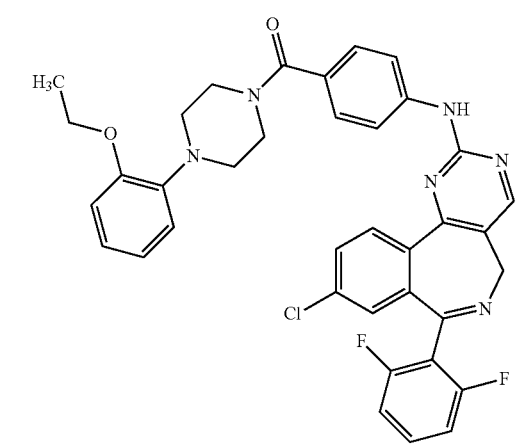 [SMILES: CCOc1ccccc1N1CCN(C(=O)c2ccc(Nc3ncc4c(n3)-c3ccc(Cl)cc3C(c3c(F)cccc3F)=NC4)cc2)CC1]
I-201
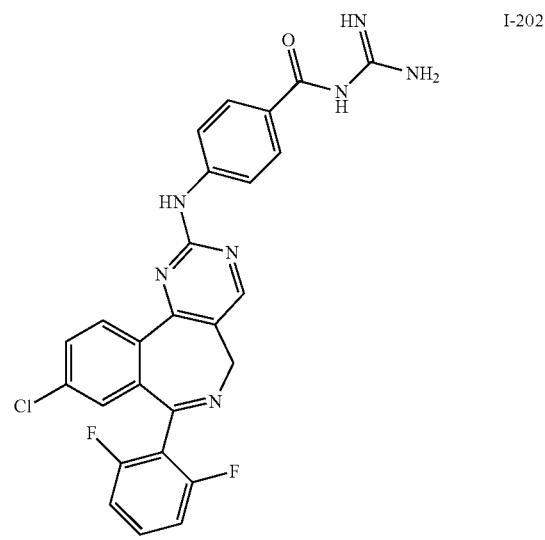
I-202

TABLE 3-continued
Aurora Kinase Inhibitors
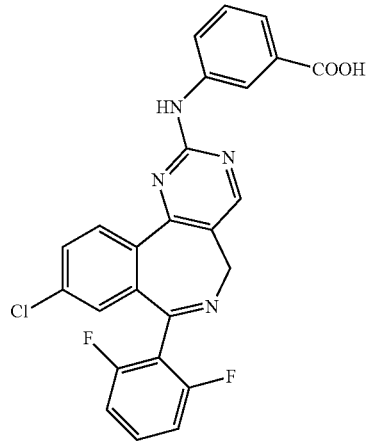 [SMILES: O=C(O)c1cccc(Nc2ncc3c(n2)-c2ccc(Cl)cc2C(c2c(F)cccc2F)=NC3)c1]
I-203
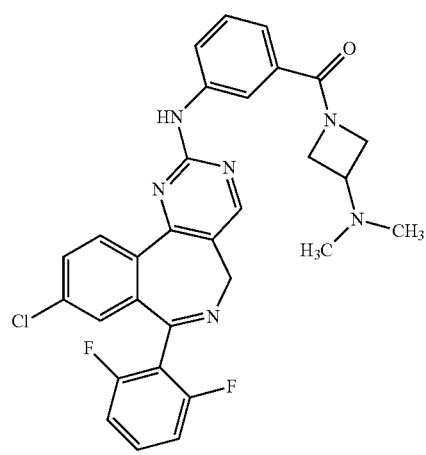 [SMILES: CN(C)C1CN(C(=O)c2cccc(Nc3ncc4c(n3)-c3ccc(Cl)cc3C(c3c(F)cccc3F)=NC4)c2)C1]
I-204
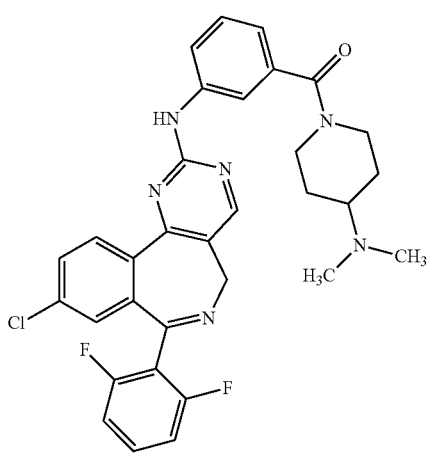 [SMILES: CN(C)C1CCN(C(=O)c2cccc(Nc3ncc4c(n3)-c3ccc(Cl)cc3C(c3c(F)cccc3F)=NC4)c2)CC1]
I-205
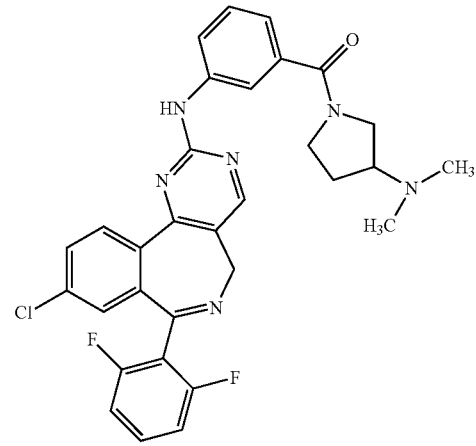 [SMILES: CN(C)C1CCN(C(=O)c2cccc(Nc3ncc4c(n3)-c3ccc(Cl)cc3C(c3c(F)cccc3F)=NC4)c2)C1]
I-206
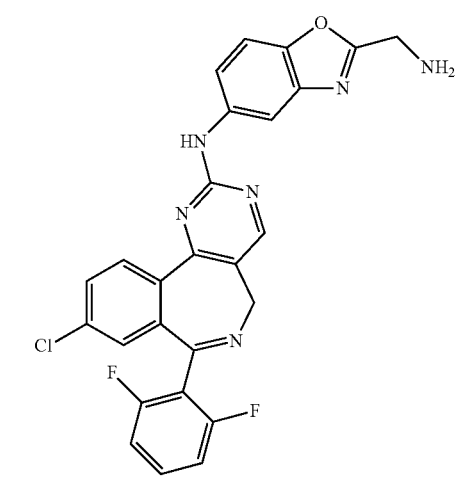 [SMILES: NCc1nc2cc(Nc3ncc4c(n3)-c3ccc(Cl)cc3C(c3c(F)cccc3F)=NC4)ccc2o1]
I-207
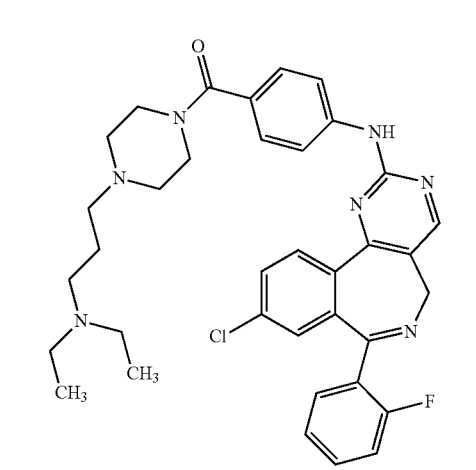 [SMILES: CCN(CC)CCCN1CCN(C(=O)c2ccc(Nc3ncc4c(n3)-c3ccc(Cl)cc3C(c3ccccc3F)=NC4)cc2)CC1]
I-208

TABLE 3-continued
Aurora Kinase Inhibitors
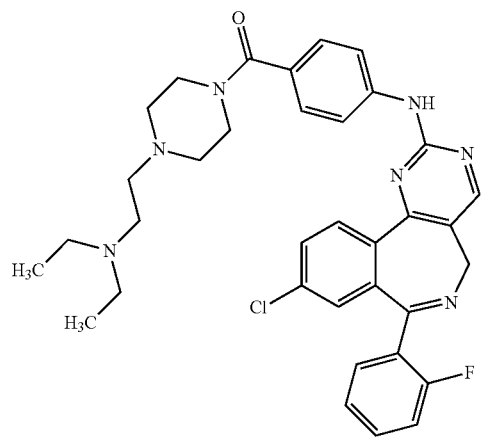 [SMILES: CCN(CC)CCN1CCN(C(=O)c2ccc(Nc3ncc4c(n3)-c3ccc(Cl)cc3C(c3ccccc3F)=NC4)cc2)CC1]
I-209
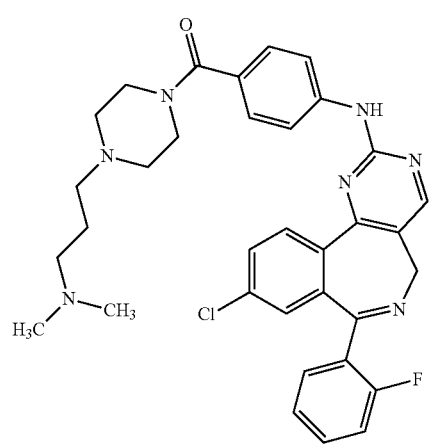 [SMILES: CN(C)CCCN1CCN(C(=O)c2ccc(Nc3ncc4c(n3)-c3ccc(Cl)cc3C(c3ccccc3F)=NC4)cc2)CC1]
I-210
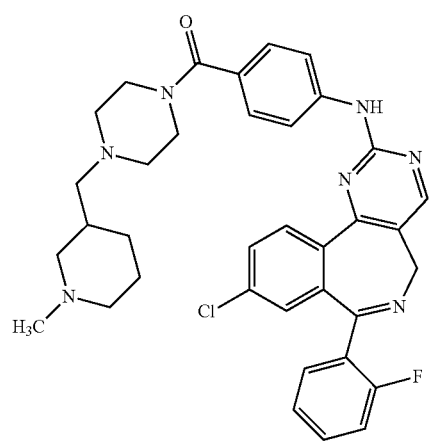 [SMILES: CN1CCCC(CN2CCN(C(=O)c3ccc(Nc4ncc5c(n4)-c4ccc(Cl)cc4C(c4ccccc4F)=NC5)cc3)CC2)C1]
I-211
TABLE 3-continued
Aurora Kinase Inhibitors
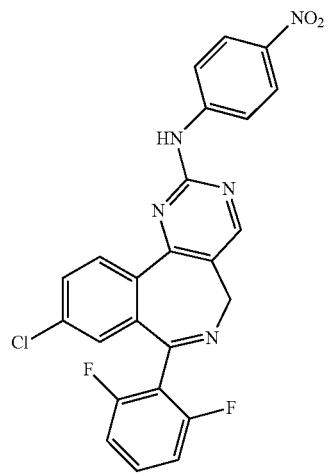 [SMILES: O=[N+]([O-])c1ccc(Nc2ncc3c(n2)-c2ccc(Cl)cc2C(c2c(F)cccc2F)=NC3)cc1]
I-212
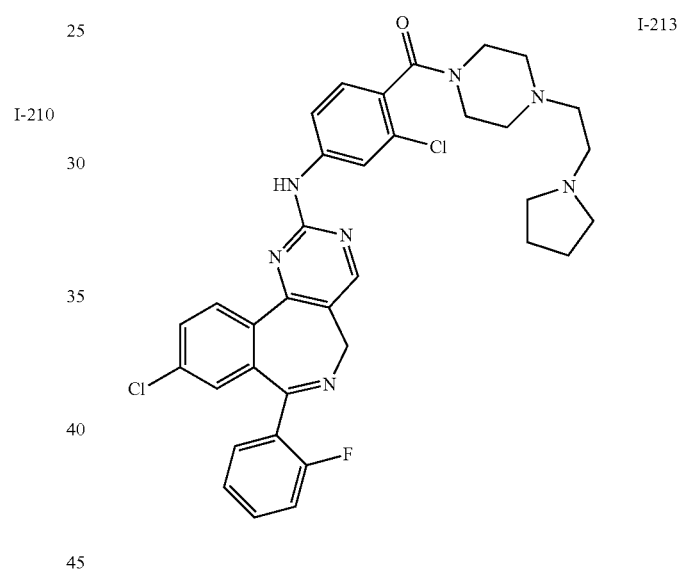
I-213
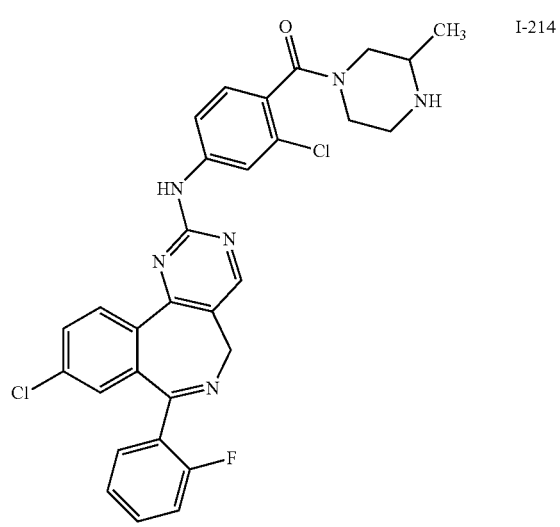
I-214

TABLE 3-continued
Aurora Kinase Inhibitors
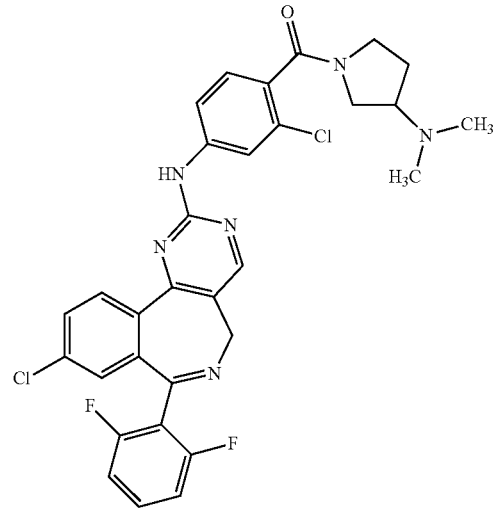 [SMILES: CN(C)C1CCN(C(=O)c2ccc(Nc3ncc4c(n3)-c3ccc(Cl)cc3C(c3c(F)cccc3F)=NC4)cc2Cl)C1]
I-215
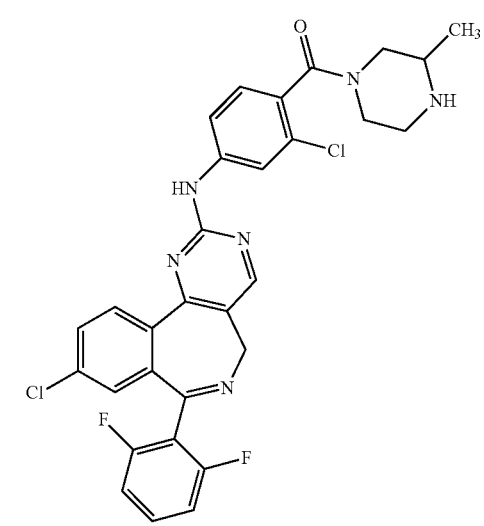 [SMILES: CC1CN(C(=O)c2ccc(Nc3ncc4c(n3)-c3ccc(Cl)cc3C(c3c(F)cccc3F)=NC4)cc2Cl)CCN1]
I-216
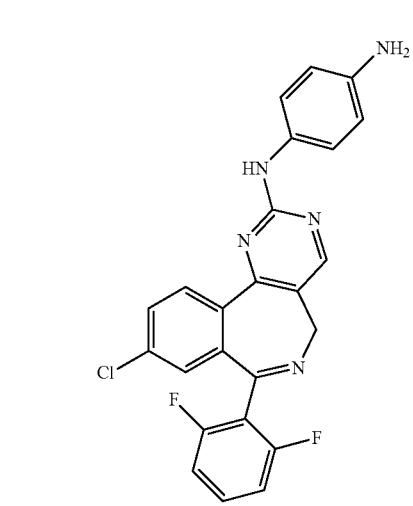 [SMILES: Nc1ccc(Nc2ncc3c(n2)-c2ccc(Cl)cc2C(c2c(F)cccc2F)=NC3)cc1]
I-217
TABLE 3-continued
Aurora Kinase Inhibitors
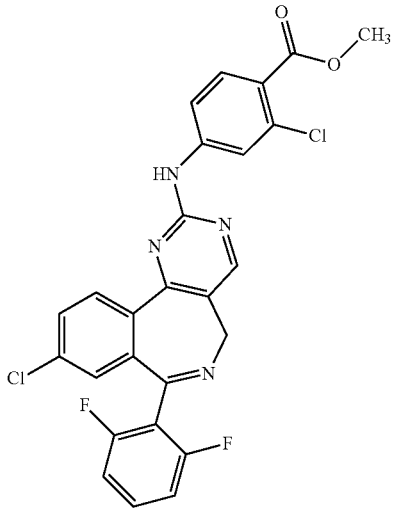 [SMILES: COC(=O)c1ccc(Nc2ncc3c(n2)-c2ccc(Cl)cc2C(c2c(F)cccc2F)=NC3)cc1Cl]
I-218
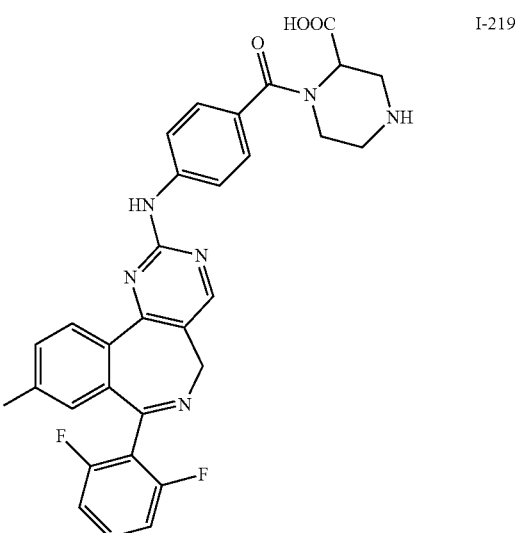
I-219
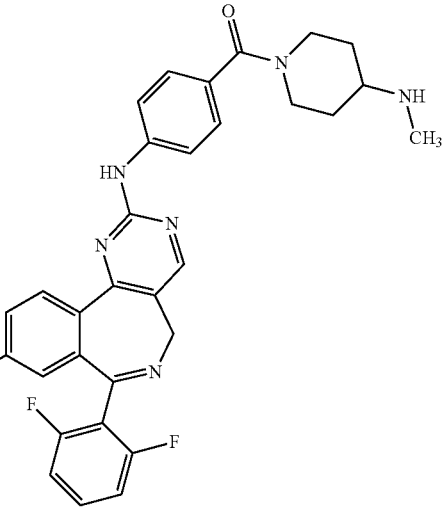
I-220

TABLE 3-continued
Aurora Kinase Inhibitors
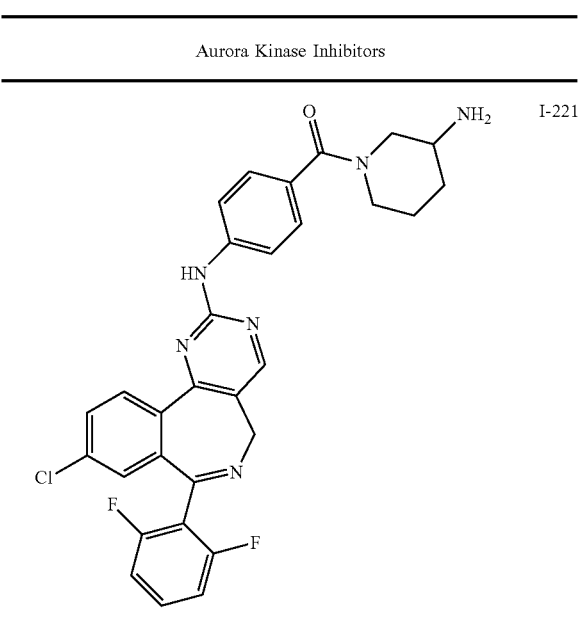
I-221
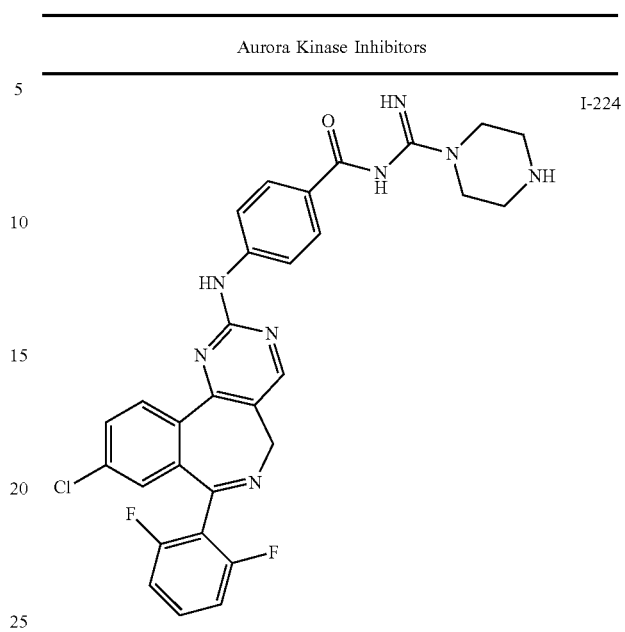
I-224
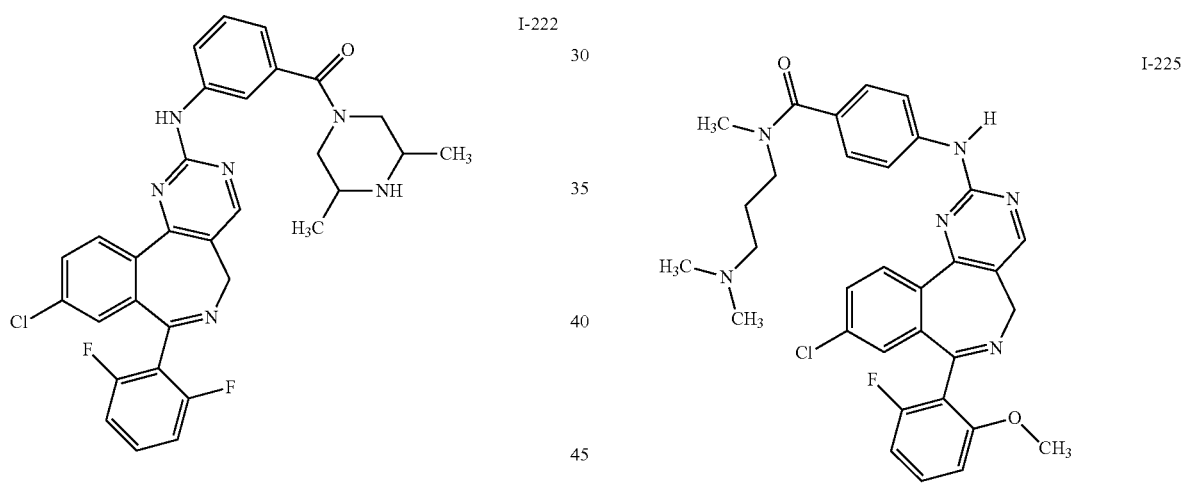
I-222
I-225
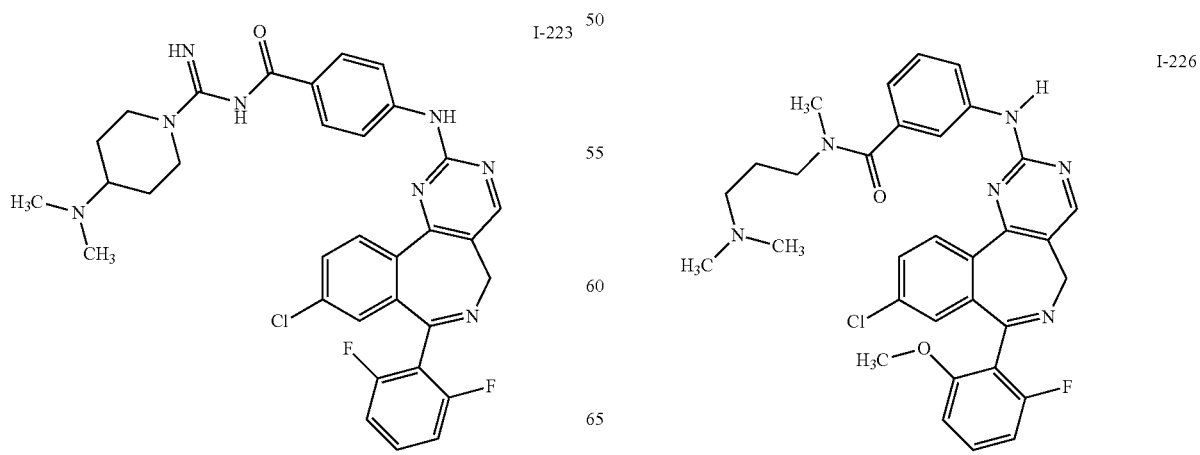
I-223
I-226

TABLE 3-continued
Aurora Kinase Inhibitors
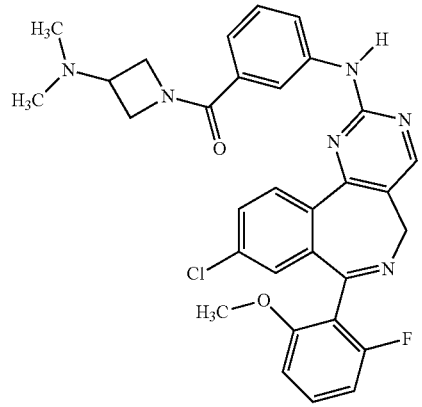 [SMILES: COc1cccc(F)c1C1=NCc2cnc(Nc3cccc(C(=O)N4CC(N(C)C)C4)c3)nc2-c2ccc(Cl)cc21] I-227
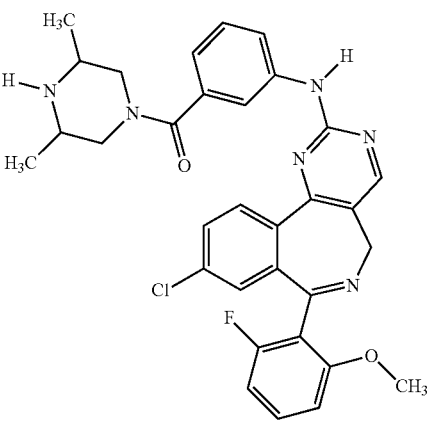 [SMILES: COc1cccc(F)c1C1=NCc2cnc(Nc3cccc(C(=O)N4CC(C)NC(C)C4)c3)nc2-c2ccc(Cl)cc21] I-228
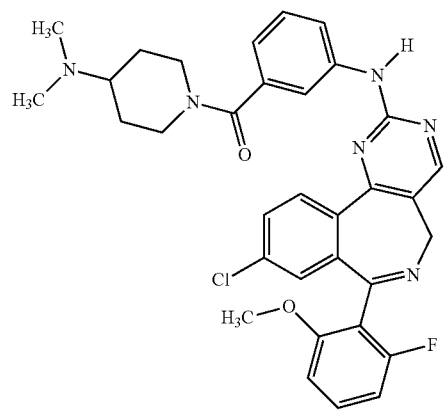 [SMILES: COc1cccc(F)c1C1=NCc2cnc(Nc3cccc(C(=O)N4CCC(N(C)C)CC4)c3)nc2-c2ccc(Cl)cc21] I-229
TABLE 3-continued
Aurora Kinase Inhibitors
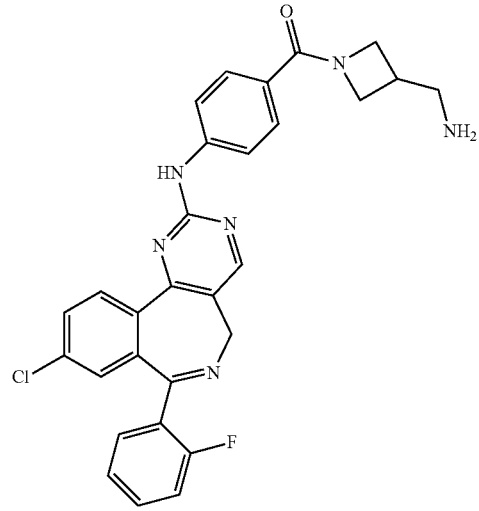 [SMILES: NCC1CN(C(=O)c2ccc(Nc3ncc4c(n3)-c3ccc(Cl)cc3C(c3ccccc3F)=NC4)cc2)C1] I-230
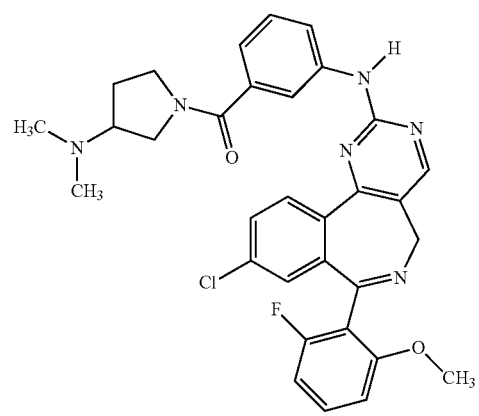 I-231
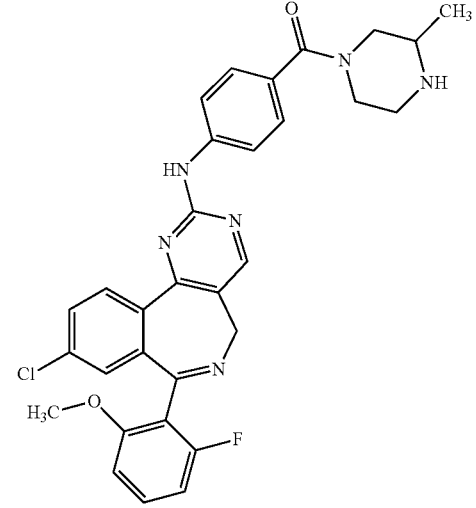 [SMILES: COc1cccc(F)c1C1=NCc2cnc(Nc3ccc(C(=O)N4CCNC(C)C4)cc3)nc2-c2ccc(Cl)cc21] I-232

TABLE 3-continued
Aurora Kinase Inhibitors
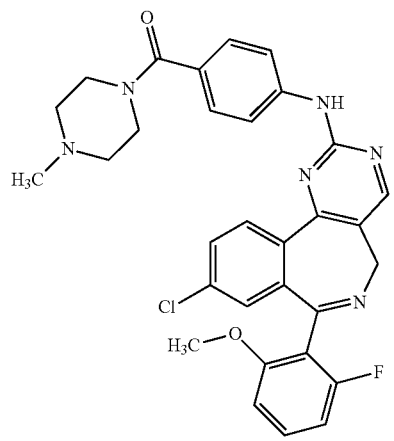 [SMILES: COc1cccc(F)c1C1=NCc2cnc(Nc3ccc(C(=O)N4CCN(C)CC4)cc3)nc2-c2ccc(Cl)cc21]
I-233
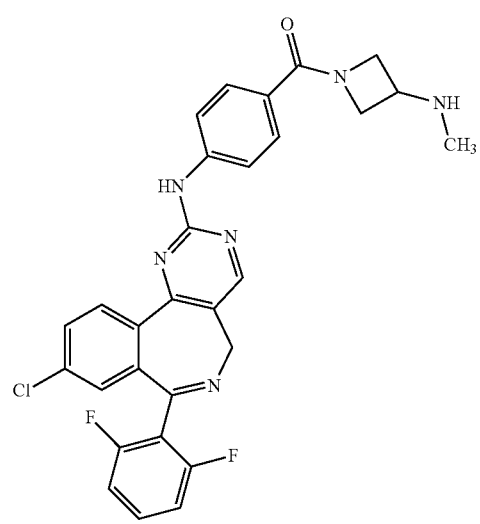 [SMILES: CNC1CN(C(=O)c2ccc(Nc3ncc4c(n3)-c3ccc(Cl)cc3C(c3c(F)cccc3F)=NC4)cc2)C1]
I-234
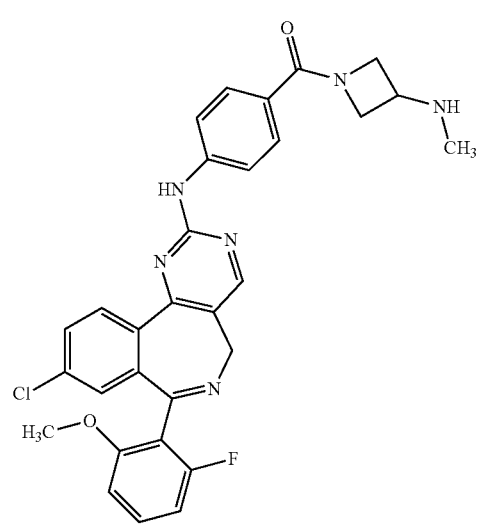 [SMILES: CNC1CN(C(=O)c2ccc(Nc3ncc4c(n3)-c3ccc(Cl)cc3C(c3c(F)cccc3OC)=NC4)cc2)C1]
I-235
TABLE 3-continued
Aurora Kinase Inhibitors
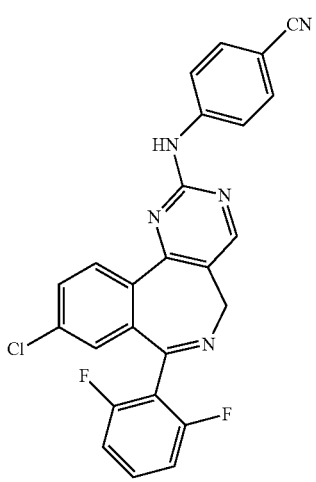 [SMILES: N#Cc1ccc(Nc2ncc3c(n2)-c2ccc(Cl)cc2C(c2c(F)cccc2F)=NC3)cc1]
I-236
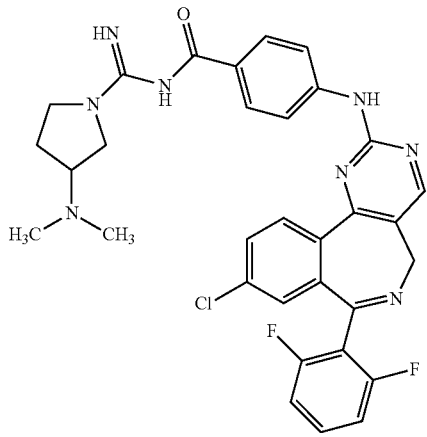 [SMILES: CN(C)C1CCN(C(=N)NC(=O)c2ccc(Nc3ncc4c(n3)-c3ccc(Cl)cc3C(c3c(F)cccc3F)=NC4)cc2)C1]
I-237
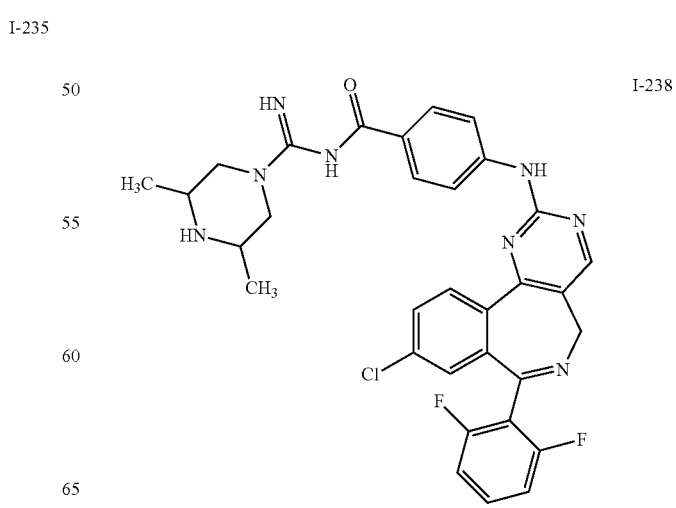
I-238

TABLE 3-continued
Aurora Kinase Inhibitors
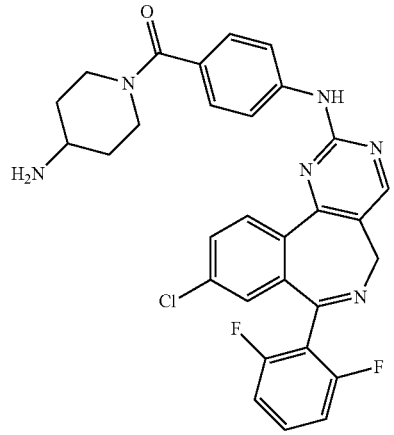 [SMILES: NC1CCN(C(=O)c2ccc(Nc3ncc4c(n3)-c3ccc(Cl)cc3C(c3c(F)cccc3F)=NC4)cc2)CC1]
I-239
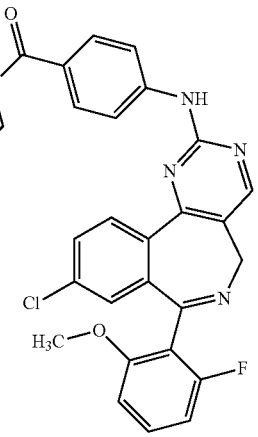
I-242
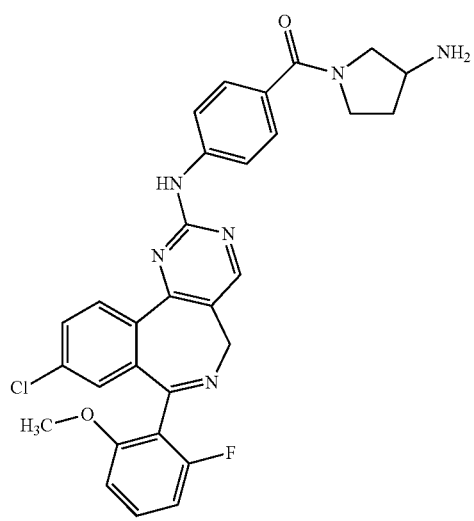 [SMILES: COc1cccc(F)c1C1=NCc2cnc(Nc3ccc(C(=O)N4CCC(N)C4)cc3)nc2-c2ccc(Cl)cc21]
I-240
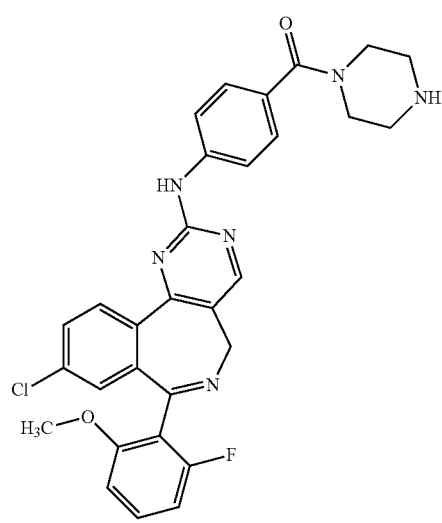 [SMILES: COc1cccc(F)c1C1=NCc2cnc(Nc3ccc(C(=O)N4CCNCC4)cc3)nc2-c2ccc(Cl)cc21]
I-243
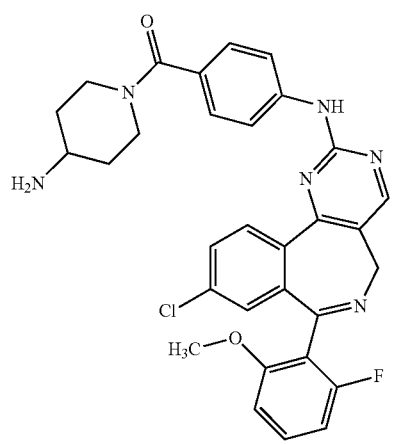
I-241
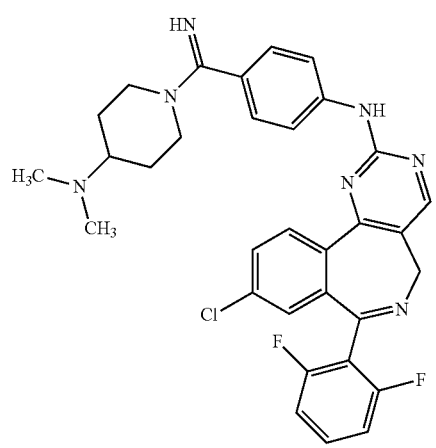 [SMILES: CN(C)C1CCN(C(=N)c2ccc(Nc3ncc4c(n3)-c3ccc(Cl)cc3C(c3c(F)cccc3F)=NC4)cc2)CC1]
I-244

TABLE 3-continued
Aurora Kinase Inhibitors
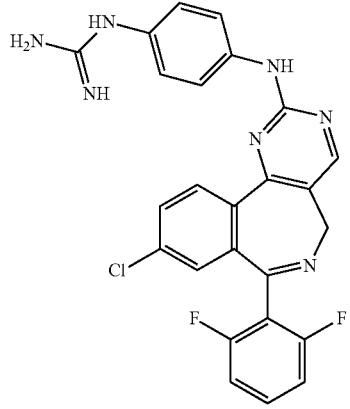 [SMILES: N=C(N)Nc1ccc(Nc2ncc3c(n2)-c2ccc(Cl)cc2C(c2c(F)cccc2F)=NC3)cc1]
I-245
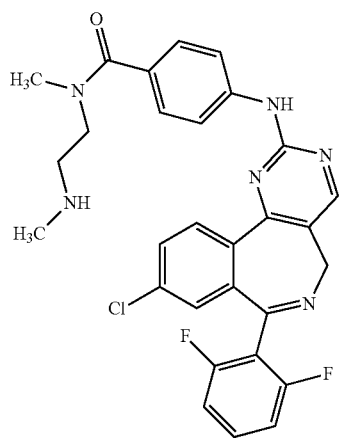 [SMILES: CNCCN(C)C(=O)c1ccc(Nc2ncc3c(n2)-c2ccc(Cl)cc2C(c2c(F)cccc2F)=NC3)cc1]
I-246
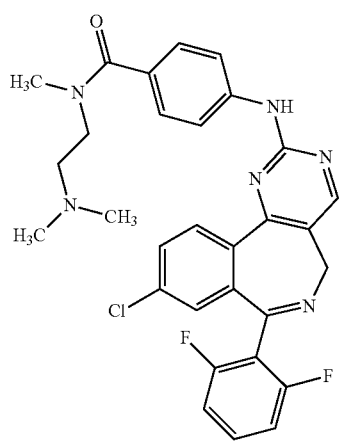 [SMILES: CN(C)CCN(C)C(=O)c1ccc(Nc2ncc3c(n2)-c2ccc(Cl)cc2C(c2c(F)cccc2F)=NC3)cc1]
I-247
TABLE 3-continued
Aurora Kinase Inhibitors
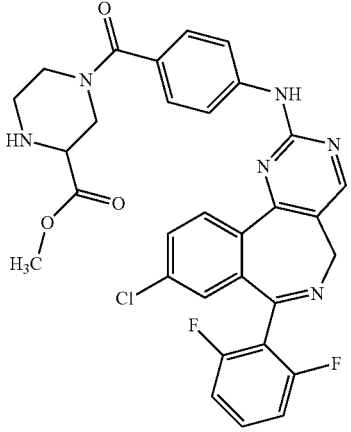 [SMILES: COC(=O)C1CN(C(=O)c2ccc(Nc3ncc4c(n3)-c3ccc(Cl)cc3C(c3c(F)cccc3F)=NC4)cc2)CCN1]
I-248
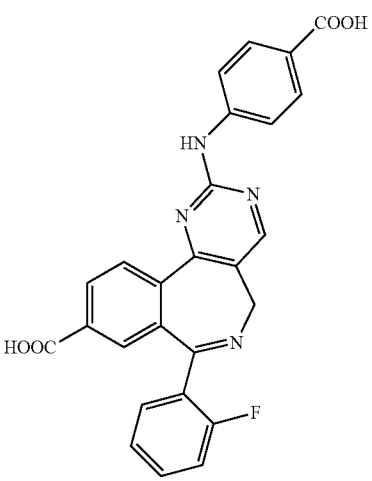 [SMILES: O=C(O)c1ccc(Nc2ncc3c(n2)-c2ccc(C(=O)O)cc2C(c2ccccc2F)=NC3)cc1]
I-249
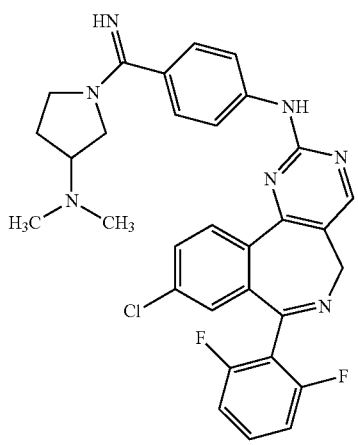 [SMILES: CN(C)C1CCN(C(=N)c2ccc(Nc3ncc4c(n3)-c3ccc(Cl)cc3C(c3c(F)cccc3F)=NC4)cc2)C1]
I-250

TABLE 3-continued
Aurora Kinase Inhibitors
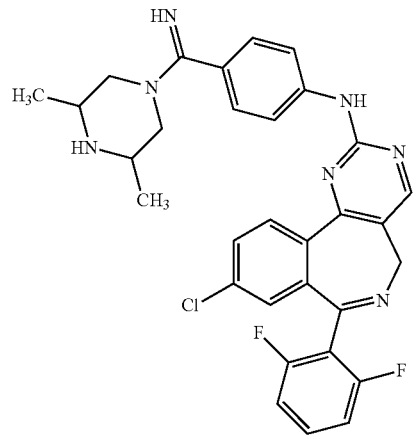 [SMILES: CC1CN(C(=N)c2ccc(Nc3ncc4c(n3)-c3ccc(Cl)cc3C(c3c(F)cccc3F)=NC4)cc2)CC(C)N1]
I-251
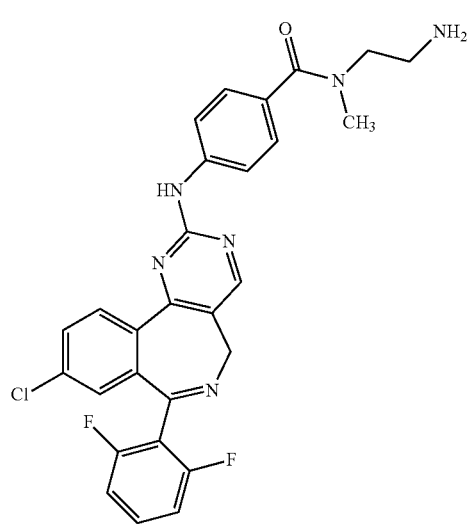 [SMILES: CN(CCN)C(=O)c1ccc(Nc2ncc3c(n2)-c2ccc(Cl)cc2C(c2c(F)cccc2F)=NC3)cc1]
I-252
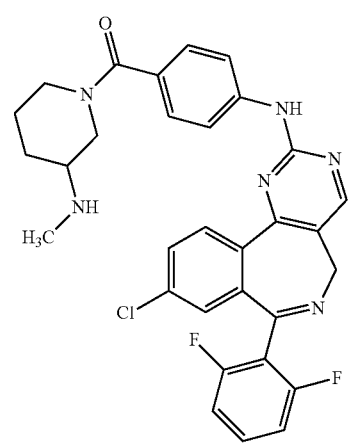 [SMILES: CNC1CCCN(C(=O)c2ccc(Nc3ncc4c(n3)-c3ccc(Cl)cc3C(c3c(F)cccc3F)=NC4)cc2)C1]
I-253
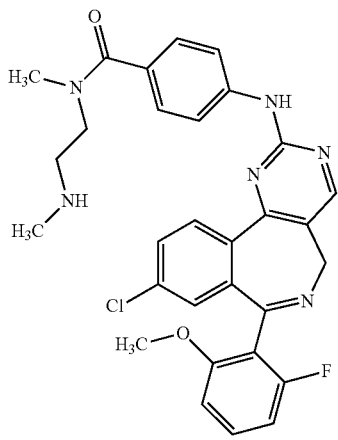 [SMILES: CNCCN(C)C(=O)c1ccc(Nc2ncc3c(n2)-c2ccc(Cl)cc2C(c2c(F)cccc2OC)=NC3)cc1]
I-254
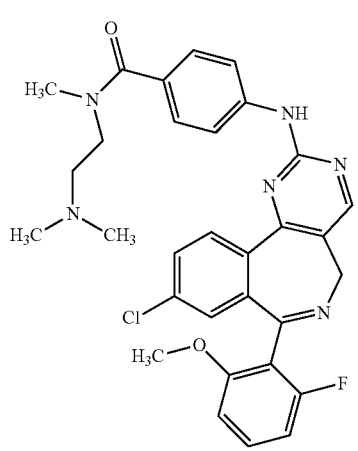 [SMILES: COc1cccc(F)c1C1=NCc2cnc(Nc3ccc(C(=O)N(C)CCN(C)C)cc3)nc2-c2ccc(Cl)cc21]
I-255
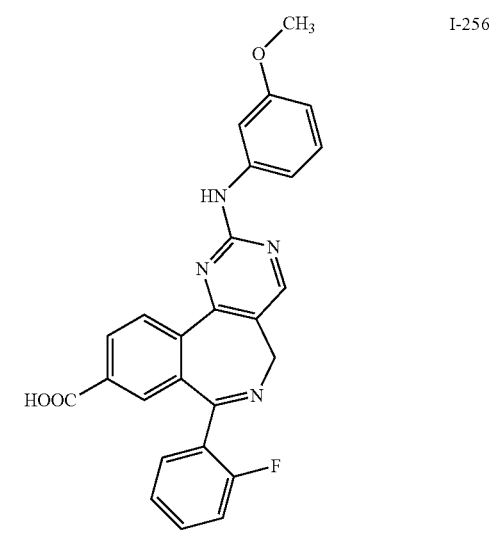
I-256

TABLE 3-continued
Aurora Kinase Inhibitors
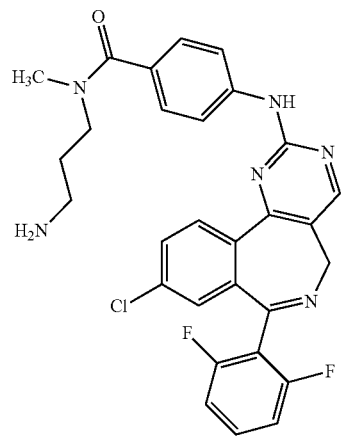 [SMILES: CN(CCCN)C(=O)c1ccc(Nc2ncc3c(n2)-c2ccc(Cl)cc2C(c2c(F)cccc2F)=NC3)cc1] I-257
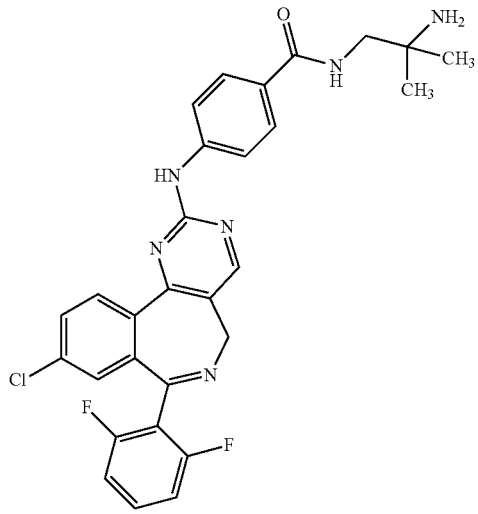 I-260
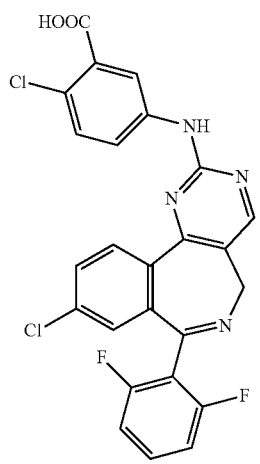 [SMILES: O=C(O)c1cc(Nc2ncc3c(n2)-c2ccc(Cl)cc2C(c2c(F)cccc2F)=NC3)ccc1Cl] I-258
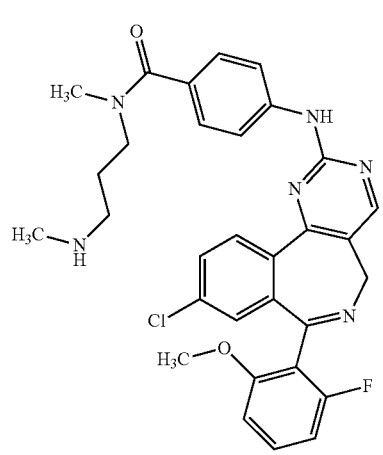 I-261
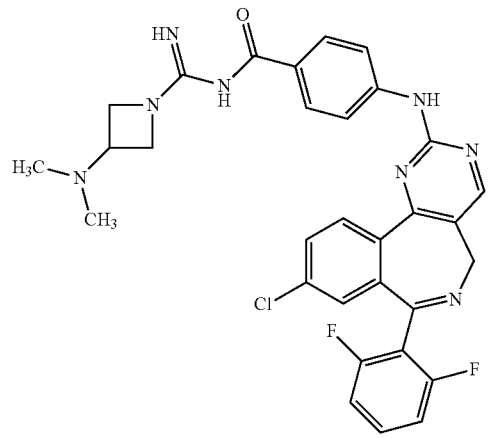 [SMILES: CN(C)C1CN(C(=N)NC(=O)c2ccc(Nc3ncc4c(n3)-c3ccc(Cl)cc3C(c3c(F)cccc3F)=NC4)cc2)C1] I-259
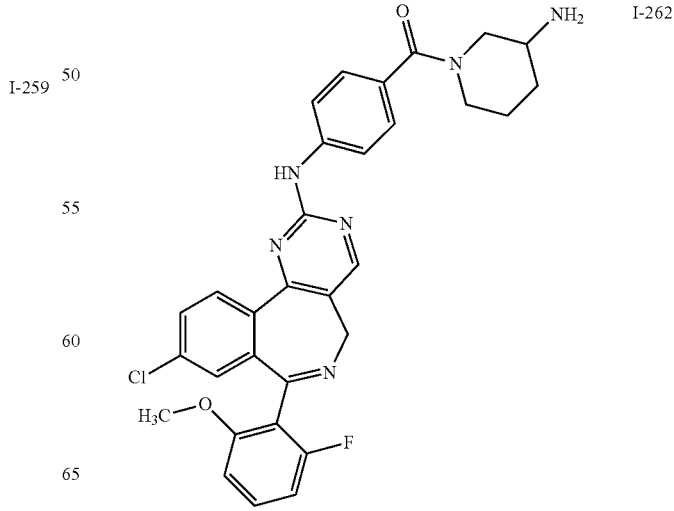 I-262

TABLE 3-continued
Aurora Kinase Inhibitors
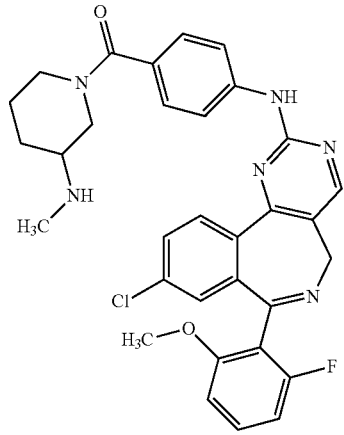 [SMILES: CNC1CCCN(C(=O)c2ccc(Nc3ncc4c(n3)-c3ccc(Cl)cc3C(c3c(F)cccc3OC)=NC4)cc2)C1]
I-263
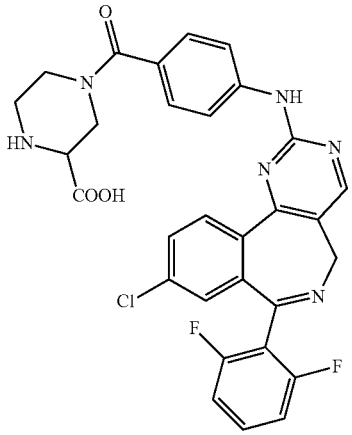
I-266
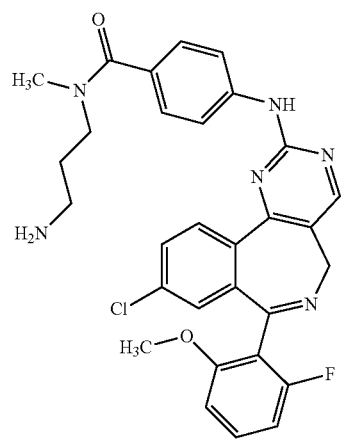 [SMILES: COc1cccc(F)c1C1=NCc2cnc(Nc3ccc(C(=O)N(C)CCCN)cc3)nc2-c2ccc(Cl)cc21]
I-264
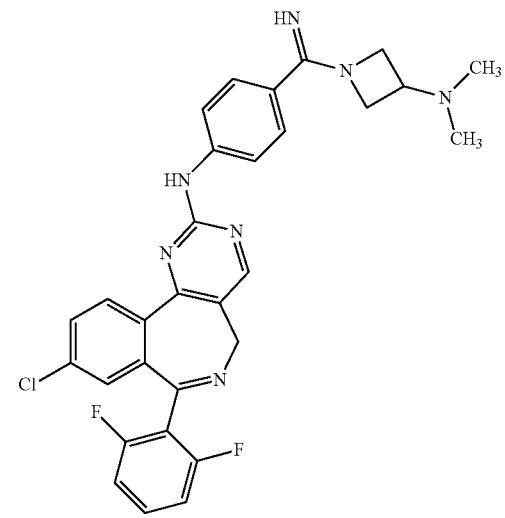
I-267
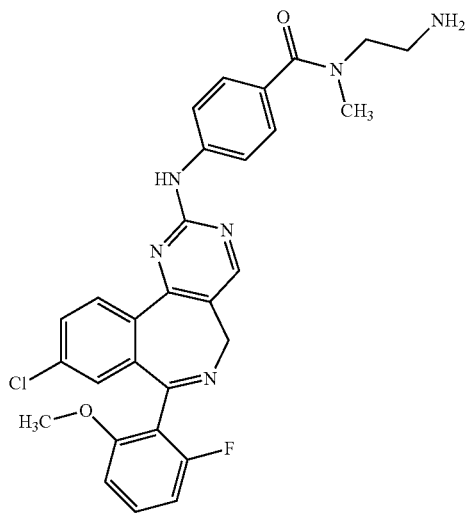 [SMILES: COc1cccc(F)c1C1=NCc2cnc(Nc3ccc(C(=O)N(C)CCN)cc3)nc2-c2ccc(Cl)cc21]
I-265
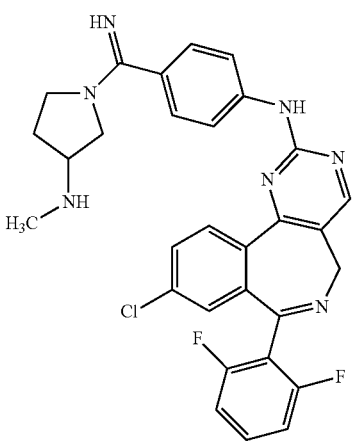 [SMILES: CNC1CCN(C(=N)c2ccc(Nc3ncc4c(n3)-c3ccc(Cl)cc3C(c3c(F)cccc3F)=NC4)cc2)C1]
I-268

TABLE 3-continued
Aurora Kinase Inhibitors
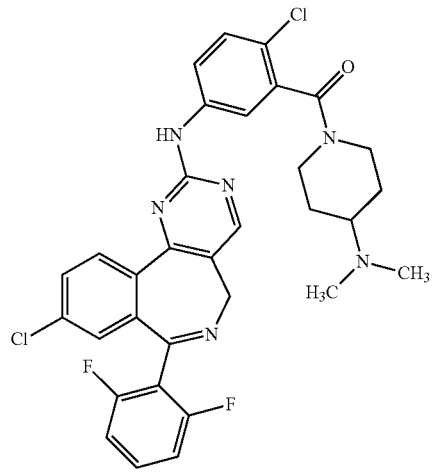 [SMILES: CN(C)C1CCN(C(=O)c2cc(Nc3ncc4c(n3)-c3ccc(Cl)cc3C(c3c(F)cccc3F)=NC4)ccc2Cl)CC1]
I-269
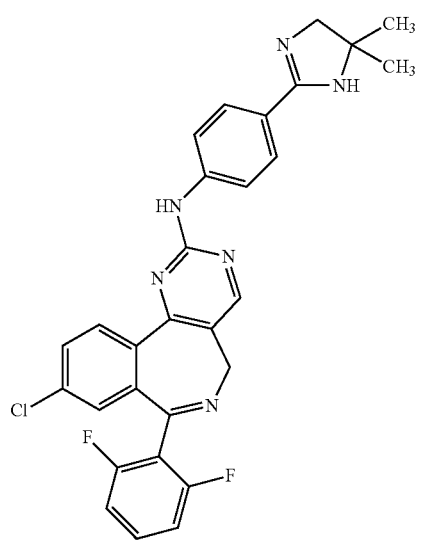 [SMILES: CC1(C)CN=C(c2ccc(Nc3ncc4c(n3)-c3ccc(Cl)cc3C(c3c(F)cccc3F)=NC4)cc2)N1]
I-270
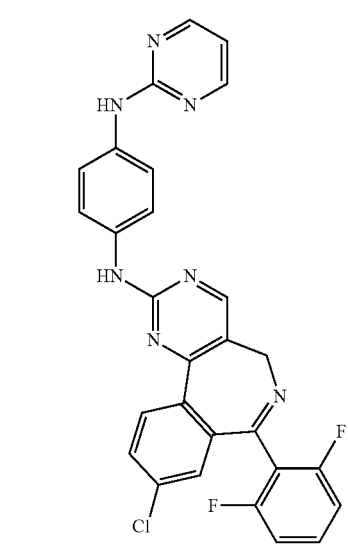 [SMILES: Fc1cccc(F)c1C1=NCc2cnc(Nc3ccc(Nc4ncccn4)cc3)nc2-c2ccc(Cl)cc21]
I-271
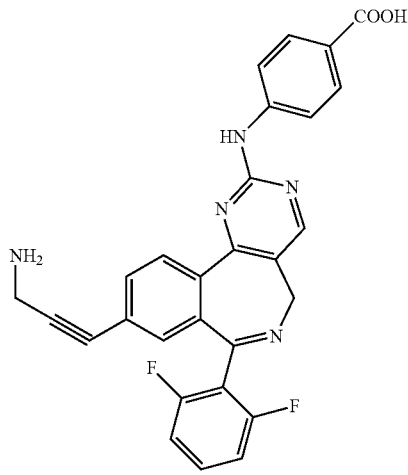 [SMILES: NCC#Cc1ccc2c(c1)C(c1c(F)cccc1F)=NCc1cnc(Nc3ccc(C(=O)O)cc3)nc1-2]
I-272
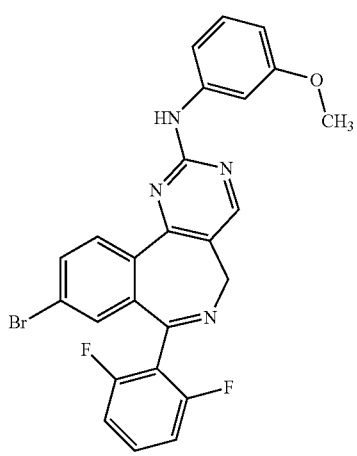 [SMILES: COc1cccc(Nc2ncc3c(n2)-c2ccc(Br)cc2C(c2c(F)cccc2F)=NC3)c1]
I-273
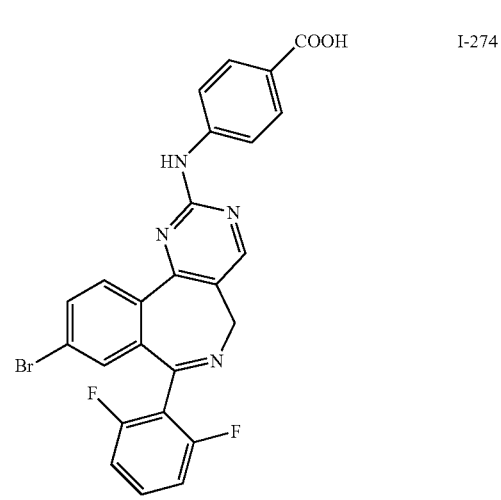
I-274

TABLE 3-continued
Aurora Kinase Inhibitors
I-275
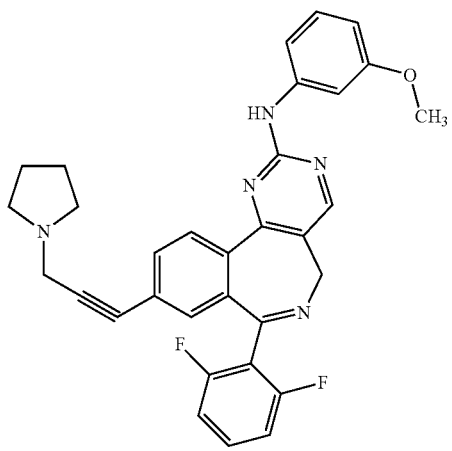 [SMILES: COc1cccc(Nc2ncc3c(n2)-c2ccc(C#CCN4CCCC4)cc2C(c2c(F)cccc2F)=NC3)c1]
I-276
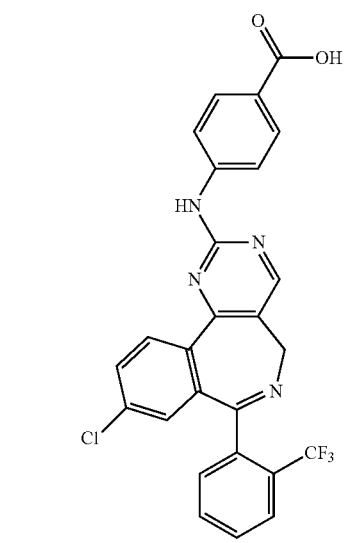 [SMILES: O=C(O)c1ccc(Nc2ncc3c(n2)-c2ccc(Cl)cc2C(c2ccccc2C(F)(F)F)=NC3)cc1]
I-277
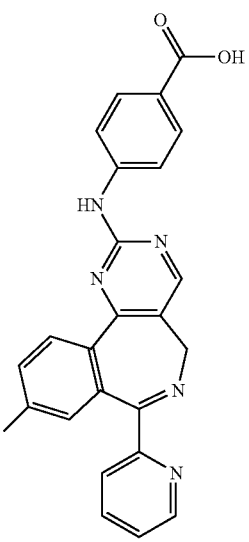
TABLE 3-continued
Aurora Kinase Inhibitors
I-278
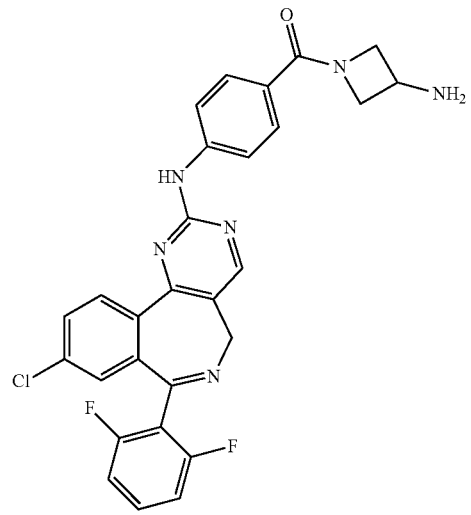 [SMILES: NC1CN(C(=O)c2ccc(Nc3ncc4c(n3)-c3ccc(Cl)cc3C(c3c(F)cccc3F)=NC4)cc2)C1]
I-279
I-280
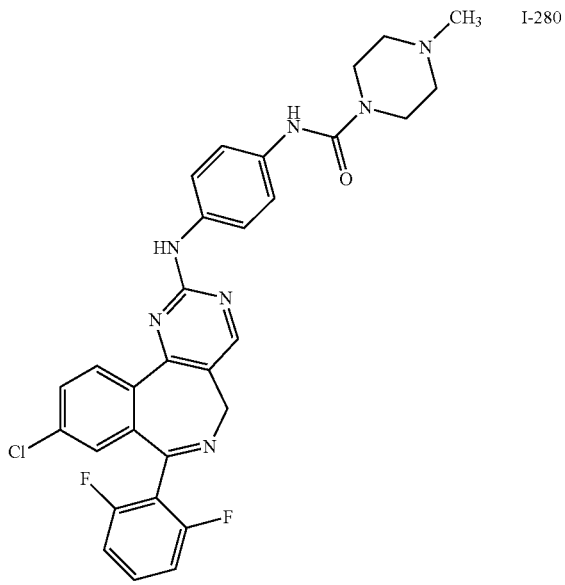

TABLE 3-continued
Aurora Kinase Inhibitors
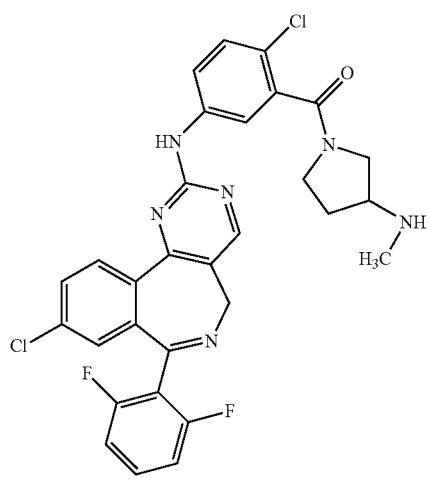 [SMILES: CNC1CCN(C(=O)c2cc(Nc3ncc4c(n3)-c3ccc(Cl)cc3C(c3c(F)cccc3F)=NC4)ccc2Cl)C1]
I-281
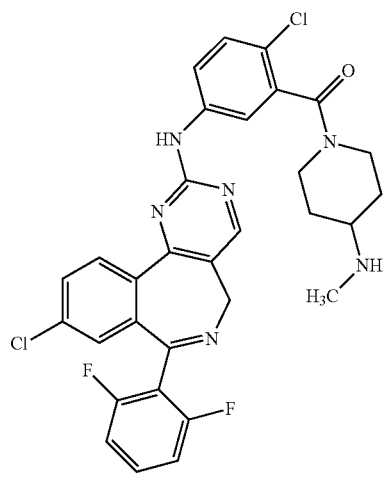 [SMILES: CNC1CCN(C(=O)c2cc(Nc3ncc4c(n3)-c3ccc(Cl)cc3C(c3c(F)cccc3F)=NC4)ccc2Cl)CC1]
I-282
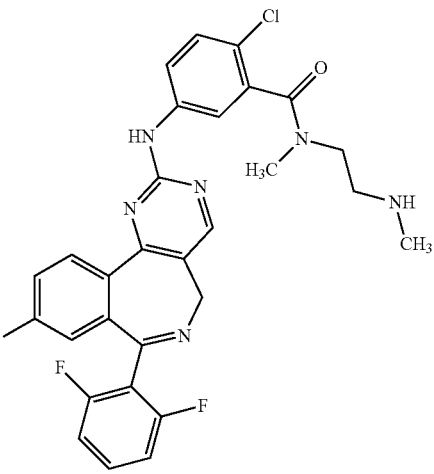
I-283
TABLE 3-continued
Aurora Kinase Inhibitors
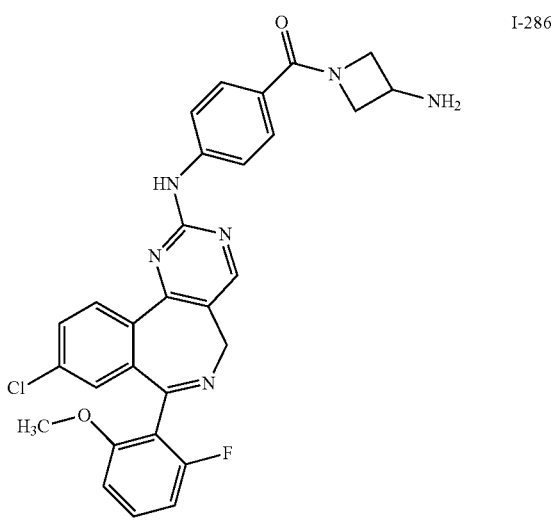
I-284
I-285
I-286

TABLE 3-continued
Aurora Kinase Inhibitors
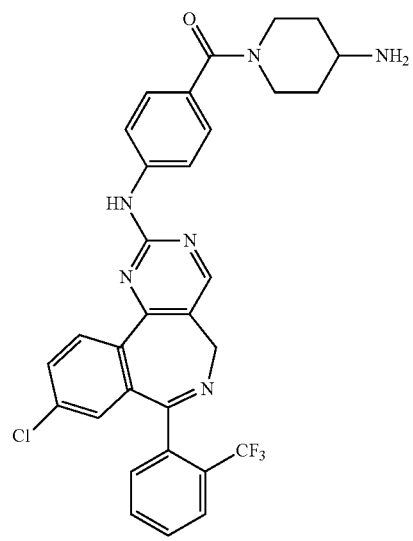 [SMILES: NC1CCN(C(=O)c2ccc(Nc3ncc4c(n3)-c3ccc(Cl)cc3C(c3ccccc3C(F)(F)F)=NC4)cc2)CC1] I-287
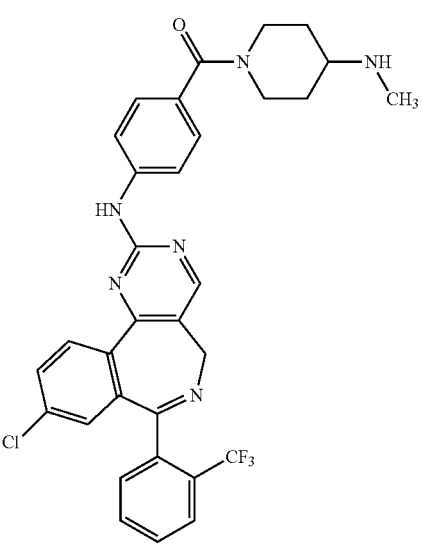 [SMILES: CNC1CCN(C(=O)c2ccc(Nc3ncc4c(n3)-c3ccc(Cl)cc3C(c3ccccc3C(F)(F)F)=NC4)cc2)CC1] I-288
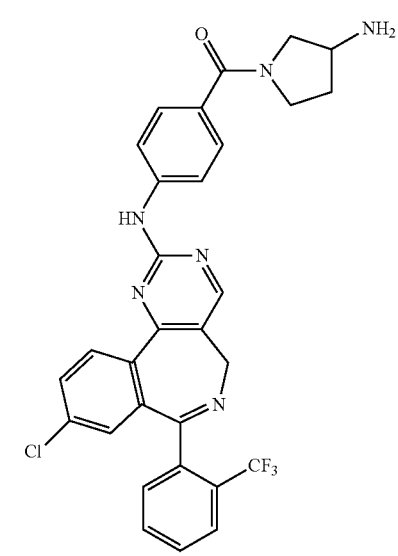 [SMILES: NC1CCN(C(=O)c2ccc(Nc3ncc4c(n3)-c3ccc(Cl)cc3C(c3ccccc3C(F)(F)F)=NC4)cc2)C1] I-289
TABLE 3-continued
Aurora Kinase Inhibitors
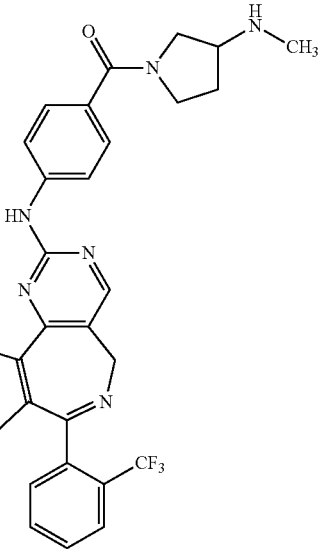 I-290
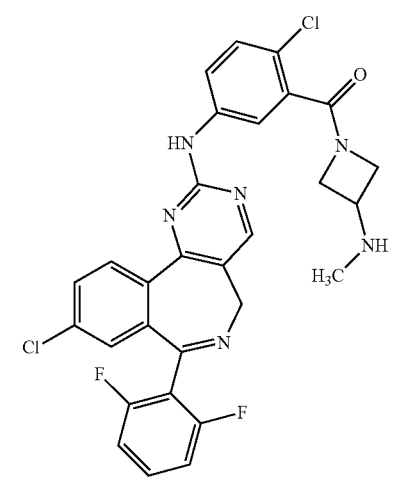 [SMILES: CNC1CN(C(=O)c2cc(Nc3ncc4c(n3)-c3ccc(Cl)cc3C(c3c(F)cccc3F)=NC4)ccc2Cl)C1] I-291
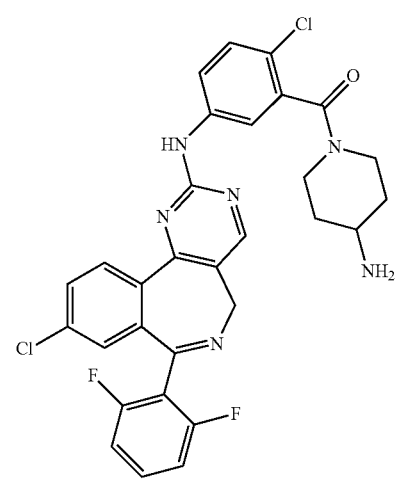 [SMILES: NC1CCN(C(=O)c2cc(Nc3ncc4c(n3)-c3ccc(Cl)cc3C(c3c(F)cccc3F)=NC4)ccc2Cl)CC1] I-292

TABLE 3-continued
Aurora Kinase Inhibitors
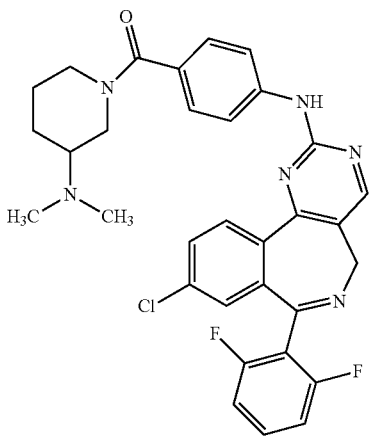 [SMILES: CN(C)C1CCCN(C(=O)c2ccc(Nc3ncc4c(n3)-c3ccc(Cl)cc3C(c3c(F)cccc3F)=NC4)cc2)C1] I-293
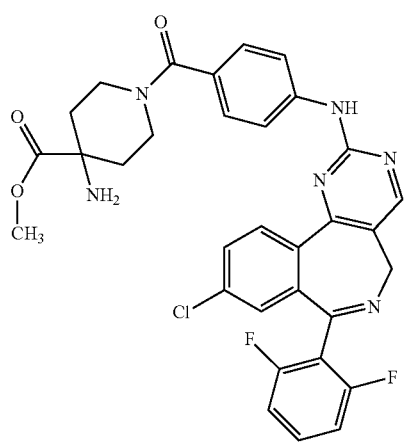 [SMILES: COC(=O)C1(N)CCN(C(=O)c2ccc(Nc3ncc4c(n3)-c3ccc(Cl)cc3C(c3c(F)cccc3F)=NC4)cc2)CC1] I-294
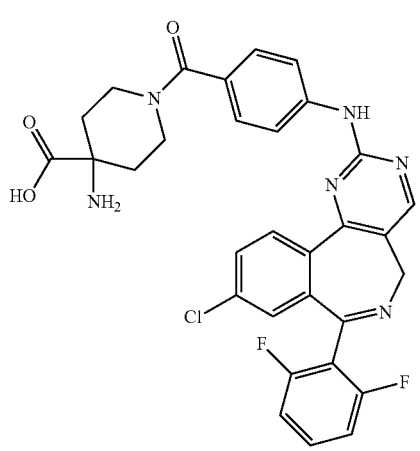 [SMILES: NC1(C(=O)O)CCN(C(=O)c2ccc(Nc3ncc4c(n3)-c3ccc(Cl)cc3C(c3c(F)cccc3F)=NC4)cc2)CC1] I-295
TABLE 3-continued
Aurora Kinase Inhibitors
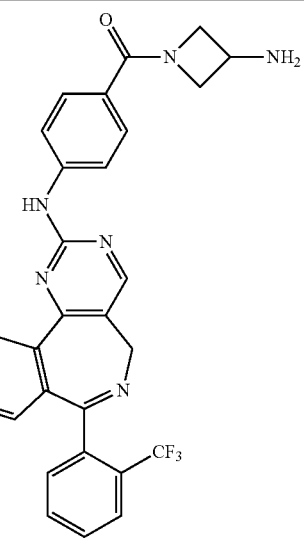 I-296
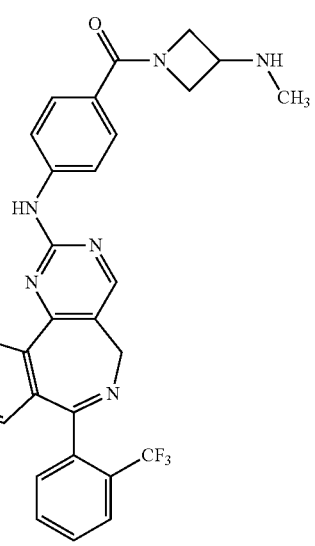 I-297
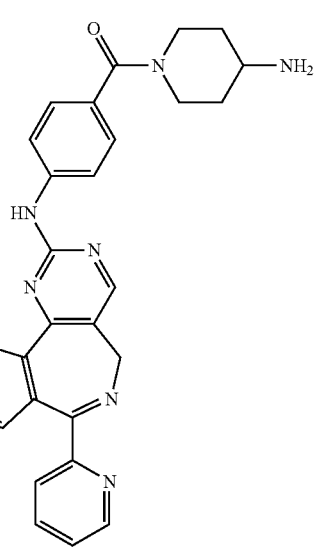 I-298

TABLE 3-continued
Aurora Kinase Inhibitors
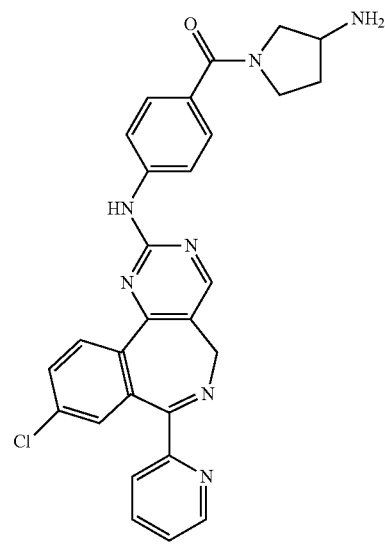 [SMILES: NC1CCN(C(=O)c2ccc(Nc3ncc4c(n3)-c3ccc(Cl)cc3C(c3ccccn3)=NC4)cc2)C1]
I-299
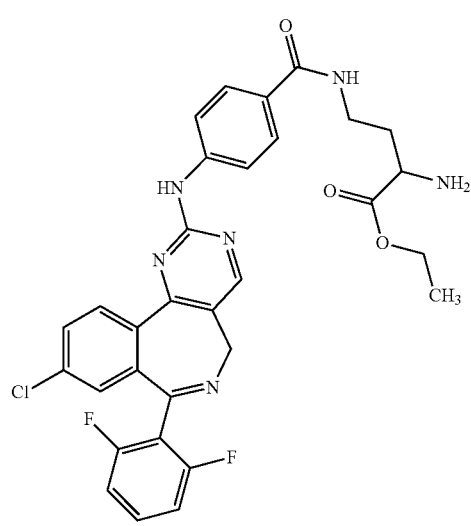 [SMILES: CCOC(=O)C(N)CCNC(=O)c1ccc(Nc2ncc3c(n2)-c2ccc(Cl)cc2C(c2c(F)cccc2F)=NC3)cc1]
I-300
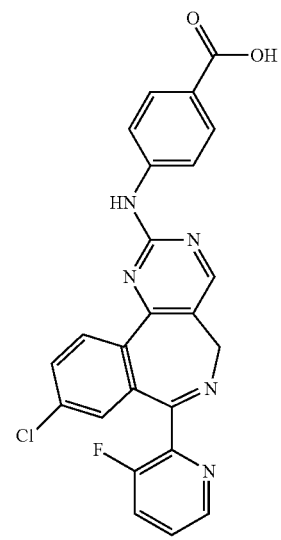 [SMILES: O=C(O)c1ccc(Nc2ncc3c(n2)-c2ccc(Cl)cc2C(c2ncccc2F)=NC3)cc1]
I-301
TABLE 3-continued
Aurora Kinase Inhibitors
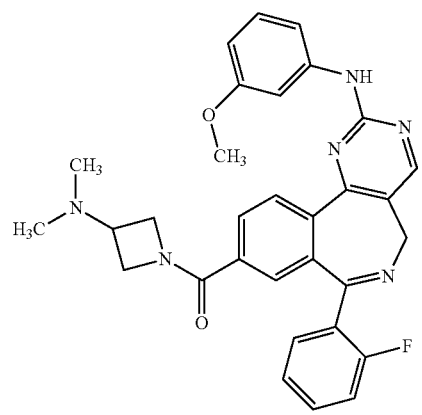 [SMILES: COc1cccc(Nc2ncc3c(n2)-c2ccc(C(=O)N4CC(N(C)C)C4)cc2C(c2ccccc2F)=NC3)c1]
I-302
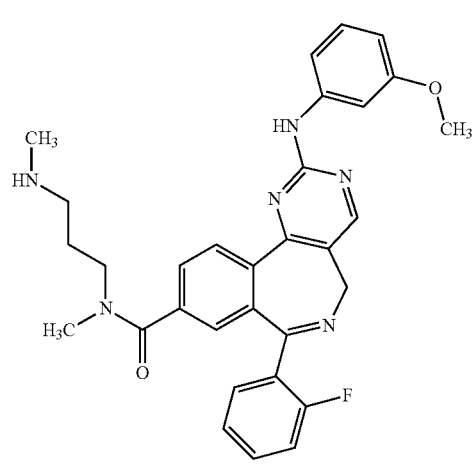 [SMILES: CNCCCN(C)C(=O)c1ccc2c(c1)C(c1ccccc1F)=NCc1cnc(Nc3cccc(OC)c3)nc1-2]
I-303
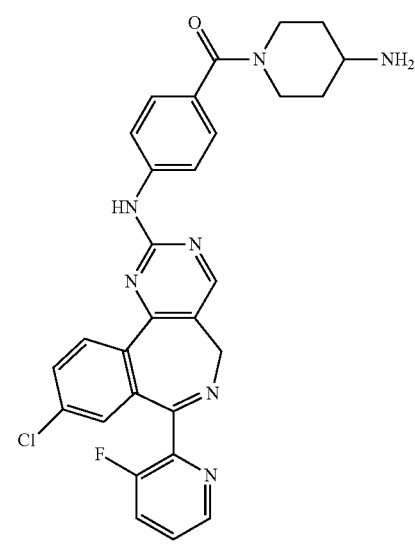 [SMILES: NC1CCN(C(=O)c2ccc(Nc3ncc4c(n3)-c3ccc(Cl)cc3C(c3ncccc3F)=NC4)cc2)CC1]
I-304

TABLE 3-continued
Aurora Kinase Inhibitors
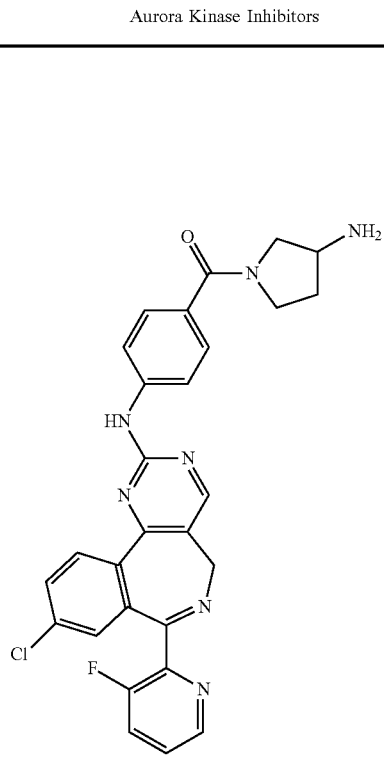
I-305
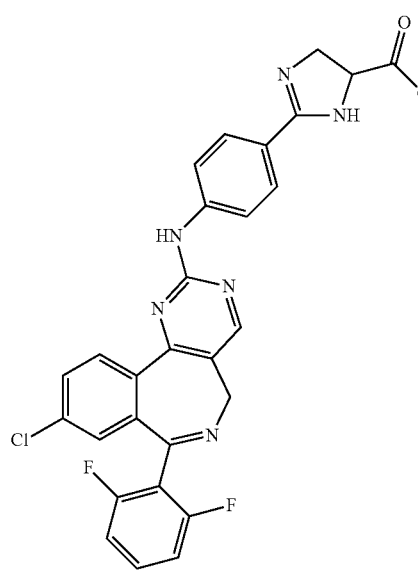
I-306
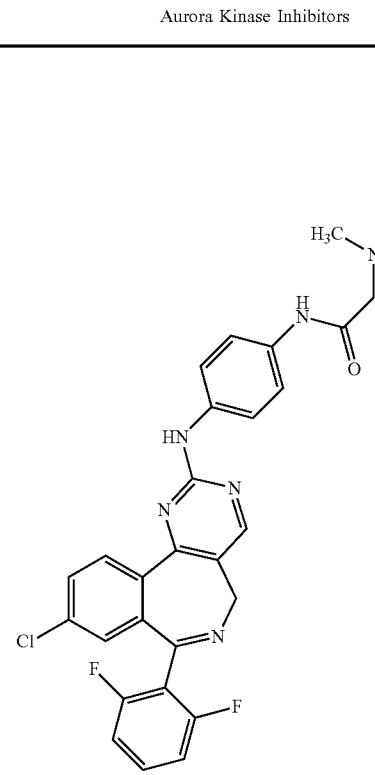
I-307
I-308

TABLE 3-continued
Aurora Kinase Inhibitors
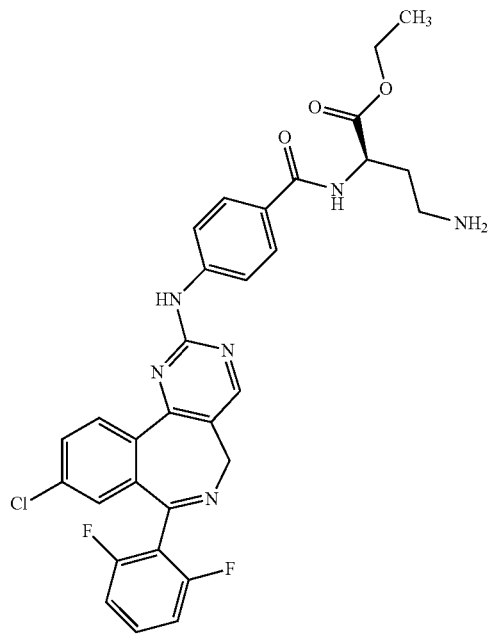 [SMILES: CCOC(=O)[C@@H](CCN)NC(=O)c1ccc(Nc2ncc3c(n2)-c2ccc(Cl)cc2C(c2c(F)cccc2F)=NC3)cc1]
I-309
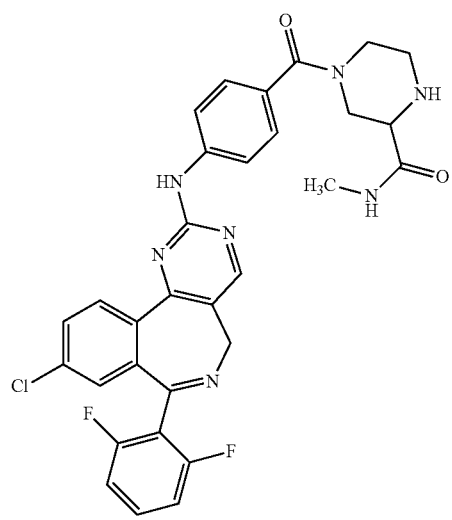 [SMILES: CNC(=O)C1CN(C(=O)c2ccc(Nc3ncc4c(n3)-c3ccc(Cl)cc3C(c3c(F)cccc3F)=NC4)cc2)CCN1]
I-310
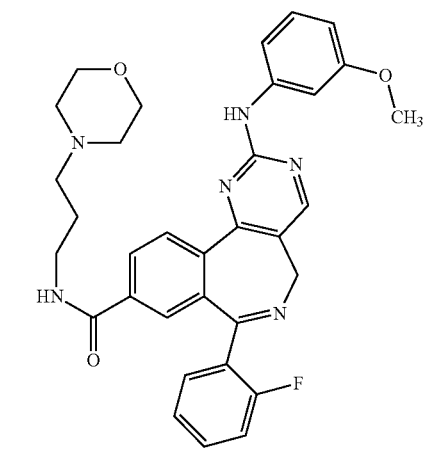 [SMILES: COc1cccc(Nc2ncc3c(n2)-c2ccc(C(=O)NCCCN4CCOCC4)cc2C(c2ccccc2F)=NC3)c1]
I-311
TABLE 3-continued
Aurora Kinase Inhibitors
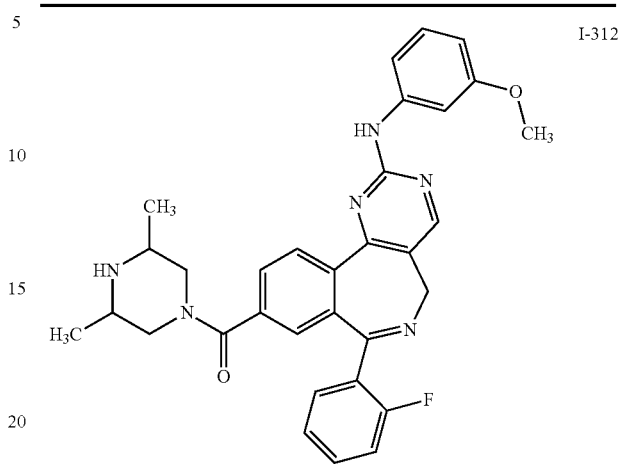
I-312
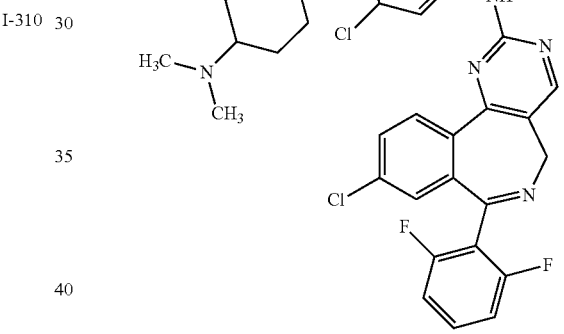
I-313
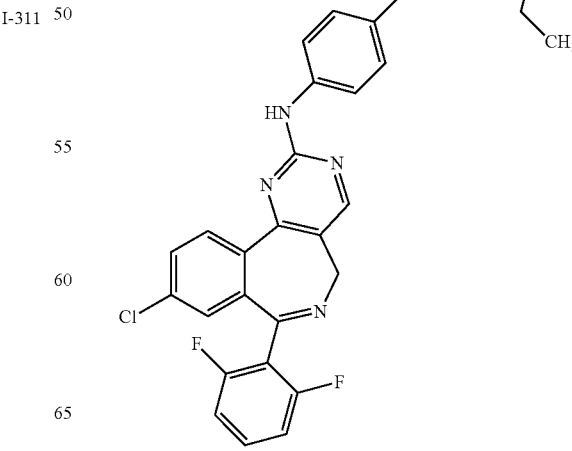
I-314

TABLE 3-continued
Aurora Kinase Inhibitors
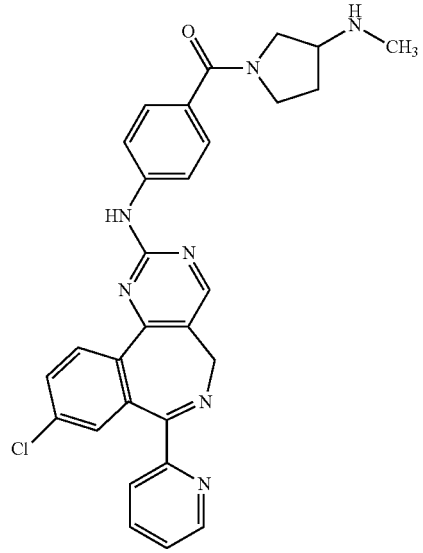 [SMILES: CNC1CCN(C(=O)c2ccc(Nc3ncc4c(n3)-c3ccc(Cl)cc3C(c3ccccn3)=NC4)cc2)C1] I-315
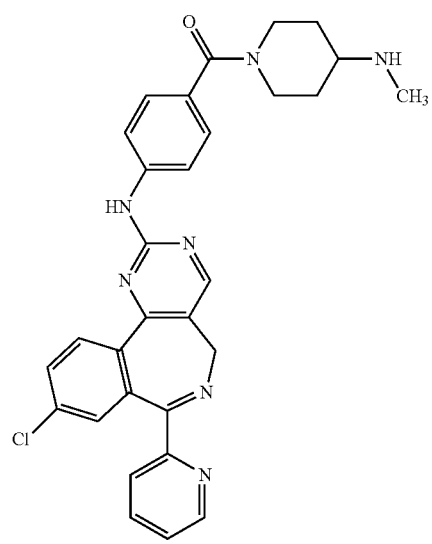 [SMILES: CNC1CCN(C(=O)c2ccc(Nc3ncc4c(n3)-c3ccc(Cl)cc3C(c3ccccn3)=NC4)cc2)CC1] I-316
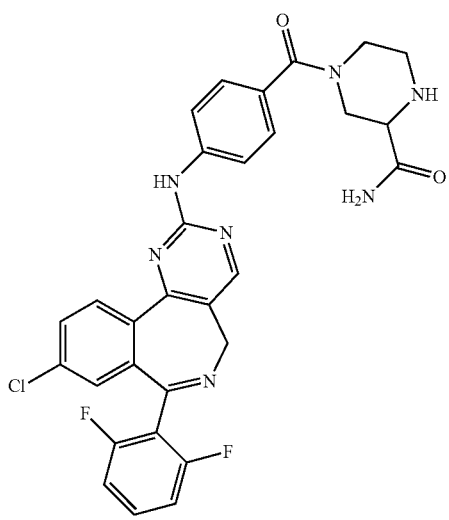 [SMILES: NC(=O)C1CN(C(=O)c2ccc(Nc3ncc4c(n3)-c3ccc(Cl)cc3C(c3c(F)cccc3F)=NC4)cc2)CCN1] I-317
TABLE 3-continued
Aurora Kinase Inhibitors
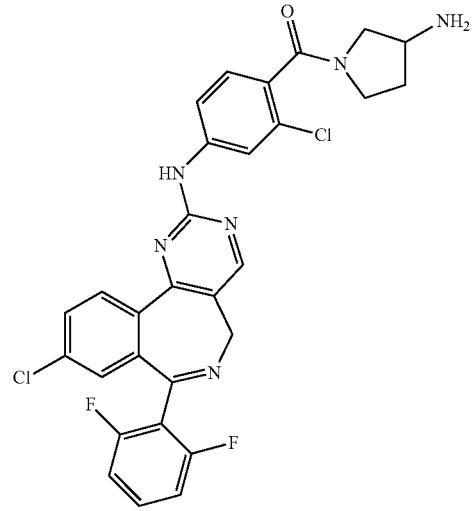 [SMILES: NC1CCN(C(=O)c2ccc(Nc3ncc4c(n3)-c3ccc(Cl)cc3C(c3c(F)cccc3F)=NC4)cc2Cl)C1] I-318
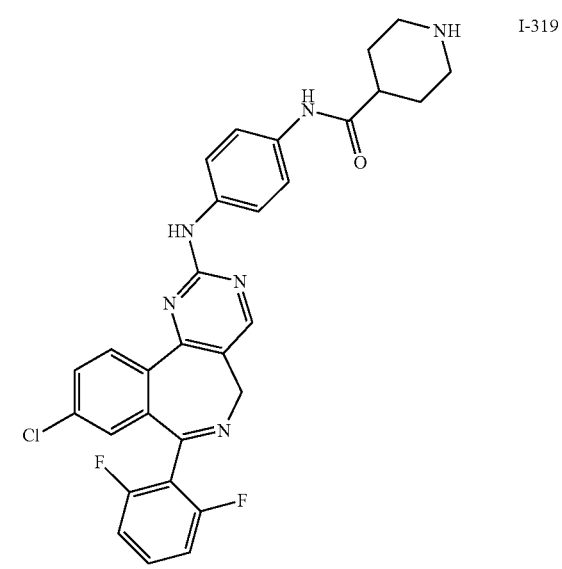 I-319
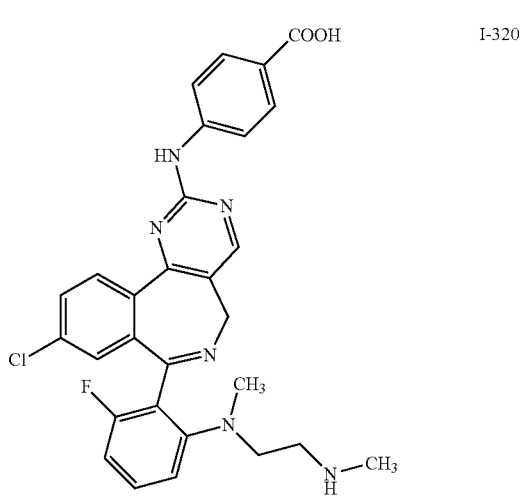 I-320

TABLE 3-continued
Aurora Kinase Inhibitors
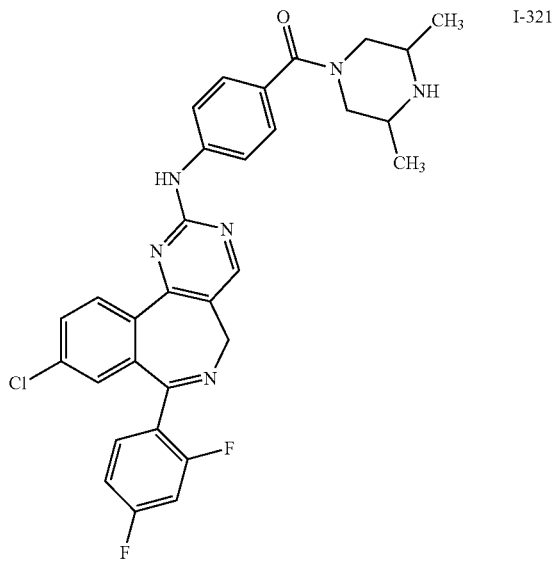 I-321
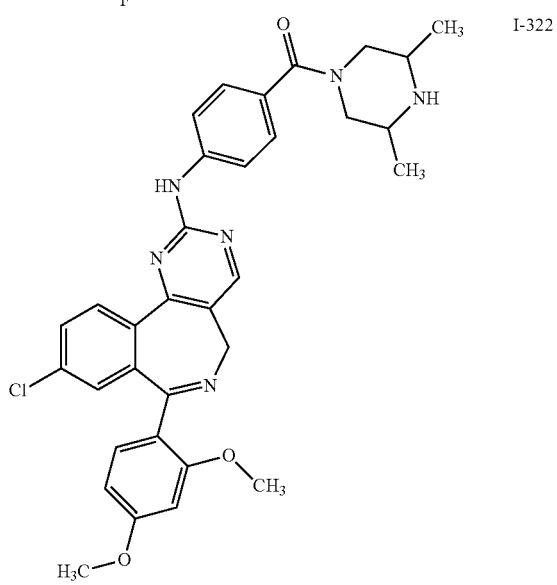 I-322
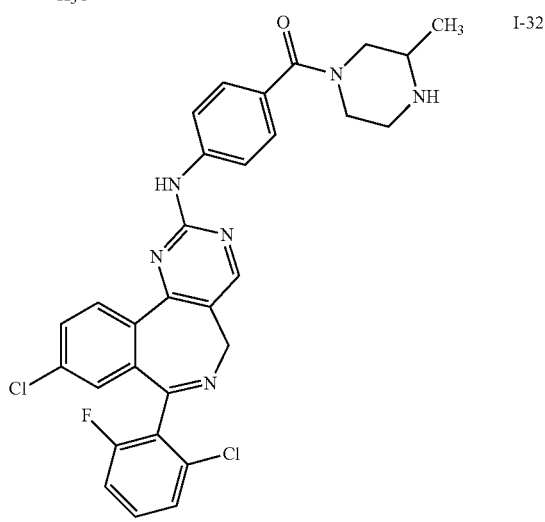 I-323
TABLE 3-continued
Aurora Kinase Inhibitors
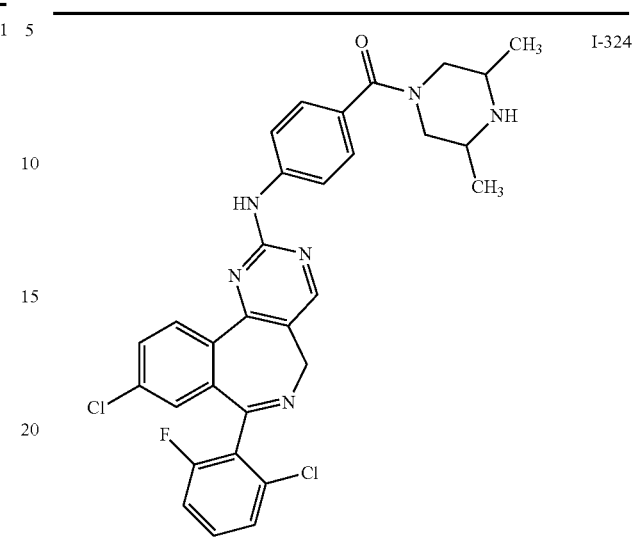 I-324
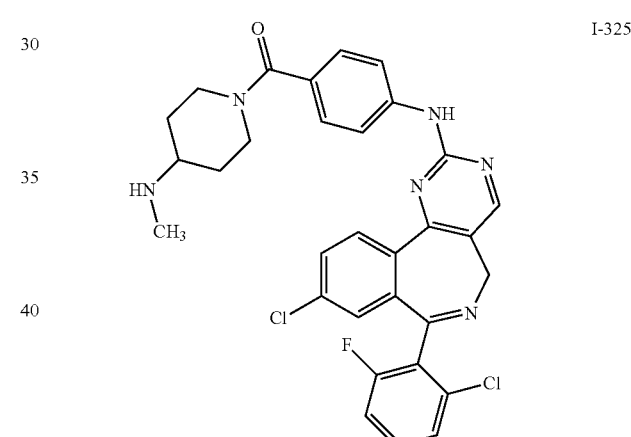 I-325
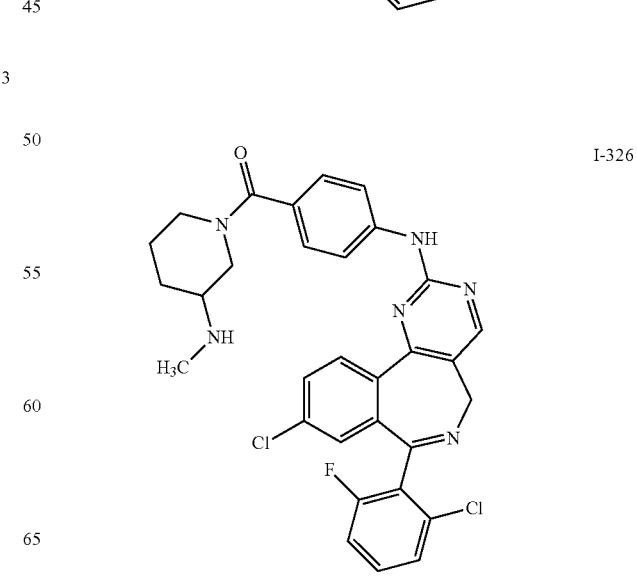 I-326

TABLE 3-continued
Aurora Kinase Inhibitors
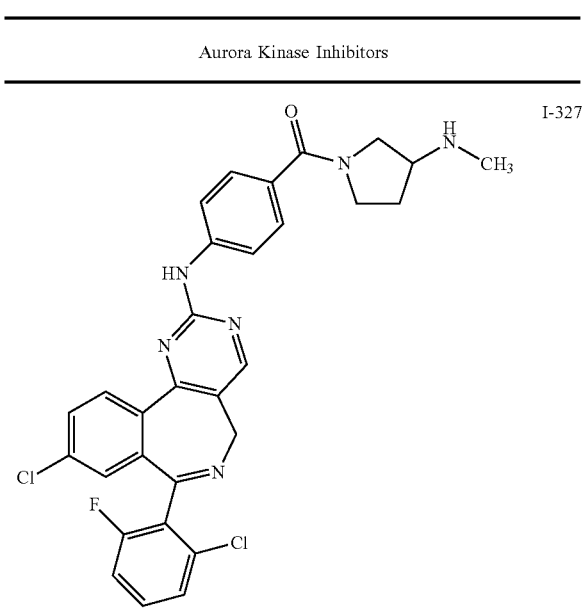
I-327
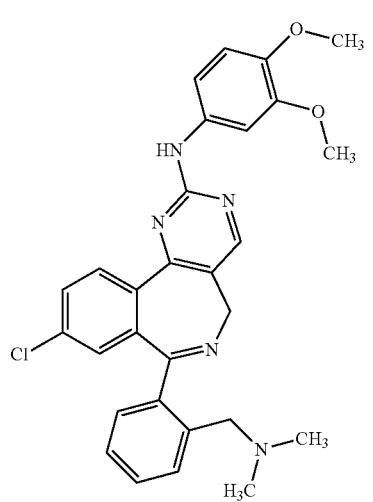 [SMILES: COc1ccc(Nc2ncc3c(n2)-c2ccc(Cl)cc2C(c2ccccc2CN(C)C)=NC3)cc1OC]
I-328
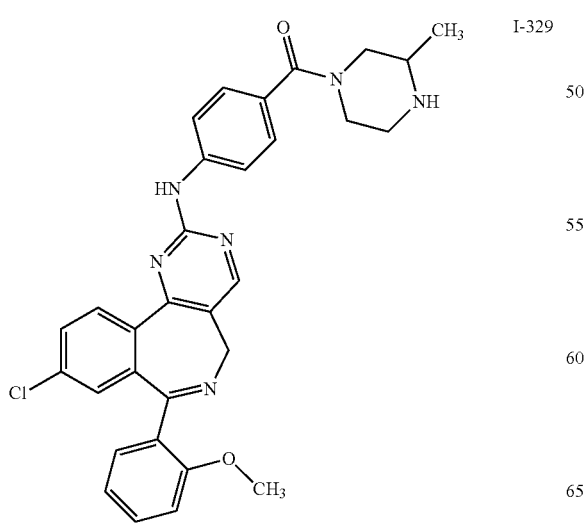
I-329
TABLE 3-continued
Aurora Kinase Inhibitors
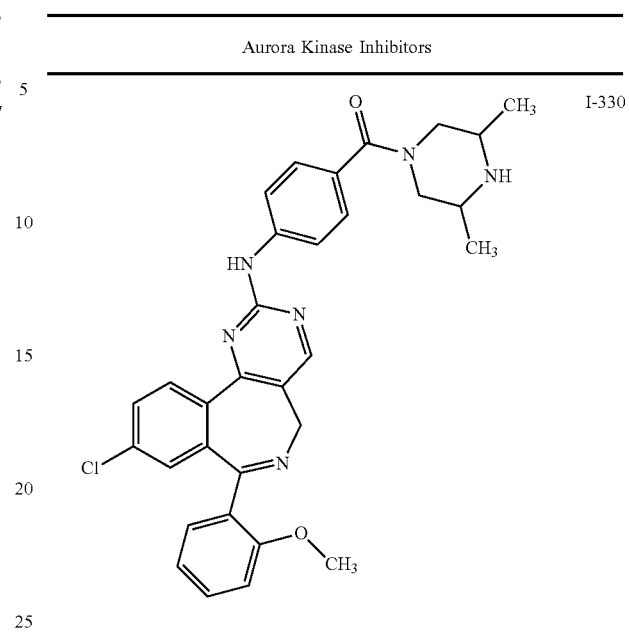
I-330
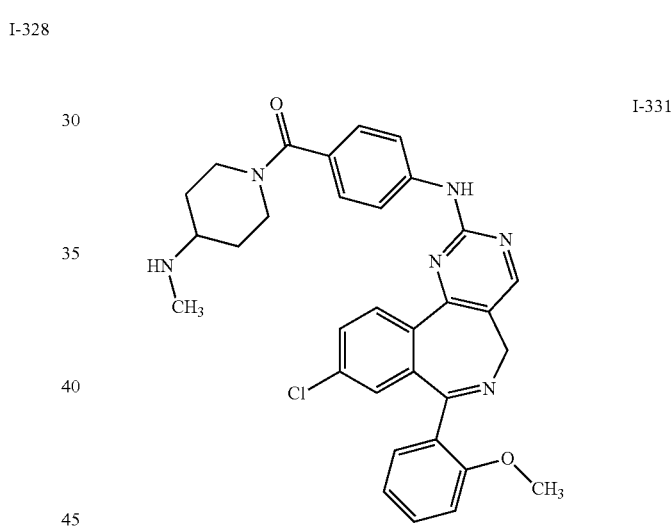
I-331
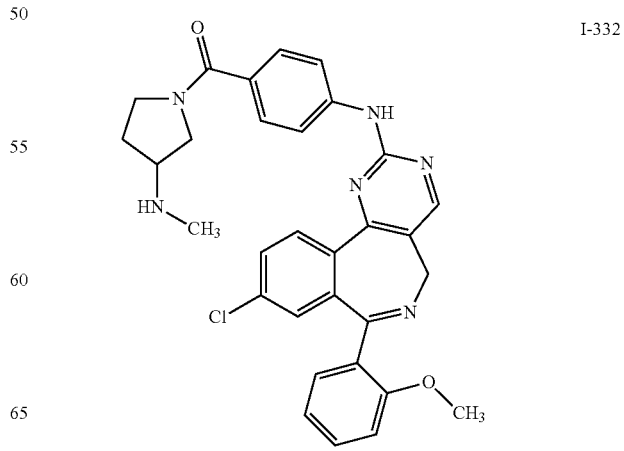
I-332

TABLE 3-continued
Aurora Kinase Inhibitors
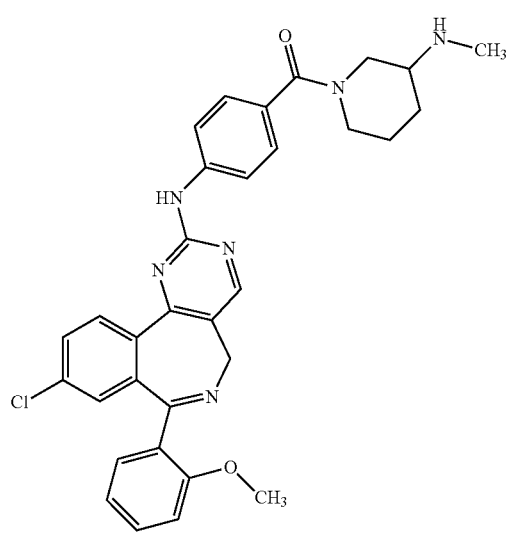 [SMILES: CNC1CCCN(C(=O)c2ccc(Nc3ncc4c(n3)-c3ccc(Cl)cc3C(c3ccccc3OC)=NC4)cc2)C1]
I-333
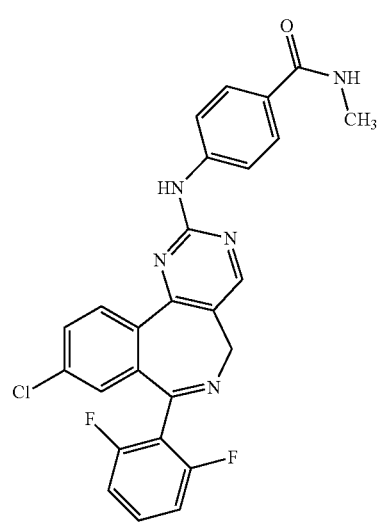 [SMILES: CNC(=O)c1ccc(Nc2ncc3c(n2)-c2ccc(Cl)cc2C(c2c(F)cccc2F)=NC3)cc1]
I-334
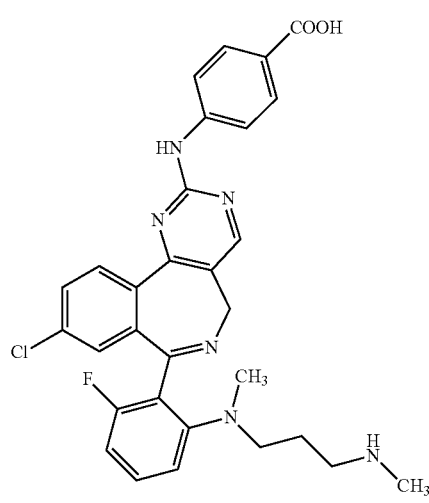 [SMILES: CNCCCN(C)c1cccc(F)c1C1=NCc2cnc(Nc3ccc(C(=O)O)cc3)nc2-c2ccc(Cl)cc21]
I-335
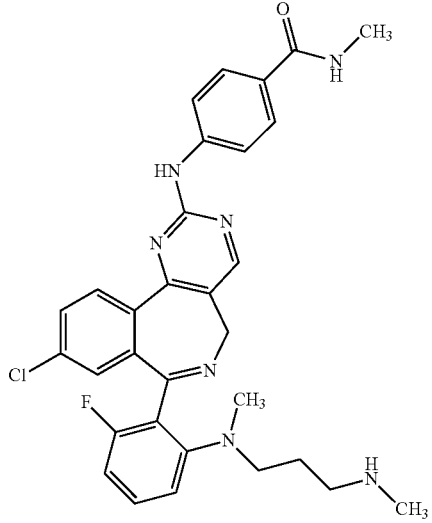 [SMILES: CNCCCN(C)c1cccc(F)c1C1=NCc2cnc(Nc3ccc(C(=O)NC)cc3)nc2-c2ccc(Cl)cc21]
I-336
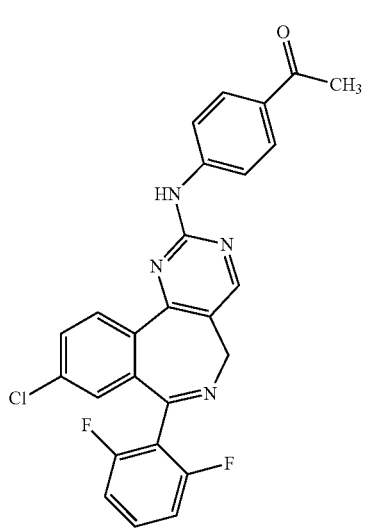 [SMILES: CC(=O)c1ccc(Nc2ncc3c(n2)-c2ccc(Cl)cc2C(c2c(F)cccc2F)=NC3)cc1]
I-337
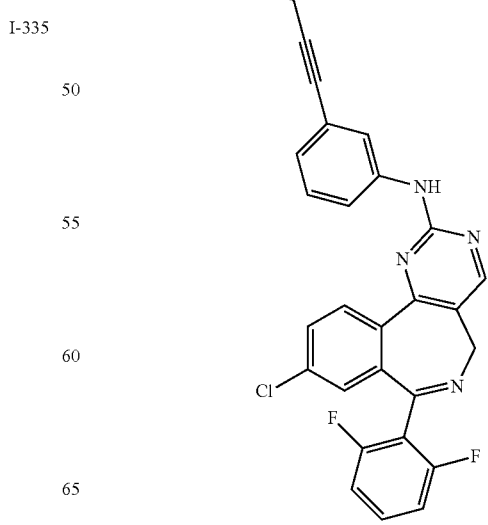
I-338

TABLE 3-continued
Aurora Kinase Inhibitors
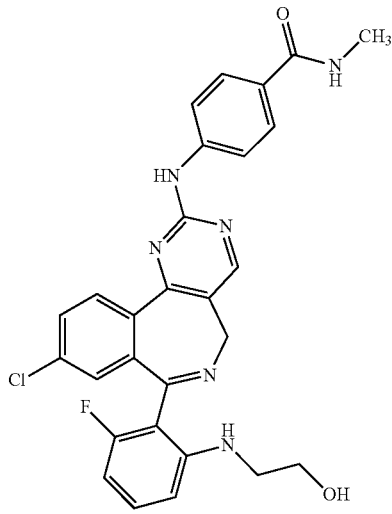 [SMILES: CNC(=O)c1ccc(Nc2ncc3c(n2)-c2ccc(Cl)cc2C(c2c(F)cccc2NCCO)=NC3)cc1]
I-339
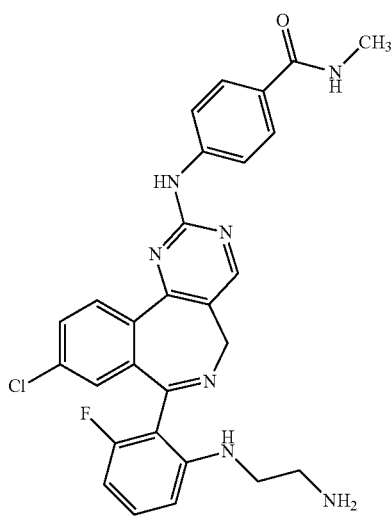 [SMILES: CNC(=O)c1ccc(Nc2ncc3c(n2)-c2ccc(Cl)cc2C(c2c(F)cccc2NCCN)=NC3)cc1]
I-340
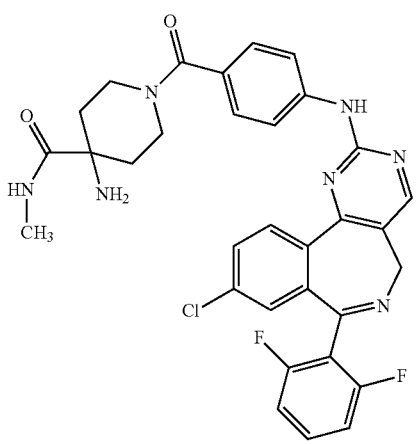 [SMILES: CNC(=O)C1(N)CCN(C(=O)c2ccc(Nc3ncc4c(n3)-c3ccc(Cl)cc3C(c3c(F)cccc3F)=NC4)cc2)CC1]
I-341
TABLE 3-continued
Aurora Kinase Inhibitors
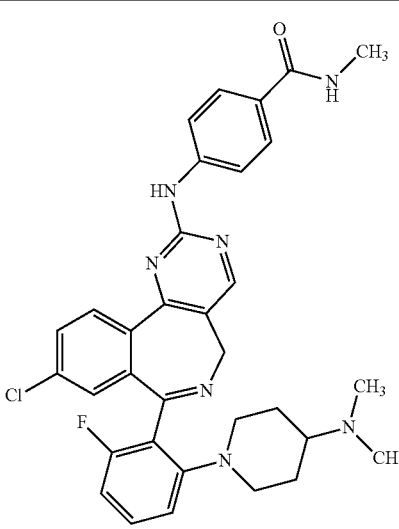
I-342
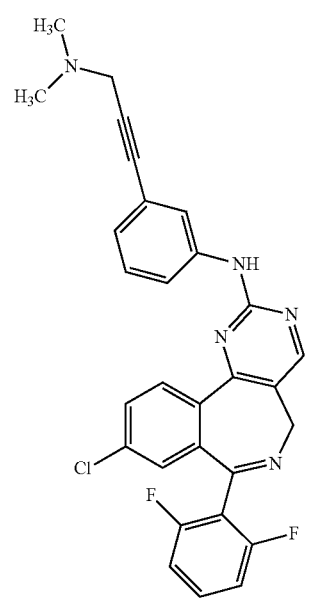 [SMILES: CN(C)CC#Cc1cccc(Nc2ncc3c(n2)-c2ccc(Cl)cc2C(c2c(F)cccc2F)=NC3)c1]
I-343
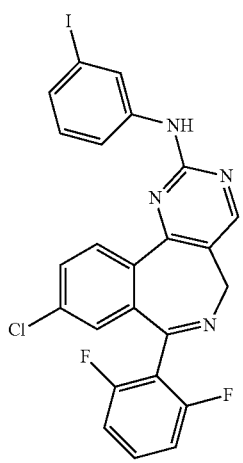 [SMILES: Fc1cccc(F)c1C1=NCc2cnc(Nc3cccc(I)c3)nc2-c2ccc(Cl)cc21]
I-344

TABLE 3-continued
Aurora Kinase Inhibitors
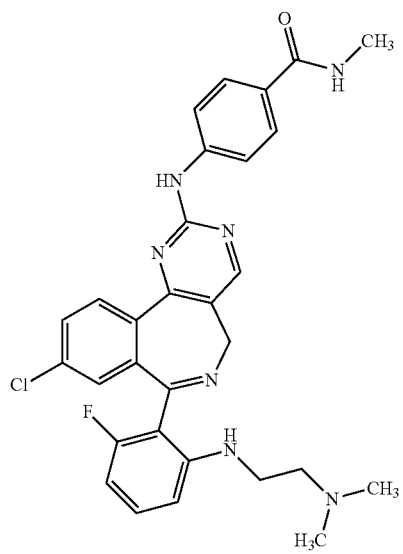 [SMILES: CNC(=O)c1ccc(Nc2ncc3c(n2)-c2ccc(Cl)cc2C(c2c(F)cccc2NCCN(C)C)=NC3)cc1]
I-345
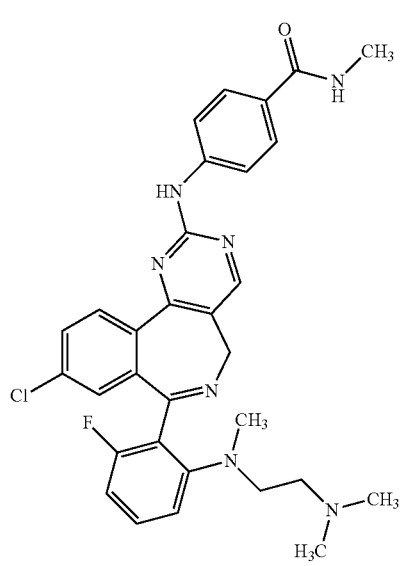 [SMILES: CNC(=O)c1ccc(Nc2ncc3c(n2)-c2ccc(Cl)cc2C(c2c(F)cccc2N(C)CCN(C)C)=NC3)cc1]
I-346
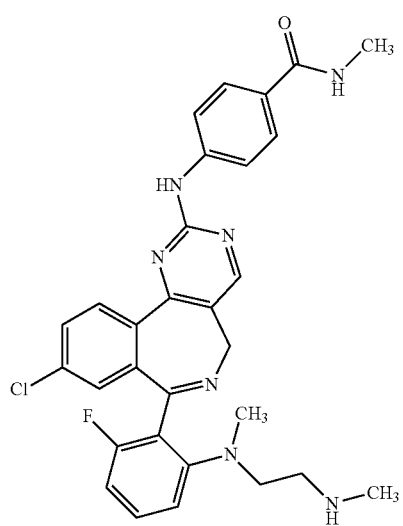 [SMILES: CNCCN(C)c1cccc(F)c1C1=NCc2cnc(Nc3ccc(C(=O)NC)cc3)nc2-c2ccc(Cl)cc21]
I-347
TABLE 3-continued
Aurora Kinase Inhibitors
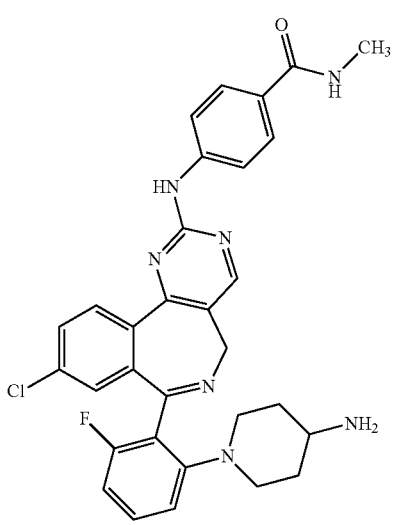 [SMILES: CNC(=O)c1ccc(Nc2ncc3c(n2)-c2ccc(Cl)cc2C(c2c(F)cccc2N2CCC(N)CC2)=NC3)cc1]
I-348
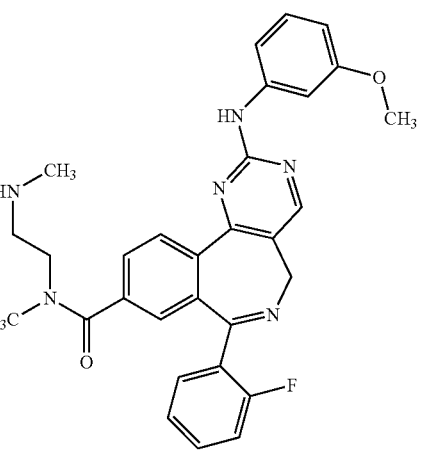
I-349
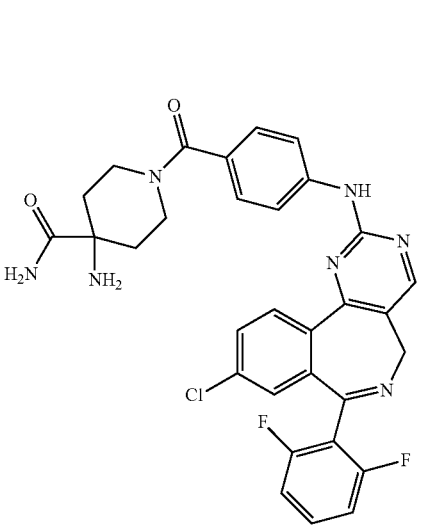 [SMILES: NC(=O)C1(N)CCN(C(=O)c2ccc(Nc3ncc4c(n3)-c3ccc(Cl)cc3C(c3c(F)cccc3F)=NC4)cc2)CC1]
I-350

TABLE 3-continued
Aurora Kinase Inhibitors
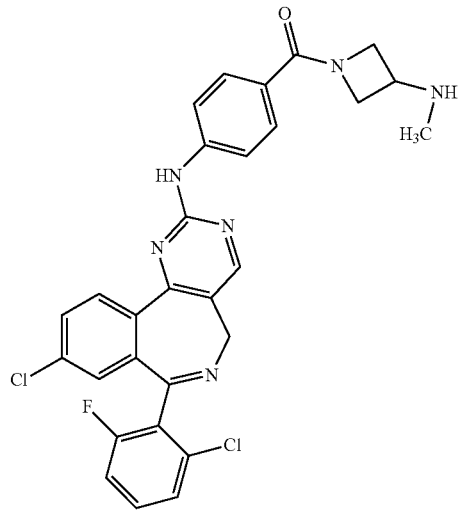 [SMILES: CNC1CN(C(=O)c2ccc(Nc3ncc4c(n3)-c3ccc(Cl)cc3C(c3c(F)cccc3Cl)=NC4)cc2)C1]
I-351
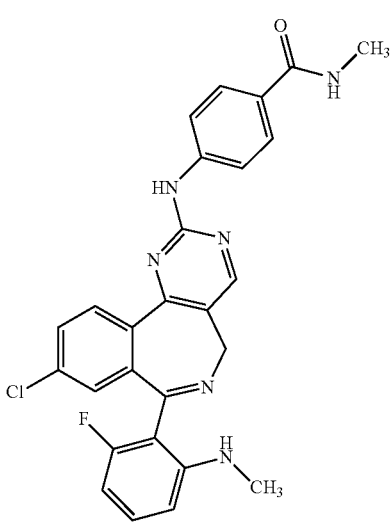
I-354
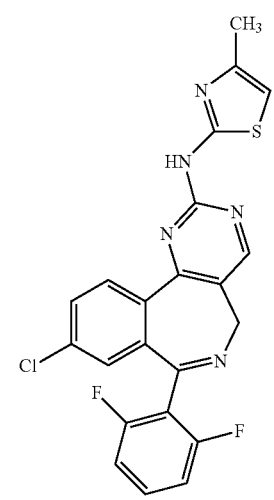 [SMILES: Cc1csc(Nc2ncc3c(n2)-c2ccc(Cl)cc2C(c2c(F)cccc2F)=NC3)n1]
I-352
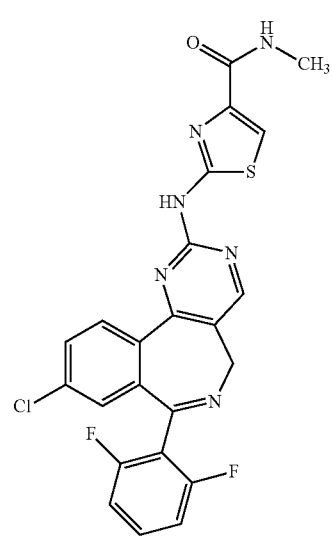
I-355
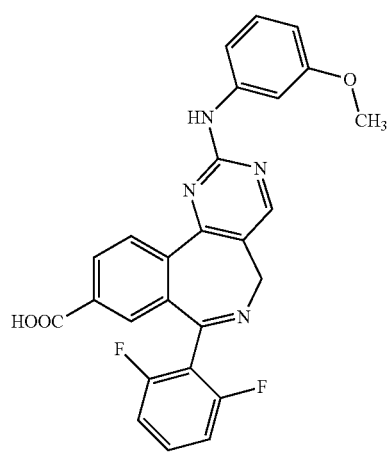 [SMILES: COc1cccc(Nc2ncc3c(n2)-c2ccc(C(=O)O)cc2C(c2c(F)cccc2F)=NC3)c1]
I-353
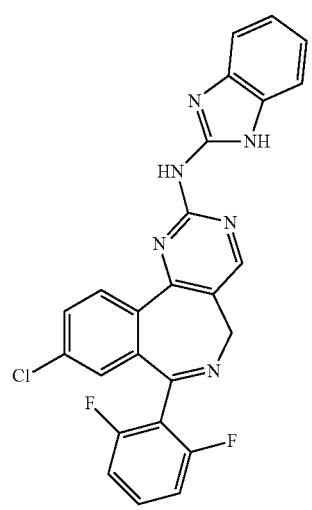 [SMILES: Fc1cccc(F)c1C1=NCc2cnc(Nc3nc4ccccc4[nH]3)nc2-c2ccc(Cl)cc21]
I-356

TABLE 3-continued
Aurora Kinase Inhibitors
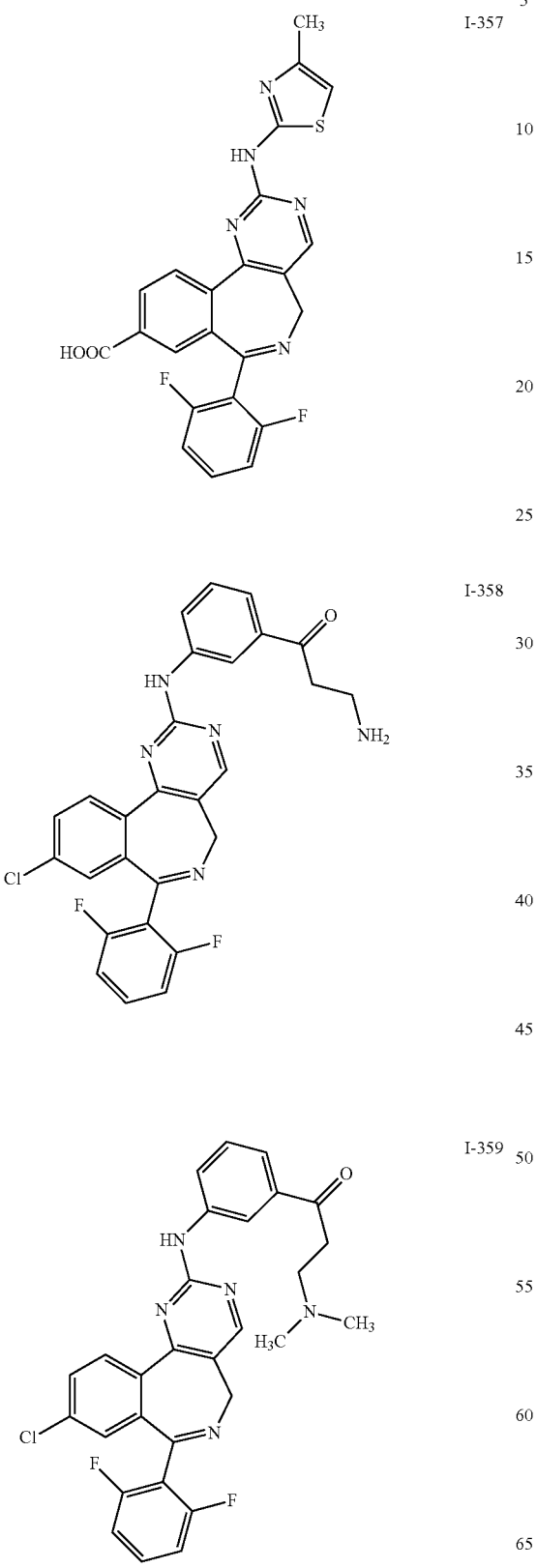
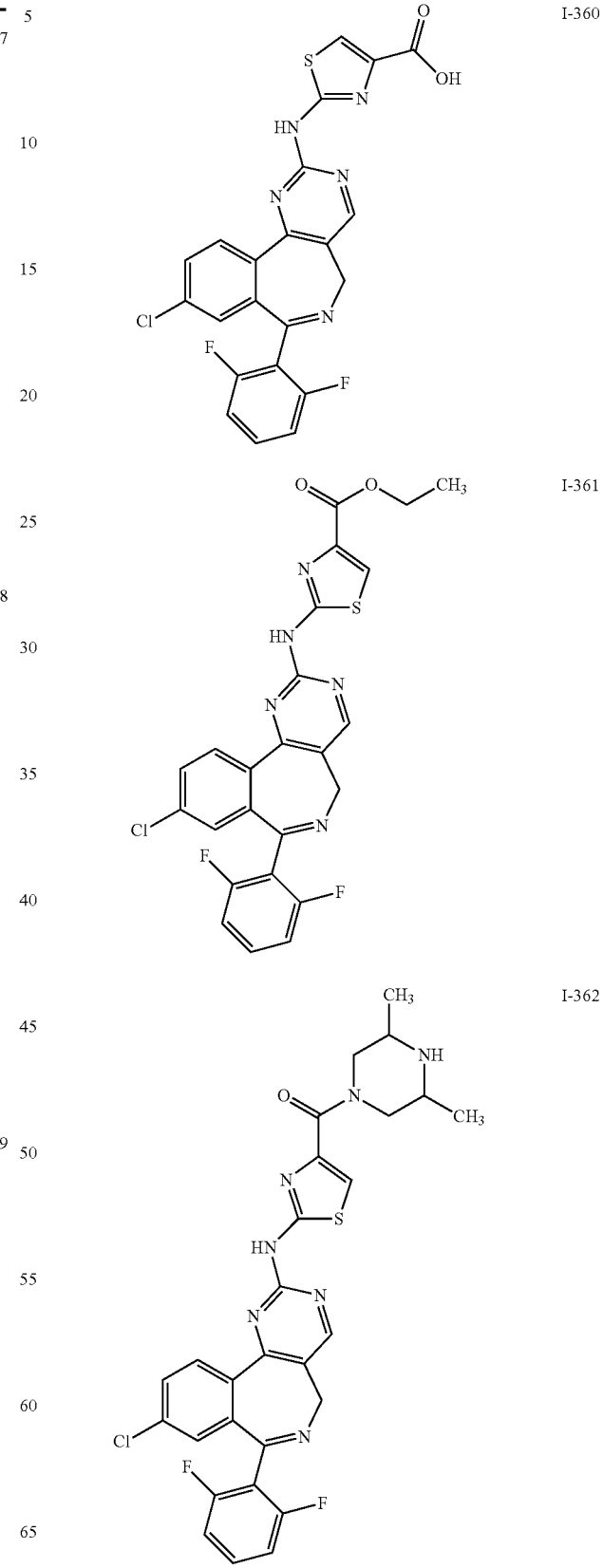

TABLE 3-continued
Aurora Kinase Inhibitors
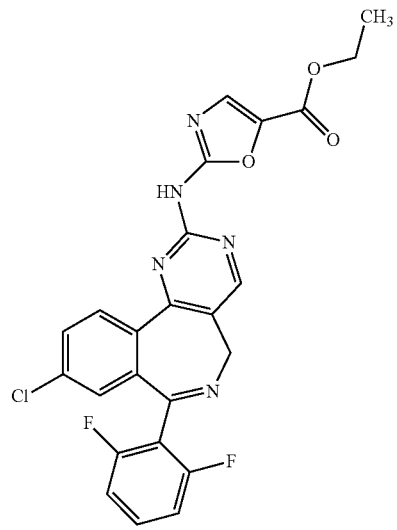 [SMILES: CCOC(=O)c1cnc(Nc2ncc3c(n2)-c2ccc(Cl)cc2C(c2c(F)cccc2F)=NC3)o1]
I-363
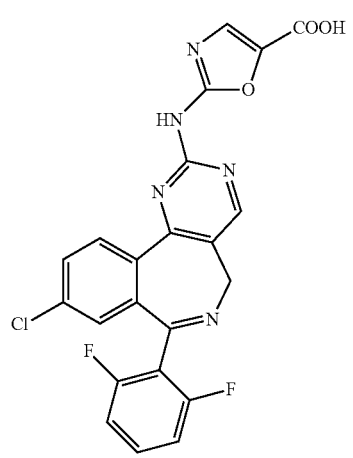 [SMILES: O=C(O)c1cnc(Nc2ncc3c(n2)-c2ccc(Cl)cc2C(c2c(F)cccc2F)=NC3)o1]
I-364
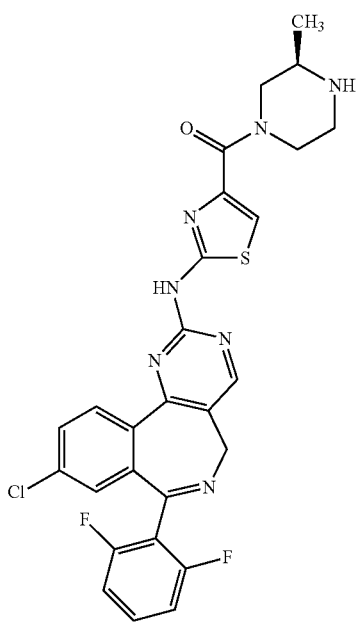 [SMILES: C[C@@H]1CN(C(=O)c2csc(Nc3ncc4c(n3)-c3ccc(Cl)cc3C(c3c(F)cccc3F)=NC4)n2)CCN1]
I-365
TABLE 3-continued
Aurora Kinase Inhibitors
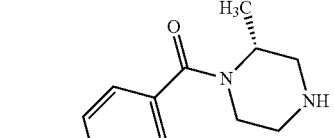
I-366
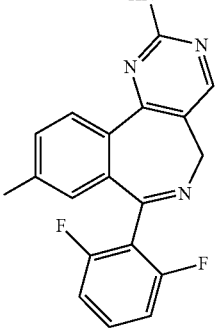
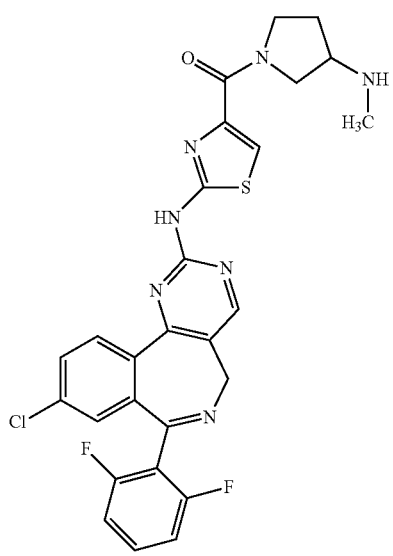 [SMILES: CNC1CCN(C(=O)c2csc(Nc3ncc4c(n3)-c3ccc(Cl)cc3C(c3c(F)cccc3F)=NC4)n2)C1]
I-367
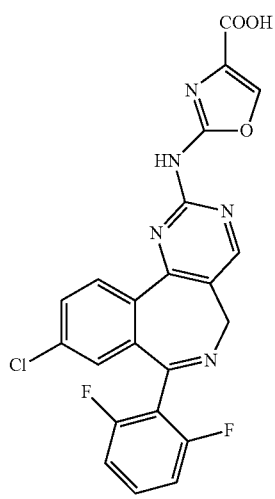 [SMILES: O=C(O)c1coc(Nc2ncc3c(n2)-c2ccc(Cl)cc2C(c2c(F)cccc2F)=NC3)n1]
I-368

TABLE 3-continued
Aurora Kinase Inhibitors
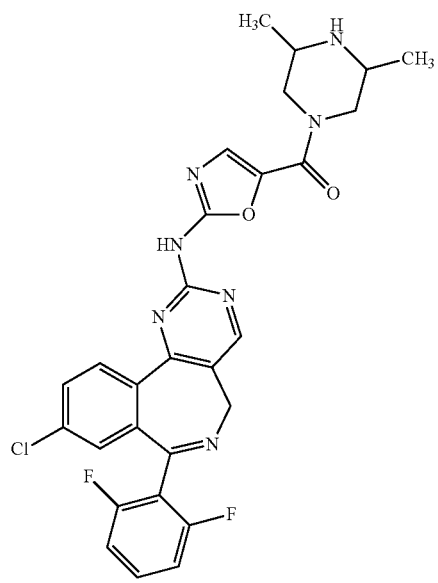 [SMILES: CC1CN(C(=O)c2cnc(Nc3ncc4c(n3)-c3ccc(Cl)cc3C(c3c(F)cccc3F)=NC4)o2)CC(C)N1]
I-369
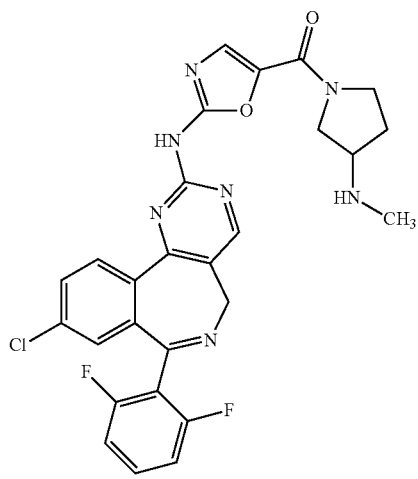 [SMILES: CNC1CCN(C(=O)c2cnc(Nc3ncc4c(n3)-c3ccc(Cl)cc3C(c3c(F)cccc3F)=NC4)o2)C1]
I-370
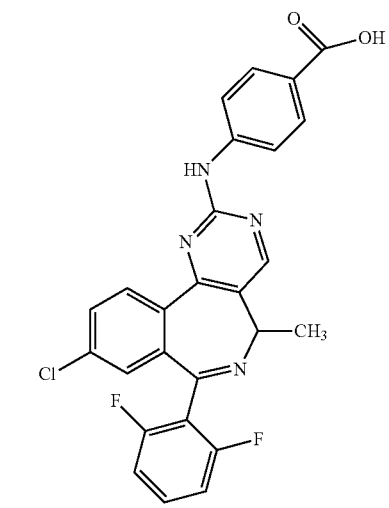 [SMILES: CC1N=C(c2c(F)cccc2F)c2cc(Cl)ccc2-c2nc(Nc3ccc(C(=O)O)cc3)ncc21]
I-371
TABLE 3-continued
Aurora Kinase Inhibitors
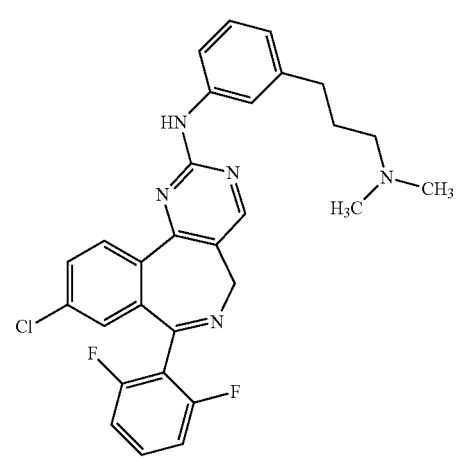 [SMILES: CN(C)CCCc1cccc(Nc2ncc3c(n2)-c2ccc(Cl)cc2C(c2c(F)cccc2F)=NC3)c1]
I-372
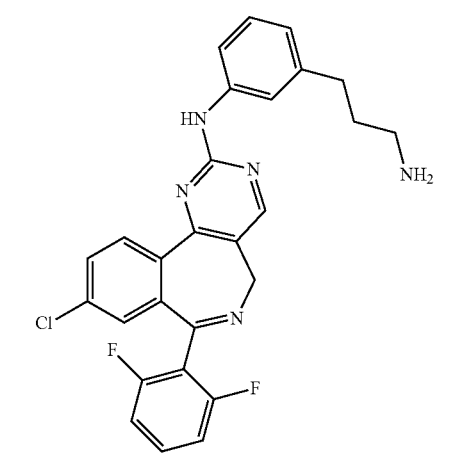 [SMILES: NCCCc1cccc(Nc2ncc3c(n2)-c2ccc(Cl)cc2C(c2c(F)cccc2F)=NC3)c1]
I-373
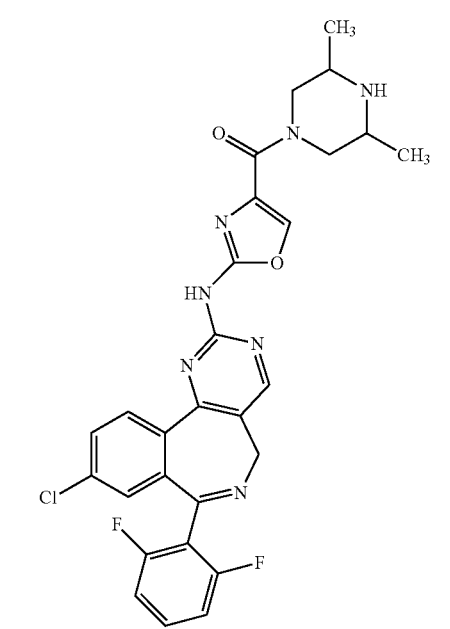 [SMILES: CC1CN(C(=O)c2coc(Nc3ncc4c(n3)-c3ccc(Cl)cc3C(c3c(F)cccc3F)=NC4)n2)CC(C)N1]
I-374

TABLE 3-continued
Aurora Kinase Inhibitors
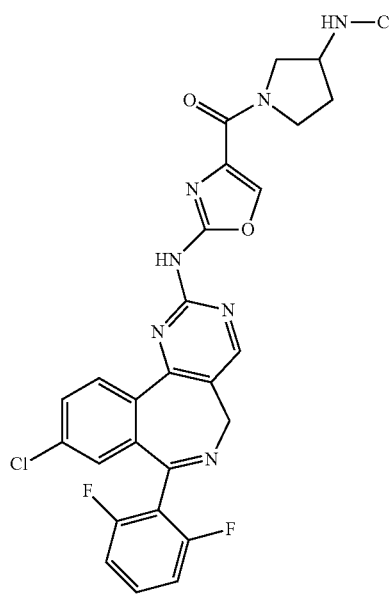
I-375
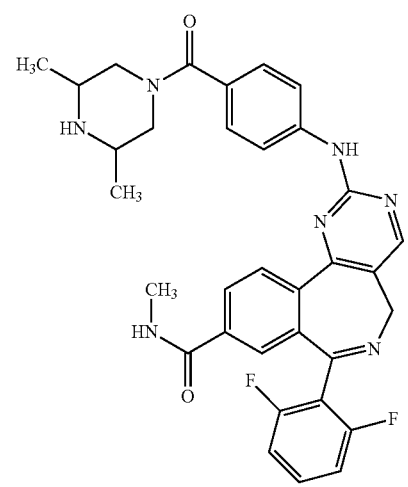 [SMILES: CNC(=O)c1ccc2c(c1)C(c1c(F)cccc1F)=NCc1cnc(Nc3ccc(C(=O)N4CC(C)NC(C)C4)cc3)nc1-2]
I-376
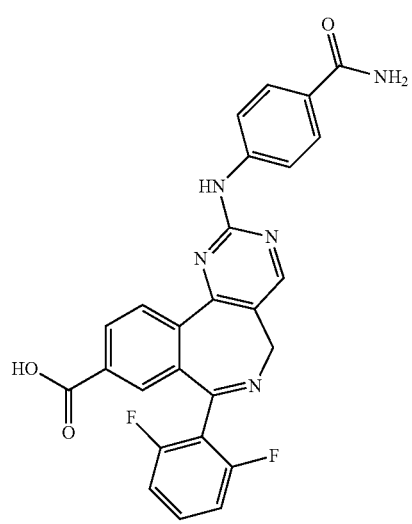 [SMILES: NC(=O)c1ccc(Nc2ncc3c(n2)-c2ccc(C(=O)O)cc2C(c2c(F)cccc2F)=NC3)cc1]
I-377
TABLE 3-continued
Aurora Kinase Inhibitors
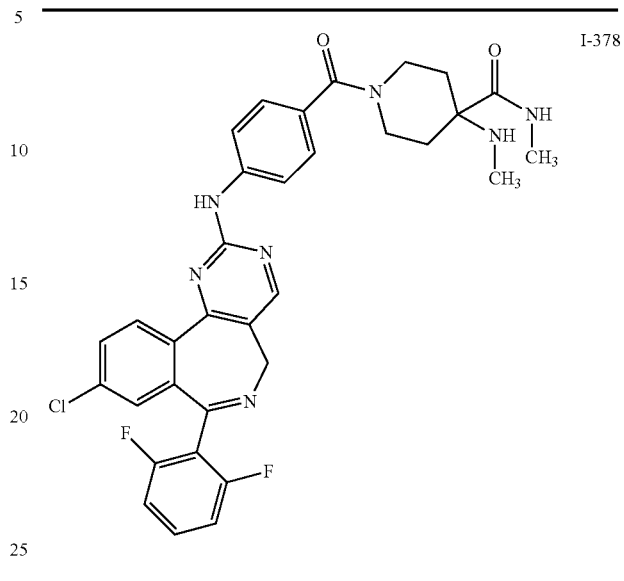
I-378
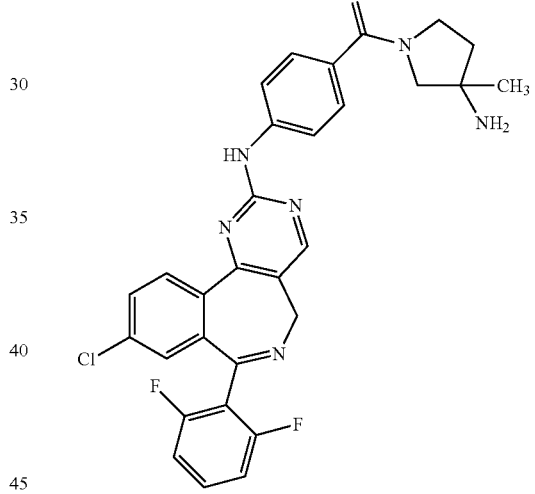
I-379
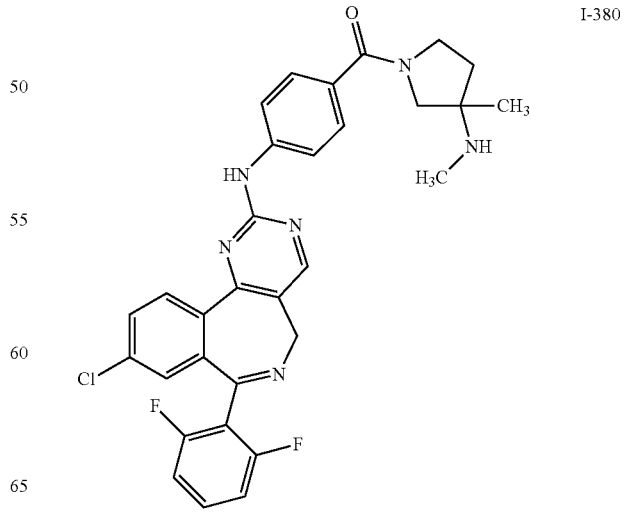
I-380

TABLE 3-continued
Aurora Kinase Inhibitors
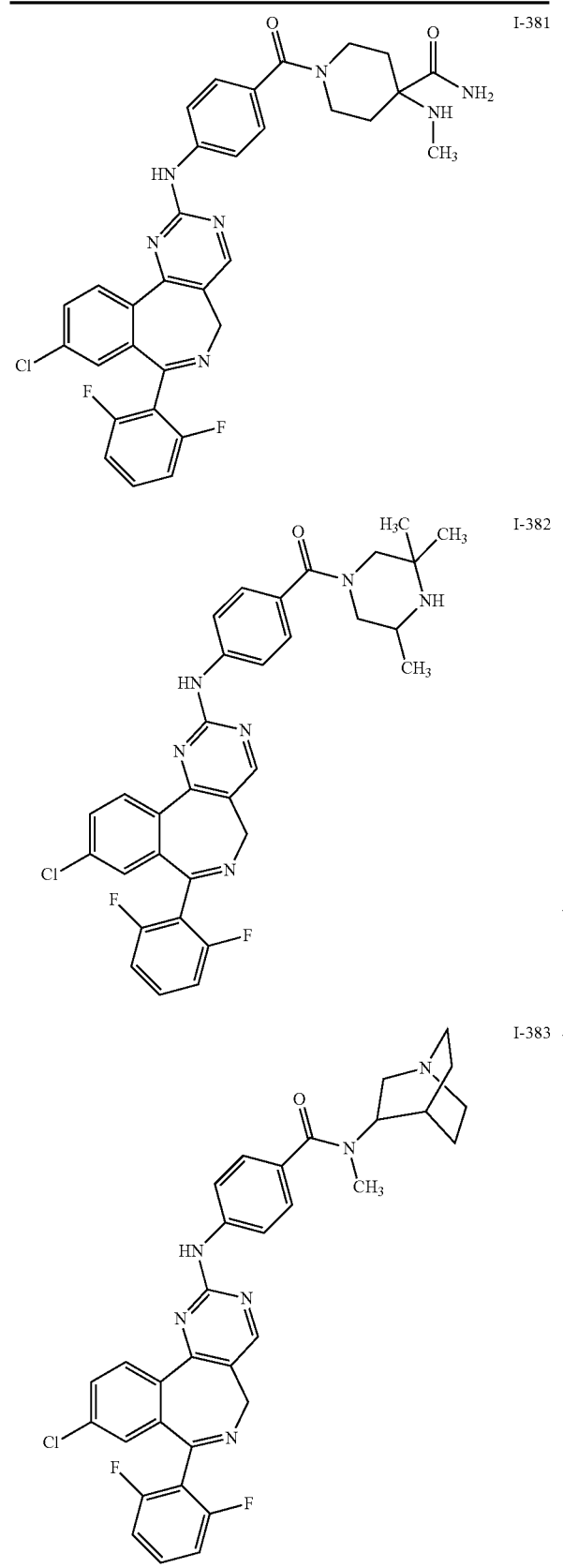

TABLE 3-continued
Aurora Kinase Inhibitors
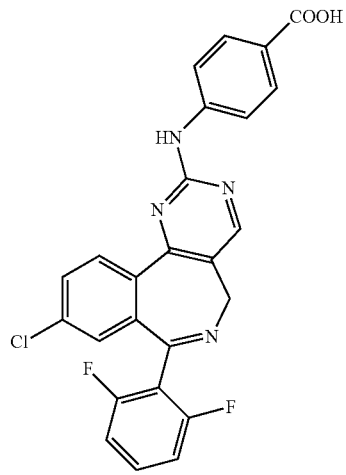 [SMILES: O=C(O)c1ccc(Nc2ncc3c(n2)-c2ccc(Cl)cc2C(c2c(F)cccc2F)=NC3)cc1]
I-387
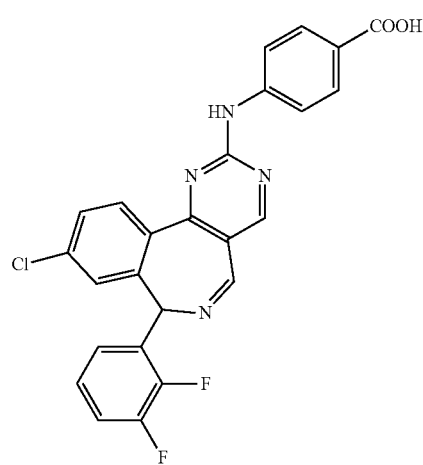 [SMILES: O=C(O)c1ccc(Nc2ncc3c(n2)-c2ccc(Cl)cc2C(c2cccc(F)c2F)N=C3)cc1]
I-388
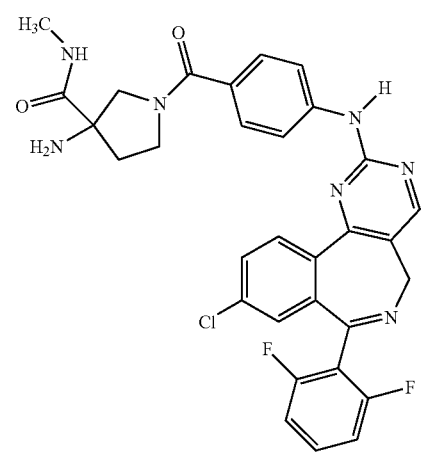 [SMILES: CNC(=O)C1(N)CCN(C(=O)c2ccc(Nc3ncc4c(n3)-c3ccc(Cl)cc3C(c3c(F)cccc3F)=NC4)cc2)C1]
I-389
TABLE 3-continued
Aurora Kinase Inhibitors
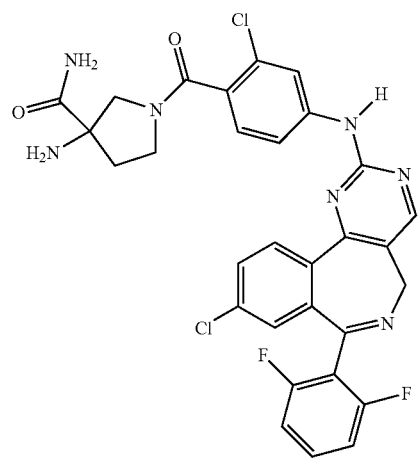 [SMILES: NC(=O)C1(N)CCN(C(=O)c2ccc(Nc3ncc4c(n3)-c3ccc(Cl)cc3C(c3c(F)cccc3F)=NC4)cc2Cl)C1]
I-390
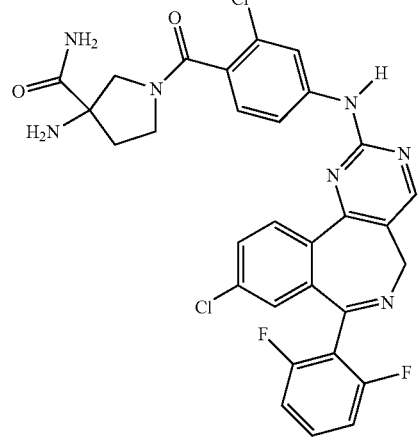
I-391
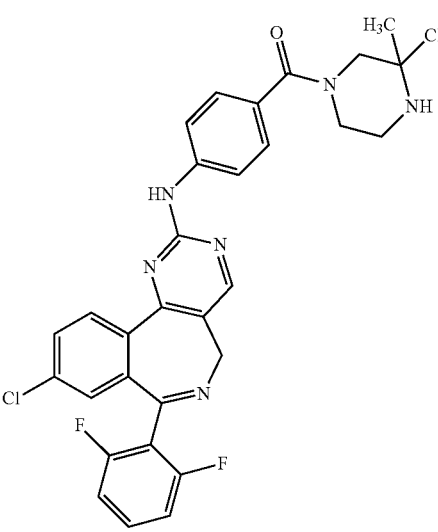
I-392

TABLE 3-continued
Aurora Kinase Inhibitors
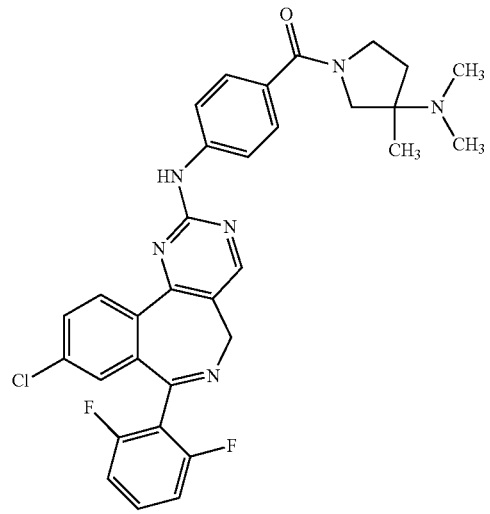 [SMILES: CN(C)C1(C)CCN(C(=O)c2ccc(Nc3ncc4c(n3)-c3ccc(Cl)cc3C(c3c(F)cccc3F)=NC4)cc2)C1]
I-393
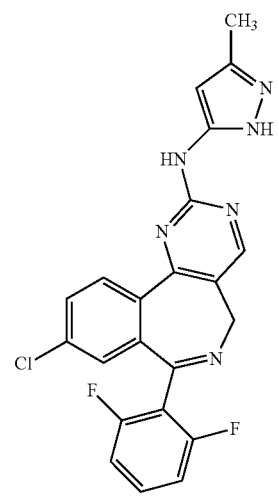 [SMILES: Cc1cc(Nc2ncc3c(n2)-c2ccc(Cl)cc2C(c2c(F)cccc2F)=NC3)[nH]n1]
I-394
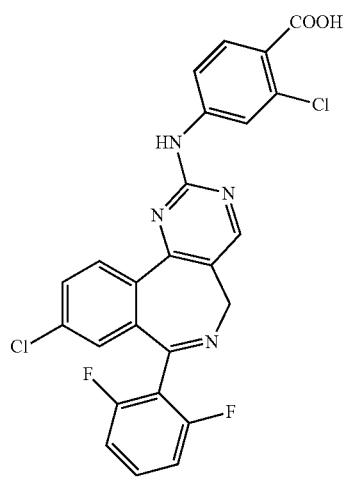 [SMILES: O=C(O)c1ccc(Nc2ncc3c(n2)-c2ccc(Cl)cc2C(c2c(F)cccc2F)=NC3)cc1Cl]
I-395
TABLE 3-continued
Aurora Kinase Inhibitors
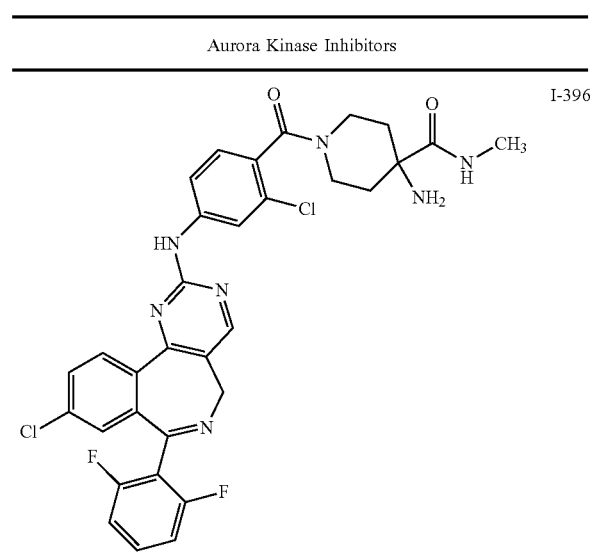
I-396
I-397
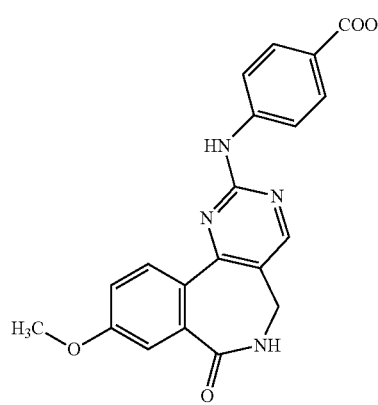
I-398

TABLE 3-continued
Aurora Kinase Inhibitors
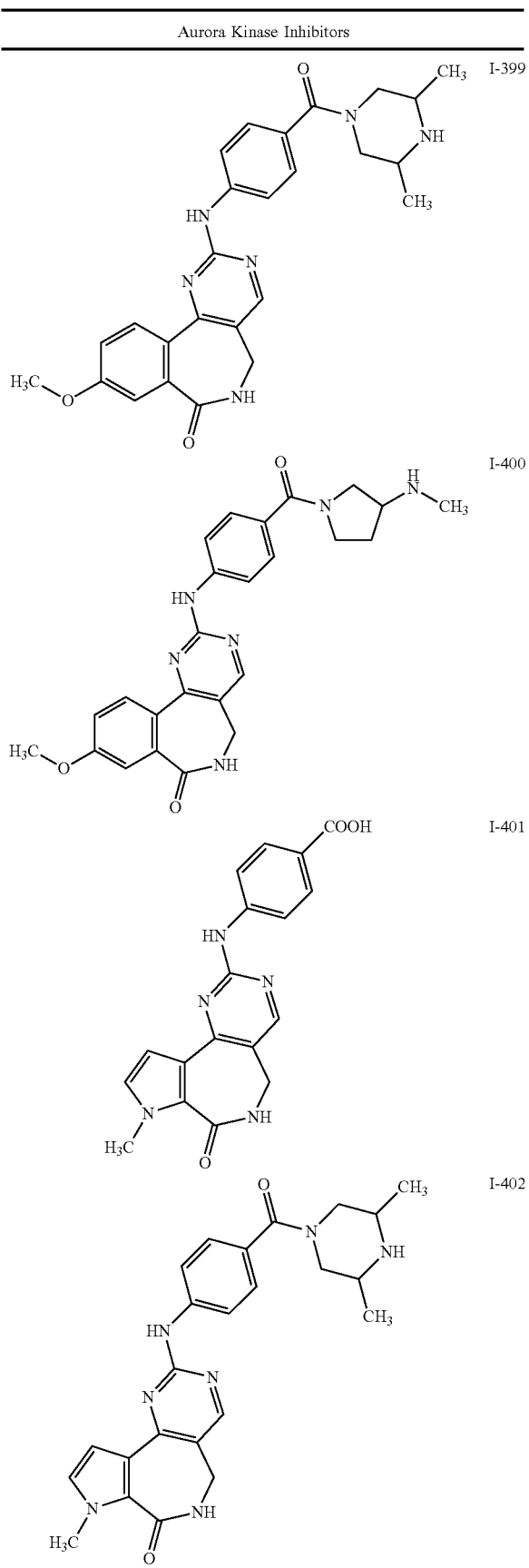
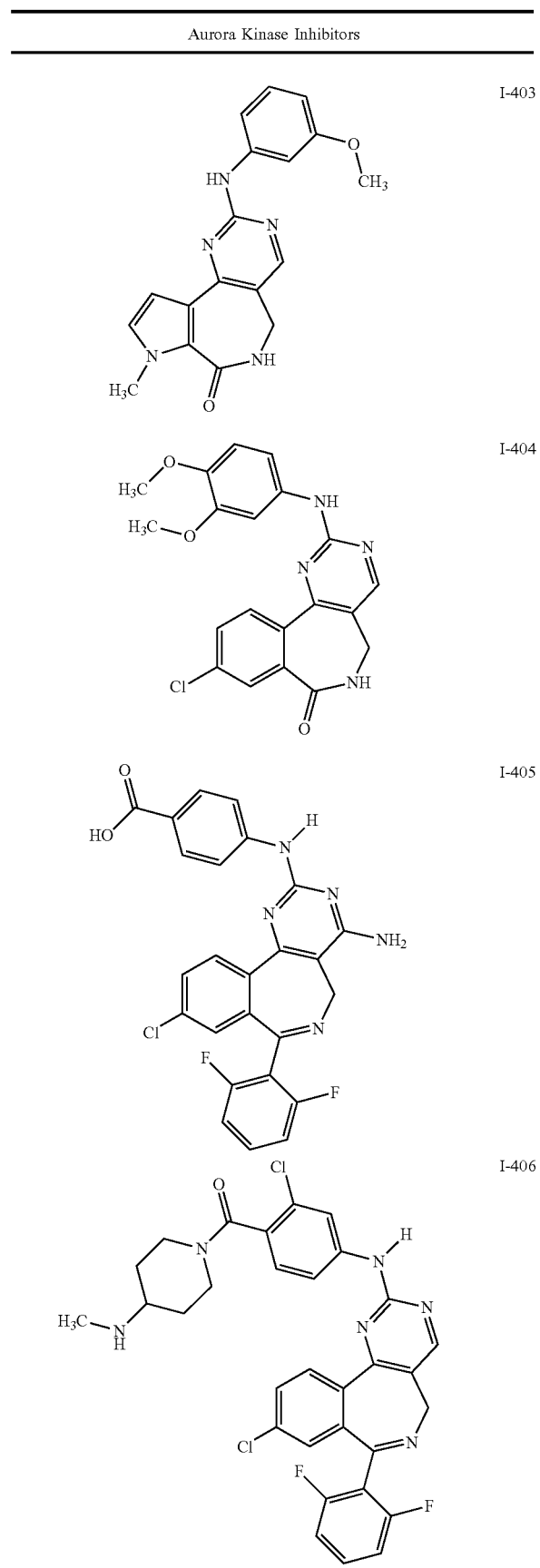

TABLE 3-continued
Aurora Kinase Inhibitors
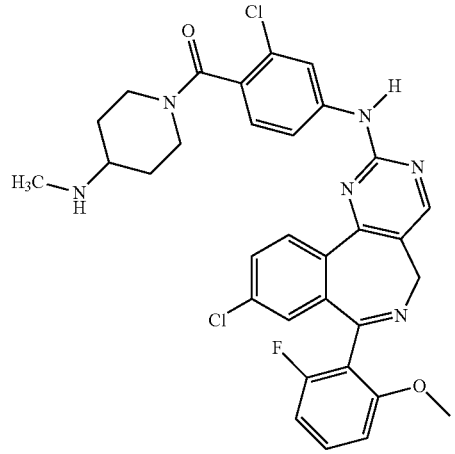
I-407
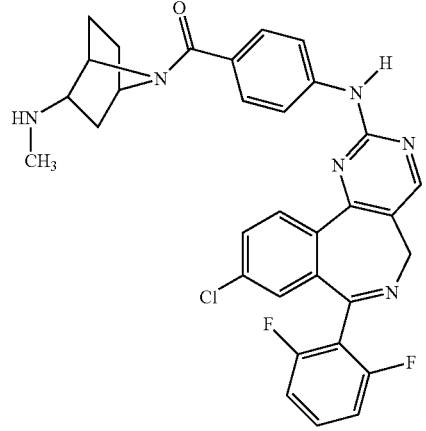
I-410
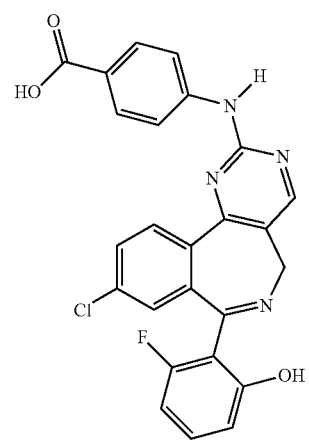 [SMILES: O=C(O)c1ccc(Nc2ncc3c(n2)-c2ccc(Cl)cc2C(c2c(O)cccc2F)=NC3)cc1]
I-408
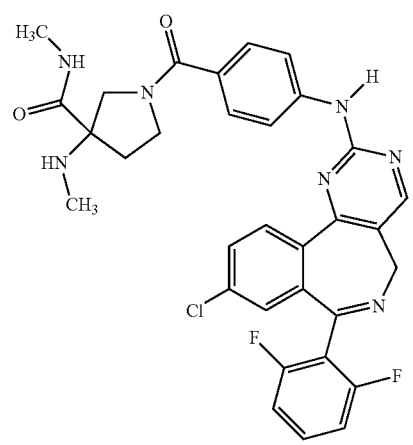
I-411
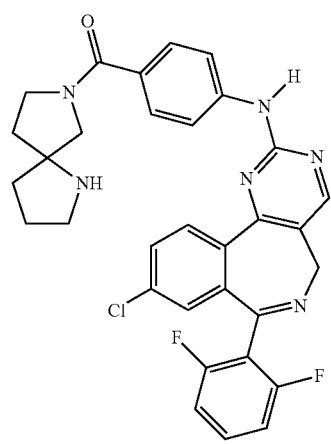 [SMILES: O=C(c1ccc(Nc2ncc3c(n2)-c2ccc(Cl)cc2C(c2c(F)cccc2F)=NC3)cc1)N1CCC2(CCCN2)C1]
I-409
I-412

TABLE 3-continued
Aurora Kinase Inhibitors
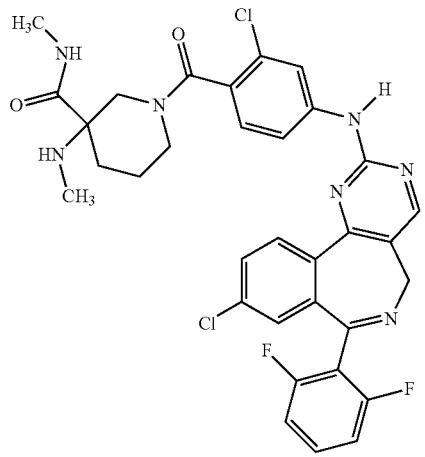 [SMILES: CNC(=O)C1(NC)CCCN(C(=O)c2ccc(Nc3ncc4c(n3)-c3ccc(Cl)cc3C(c3c(F)cccc3F)=NC4)cc2Cl)C1]
I-413
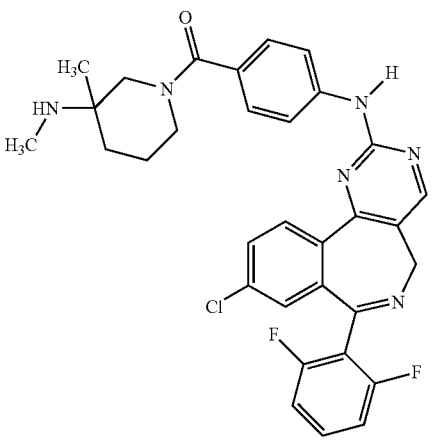 [SMILES: CNC1(C)CCCN(C(=O)c2ccc(Nc3ncc4c(n3)-c3ccc(Cl)cc3C(c3c(F)cccc3F)=NC4)cc2)C1]
I-414
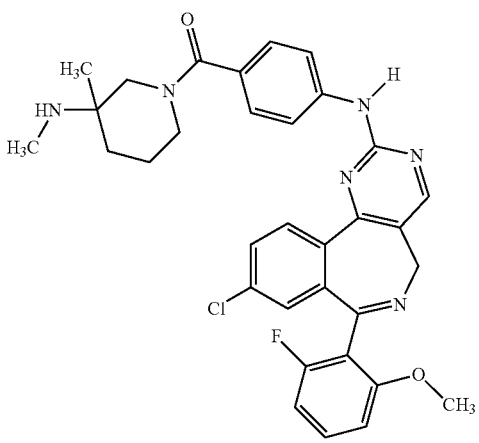
I-415
TABLE 3-continued
Aurora Kinase Inhibitors
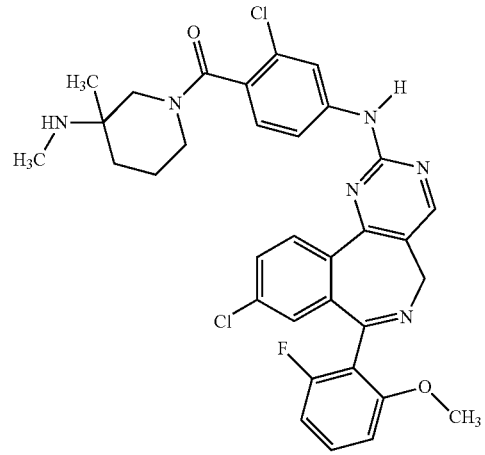
I-416
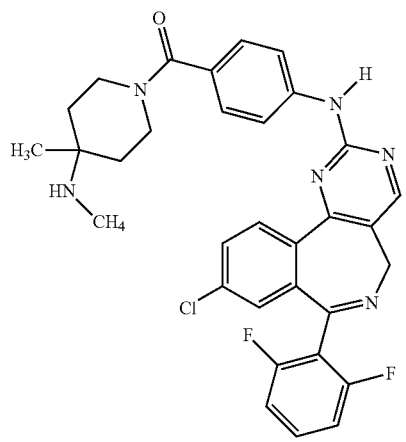 [SMILES: CNC1(C)CCN(C(=O)c2ccc(Nc3ncc4c(n3)-c3ccc(Cl)cc3C(c3c(F)cccc3F)=NC4)cc2)CC1]
I-417
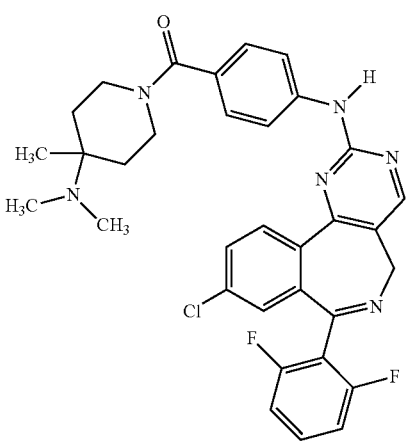 [SMILES: CN(C)C1(C)CCN(C(=O)c2ccc(Nc3ncc4c(n3)-c3ccc(Cl)cc3C(c3c(F)cccc3F)=NC4)cc2)CC1]
I-418

TABLE 3-continued
Aurora Kinase Inhibitors
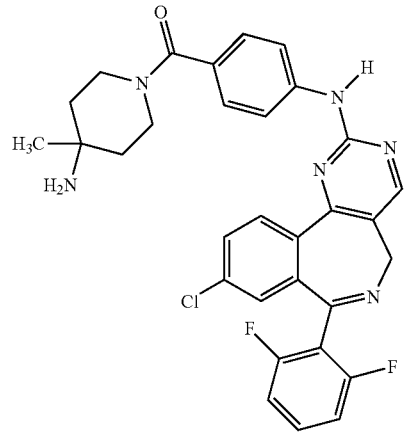 [SMILES: CC1(N)CCN(C(=O)c2ccc(Nc3ncc4c(n3)-c3ccc(Cl)cc3C(c3c(F)cccc3F)=NC4)cc2)CC1]
I-419
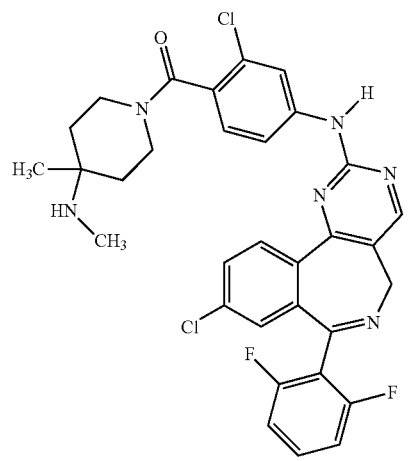 [SMILES: CNC1(C)CCN(C(=O)c2ccc(Nc3ncc4c(n3)-c3ccc(Cl)cc3C(c3c(F)cccc3F)=NC4)cc2Cl)CC1]
I-420
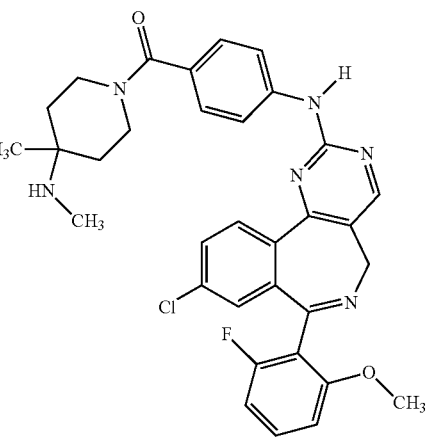
I-421
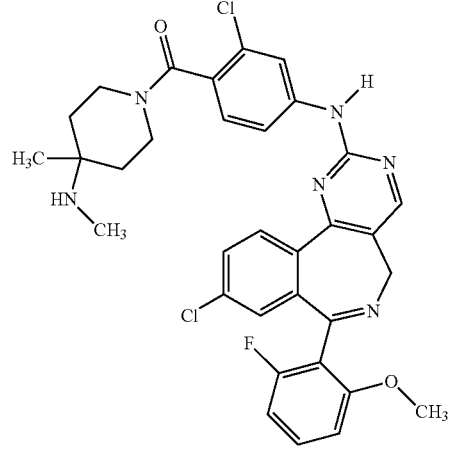
I-422
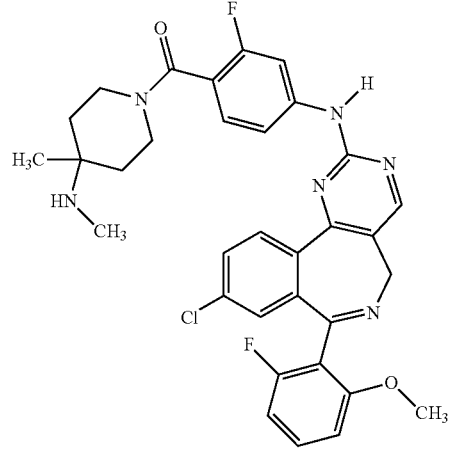
I-423
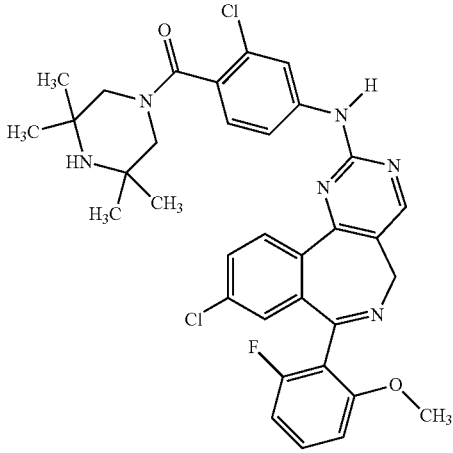
I-424

TABLE 3-continued
Aurora Kinase Inhibitors
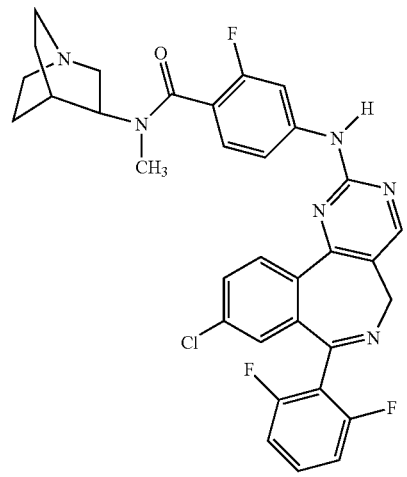 [SMILES: CN(C(=O)c1ccc(Nc2ncc3c(n2)-c2ccc(Cl)cc2C(c2c(F)cccc2F)=NC3)cc1F)C1CN2CCC1CC2]
I-425
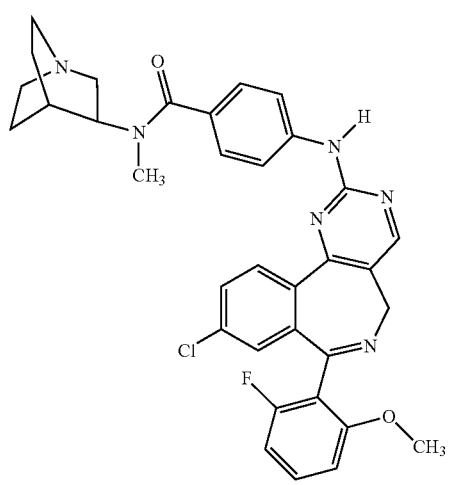 [SMILES: COc1cccc(F)c1C1=NCc2cnc(Nc3ccc(C(=O)N(C)C4CN5CCC4CC5)cc3)nc2-c2ccc(Cl)cc21]
I-426
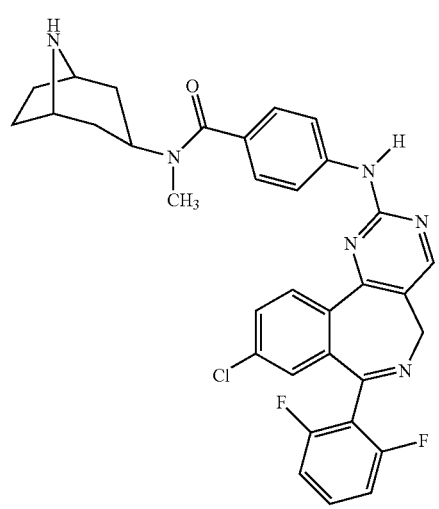 [SMILES: CN(C(=O)c1ccc(Nc2ncc3c(n2)-c2ccc(Cl)cc2C(c2c(F)cccc2F)=NC3)cc1)C1CC2CCC(C1)N2]
I-427
TABLE 3-continued
Aurora Kinase Inhibitors
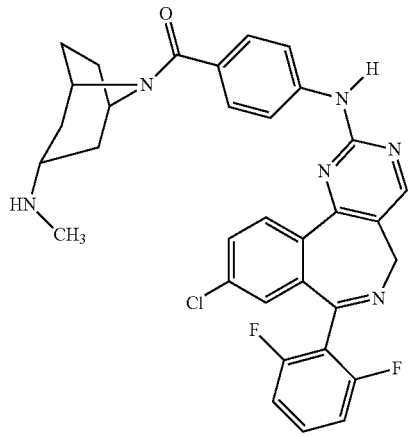 [SMILES: CNC1CC2CCC(C1)N2C(=O)c1ccc(Nc2ncc3c(n2)-c2ccc(Cl)cc2C(c2c(F)cccc2F)=NC3)cc1]
I-428
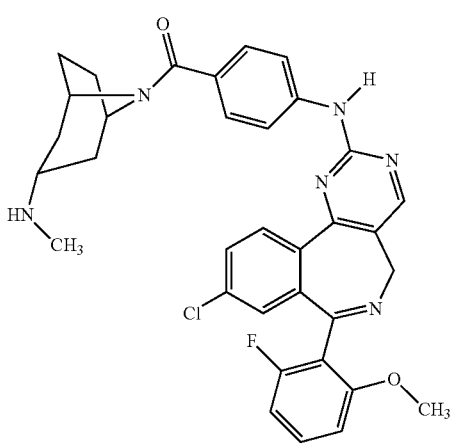 [SMILES: CNC1CC2CCC(C1)N2C(=O)c1ccc(Nc2ncc3c(n2)-c2ccc(Cl)cc2C(c2c(F)cccc2OC)=NC3)cc1]
I-429
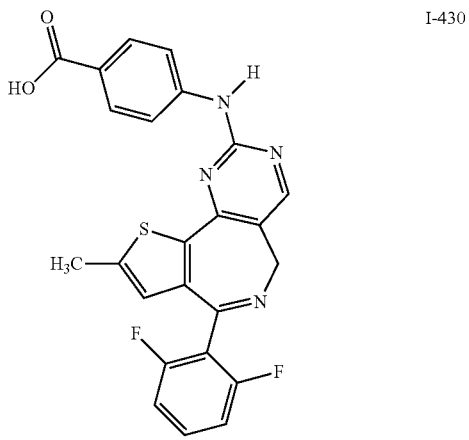
I-430

TABLE 3-continued
Aurora Kinase Inhibitors
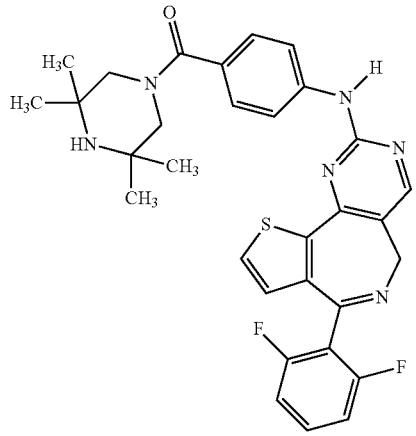 [SMILES: CC1(C)CN(C(=O)c2ccc(Nc3ncc4c(n3)-c3sccc3C(c3c(F)cccc3F)=NC4)cc2)CC(C)(C)N1]
I-431
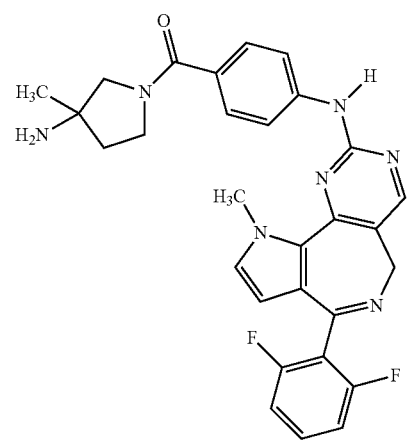 [SMILES: Cn1ccc2c1-c1nc(Nc3ccc(C(=O)N4CCC(C)(N)C4)cc3)ncc1CN=C2c1c(F)cccc1F]
I-432
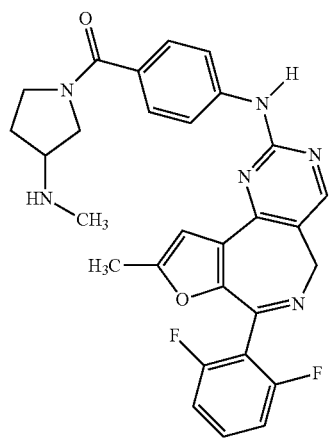 [SMILES: CNC1CCN(C(=O)c2ccc(Nc3ncc4c(n3)-c3cc(C)oc3C(c3c(F)cccc3F)=NC4)cc2)C1]
I-433
TABLE 3-continued
Aurora Kinase Inhibitors
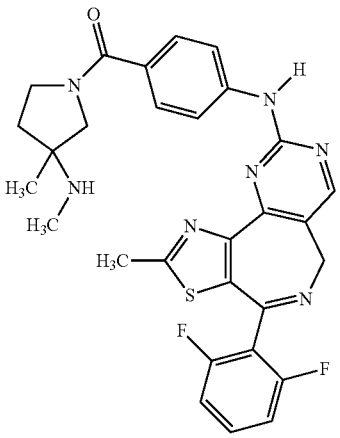 [SMILES: CNC1(C)CCN(C(=O)c2ccc(Nc3ncc4c(n3)-c3nc(C)sc3C(c3c(F)cccc3F)=NC4)cc2)C1]
I-434
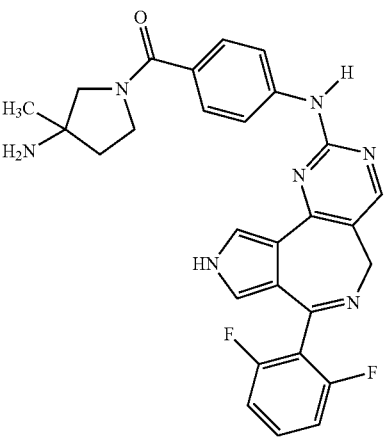 [SMILES: CC1(N)CCN(C(=O)c2ccc(Nc3ncc4c(n3)-c3c[nH]cc3C(c3c(F)cccc3F)=NC4)cc2)C1]
I-435
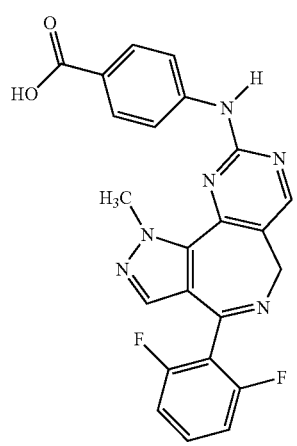 [SMILES: Cn1ncc2c1-c1nc(Nc3ccc(C(=O)O)cc3)ncc1CN=C2c1c(F)cccc1F]
I-436

TABLE 3-continued
Aurora Kinase Inhibitors
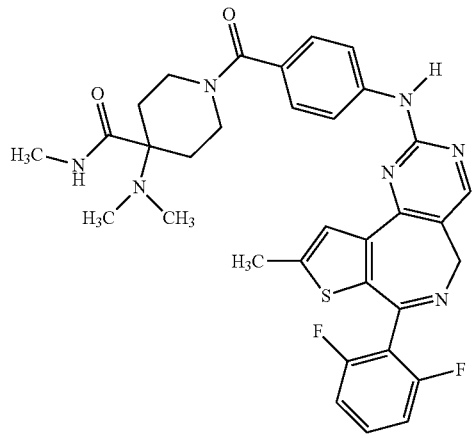 [SMILES: CNC(=O)C1(N(C)C)CCN(C(=O)c2ccc(Nc3ncc4c(n3)-c3cc(C)sc3C(c3c(F)cccc3F)=NC4)cc2)CC1]
I-437
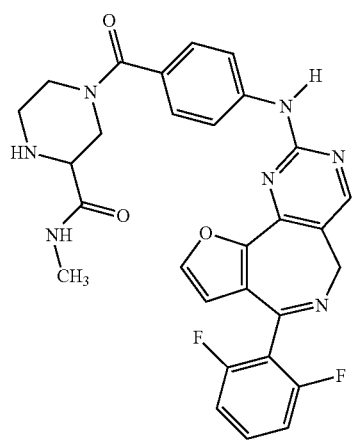 [SMILES: CNC(=O)C1CN(C(=O)c2ccc(Nc3ncc4c(n3)-c3occc3C(c3c(F)cccc3F)=NC4)cc2)CCN1]
I-438
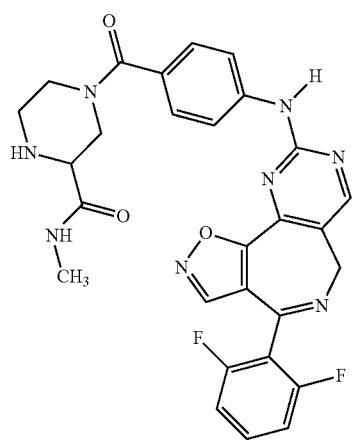 [SMILES: CNC(=O)C1CN(C(=O)c2ccc(Nc3ncc4c(n3)-c3oncc3C(c3c(F)cccc3F)=NC4)cc2)CCN1]
I-439
TABLE 3-continued
Aurora Kinase Inhibitors
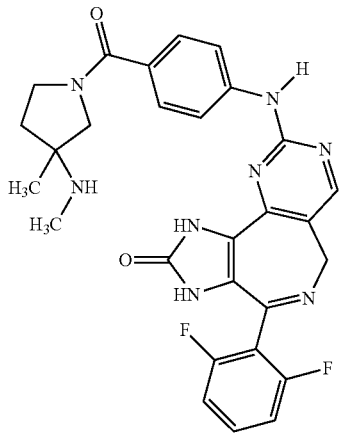 [SMILES: CNC1(C)CCN(C(=O)c2ccc(Nc3ncc4c(n3)-c3[nH]c(=O)[nH]c3C(c3c(F)cccc3F)=NC4)cc2)C1]
I-440
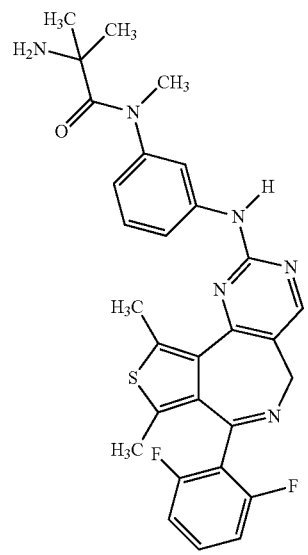 [SMILES: Cc1sc(C)c2c1C(c1c(F)cccc1F)=NCc1cnc(Nc3cccc(N(C)C(=O)C(C)(C)N)c3)nc1-2]
I-441
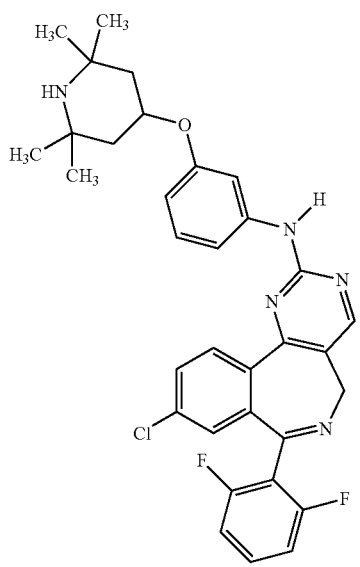 [SMILES: CC1(C)CC(Oc2cccc(Nc3ncc4c(n3)-c3ccc(Cl)cc3C(c3c(F)cccc3F)=NC4)c2)CC(C)(C)N1]
I-442

TABLE 3-continued
Aurora Kinase Inhibitors
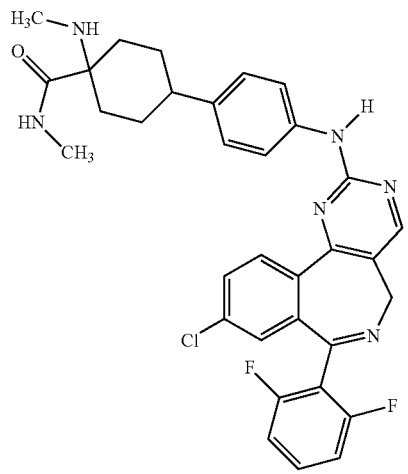 [SMILES: CNC(=O)C1(NC)CCC(c2ccc(Nc3ncc4c(n3)-c3ccc(Cl)cc3C(c3c(F)cccc3F)=NC4)cc2)CC1]
I-443
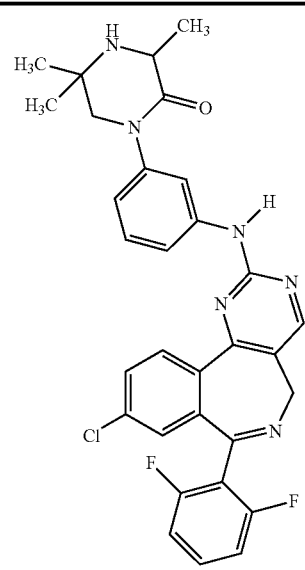
I-446
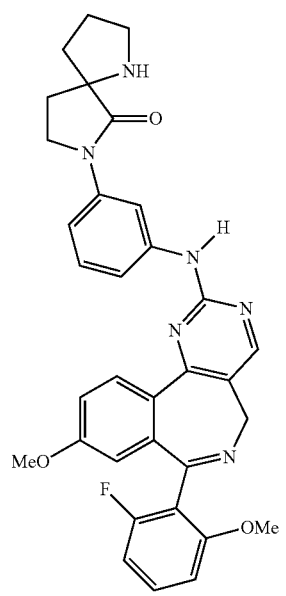 [SMILES: COc1ccc2c(c1)C(c1c(F)cccc1OC)=NCc1cnc(Nc3cccc(N4CCC5(CCCN5)C4=O)c3)nc1-2]
I-444
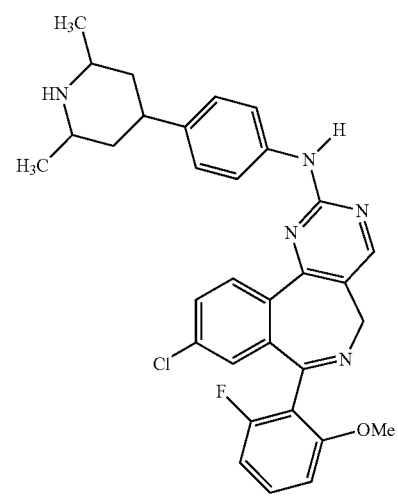
I-447
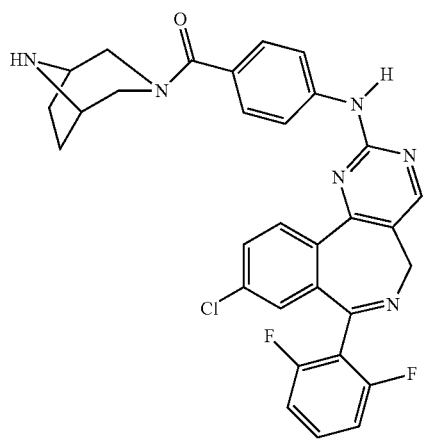 [SMILES: O=C(c1ccc(Nc2ncc3c(n2)-c2ccc(Cl)cc2C(c2c(F)cccc2F)=NC3)cc1)N1CC2CCC(C1)N2]
I-445
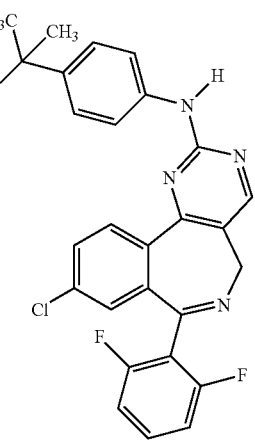
I-448

TABLE 3-continued
Aurora Kinase Inhibitors
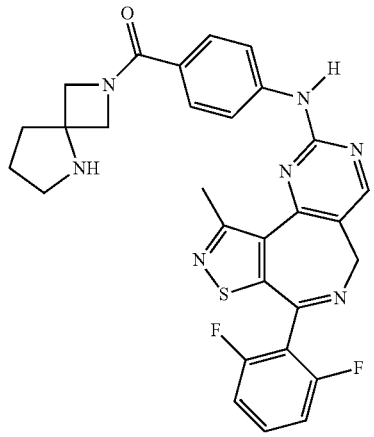 [SMILES: Cc1nsc2c1-c1nc(Nc3ccc(C(=O)N4CC5(CCCN5)C4)cc3)ncc1CN=C2c1c(F)cccc1F]
I-449
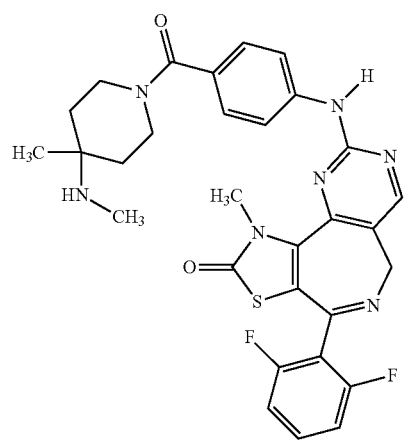 [SMILES: CNC1(C)CCN(C(=O)c2ccc(Nc3ncc4c(n3)-c3c(sc(=O)n3C)C(c3c(F)cccc3F)=NC4)cc2)CC1]
I-450
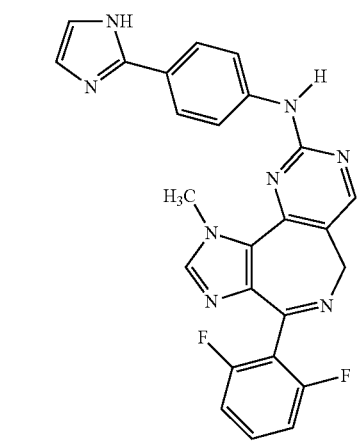 [SMILES: Cn1cnc2c1-c1nc(Nc3ccc(-c4ncc[nH]4)cc3)ncc1CN=C2c1c(F)cccc1F]
I-451
TABLE 3-continued
Aurora Kinase Inhibitors
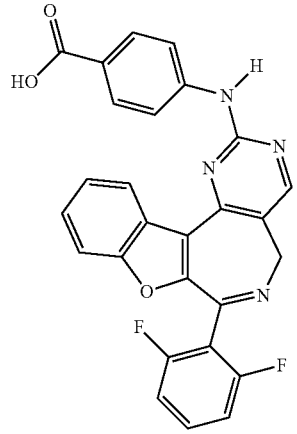 [SMILES: O=C(O)c1ccc(Nc2ncc3c(n2)-c2c(oc4ccccc24)C(c2c(F)cccc2F)=NC3)cc1]
I-452
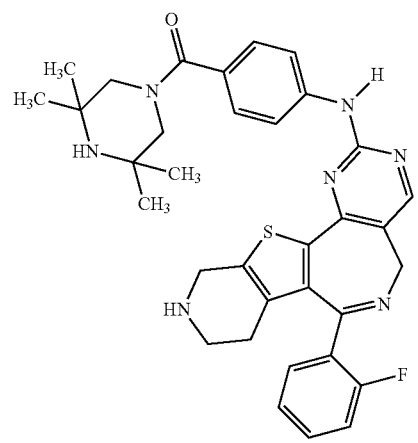 [SMILES: CC1(C)CN(C(=O)c2ccc(Nc3ncc4c(n3)-c3sc5c(c3C(c3ccccc3F)=NC4)CCNC5)cc2)CC(C)(C)N1]
I-453
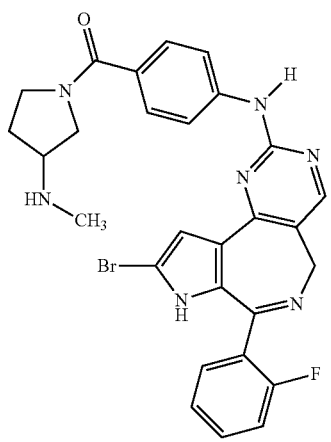 [SMILES: CNC1CCN(C(=O)c2ccc(Nc3ncc4c(n3)-c3cc(Br)[nH]c3C(c3ccccc3F)=NC4)cc2)C1]
I-454

TABLE 3-continued
Aurora Kinase Inhibitors
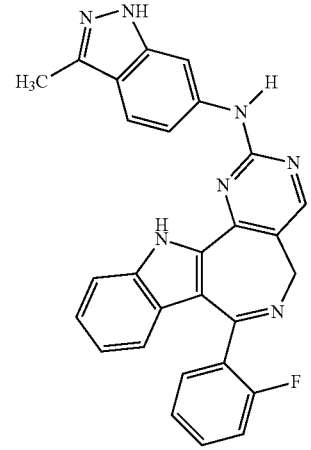 [SMILES: Cc1n[nH]c2cc(Nc3ncc4c(n3)-c3[nH]c5ccccc5c3C(c3ccccc3F)=NC4)ccc12]
I-455
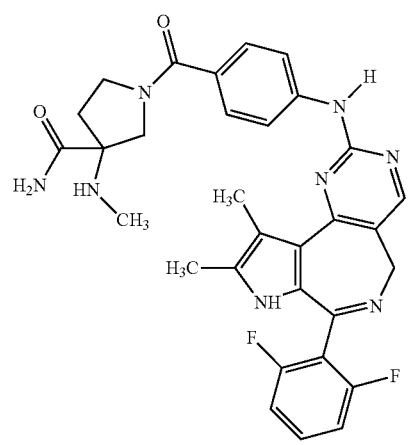 [SMILES: CNC1(C(N)=O)CCN(C(=O)c2ccc(Nc3ncc4c(n3)-c3c([nH]c(C)c3C)C(c3c(F)cccc3F)=NC4)cc2)C1]
I-456
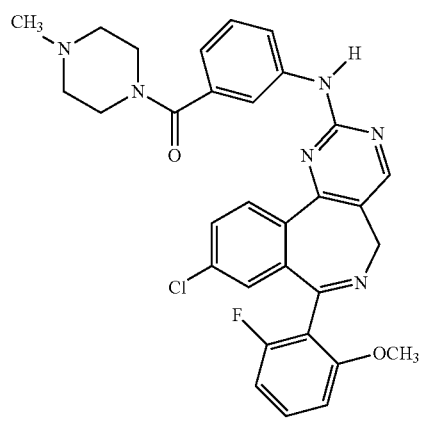 [SMILES: COc1cccc(F)c1C1=NCc2cnc(Nc3cccc(C(=O)N4CCN(C)CC4)c3)nc2-c2ccc(Cl)cc21]
I-457
TABLE 3-continued
Aurora Kinase Inhibitors
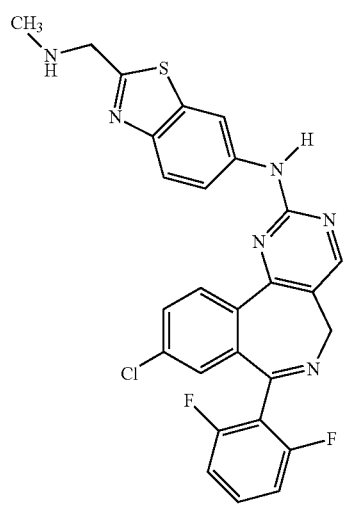 [SMILES: CNCc1nc2ccc(Nc3ncc4c(n3)-c3ccc(Cl)cc3C(c3c(F)cccc3F)=NC4)cc2s1]
I-458
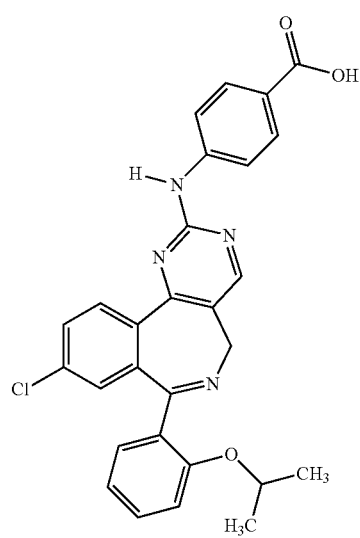
I-459
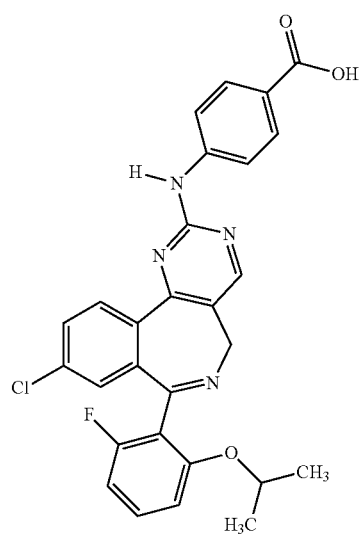 [SMILES: CC(C)Oc1cccc(F)c1C1=NCc2cnc(Nc3ccc(C(=O)O)cc3)nc2-c2ccc(Cl)cc21]
I-460

TABLE 3-continued
Aurora Kinase Inhibitors
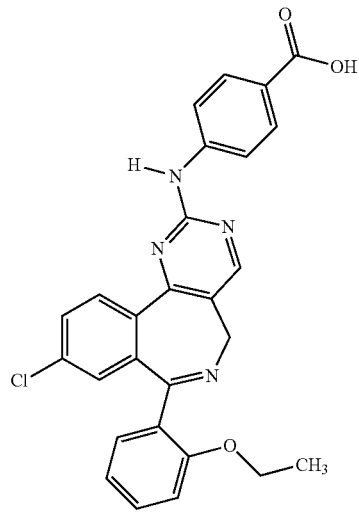 [SMILES: CCOc1ccccc1C1=NCc2cnc(Nc3ccc(C(=O)O)cc3)nc2-c2ccc(Cl)cc21]
I-461
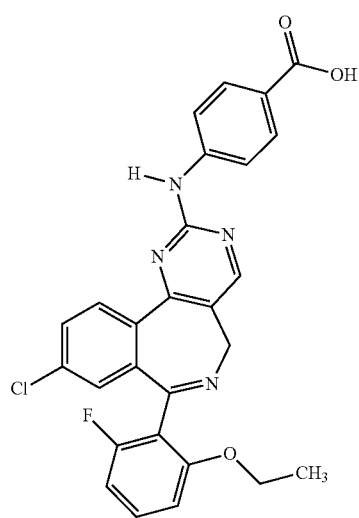 [SMILES: CCOc1cccc(F)c1C1=NCc2cnc(Nc3ccc(C(=O)O)cc3)nc2-c2ccc(Cl)cc21]
I-462
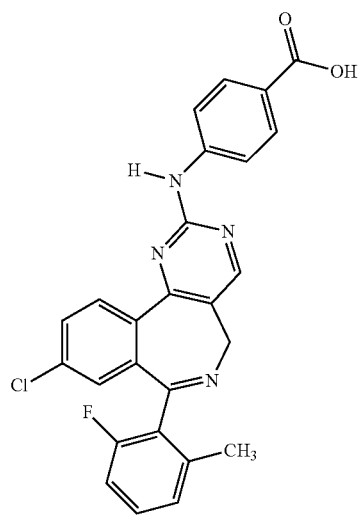 [SMILES: Cc1cccc(F)c1C1=NCc2cnc(Nc3ccc(C(=O)O)cc3)nc2-c2ccc(Cl)cc21]
I-463
TABLE 3-continued
Aurora Kinase Inhibitors
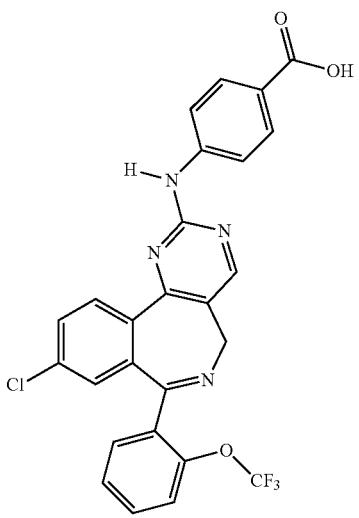 [SMILES: O=C(O)c1ccc(Nc2ncc3c(n2)-c2ccc(Cl)cc2C(c2ccccc2OC(F)(F)F)=NC3)cc1]
I-464
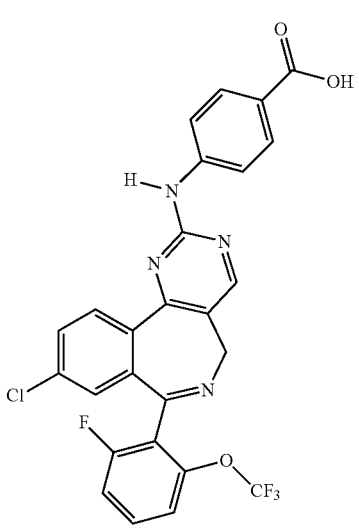 [SMILES: O=C(O)c1ccc(Nc2ncc3c(n2)-c2ccc(Cl)cc2C(c2c(F)cccc2OC(F)(F)F)=NC3)cc1]
I-465
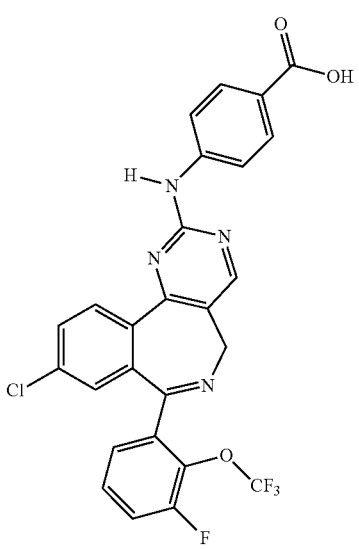 [SMILES: O=C(O)c1ccc(Nc2ncc3c(n2)-c2ccc(Cl)cc2C(c2cccc(F)c2OC(F)(F)F)=NC3)cc1]
I-466

TABLE 3-continued
Aurora Kinase Inhibitors
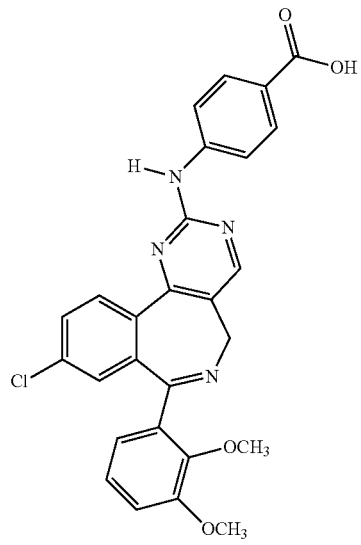 [SMILES: COc1cccc(C2=NCc3cnc(Nc4ccc(C(=O)O)cc4)nc3-c3ccc(Cl)cc32)c1OC]
I-467
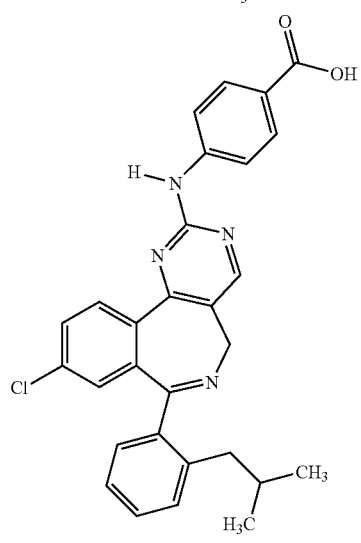
I-468
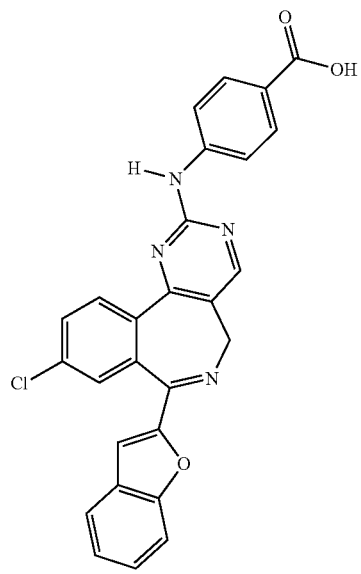 [SMILES: O=C(O)c1ccc(Nc2ncc3c(n2)-c2ccc(Cl)cc2C(c2cc4ccccc4o2)=NC3)cc1]
I-469
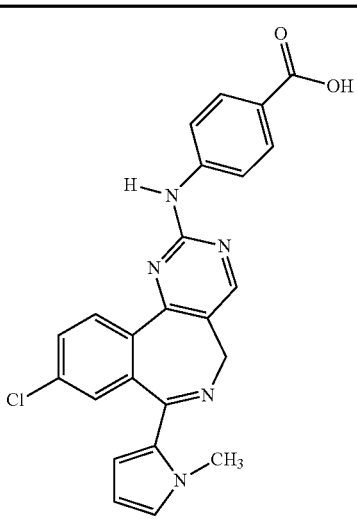
I-470
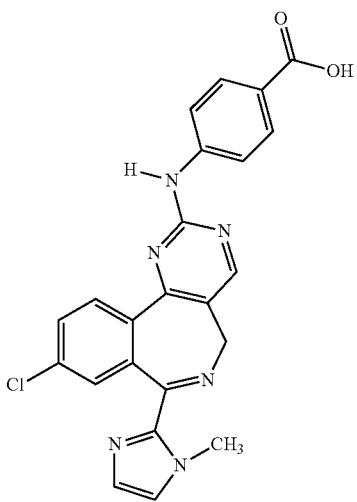 [SMILES: Cn1ccnc1C1=NCc2cnc(Nc3ccc(C(=O)O)cc3)nc2-c2ccc(Cl)cc21]
I-471
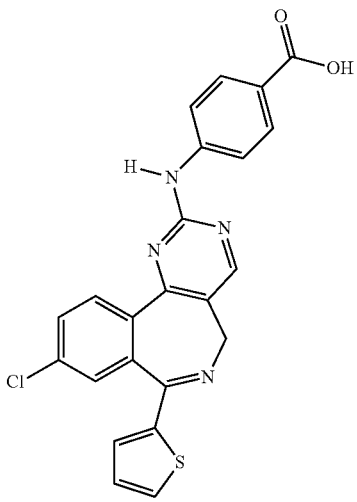 [SMILES: O=C(O)c1ccc(Nc2ncc3c(n2)-c2ccc(Cl)cc2C(c2cccs2)=NC3)cc1]
I-472

TABLE 3-continued
Aurora Kinase Inhibitors
I-473
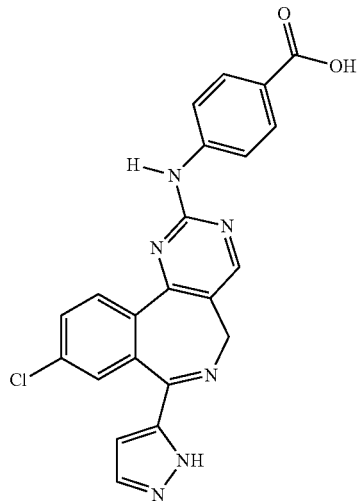 [SMILES: O=C(O)c1ccc(Nc2ncc3c(n2)-c2ccc(Cl)cc2C(c2ccn[nH]2)=NC3)cc1]
I-474
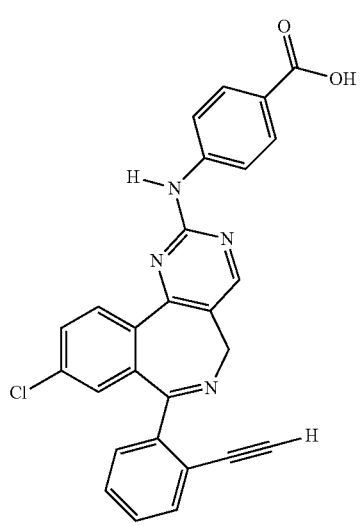 [SMILES: C#Cc1ccccc1C1=NCc2cnc(Nc3ccc(C(=O)O)cc3)nc2-c2ccc(Cl)cc21]
I-475
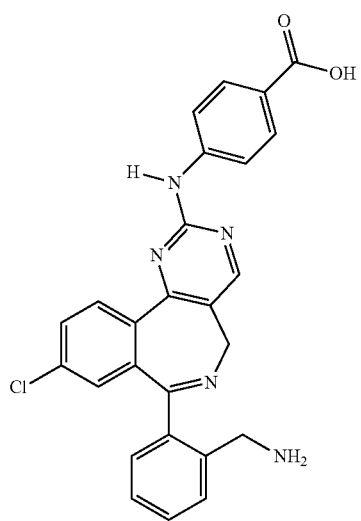 [SMILES: NCc1ccccc1C1=NCc2cnc(Nc3ccc(C(=O)O)cc3)nc2-c2ccc(Cl)cc21]
I-476
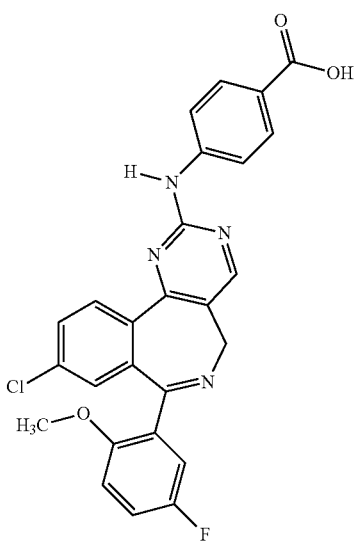 [SMILES: COc1ccc(F)cc1C1=NCc2cnc(Nc3ccc(C(=O)O)cc3)nc2-c2ccc(Cl)cc21]
I-477
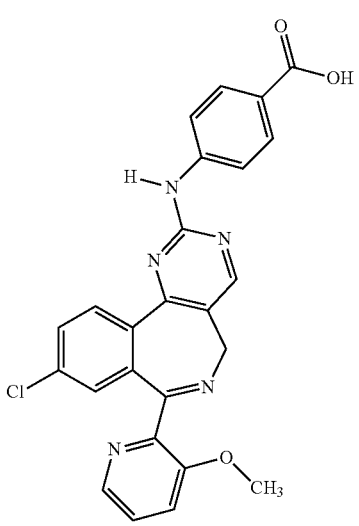 [SMILES: COc1cccnc1C1=NCc2cnc(Nc3ccc(C(=O)O)cc3)nc2-c2ccc(Cl)cc21]
I-478
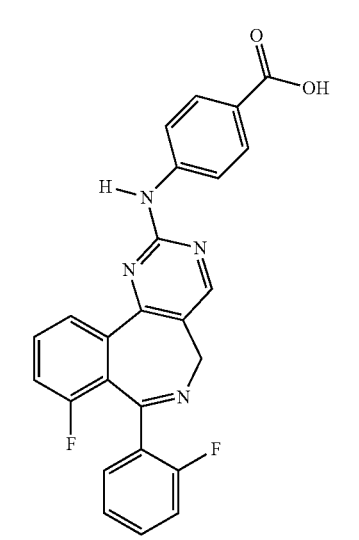 [SMILES: O=C(O)c1ccc(Nc2ncc3c(n2)-c2cccc(F)c2C(c2ccccc2F)=NC3)cc1]

TABLE 3-continued
Aurora Kinase Inhibitors
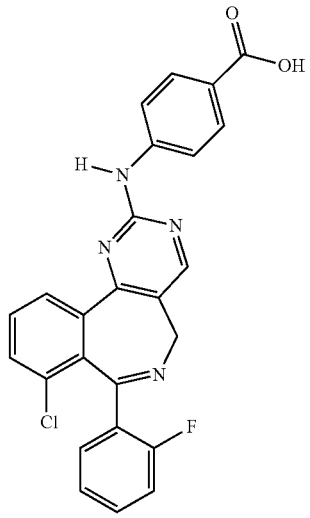 [SMILES: O=C(O)c1ccc(Nc2ncc3c(n2)-c2cccc(Cl)c2C(c2ccccc2F)=NC3)cc1]
I-479
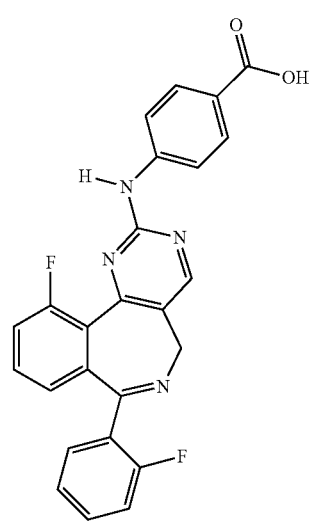 [SMILES: O=C(O)c1ccc(Nc2ncc3c(n2)-c2c(F)cccc2C(c2ccccc2F)=NC3)cc1]
I-480
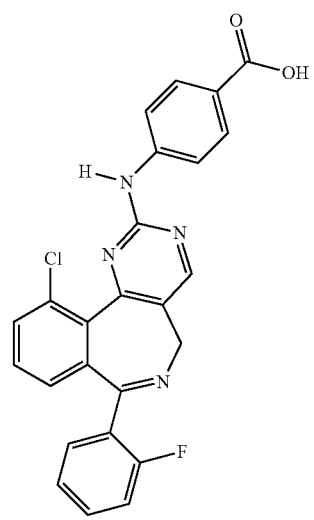 [SMILES: O=C(O)c1ccc(Nc2ncc3c(n2)-c2c(Cl)cccc2C(c2ccccc2F)=NC3)cc1]
I-481
TABLE 3-continued
Aurora Kinase Inhibitors
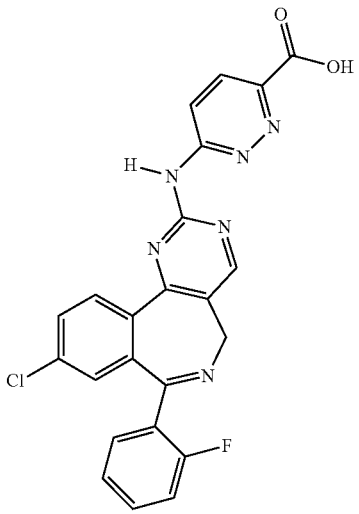 [SMILES: O=C(O)c1ccc(Nc2ncc3c(n2)-c2ccc(Cl)cc2C(c2ccccc2F)=NC3)nn1]
I-482
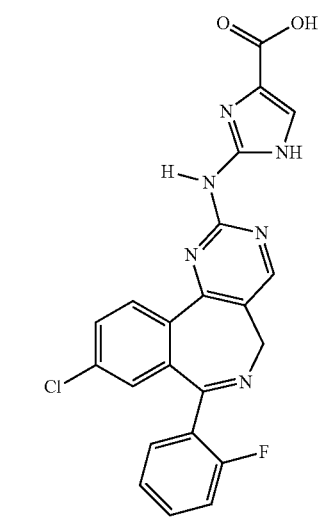 [SMILES: O=C(O)c1c[nH]c(Nc2ncc3c(n2)-c2ccc(Cl)cc2C(c2ccccc2F)=NC3)n1]
I-483
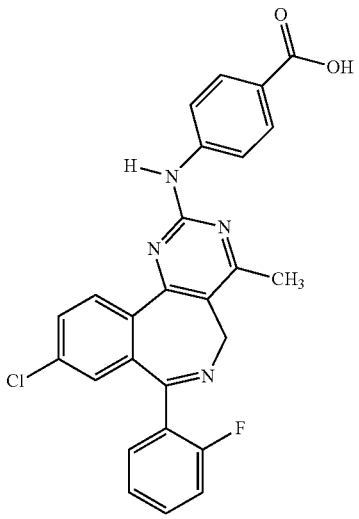 [SMILES: Cc1nc(Nc2ccc(C(=O)O)cc2)nc2c1CN=C(c1ccccc1F)c1cc(Cl)ccc1-2]
I-484

TABLE 3-continued
Aurora Kinase Inhibitors
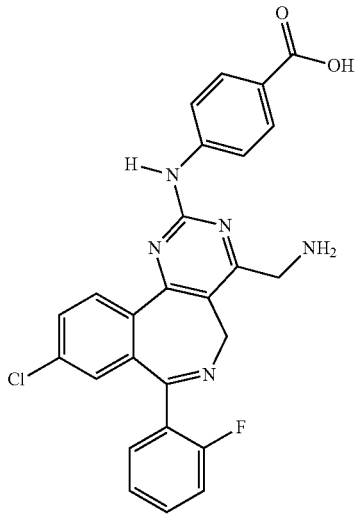 [SMILES: NCc1nc(Nc2ccc(C(=O)O)cc2)nc2c1CN=C(c1ccccc1F)c1cc(Cl)ccc1-2]
I-485
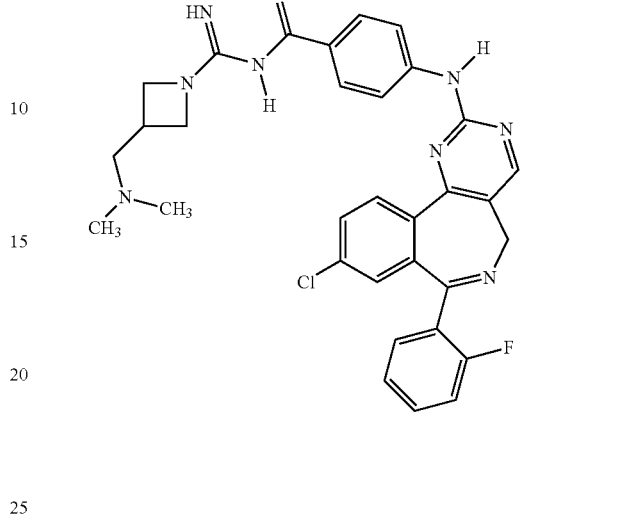
I-488
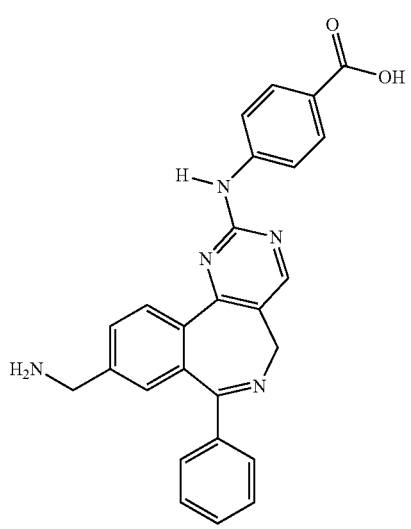 [SMILES: NCc1ccc2c(c1)C(c1ccccc1)=NCc1cnc(Nc3ccc(C(=O)O)cc3)nc1-2]
I-486
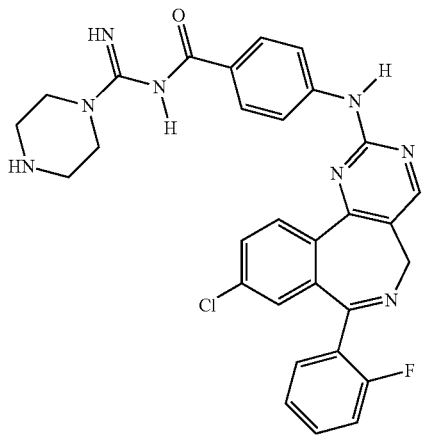
I-489
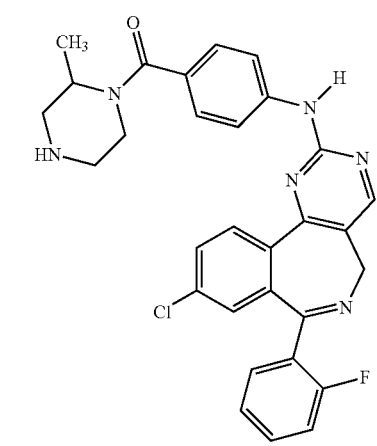 [SMILES: CC1CNCCN1C(=O)c1ccc(Nc2ncc3c(n2)-c2ccc(Cl)cc2C(c2ccccc2F)=NC3)cc1]
I-487
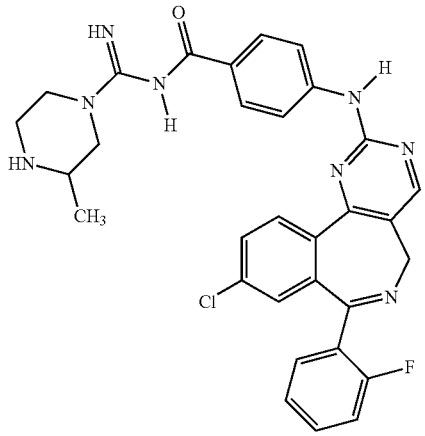 [SMILES: CC1CN(C(=N)NC(=O)c2ccc(Nc3ncc4c(n3)-c3ccc(Cl)cc3C(c3ccccc3F)=NC4)cc2)CCN1]
I-490

TABLE 3-continued
Aurora Kinase Inhibitors
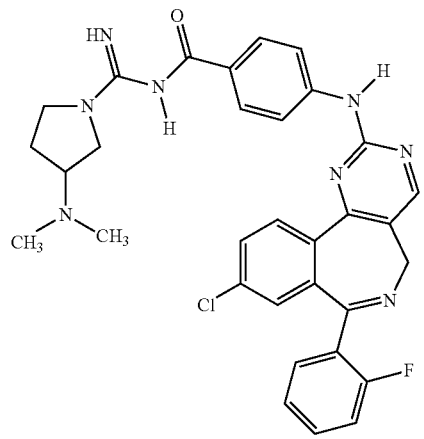 [SMILES: CN(C)C1CCN(C(=N)NC(=O)c2ccc(Nc3ncc4c(n3)-c3ccc(Cl)cc3C(c3ccccc3F)=NC4)cc2)C1]
I-491
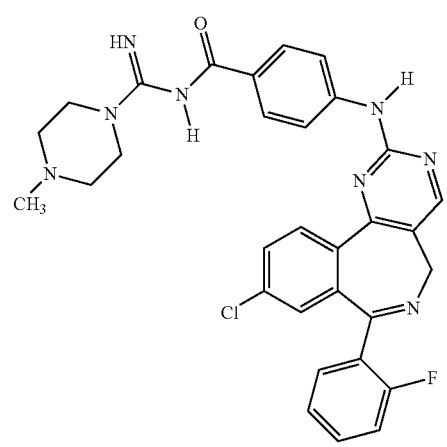 [SMILES: CN1CCN(C(=N)NC(=O)c2ccc(Nc3ncc4c(n3)-c3ccc(Cl)cc3C(c3ccccc3F)=NC4)cc2)CC1]
I-492
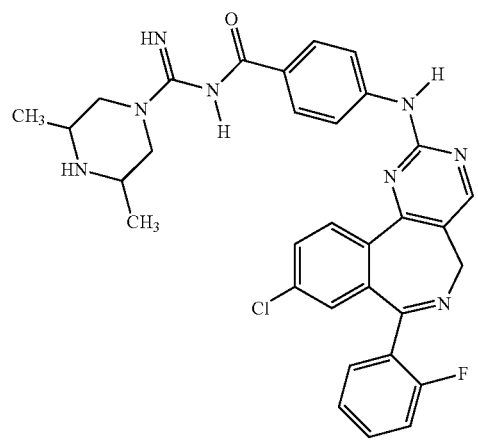 [SMILES: CC1CN(C(=N)NC(=O)c2ccc(Nc3ncc4c(n3)-c3ccc(Cl)cc3C(c3ccccc3F)=NC4)cc2)CC(C)N1]
I-493
TABLE 3-continued
Aurora Kinase Inhibitors
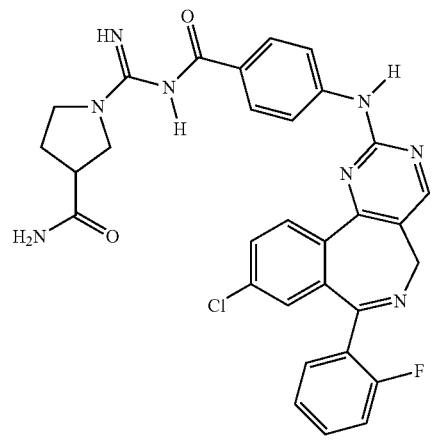 [SMILES: N=C(NC(=O)c1ccc(Nc2ncc3c(n2)-c2ccc(Cl)cc2C(c2ccccc2F)=NC3)cc1)N1CCC(C(N)=O)C1]
I-494
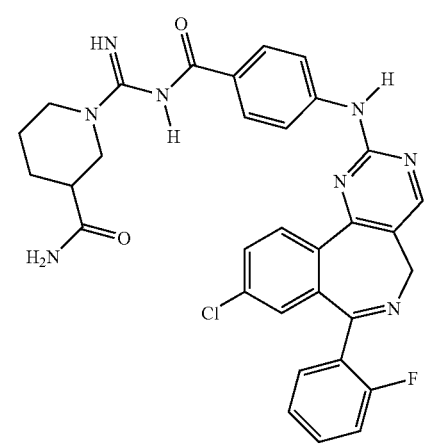 [SMILES: N=C(NC(=O)c1ccc(Nc2ncc3c(n2)-c2ccc(Cl)cc2C(c2ccccc2F)=NC3)cc1)N1CCCC(C(N)=O)C1]
I-495
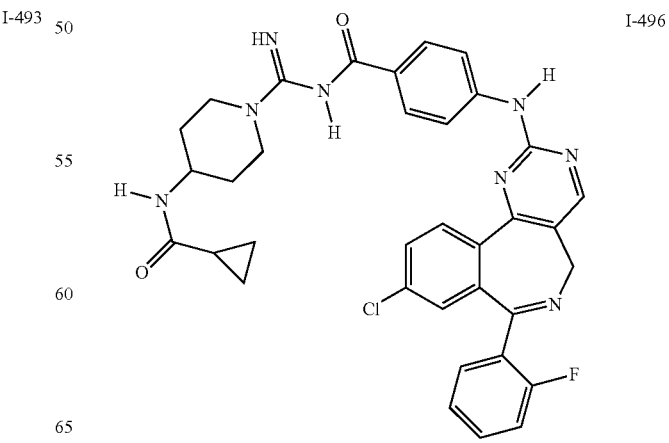
I-496

TABLE 3-continued
Aurora Kinase Inhibitors
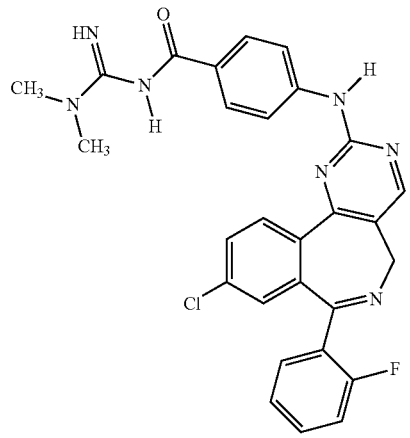 [SMILES: CN(C)C(=N)NC(=O)c1ccc(Nc2ncc3c(n2)-c2ccc(Cl)cc2C(c2ccccc2F)=NC3)cc1]
I-497
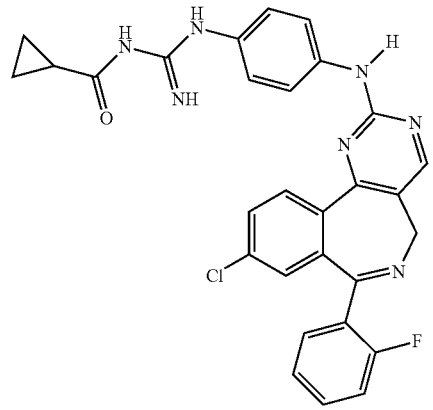 [SMILES: N=C(NC(=O)C1CC1)Nc1ccc(Nc2ncc3c(n2)-c2ccc(Cl)cc2C(c2ccccc2F)=NC3)cc1]
I-498
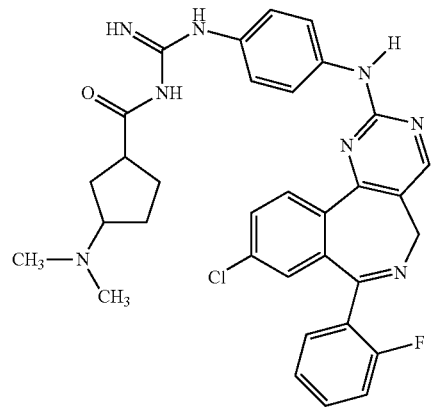 [SMILES: CN(C)C1CCC(C(=O)NC(=N)Nc2ccc(Nc3ncc4c(n3)-c3ccc(Cl)cc3C(c3ccccc3F)=NC4)cc2)C1]
I-499
TABLE 3-continued
Aurora Kinase Inhibitors
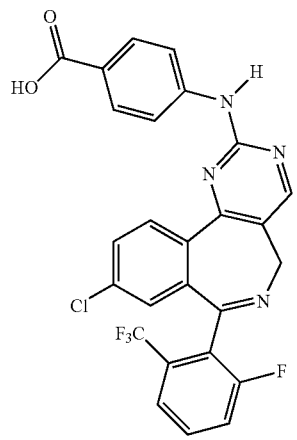 [SMILES: O=C(O)c1ccc(Nc2ncc3c(n2)-c2ccc(Cl)cc2C(c2c(F)cccc2C(F)(F)F)=NC3)cc1]
I-500
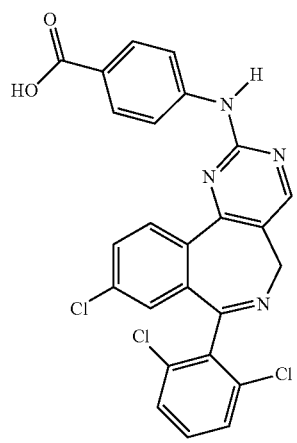
I-501
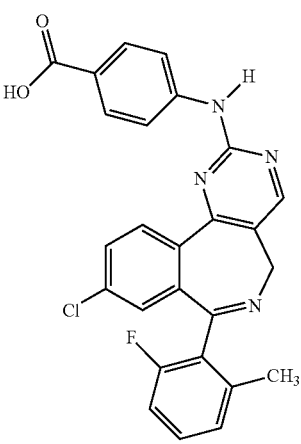 [SMILES: Cc1cccc(F)c1C1=NCc2cnc(Nc3ccc(C(=O)O)cc3)nc2-c2ccc(Cl)cc21]
I-502

TABLE 3-continued
Aurora Kinase Inhibitors
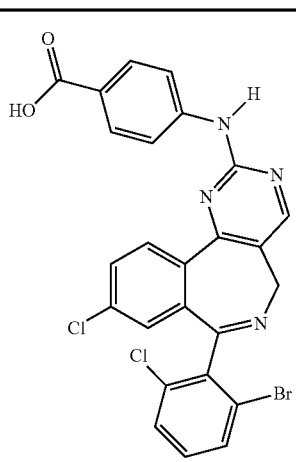
I-503
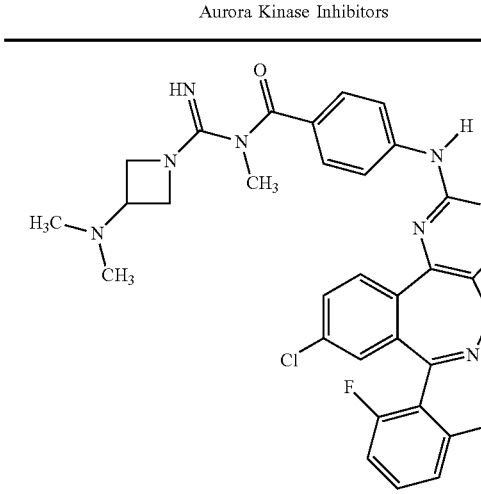
I-506
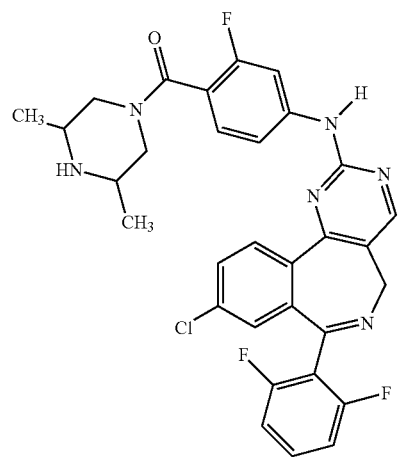 [SMILES: CC1CN(C(=O)c2ccc(Nc3ncc4c(n3)-c3ccc(Cl)cc3C(c3c(F)cccc3F)=NC4)cc2F)CC(C)N1]
I-504
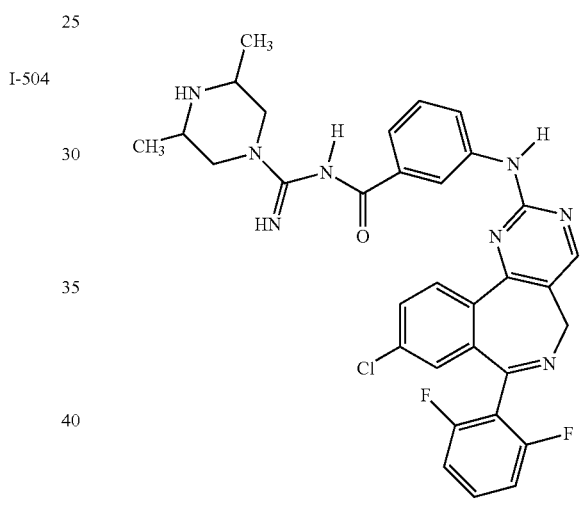
I-507
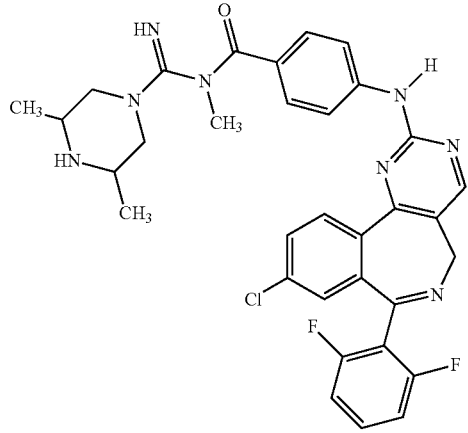 [SMILES: CC1CN(C(=N)N(C)C(=O)c2ccc(Nc3ncc4c(n3)-c3ccc(Cl)cc3C(c3c(F)cccc3F)=NC4)cc2)CC(C)N1]
I-505
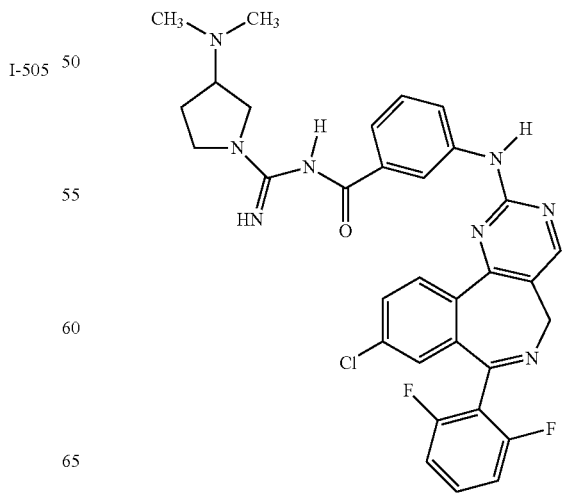
I-508

TABLE 3-continued
Aurora Kinase Inhibitors
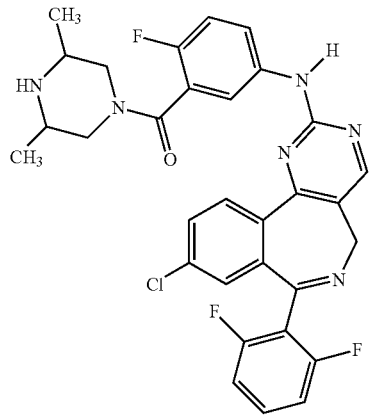 [SMILES: CC1CN(C(=O)c2cc(Nc3ncc4c(n3)-c3ccc(Cl)cc3C(c3c(F)cccc3F)=NC4)ccc2F)CC(C)N1]
I-509
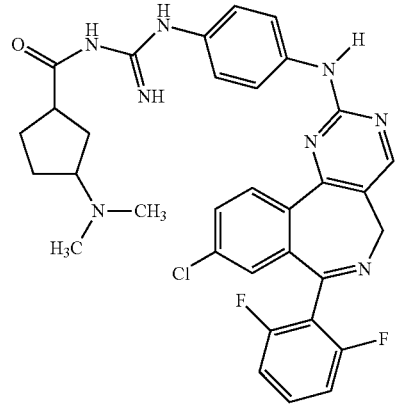 [SMILES: CN(C)C1CCC(C(=O)NC(=N)Nc2ccc(Nc3ncc4c(n3)-c3ccc(Cl)cc3C(c3c(F)cccc3F)=NC4)cc2)C1]
I-510
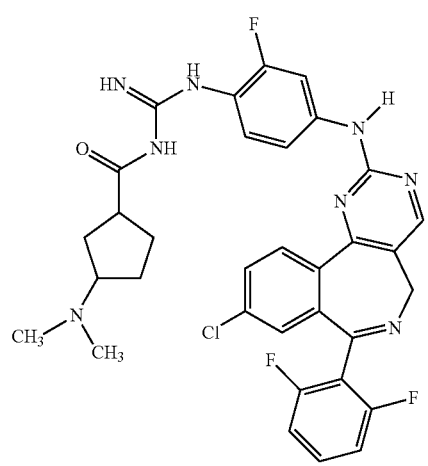 [SMILES: CN(C)C1CCC(C(=O)NC(=N)Nc2ccc(Nc3ncc4c(n3)-c3ccc(Cl)cc3C(c3c(F)cccc3F)=NC4)cc2F)C1]
I-511
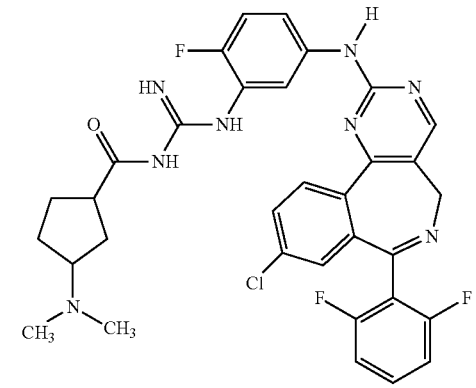 [SMILES: CN(C)C1CCC(C(=O)NC(=N)Nc2cc(Nc3ncc4c(n3)-c3ccc(Cl)cc3C(c3c(F)cccc3F)=NC4)ccc2F)C1]
I-512
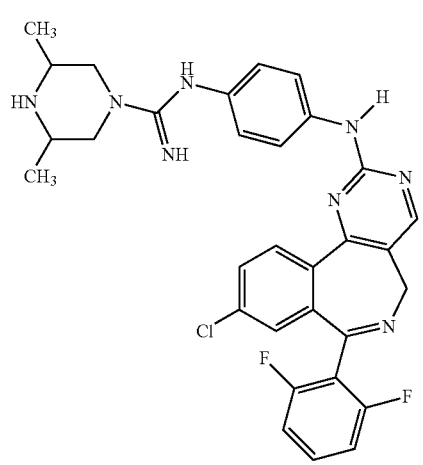 [SMILES: CC1CN(C(=N)Nc2ccc(Nc3ncc4c(n3)-c3ccc(Cl)cc3C(c3c(F)cccc3F)=NC4)cc2)CC(C)N1]
I-513
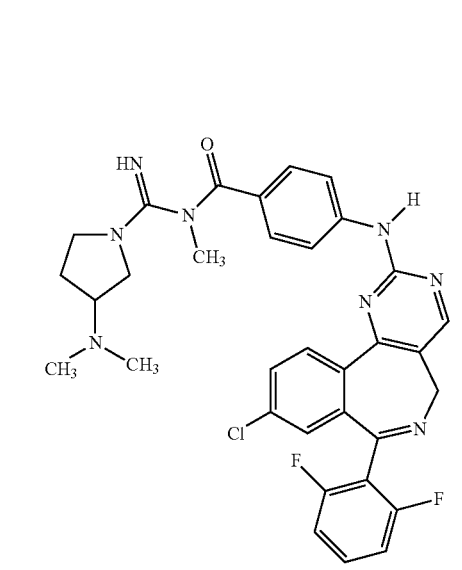 [SMILES: CN(C(=N)N1CCC(N(C)C)C1)C(=O)c1ccc(Nc2ncc3c(n2)-c2ccc(Cl)cc2C(c2c(F)cccc2F)=NC3)cc1]
I-514

TABLE 3-continued
Aurora Kinase Inhibitors
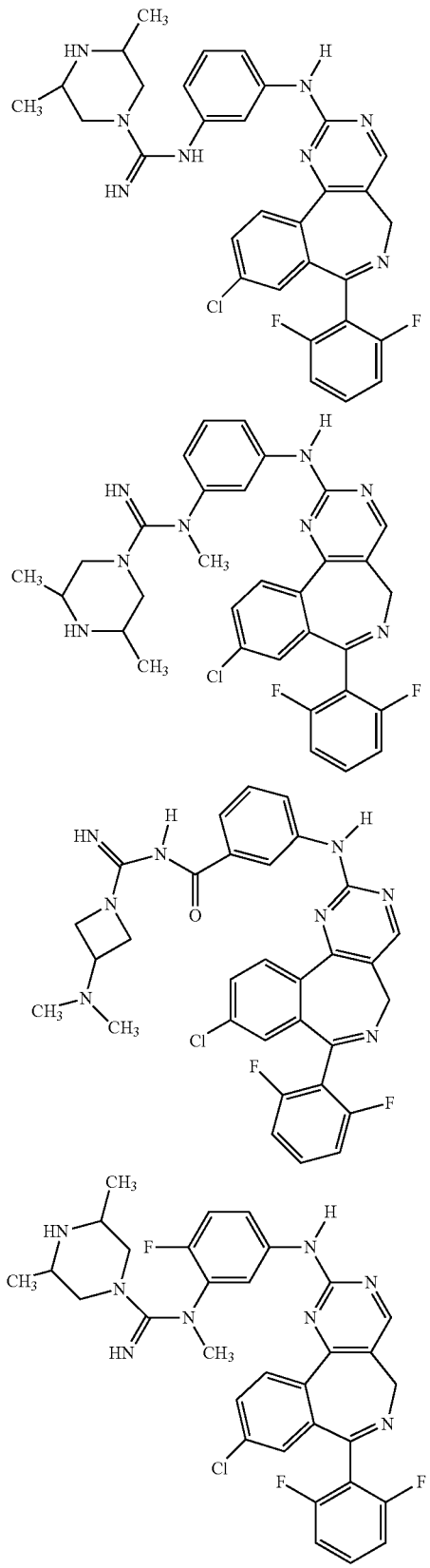
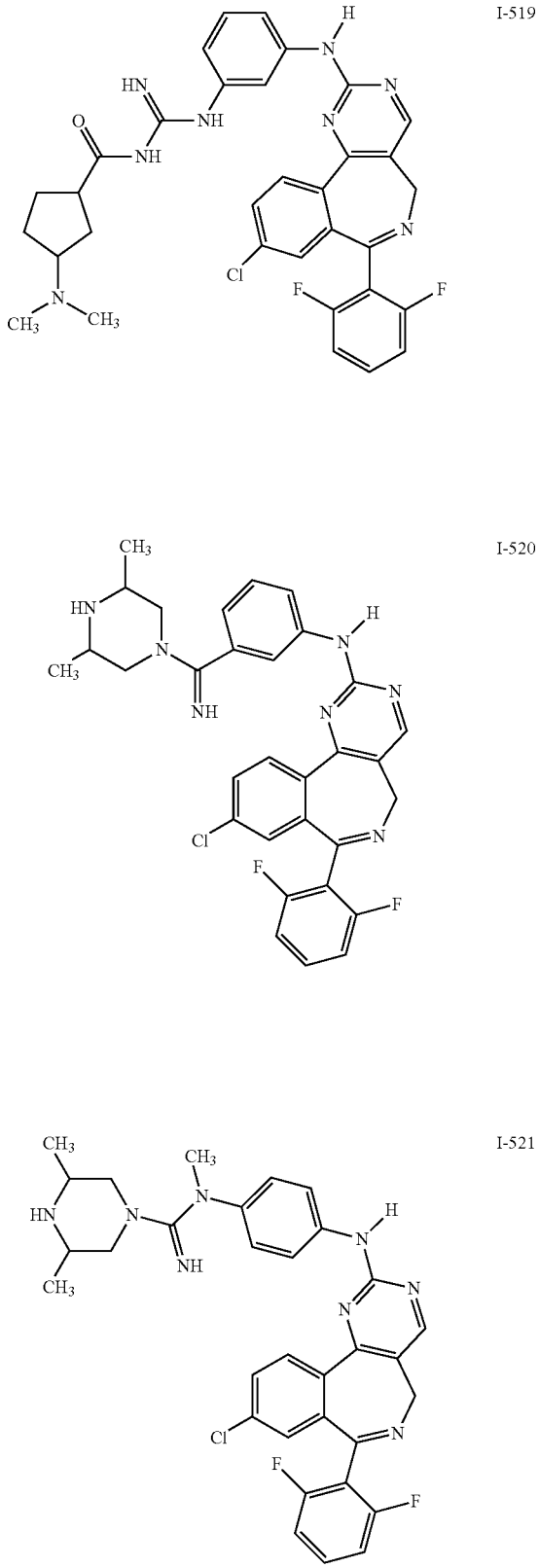

TABLE 3-continued
Aurora Kinase Inhibitors
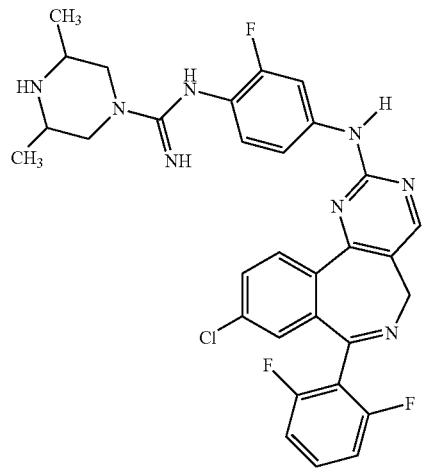 [SMILES: CC1CN(C(=N)Nc2ccc(Nc3ncc4c(n3)-c3ccc(Cl)cc3C(c3c(F)cccc3F)=NC4)cc2F)CC(C)N1]
I-522
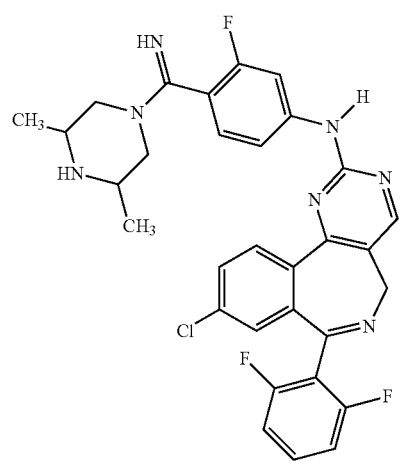 [SMILES: CC1CN(C(=N)c2ccc(Nc3ncc4c(n3)-c3ccc(Cl)cc3C(c3c(F)cccc3F)=NC4)cc2F)CC(C)N1]
I-523
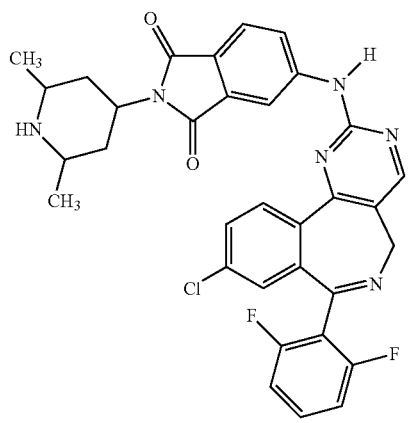 [SMILES: CC1CC(N2C(=O)c3ccc(Nc4ncc5c(n4)-c4ccc(Cl)cc4C(c4c(F)cccc4F)=NC5)cc3C2=O)CC(C)N1]
I-524
TABLE 3-continued
Aurora Kinase Inhibitors
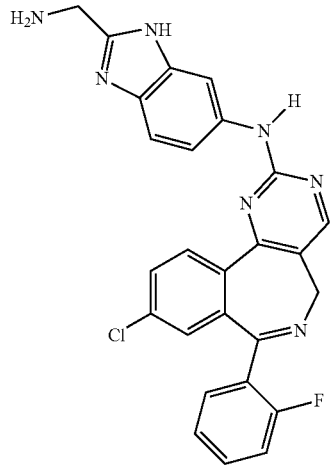 [SMILES: NCc1nc2ccc(Nc3ncc4c(n3)-c3ccc(Cl)cc3C(c3ccccc3F)=NC4)cc2[nH]1]
I-525
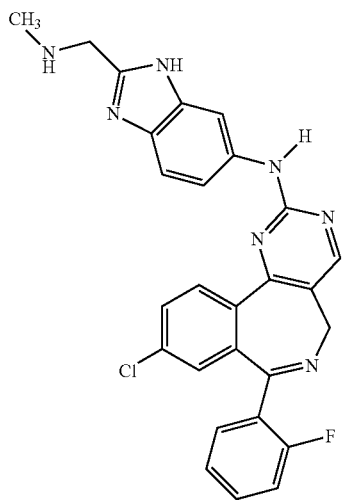 [SMILES: CNCc1nc2ccc(Nc3ncc4c(n3)-c3ccc(Cl)cc3C(c3ccccc3F)=NC4)cc2[nH]1]
I-526
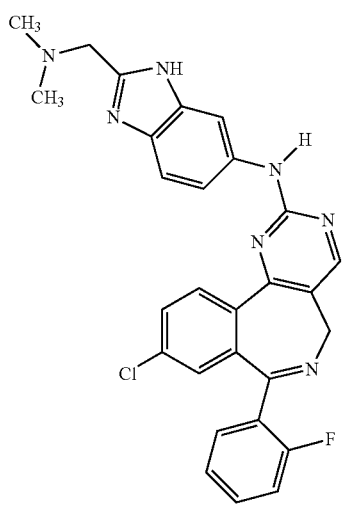 [SMILES: CN(C)Cc1nc2ccc(Nc3ncc4c(n3)-c3ccc(Cl)cc3C(c3ccccc3F)=NC4)cc2[nH]1]
I-527

TABLE 3-continued
Aurora Kinase Inhibitors
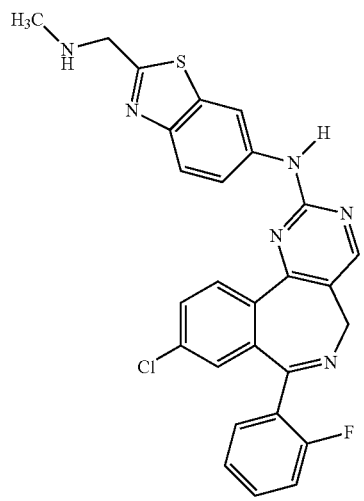 [SMILES: CNCc1nc2ccc(Nc3ncc4c(n3)-c3ccc(Cl)cc3C(c3ccccc3F)=NC4)cc2s1]
I-528
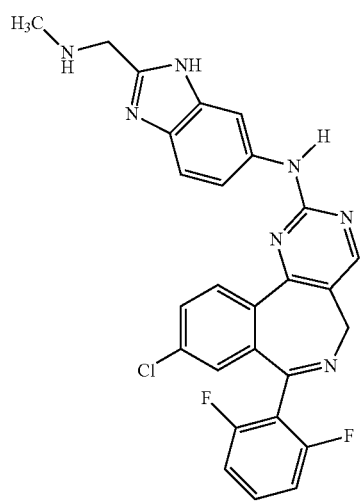 [SMILES: CNCc1nc2ccc(Nc3ncc4c(n3)-c3ccc(Cl)cc3C(c3c(F)cccc3F)=NC4)cc2[nH]1]
I-529
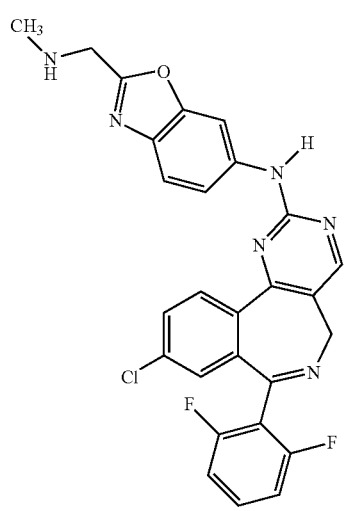 [SMILES: CNCc1nc2ccc(Nc3ncc4c(n3)-c3ccc(Cl)cc3C(c3c(F)cccc3F)=NC4)cc2o1]
I-530
TABLE 3-continued
Aurora Kinase Inhibitors
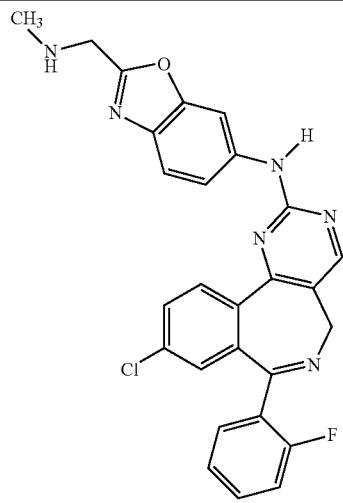
I-531
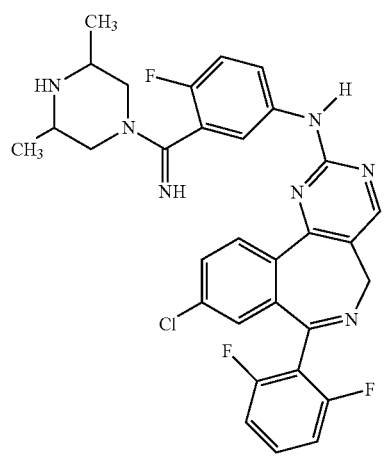 [SMILES: CC1CN(C(=N)c2cc(Nc3ncc4c(n3)-c3ccc(Cl)cc3C(c3c(F)cccc3F)=NC4)ccc2F)CC(C)N1]
I-532
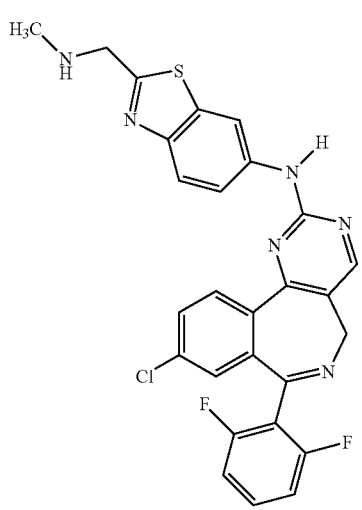 [SMILES: CNCc1nc2ccc(Nc3ncc4c(n3)-c3ccc(Cl)cc3C(c3c(F)cccc3F)=NC4)cc2s1]
I-533

TABLE 3-continued

Aurora Kinase Inhibitors

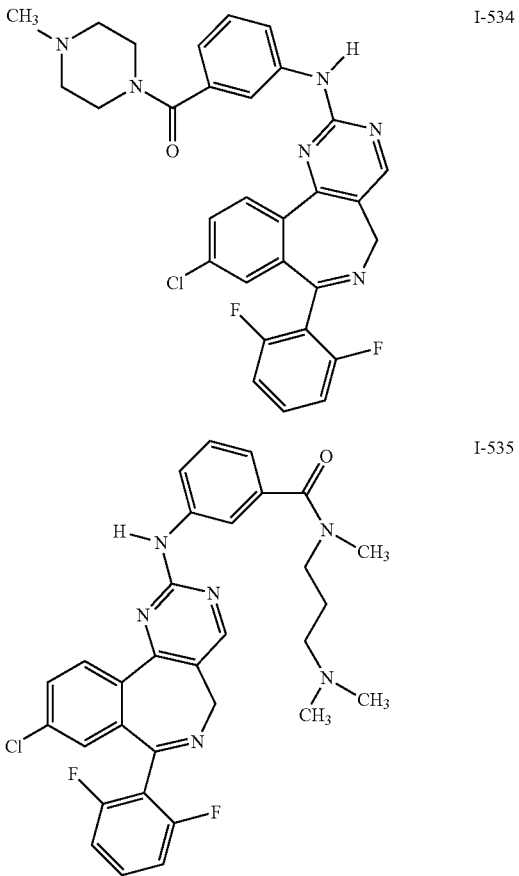

I-534

I-535

The compounds in Table 3 above also may be identified by the following chemical names:

I-1: 4-[9-Chloro-7-(2-fluoro-phenyl)-5H-benzo[c]pyrimido[4,5-e]azepin-2-ylamino]-N-(2-methylamino-ethyl)-benzamide I-2: N-(2-Amino-ethyl)-4-[9-chloro-7-(2-fluoro-phenyl)-5H-benzo[c]pyrimido[4,5-e]azepin-2-ylamino]-N-methyl-benzamide I-3: 4-[9-Chloro-7-(2-fluoro-phenyl)-5H-benzo[c]pyrimido[4,5-e]azepin-2-ylamino]-N-methyl-N-(2-methylamino-ethyl)-benzamide I-4: 4-[9-Chloro-7-(2-fluoro-phenyl)-5H-benzo[c]pyrimido[4,5-e]azepin-2-ylamino]-N-(2-dimethylamino-ethyl)-benzamide I-5: 4-[9-Chloro-7-(2-fluoro-phenyl)-5H-benzo[c]pyrimido[4,5-e]azepin-2-ylamino]-N-(2-dimethylamino-ethyl)-N-methyl-benzamide I-6: 4-[9-Chloro-7-(2-fluoro-phenyl)-5H-benzo[c]pyrimido[4,5-e]azepin-2-ylamino]-N-(3-dimethylamino-propyl)-benzamide I-7: 4-[9-Chloro-7-(2-fluoro-phenyl)-5H-benzo[c]pyrimido[4,5-e]azepin-2-ylamino]-N-(3-dimethylamino-propyl)-N-methyl-benzamide I-8: {4-[9-Chloro-7-(2-fluoro-phenyl)-5H-benzo[c]pyrimido[4,5-e]azepin-2-ylamino]-phenyl}-piperazin-1-yl-methanone I-9: {4-[9-Chloro-7-(2-fluoro-phenyl)-5H-benzo[c]pyrimido[4,5-e]azepin-2-ylamino]-phenyl}-(4-methyl-piperazin-1-yl)-methanone I-10: {4-[9-Chloro-7-(2-chloro-phenyl)-5H-benzo[c]pyrimido[4,5-e]azepin-2-ylamino]-phenyl}-(4-methyl-piperazin-1-yl)-methanone I-11: [4-(9-Chloro-7-o-tolyl-5H-benzo[c]pyrimido[4,5-e]azepin-2-ylamino)-phenyl]-(4-methyl-piperazin-1-yl)-methanone I-12: {4-[9-Chloro-7-(2-methoxy-phenyl)-5H-benzo[c]pyrimido[4,5-e]azepin-2-ylamino]-phenyl}-(4-methyl-piperazin-1-yl)-methanone I-13: {4-[9-Chloro-7-(4-fluoro-phenyl)-5H-benzo[c]pyrimido[4,5-e]azepin-2-ylamino]-phenyl}-(4-methyl-piperazin-1-yl)-methanone I-14: {4-[7-(2-Fluoro-phenyl)-9-methyl-5H-benzo[c]pyrimido[4,5-e]azepin-2-ylamino]-phenyl}-(4-methyl-piperazin-1-yl)-methanone I-15: 2-{3-[9-Chloro-7-(2-fluoro-phenyl)-5H-benzo[c]pyrimido[4,5-e]azepin-2-ylamino]-phenyl}-1-(4-methyl-piperazin-1-yl)-ethanone I-16: 4-[9-Chloro-7-(2-fluoro-phenyl)-5H-benzo[c]pyrimido[4,5-e]azepin-2-ylamino]-N-piperidin-4-yl-benzamide I-17: (4-Amino-piperidin-1-yl)-{4-[9-chloro-7-(2-fluoro-phenyl)-5H-benzo[c]pyrimido[4,5-e]azepin-2-ylamino]-phenyl}-methanone I-18: {4-[9-Chloro-7-(2-fluoro-phenyl)-5H-benzo[c]pyrimido[4,5-e]azepin-2-ylamino]-phenyl}-(4-dimethylamino-piperidin-1-yl)-methanone I-19: 4-[9-Chloro-7-(2-fluoro-phenyl)-5H-benzo[c]pyrimido[4,5-e]azepin-2-ylamino]-N-[3-(4-methyl-piperazin-1-yl)-propyl]-benzamide I-20: 4-[9-Chloro-7-(2-chloro-phenyl)-5H-benzo[c]pyrimido[4,5-e]azepin-2-ylamino]-N-[3-(4-methyl-piperazin-1-yl)-propyl]-benzamide I-21: 4-(9-Chloro-7-o-tolyl-5H-benzo[c]pyrimido[4,5-e]azepin-2-ylamino)-N-[3-(4-methyl-piperazin-1-yl)-propyl]-benzamide I-22: 4-[9-Chloro-7-(2-methoxy-phenyl)-5H-benzo[c]pyrimido[4,5-e]azepin-2-ylamino]-N-[3-(4-methyl-piperazin-1-yl)-propyl]-benzamide I-23: 4-[9-Chloro-7-(4-fluoro-phenyl)-5H-benzo[c]pyrimido[4,5-e]azepin-2-ylamino]-N-[3-(4-methyl-piperazin-1-yl)-propyl]-benzamide I-24: 4-[7-(2-Fluoro-phenyl)-9-methyl-5H-benzo[c]pyrimido[4,5-e]azepin-2-ylamino]-N-[3-(4-methyl-piperazin-1-yl)-propyl]-benzamide I-25: 2-{3-[9-Chloro-7-(2-fluoro-phenyl)-5H-benzo[c]pyrimido[4,5-e]azepin-2-ylamino]-phenyl}-N-[3-(4-methyl-piperazin-1-yl)-propyl]-acetamide I-26: {4-[9-Chloro-7-(2-fluoro-phenyl)-5H-benzo[c]pyrimido[4,5-e]azepin-2-ylamino]-phenyl}-morpholin-4-yl-methanone I-27: 4-[9-Chloro-7-(2-fluoro-phenyl)-5H-benzo[c]pyrimido[4,5-e]azepin-2-ylamino]-N,N-bis-(2-hydroxy-ethyl)-benzamide I-28: {4-[9-Chloro-7-(2-chloro-phenyl)-5H-benzo[c]pyrimido[4,5-e]azepin-2-ylamino]-phenyl}-morpholin-4-yl-methanone I-29: 4-[9-Chloro-7-(2-fluoro-phenyl)-5H-benzo[c]pyrimido[4,5-e]azepin-2-ylamino]-N-(2-morpholin-4-yl-ethyl)-benzamide I-30: 4-[9-Chloro-7-(2-chloro-phenyl)-5H-benzo[e]pyrimido[4,5-e]azepin-2-ylamino]-N-(2-morpholin-4-yl-ethyl)-benzamide I-31: 4-(9-Chloro-7-o-tolyl-5H-benzo[c]pyrimido[4,5-e]azepin-2-ylamino)-N-(2-morpholin-4-yl-ethyl)-benzamide I-32: 4-[9-Chloro-7-(2-methoxy-phenyl)-5H-benzo[c]pyrimido[4,5-e]azepin-2-ylamino]-N-(3-morpholin-4-yl-propyl)-benzamide
I-33: 4-[9-Chloro-7-(4-fluoro-phenyl)-5H-benzo[c]pyrimido[4,5-e]azepin-2-ylamino]-N-(2-morpholin-4-yl-ethyl)-benzamide
I-34: 4-[9-Chloro-7-(2-chloro-phenyl)-5H-benzo[c]pyrimido[4,5-e]azepin-2-ylamino]-2-hydroxy-N-(2-morpholin-4-yl-ethyl)-benzamide
I-35: [9-Chloro-7-(2-chloro-phenyl)-5H-benzo[c]pyrimido[4,5-e]azepin-2-yl]-pyridin-2-yl-amine
I-36: [9-Chloro-7-(2-fluoro-phenyl)-5H-benzo[c]pyrimido[4,5-e]azepin-2-yl]-(3,5-dichloro-phenyl)-amine
I-37: [9-Chloro-7-(2-fluoro-phenyl)-5H-benzo[c]pyrimido[4,5-e]azepin-2-yl]-(4-methoxy-phenyl)-amine
I-38: [9-Chloro-7-(2-fluoro-phenyl)-5H-benzo[c]pyrimido[4,5-e]azepin-2-yl]-(4-ethoxy-phenyl)-amine
I-39: [9-Chloro-7-(2-fluoro-phenyl)-5H-benzo[c]pyrimido[4,5-e]azepin-2-yl]-(3-methoxy-phenyl)-amine
I-40: [9-Chloro-7-(2-fluoro-phenyl)-5H-benzo[c]pyrimido[4,5-e]azepin-2-yl]-(2-methoxy-phenyl)-amine
I-41: [9-Chloro-7-(2-fluoro-phenyl)-5H-benzo[c]pyrimido[4,5-e]azepin-2-yl]-(4-chloro-phenyl)-amine
I-42: [9-Chloro-7-(2-chloro-phenyl)-5H-benzo[c]pyrimido[4,5-e]azepin-2-yl]-(4-chloro-phenyl)-amine
I-43: [9-Chloro-7-(2-fluoro-phenyl)-5H-benzo[c]pyrimido[4,5-e]azepin-2-yl]-(3-chloro-phenyl)-amine
I-44: [9-Chloro-7-(2-fluoro-phenyl)-5H-benzo[c]pyrimido[4,5-e]azepin-2-yl]-(2-chloro-phenyl)-amine
I-45: 4-[9-Chloro-7-(2-chloro-phenyl)-5H-benzo[c]pyrimido[4,5-e]azepin-2-ylamino]-phenol
I-46: [9-Chloro-7-(2-fluoro-phenyl)-5H-benzo[c]pyrimido[4,5-e]azepin-2-yl]-(4-morpholin-4-yl-phenyl)-amine
I-47: [9-Chloro-7-(2-fluoro-phenyl)-5H-benzo[c]pyrimido[4,5-e]azepin-2-yl]-[4-(4-methyl-piperazin-1-yl)-phenyl]-amine
I-48: [9-Chloro-7-(2-fluoro-phenyl)-5H-benzo[c]pyrimido[4,5-e]azepin-2-yl]-(4-pyridin-4-ylmethyl-phenyl)-amine
I-49: 4-[9-Chloro-7-(2-fluoro-phenyl)-5H-benzo[c]pyrimido[4,5-e]azepin-2-ylamino]-benzonitrile
I-50: [9-Chloro-7-(2-fluoro-phenyl)-5H-benzo[c]pyrimido[4,5-e]azepin-2-yl]-(4-nitro-phenyl)-amine
I-51: 4-[7-(2-Fluoro-phenyl)-5H-benzo[c]pyrimido[4,5-e]azepin-2-ylamino]-benzoic acid
I-52: 4-[9-Chloro-7-(2-fluoro-phenyl)-5H-benzo[c]pyrimido[4,5-e]azepin-2-ylamino]-benzoic acid
I-53: 4-[9-Chloro-7-(2-chloro-phenyl)-5H-benzo[c]pyrimido[4,5-e]azepin-2-ylamino]-benzoic acid
I-54: 4-(9-Chloro-7-o-tolyl-5H-benzo[c]pyrimido[4,5-e]azepin-2-ylamino)-benzoic acid
I-55: 4-[9-Chloro-7-(2-methoxy-phenyl)-5H-benzo[c]pyrimido[4,5-e]azepin-2-ylamino]-benzoic acid
I-56: 4-[9-Chloro-7-(4-fluoro-phenyl)-5H-benzo[c]pyrimido[4,5-e]azepin-2-ylamino]-benzoic acid
I-57: 4-[9-Fluoro-7-(2-fluoro-phenyl)-5H-benzo[c]pyrimido[4,5-e]azepin-2-ylamino]-benzoic acid
I-58: 4-[7-(2-Fluoro-phenyl)-9-methyl-5H-benzo[c]pyrimido[4,5-e]azepin-2-ylamino]-benzoic acid
I-59: 4-[10-Fluoro-7-(2-fluoro-phenyl)-5H-benzo[c]pyrimido[4,5-e]azepin-2-ylamino]-benzoic acid
I-60: 4-[10-Chloro-7-(2-fluoro-phenyl)-5H-benzo[c]pyrimido[4,5-e]azepin-2-ylamino]-benzoic acid
I-61: 4-[10-Bromo-7-(2-fluoro-phenyl)-5H-benzo[c]pyrimido[4,5-e]azepin-2-ylamino]-benzoic acid
I-62: 4-[7-(2-Fluoro-phenyl)-10-methoxy-5H-benzo[c]pyrimido[4,5-e]azepin-2-ylamino]-benzoic acid
I-63: 4-[9-Chloro-7-(2-chloro-phenyl)-5H-benzo[c]pyrimido[4,5-e]azepin-2-ylamino]-benzamide
I-64: 3-[9-Chloro-7-(2-chloro-phenyl)-5H-benzo[c]pyrimido[4,5-e]azepin-2-ylamino]-benzamide
I-65: {3-[9-Chloro-7-(2-chloro-phenyl)-5H-benzo[c]pyrimido[4,5-e]azepin-2-ylamino]-phenyl}-acetic acid
I-66: 2-{3-[9-Chloro-7-(2-chloro-phenyl)-5H-benzo[c]pyrimido[4,5-e]azepin-2-ylamino]-phenyl}-acetamide
I-67: 4-[9-Chloro-7-(2-fluoro-phenyl)-5H-benzo[c]pyrimido[4,5-e]azepin-2-ylamino]-benzenesulfonic acid
I-68: 4-[9-Chloro-7-(2-fluoro-phenyl)-5H-benzo[c]pyrimido[4,5-e]azepin-2-ylamino]-benzenesulfonamide
I-69: 4-[9-Chloro-7-(2-chloro-phenyl)-5H-benzo[c]pyrimido[4,5-e]azepin-2-ylamino]-N-(5-methyl-isoxazol-3-yl)-benzenesulfonamide
I-70: [9-Chloro-7-(2-fluoro-phenyl)-5H-benzo[c]pyrimido[4,5-e]azepin-2-yl]-(4-trifluoromethanesulfonyl-phenyl)-amine
I-71: [9-Chloro-7-(2-fluoro-phenyl)-5H-benzo[c]pyrimido[4,5-e]azepin-2-yl]-(3,4-dimethoxy-phenyl)-amine
I-72: [9-Chloro-7-(2-fluoro-phenyl)-6,7-dihydro-5H-benzo[c]pyrimido-[4,5-e]azepin-2-yl]-(3,4-dimethoxy-phenyl)-amine
I-73: [9-Chloro-7-(2-chloro-phenyl)-5H-benzo[c]pyrimido[4,5-e]azepin-2-yl]-(3,4-dimethoxy-phenyl)-amine
I-74: (9-Chloro-7-o-tolyl-5H-benzo[c]pyrimido[4,5-e]azepin-2-yl)-(3,4-dimethoxy-phenyl)-amine
I-75: (3,4-Dimethoxy-phenyl)-[7-(2-fluoro-phenyl)-9-methyl-5H-benzo[c]pyrimido[4,5-e]azepin-2-yl]-amine
I-76: (3,4-Dimethoxy-phenyl)-[7-(2-fluoro-phenyl)-9-isopropyl-5H-benzo[c]pyrimido[4,5-e]azepin-2-yl]-amine
I-77: (3,4-Dimethoxy-phenyl)-[10-fluoro-7-(2-fluoro-phenyl)-5H-benzo[c]pyrimido[4,5-e]azepin-2-yl]-amine
I-78: [10-Bromo-7-(2-fluoro-phenyl)-5H-benzo[c]pyrimido[4,5-e]azepin-2-yl]-(3,4-dimethoxy-phenyl)-amine
I-79: (3,4-Dimethoxy-phenyl)-[7-(2-fluoro-phenyl)-10-trifluoromethyl-5H-benzo[c]pyrimido[4,5-e]azepin-2-yl]-amine
I-80: (3,4-Dimethoxy-phenyl)-[7-(2-fluoro-phenyl)-10-methyl-5H-benzo[c]pyrimido[4,5-e]azepin-2-yl]-amine
I-81: (3,4-Dimethoxy-phenyl)-[7-(2-fluoro-phenyl)-10-methoxy-5H-benzo[c]pyrimido[4,5-e]azepin-2-yl]-amine
I-82: (3,4-Dimethoxy-phenyl)-[7-(2-fluoro-phenyl)-11-methyl-5H-benzo[c]pyrimido[4,5-e]azepin-2-yl]-amine
I-83: [9-Chloro-7-(2-fluoro-phenyl)-5H-benzo[c]pyrimido[4,5-e]azepin-2-yl]-(2,3-dihydro-benzo[1,4]dioxin-6-yl)-amine
I-84: [9-Chloro-7-(2-fluoro-phenyl)-5H-benzo[c]pyrimido[4,5-e]azepin-2-yl]-(4-fluoro-3-methoxy-phenyl)-amine
I-85: 4-[9-Chloro-7-(2-fluoro-phenyl)-5H-benzo[c]pyrimido[4,5-e]azepin-2-ylamino]-2-hydroxy-benzoic acid
I-86: 4-[9-Chloro-7-(2-chloro-phenyl)-5H-benzo[c]pyrimido[4,5-e]azepin-2-ylamino]-2-hydroxy-benzoic acid
I-87: [9-Chloro-7-(2-fluoro-phenyl)-5H-benzo[c]pyrimido[4,5-e]azepin-2-yl]-(3,4-dichloro-phenyl)-amine
I-88: [9-Chloro-7-(2-chloro-phenyl)-5H-benzo[c]pyrimido[4,5-e]azepin-2-yl]-(3,5-dimethoxy-phenyl)-amine
I-89: [9-Chloro-7-(2-fluoro-phenyl)-5H-benzo[c]pyrimido[4,5-e]azepin-2-yl]-(3,5-dimethyl-phenyl)-amine
I-90: [9-Chloro-7-(2-fluoro-phenyl)-5H-benzo[c]pyrimido[4,5-e]azepin-2-yl]-phenyl-amine
I-91: 4-[9-Chloro-7-(2,5-difluoro-phenyl)-5H-benzo[c]pyrimido[4,5-e]azepin-2-ylamino]-benzoic acid
I-92: 4-[9-Chloro-7-(2,3-difluoro-phenyl)-5H-benzo[c]pyrimido[4,5-e]azepin-2-ylamino]-benzoic acid I-93: (3-Dimethylamino-pyrrolidin-1-yl)-{4-[7-(2-fluoro-phenyl)-9-methoxy-5H-benzo[c]pyrimido[4,5-e]azepin-2-ylamino]-phenyl}-methanone
I-94: 4-[9-Chloro-7-(2,5-dimethoxy-phenyl)-5H-benzo[c]pyrimido-[4,5-e]azepin-2-ylamino]-benzoic acid
I-95: 4-[7-(2-Fluoro-phenyl)-9-methoxy-5H-benzo[c]pyrimido[4,5-e]azepin-2-ylamino]-N,N-bis-(2-hydroxy-ethyl)-benzamide
I-96: 4-[9-Chloro-7-(2,4-difluoro-phenyl)-5H-benzo[c]pyrimido[4,5-e]azepin-2-ylamino]-benzoic acid
I-97: 4-[9-Chloro-7-(2,4-difluoro-phenyl)-7H-benzo[c]pyrimido[4,5-e]azepin-2-ylamino]-benzoic acid
I-98: {4-[9-Chloro-7-(2-fluoro-phenyl)-5H-benzo[c]pyrimido[4,5-e]azepin-2-ylamino]-phenyl}-(3-dimethyl-amino-azetidin-1-yl)-methanone
I-99: 4-[9-Chloro-7-(2-fluoro-phenyl)-5H-benzo[c]pyrimido[4,5-e]azepin-2-ylamino]-N-methyl-N-(1-methyl-pyrrolidin-3-yl)-benzamide
I-100: {4-[9-Chloro-7-(2-fluoro-phenyl)-5H-benzo[c]pyrimido[4,5-e]azepin-2-ylamino]-phenyl}-(3-dimethyl-amino-pyrrolidin-1-yl)-methanone
I-101: 4-[9-Chloro-7-(2,4-dimethoxy-phenyl)-5H-benzo[c]pyrimido-[4,5-e]azepin-2-ylamino]-benzoic acid
I-102: {4-[9-Chloro-7-(2-fluoro-phenyl)-5H-benzo[c]pyrimido[4,5-e]azepin-2-ylamino]-phenyl}-(3-methyl-amino-pyrrolidin-1-yl)-methanone
I-103: (3-Amino-pyrrolidin-1-yl)-{4-[9-chloro-7-(2-fluoro-phenyl)-5H-benzo[c]pyrimido[4,5-e]azepin-2-ylamino]-phenyl}-methanone
I-104: 4-[9-Chloro-7-(2,3-difluoro-phenyl)-5H-benzo[c]pyrimido[4,5-e]azepin-2-ylamino]-benzoic acid methyl ester
I-105: 4-[9-Chloro-7-(2,5-difluoro-phenyl)-5H-benzo[c]pyrimido[4,5-e]azepin-2-ylamino]-benzoic acid methyl ester
I-106: {4-[9-Chloro-7-(2-fluoro-phenyl)-5H-benzo[c]pyrimido[4,5-e]azepin-2-ylamino]-phenyl}-phosphonic acid
I-107: N-{4-[9-Chloro-7-(2-fluoro-phenyl)-5H-benzo[c]pyrimido[4,5-e]azepin-2-ylamino]-phenyl}-methanesulfonamide
I-108: N-{4-[9-Chloro-7-(2-fluoro-phenyl)-5H-benzo[c]pyrimido[4,5-e]azepin-2-ylamino]-phenyl}-N-methyl-acetamide
I-109: 2-{4-[9-Chloro-7-(2-fluoro-phenyl)-5H-benzo[c]pyrimido[4,5-e]azepin-2-ylamino]-benzoylamino}-succinic acid
I-110: [9-Chloro-7-(2-fluoro-phenyl)-4-methyl-5H-benzo[c]pyrimido-[4,5-e]azepin-2-yl]-(3,4-dimethoxy-phenyl)-amine
I-111: {4-[9-Chloro-7-(2-fluoro-phenyl)-5H-benzo[c]pyrimido[4,5-e]azepin-2-ylamino]-phenyl}-(3,5-dimethyl-piperazin-1-yl)-methanone
I-112: 1-{4-[9-Chloro-7-(2-fluoro-phenyl)-5H-benzo[c]pyrimido[4,5-e]azepin-2-ylamino]-benzoyl}-pyrrolidine-2-carboxylic acid
I-113: {4-[9-Chloro-7-(2-fluoro-phenyl)-5H-benzo[c]pyrimido[4,5-e]azepin-2-ylamino]-phenyl}-(3-methyl-piperazin-1-yl)-methanone
I-114: [9-Chloro-7-(2-fluoro-phenyl)-5H-benzo[c]pyrimido[4,5-e]azepin-2-yl]-[4-(2H-tetrazol-5-yl)-phenyl]-amine
I-115: N-{4-[9-Chloro-7-(2-fluoro-phenyl)-5H-benzo[c]pyrimido[4,5-e]azepin-2-ylamino]-phenyl}-acetamide
I-116: 5-[9-Chloro-7-(2-fluoro-phenyl)-5H-benzo[c]pyrimido[4,5-e]azepin-2-ylamino]-2-fluoro-benzoic acid
I-117: N-(3-Amino-propyl)-4-[9-chloro-7-(2-fluoro-phenyl)-5H-benzo[c]pyrimido[4,5-e]azepin-2-ylamino]-N-methyl-benzamide
I-118: 2-{4-[9-Chloro-7-(2-fluoro-phenyl)-5H-benzo[c]pyrimido[4,5-e]azepin-2-ylamino]-benzoylamino}-propionic acid
I-119: 5-[9-Chloro-7-(2-fluoro-phenyl)-5H-benzo[c]pyrimido[4,5-e]azepin-2-ylamino]-pyridine-2-carboxylic acid
I-120: 2-{4-[9-Chloro-7-(2-fluoro-phenyl)-5H-benzo[c]pyrimido[4,5-e]azepin-2-ylamino]-phenyl}-N-(2-morpholin-4-yl-ethyl)-acetamide
I-121: 5-[9-Chloro-7-(2-fluoro-phenyl)-5H-benzo[c]pyrimido[4,5-e]azepin-2-ylamino]-2-methoxy-benzoic acid
I-122: 5-[9-Chloro-7-(2-fluoro-phenyl)-5H-benzo[c]pyrimido[4,5-e]azepin-2-ylamino]-2-methyl-benzoic acid
I-123: 6-[9-Chloro-7-(2-fluoro-phenyl)-5H-benzo[c]pyrimido[4,5-e]azepin-2-ylamino]-nicotinic acid
I-124: 4-[9-Chloro-7-(2-fluoro-phenyl)-5H-benzo[c]pyrimido[4,5-e]azepin-2-ylamino]-N-(2-morpholin-4-yl-ethyl)-benzenesulfonamide
I-125: 2-Chloro-5-[9-chloro-7-(2-fluoro-phenyl)-5H-benzo[c]pyrimido-[4,5-e]azepin-2-ylamino]-benzoic acid
I-126: {4-[9-Chloro-7-(2-fluoro-phenyl)-5H-benzo[c]pyrimido[4,5-e]azepin-2-ylamino]-phenyl}-acetic acid
I-127: 4-[9-Chloro-7-(2-fluoro-phenyl)-5H-benzo[c]pyrimido[4,5-e]azepin-2-ylamino]-2-trifluoromethyl-benzoic acid
I-128: 4-[9-Chloro-7-(2-fluoro-phenyl)-5H-benzo[c]pyrimido[4,5-e]azepin-2-ylamino]-N-methyl-N-(1-methyl-piperidin-4-yl)-benzamide
I-129: N-(3-Amino-propyl)-4-[9-chloro-7-(2-fluoro-phenyl)-5H-benzo[c]pyrimido[4,5-e]azepin-2-ylamino]-benzamide
I-130: 4-[9-Chloro-7-(2-fluoro-phenyl)-5H-benzo[c]pyrimido[4,5-e]azepin-2-ylamino]-N-(3-methylamino-propyl)-benzamide
I-131: N-(2-Amino-2-methyl-propyl)-4-[9-chloro-7-(2-fluoro-phenyl)-5H-benzo[c]pyrimido[4,5-e]azepin-2-ylamino]-benzamide
I-132: 2-(3,4-Dimethoxy-phenylamino)-7-(2-fluoro-phenyl)-5H-benzo[c]pyrimido[4,5-e]azepine-10-carboxylic acid
I-133: 4-[9-Chloro-7-(2-fluoro-phenyl)-5H-benzo[c]pyrimido[4,5-e]azepin-2-ylamino]-2-methyl-benzoic acid
I-134: 2-Chloro-4-[9-chloro-7-(2-fluoro-phenyl)-5H-benzo[c]pyrimido-[4,5-e]azepin-2-ylamino]-benzoic acid
I-135: 4-[9-Chloro-7-(2,6-difluoro-phenyl)-5H-benzo[c]pyrimido[4,5-e]azepin-2-ylamino]-benzoic acid
I-136: 4-[9-Chloro-7-(2-fluoro-phenyl)-5H-benzo[c]pyrimido[4,5-e]azepin-2-ylamino]-2-fluoro-benzoic acid
I-137: 4-[7-(2-Fluoro-phenyl)-9-methoxy-5H-benzo[c]pyrimido[4,5-e]azepin-2-ylamino]-benzoic acid
I-138: (3,4-Dimethoxy-phenyl)-[7-(2-fluoro-phenyl)-9-methoxy-5H-benzo[c]pyrimido[4,5-e]azepin-2-yl]-amine
I-139: [9,10-Dichloro-7-(2-fluoro-phenyl)-5H-benzo[c]pyrimido[4,5-e]azepin-2-yl]-(3,4-dimethoxy-phenyl)-amine
I-140: 4-[9,10-Dichloro-7-(2-fluoro-phenyl)-5H-benzo[c]pyrimido[4,5-e]azepin-2-ylamino]-benzoic acid
I-141: 4-[9-Chloro-7-(2-fluoro-phenyl)-5H-benzo[c]pyrimido[4,5-e]azepin-2-ylamino]-2-methoxy-benzoic acid
I-142: N-(2-Amino-ethyl)-4-[9-chloro-7-(2-fluoro-phenyl)-5H-benzo[c]pyrimido[4,5-e]azepin-2-ylamino]-benzamide
I-143: 4-(9-Chloro-7-phenyl-5H-benzo[c]pyrimido[4,5-e]azepin-2-ylamino)-benzoic acid I-144: [7-(2-Bromo-phenyl)-9-chloro-5H-benzo[c]pyrimido[4,5-e]azepin-2-yl]-(3,4-dimethoxy-phenyl)-amine I-145: 2-{4-[9-Chloro-7-(2-fluoro-phenyl)-5H-benzo[c]pyrimido[4,5-e]azepin-2-ylamino]-phenyl}-1-(4-methyl-piperazin-1-yl)-ethanone I-146: 3-[9-Chloro-7-(2-fluoro-phenyl)-5H-benzo[c]pyrimido[4,5-e]azepin-2-ylamino]-benzoic acid I-147: 4-[9-Chloro-7-(2-fluoro-phenyl)-5H-benzo[c]pyrimido[4,5-e]azepin-2-ylamino]-N-[2-(1H-imidazol-4-yl)-ethyl]-benzamide I-148: 4-[7-(2-Fluoro-phenyl)-9-methyl-5H-benzo[c]pyrimido[4,5-e]azepin-2-ylamino]-N-(2-morpholin-4-yl-ethyl)-benzamide I-149: {3-[9-Chloro-7-(2-fluoro-phenyl)-5H-benzo[c]pyrimido[4,5-e]azepin-2-ylamino]-phenyl}-acetic acid I-150: 4-[9-Chloro-7-(2-fluoro-phenyl)-5H-benzo[c]pyrimido[4,5-e]azepin-2-ylamino]-N-(2-pyridin-4-yl-ethyl)-benzamide I-151: 4-[9-Chloro-7-(2-fluoro-phenyl)-5H-benzo[c]pyrimido[4,5-e]azepin-2-ylamino]-N-(2-pyridin-3-yl-ethyl)-benzamide I-152: (9-Chloro-7-phenyl-5H-benzo[c]pyrimido[4,5-e]azepin-2-yl)-(3,4-dimethoxy-phenyl)-amine I-153: 4-[7-(2-Fluoro-phenyl)-10-methyl-5H-benzo[c]pyrimido[4,5-e]azepin-2-ylamino]-benzoic acid I-154: (3,4-Dimethoxy-phenyl)-[7-(2-fluoro-phenyl)-5H-benzo[c]pyrimido-[4,5-e]azepin-2-yl]-amine I-155: 4-[9-Chloro-7-(4-methoxy-phenyl)-5H-benzo[c]pyrimido[4,5-e]azepin-2-ylamino]-benzoic acid I-156: 4-[9-Chloro-7-(3-methoxy-phenyl)-5H-benzo[c]pyrimido[4,5-e]azepin-2-ylamino]-benzoic acid I-157: 4-[9-Chloro-7-(3-fluoro-phenyl)-5H-benzo[c]pyrimido[4,5-e]azepin-2-ylamino]-N-[3-(4-methyl-piperazin-1-yl)-propyl]-benzamide I-158: 4-[9-Chloro-7-(3-fluoro-phenyl)-5H-benzo[c]pyrimido[4,5-e]azepin-2-ylamino]-N-(2-morpholin-4-yl-ethyl)-benzamide I-159: {4-[9-Chloro-7-(3-fluoro-phenyl)-5H-benzo[c]pyrimido[4,5-e]azepin-2-ylamino]-phenyl}-(4-methyl-piperazin-1-yl)-methanone I-160: 4-[9-Chloro-7-(2-fluoro-phenyl)-5H-benzo[c]pyrimido[4,5-e]azepin-2-ylamino]-N-methyl-N-(2-pyridin-2-yl-ethyl)-benzamide I-161: 4-[9-Chloro-7-(2-fluoro-phenyl)-5H-benzo[c]pyrimido[4,5-e]azepin-2-ylamino]-N-(2-pyridin-2-yl-ethyl)-benzamide I-162: 4-[9-Chloro-7-(3-fluoro-phenyl)-5H-benzo[c]pyrimido[4,5-e]azepin-2-ylamino]-benzoic acid I-163: {3-[9-Chloro-7-(2-fluoro-phenyl)-5H-benzo[c]pyrimido[4,5-e]azepin-2-ylamino]-phenyl}-(4-methyl-piperazin-1-yl)-methanone I-164: 9-Chloro-7-(2-fluorophenyl)-N-{4-[(4-pyridin-2-ylpiperazin-1-yl)carbonyl]phenyl}-5H-pyrimido [5,4-d][2]benzazepin-2-amine I-165: 9-Chloro-7-(2-fluorophenyl)-N-(4-{[4-(2-morpholin-4-yl-2-oxoethyl)piperazin-1-yl]carbonyl}phenyl)-5H-pyrimido-[5,4-d][2]benzazepin-2-amine I-166: 9-Chloro-7-(2-fluorophenyl)-N-(4-{[4-(2-furoyl)piperazin-1-yl]carbonyl}phenyl)-5H-pyrimido[5,4-d][2]benzazepin-2-amine I-167: Benzyl-4-(4-{[9-chloro-7-(2-fluorophenyl)-5H-pyrimido-[5,4-d][2]benzazepin-2-yl]amino}benzoyl)piperazine-1-carboxylate I-168: Ethyl-4-(4-{[19-chloro-7-(2-fluorophenyl)-5H-pyrimido-[5,4-d][2]benzazepin-2-yl]amino}benzoyl)piperazine-1-carboxylate I-169: 2-[4-(4-{[9-Chloro-7-(2-fluorophenyl)-5H-pyrimido[5,4-d][2]benzazepin-2-yl]amino}benzoyl)piperazin-1-yl]benzoic acid I-170: 2-[4-(4-{[9-Chloro-7-(2-fluorophenyl)-5H-pyrimido[5,4-d][2]benzazepin-2-yl]amino}benzoyl)piperazin-1-yl]-N-isopropylacetamide I-171: 9-Chloro-7-(2-fluorophenyl)-N-(4-{[4-(2-pyrrolidin-1-ylethyl)piperazin-1-yl]carbonyl}phenyl)-5H-pyrimido[5,4-d][2]benzazepin-2-amine I-172: N-[2-(aminocarbonyl)phenyl]-4-{[9-chloro-7-(2-fluorophenyl)-5H-pyrimido[5,4-d][2]benzazepin-2-yl]amino}benzamide I-173: 9-Chloro-7-(2-fluorophenyl)-N-{4-[(4-pyrimidin-2-ylpiperazin-1-yl)carbonyl]phenyl}-5H-pyrimido[5,4-d][2]benzazepin-2-amine I-174: 4-{[9-Chloro-7-(2-chloro-6-fluorophenyl)-5H-pyrimido-[5,4-d][2]benzazepin-2-yl]amino}benzoic acid I-175: 9-Chloro-7-(2,6-difluorophenyl)-N-{4-[(3,5-dimethylpiperazin-1-yl)carbonyl]phenyl}-5H-pyrimido[5,4-d][2]benzazepin-2-amine I-176: 9-Chloro-7-(2,6-difluorophenyl)-N-(4-{[3-(dimethylamino)pyrrolidin-1-yl]carbonyl}phenyl)-5H-pyrimido[5,4-d][2]benzazepin-2-amine I-177: 9-Chloro-N-{4-[(3,5-dimethylpiperazin-1-yl)carbonyl]phenyl}-7-(2-fluoro-6-methoxyphenyl)-5H-pyrimido[5,4-d][2]benzazepin-2-amine I-178: 9-Chloro-N-(4-{[3-(dimethylamino)pyrrolidin-1-yl]carbonyl}phenyl)-7-(2-fluoro-6-methoxyphenyl)-5H-pyrimido[5,4-d][2]benzazepin-2-amine I-179: 9-Chloro-N-(4-{[3-(dimethylamino)azetidin-1-yl]carbonyl}phenyl)-7-(2-fluoro-6-methoxyphenyl)-5H-pyrimido[5,4-d][2]benzazepin-2-amine I-180: 9-Chloro-7-(2,6-difluorophenyl)-N-(4-{[3-(dimethylamino)azetidin-1-yl]carbonyl}phenyl)-5H-pyrimido[5,4-d][2]benzazepin-2-amine I-181: {4-[9-Chloro-7-(2-fluoro-phenyl)-5H-benzo[c]pyrimido[4,5-e]azepin-2-ylamino]-phenyl}-[4-(3-piperidin-1-yl-propyl)-piperazin-1-yl]-methanone I-182: {4-[9-Chloro-7-(2-fluoro-phenyl)-5H-benzo[c]pyrimido[4,5-e]azepin-2-ylamino]-phenyl}-[4-(2-piperidin-1-yl-ethyl)-piperazin-1-yl]-methanone I-183: {4-[9-Chloro-7-(2,6-difluoro-phenyl)-5H-benzo[c]pyrimido[4,5-e]azepin-2-ylamino]-phenyl}-(4-dimethylamino-piperidin-1-yl)-methanone I-184: {4-[9-Chloro-7-(2,6-difluoro-phenyl)-5H-benzo[c]pyrimido[4,5-e]azepin-2-ylamino]-phenyl}-(4-methyl-piperazin-1-yl)-methanone I-185: 4-[9-Chloro-7-(2,6-difluoro-phenyl)-5H-benzo[c]pyrimido[4,5-e]azepin-2-ylamino]-N-(3-dimethylamino-propyl)-N-methyl-benzamide I-186: {4-[9-Chloro-7-(2-fluoro-6-methoxy-phenyl)-5H-benzo[c]pyrimido-[4,5-e]azepin-2-ylamino]-phenyl}-(4-dimethylamino-piperidin-1-yl)-methanone I-187: {4-[9-Chloro-7-(2-fluoro-phenyl)-5H-benzo[c]pyrimido[4,5-e]azepin-2-ylamino]-phenyl}-[4-(2-dipropylamino-ethyl)-piperazin-1-yl]-methanone I-188: {4-[9-Chloro-7-(2-fluoro-phenyl)-5H-benzo[c]pyrimido[4,5-e]azepin-2-ylamino]-phenyl}-[4-(3-pyrrolidin-1-yl-propyl)-piperazin-1-yl]-methanone I-189: {4-[9-Chloro-7-(2-fluoro-phenyl)-5H-benzo[c]pyrimido[4,5-e]azepin-2-ylamino]-phenyl}-[4-(2-morpholin-4-yl-ethyl)-piperazin-1-yl]-methanone I-190: 4-[9-Chloro-7-(2-fluoro-6-methoxy-phenyl)-5H-benzo[c]pyrimido[4,5-e]azepin-2-ylamino]-benzoic acid I-191: {4-[9-Chloro-7-(2,6-difluoro-phenyl)-5H-benzo[c]pyrimido[4,5-e]azepin-2-ylamino]-phenyl}-(3(S)-methyl-piperazin-1-yl)-methanone I-192: (3-Amino-azetidin-1-yl)-{4-[9-chloro-7-(2-fluoro-phenyl)-5H-benzo[c]pyrimido[4,5-e]azepin-2-ylamino]-phenyl}-methanone I-193: {4-[9-Chloro-7-(2-fluoro-phenyl)-5H-benzo[c]pyrimido[4,5-e]azepin-2-ylamino]-phenyl}-(3-dimethylaminomethyl-azetidin-1-yl)-methanone I-194: {4-[9-Chloro-7-(2,6-difluoro-phenyl)-5H-benzo[c]pyrimido[4,5-e]azepin-2-ylamino]-phenyl}-(3(R)-methyl-piperazin-1-yl)-methanone I-195: {4-[9-Chloro-7-(2,6-difluoro-phenyl)-5H-benzo[c]pyrimido[4,5-e]azepin-2-ylamino]-phenyl}-piperazin-1-yl-methanone I-196: (3-Amino-pyrrolidin-1-yl)-{4-[9-chloro-7-(2,6-difluoro-phenyl)-5H-benzo[c]pyrimido[4,5-e]azepin-2-ylamino]-phenyl}-methanone I-197: {4-[9-Chloro-7-(2,6-difluoro-phenyl)-5H-benzo[c]pyrimido[4,5-e]azepin-2-ylamino]-phenyl}-(3-methyl-amino-pyrrolidin-1-yl)-methanone I-198: 4-[9-Chloro-7-(2,6-difluoro-phenyl)-5H-benzo[c]pyrimido[4,5-e]azepin-2-ylamino]-N-methyl-N-(3-methyl-amino-propyl)-benzamide I-199: {4-[9-Chloro-7-(2-fluoro-6-methoxy-phenyl)-5H-benzo[c]pyrimido[4,5-e]azepin-2-ylamino]-phenyl}-(3-methylamino-pyrrolidin-1-yl)-methanone I-200: 4-[9-Chloro-7-(2-fluoro-phenyl)-5H-benzo[c]pyrimido[4,5-e]azepin-2-ylamino]-cyclohexanecarboxylic acid I-201: 9-chloro-N-(4-{[4-(2-ethoxyphenyl)piperazin-1-yl]carbonyl}phenyl)-7-(2-fluorophenyl)-5H-pyrimido[5,4-d][2]benzazepin-2-amine I-202: N-[amino(imino)methyl]-4-{9-chloro-7-(2,6-difluorophenyl)-5H-pyrimido[5,4-d][2]benzazepin-2-yl]amino}benzamide I-203: 3-{[9-chloro-7-(2,6-difluorophenyl)-5H-pyrimido[5,4-d][2]benzazepin-2-yl]amino}benzoic acid I-204: 9-chloro-7-(2,6-difluorophenyl)-N-(3-{[3-(dimethylamino)azetidin-1-yl]carbonyl}phenyl)-5H-pyrimido[5,4-d][2]benzazepin-2-amine I-205: 9-chloro-7-(2,6-difluorophenyl)-N-(3-{[4-(dimethylamino)piperidin-1-yl]carbonyl}phenyl)-5H-pyrimido[5,4-d][2]benzazepin-2-amine I-206: 9-chloro-7-(2,6-difluorophenyl)-N-(3-{[3-(dimethylamino)pyrrolidin-1-yl]carbonyl}phenyl)-5H-pyrimido[5,4-d][2]benzazepin-2-amine I-207: N-[2-(aminomethyl)-1,3-benzoxazol-5-yl]-9-chloro-7-(2,6-difluorophenyl)-5H-pyrimido[5,4-d][2]benzazepin-2-amine I-208: 9-chloro-N-[4-({4-[3-(diethylamino)propyl]piperazin-1-yl}carbonyl)phenyl]-7-(2-fluorophenyl)-5H-pyrimido[5,4-d][2]benzazepin-2-amine I-209: 9-chloro-N-[4-({4-[2-(diethylamino)ethyl]piperazin-1-yl}carbonyl)phenyl]-7-(2-fluorophenyl)-5H-pyrimido[5,4-d][2]benzazepin-2-amine I-210: 9-chloro-N-[4-({4-[3-(dimethylamino)propyl]piperazin-1-yl}carbonyl)phenyl]-7-(2-fluorophenyl)-5H-pyrimido[5,4-d][2]benzazepin-2-amine I-211: 9-chloro-7-(2-fluorophenyl)-N-[4-({4-[(1-methylpiperidin-3-yl)methyl]piperazin-1-yl}carbonyl)phenyl]-5H-pyrimido[5,4-d][2]benzazepin-2-amine I-212: 9-chloro-7-(2,6-difluorophenyl)-N-(4-nitrophenyl)-5H-pyrimido[5,4-d][2]benzazepin-2-amine I-213: 9-chloro-N-(3-chloro-4-{[4-(2-pyrrolidin-1-ylethyl)piperazin-1-yl]carbonyl}phenyl)-7-(2-fluorophenyl)-5H-pyrimido[5,4-d][2]benzazepin-2-amine I-214: 9-chloro-N-{3-chloro-4-[(3-methylpiperazin-1-yl)carbonyl]phenyl}-7-(2-fluorophenyl)-5H-pyrimido[5,4-d][2]benzazepin-2-amine I-215: 9-chloro-N-(3-chloro-4-{[3-(dimethylamino)pyrrolidin-1-yl]carbonyl}phenyl)-7-(2,6-difluorophenyl)-5H-pyrimido[5,4-d][2]benzazepin-2-amine I-216: 9-chloro-N-{3-chloro-4-[(3-methylpiperazin-1-yl)carbonyl]phenyl}-7-(2,6-difluorophenyl)-5H-pyrimido[5,4-d][2]benzazepin-2-amine I-217: N-[9-chloro-7-(2,6-difluorophenyl)-5H-pyrimido[5,4-d][2]benzazepin-2-yl]benzene-1,4-diamine I-218: methyl 2-chloro-4-{[9-chloro-7-(2,6-difluorophenyl)-5H-pyrimido[5,4-d][2]benzazepin-2-yl]amino}benzoate I-219: 1-(4-{[9-chloro-7-(2,6-difluorophenyl)-5H-pyrimido[5,4-d][2]benzazepin-2-yl]amino}benzoyl)piperazine-2-carboxylic acid I-220: 9-chloro-7-(2,6-difluorophenyl)-N-(4-{[4-(methylamino)piperidin-1-yl]carbonyl}phenyl)-5H-pyrimido[5,4-d][2]benzazepin-2-amine I-221: N-{4-[(3-aminopiperidin-1-yl)carbonyl]phenyl}-9-chloro-7-(2,6-difluorophenyl)-5H-pyrimido[5,4-d][2]benzazepin-2-amine I-222: 9-chloro-7-(2,6-difluorophenyl)-N-{3-[(3,5-dimethylpiperazin-1-yl)carbonyl]phenyl}-5H-pyrimido[5,4-d][2]benzazepin-2-amine I-223: 4-{[9-chloro-7-(2,6-difluorophenyl)-5H-pyrimido[5,4-d][2]benzazepin-2-yl]amino}-N-[[4-(dimethylamino)piperidin-1-yl](imino)methyl]benzamide I-224: 4-{[9-chloro-7-(2,6-difluorophenyl)-5H-pyrimido[5,4-d][2]benzazepin-2-yl]amino}-N-[imino(piperazin-1-yl)methyl]benzamide I-225: 4-{[9-chloro-7-(2-fluoro-6-methoxyphenyl)-5H-pyrimido[5,4-d][2]benzazepin-2-yl]amino}-N-[3-(dimethylamino)propyl]-N-methylbenzamide I-226: 3-{[9-chloro-7-(2-fluoro-6-methoxyphenyl)-5H-pyrimido[5,4-d][2]benzazepin-2-yl]amino}-N-[3-(dimethylamino)propyl]-N-methylbenzamide I-227: 9-chloro-N-(3-{[3-(dimethylamino)azetidin-1-yl]carbonyl}phenyl)-7-(2-fluoro-6-methoxyphenyl)-5H-pyrimido[5,4-d][2]benzazepin-2-amine I-228: 9-chloro-N-{3-[(3,5-dimethylpiperazin-1-yl)carbonyl]phenyl}-7-(2-fluoro-6-methoxyphenyl)-5H-pyrimido[5,4-d][2]benzazepin-2-amine I-229: 9-chloro-N-(3-{[4-(dimethylamino)piperidin-1-yl]carbonyl}phenyl)-7-(2-fluoro-6-methoxyphenyl)-5H-pyrimido[5,4-d][2]benzazepin-2-amine I-230: N-(4-{[3-(aminomethyl)azetidin-1-yl]carbonyl}phenyl)-9-chloro-7-(2-fluorophenyl)-5H-pyrimido[5,4-d][2]benzazepin-2-amine I-231: 9-chloro-N-(3-{[3-(dimethylamino)pyrrolidin-1-yl]carbonyl}phenyl)-7-(2-fluoro-6-methoxyphenyl)-5H-pyrimido[5,4-d][2]benzazepin-2-amine I-232: 9-chloro-7-(2-fluoro-6-methoxyphenyl)-N-{4-[(3-methylpiperazin-1-yl)carbonyl]phenyl}-5H-pyrimido[5,4-d][2]benzazepin-2-amine I-233: 9-chloro-7-(2-fluoro-6-methoxyphenyl)-N-{4-[(4-methylpiperazin-1-yl)carbonyl]phenyl}-5H-pyrimido[5,4-d][2]benzazepin-2-amine I-234: 9-chloro-7-(2,6-difluorophenyl)-N-(4-{[3-(methylamino)azetidin-1-yl]carbonyl}phenyl)-5H-pyrimido[5,4-d][2]benzazepin-2-amine I-235: 9-chloro-7-(2-fluoro-6-methoxyphenyl)-N-(4-{[3-(methylamino)azetidin-1-yl]carbonyl}phenyl)-5H-pyrimido[5,4-d][2]benzazepin-2-amine I-236: 4-{[9-chloro-7-(2,6-difluorophenyl)-5H-pyrimido[5,4-d][2]benzazepin-2-yl]amino}benzonitrile I-237: 4-{[9-chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide I-238: 4-{[9-chloro-7-(2,6-difluorophenyl)-5H-pyrimido[5,4-d][2]benzazepin-2-yl]amino}-N-[(3, 5-dimethylpiperazin-1-yl) (imino)methyl]benzamide I-239: N-{4-[(4-aminopiperidin-1-yl)carbonyl]phenyl}-9-chloro-7-(2,6-difluorophenyl)-5H-pyrimido[5,4-d][2]benzazepin-2-amine I-240: N-{4-[(3-aminopyrrolidin-1-yl)carbonyl]phenyl}-9-chloro-7-(2-fluoro-6-methoxyphenyl)-5H-pyrimido[5,4-d][2]benzazepin-2-amine I-241: N-{4-[(4-aminopiperidin-1-yl)carbonyl]phenyl}-9-chloro-7-(2-fluoro-6-methoxyphenyl)-5H-pyrimido[5,4-d][2]benzazepin-2-amine I-242: 9-chloro-7-(2-fluoro-6-methoxyphenyl)-N-(4-{[4-(methylamino)piperidin-1-yl]carbonyl}phenyl)-5H-pyrimido[5,4-d][2]benzazepin-2-amine I-243: 9-chloro-7-(2-fluoro-6-methoxyphenyl)-N-[4-(piperazin-1-ylcarbonyl)phenyl]-5H-pyrimido[5,4-d][2]benzazepin-2-amine I-244: 9-chloro-7-(2,6-difluorophenyl)-N-{4-[[4-(dimethylamino)piperidin-1-yl](imino)methyl]phenyl}-5H-pyrimido[5,4-d][2]benzazepin-2-amine I-245: N-(4-{[9-chloro-7-(2,6-difluorophenyl)-5H-pyrimido[5,4-d][2]benzazepin-2-yl]amino}phenyl)guanidine I-246: 4-{[9-chloro-7-(2,6-difluorophenyl)-5H-pyrimido[5,4-d][2]benzazepin-2-yl]amino}-N-methyl-N-[2-(methylamino)ethyl]benzamide I-247: 4-{[9-chloro-7-(2,6-difluorophenyl)-5H-pyrimido[5,4-d][2]benzazepin-2-yl]amino}-N-[2-(dimethylamino)ethyl]-N-methylbenzamide I-248: methyl 4-(4-{[9-chloro-7-(2,6-difluorophenyl)-5H-pyrimido[5,4-d][2]benzazepin-2-yl]amino}benzoyl)piperazine-2-carboxylate I-249: 2-[(4-carboxyphenyl)amino]-7-(2-fluorophenyl)-5H-pyrimido[5,4-d][2]benzazepine-9-carboxylic acid I-250: 9-chloro-7-(2,6-difluorophenyl)-N-{4-[[3-(dimethylamino)pyrrolidin-1-yl](imino)methyl]phenyl}-5H-pyrimido[5,4-d][2]benzazepin-2-amine I-251: 9-chloro-7-(2,6-difluorophenyl)-N-{4-[(3,5-dimethylpiperazin-1-yl)(imino)methyl]phenyl}-5H-pyrimido[5,4-d][2]benzazepin-2-amine I-252: N-(2-aminoethyl)-4-{[9-chloro-7-(2,6-difluorophenyl)-5H-pyrimido[5,4-d][2]benzazepin-2-yl]amino}-N-methylbenzamide I-253: 9-chloro-7-(2,6-difluorophenyl)-N-(4-{[3-(methylamino)piperidin-1-yl]carbonyl}phenyl)-5H-pyrimido[5,4-d][2]benzazepin-2-amine I-254: 4-{[9-chloro-7-(2-fluoro-6-methoxyphenyl)-5H-pyrimido[5,4-d][2]benzazepin-2-yl]amino}-N-methyl-N-[2-(methylamino)ethyl]benzamide I-255: 4-{[9-chloro-7-(2-fluoro-6-methoxyphenyl)-5H-pyrimido[5,4-d][2]benzazepin-2-yl]amino}-N-[2-(dimethylamino)ethyl]-N-methylbenzamide I-256: 7-(2-fluorophenyl)-2-[(3-methoxyphenyl)amino]-5H-pyrimido[5,4-d][2]benzazepine-9-carboxylic acid I-257: N-(3-aminopropyl)-4-{[9-chloro-7-(2,6-difluorophenyl)-5H-pyrimido[5,4-d][2]benzazepin-2-yl]amino}-N-methylbenzamide I-258: 2-chloro-5-{[9-chloro-7-(2,6-difluorophenyl)-5H-pyrimido[5,4-d][2]benzazepin-2-yl]amino}benzoic acid I-259: 4-{[9-chloro-7-(2,6-difluorophenyl)-5H-pyrimido[5,4-d][2]benzazepin-2-yl]amino}-N-[[13-(dimethylamino)azetidin-1-yl](imino)methyl]benzamide I-260: N-(2-amino-2-methylpropyl)-4-{[9-chloro-7-(2,6-difluorophenyl)-5H-pyrimido[5,4-d][2]benzazepin-2-yl]amino}benzamide I-261: 4-{[9-chloro-7-(2-fluoro-6-methoxyphenyl)-5H-pyrimido[5,4-d][2]benzazepin-2-yl]amino}-N-methyl-N-[3-(methylamino)propyl]benzamide I-262: N-{4-[(3-aminopiperidin-1-yl)carbonyl]phenyl}-9-chloro-7-(2-fluoro-6-methoxyphenyl)-5H-pyrimido[5,4-d][2]benzazepin-2-amine I-263: 9-chloro-7-(2-fluoro-6-methoxyphenyl)-N-(4-{[3-(methylamino)piperidin-1-yl]carbonyl}phenyl)-5H-pyrimido[5,4-d][2]benzazepin-2-amine I-264: N-(3-aminopropyl)-4-{[9-chloro-7-(2-fluoro-6-methoxyphenyl)-5H-pyrimido[5,4-d][2]benzazepin-2-yl]amino}-N-methylbenzamide I-265: N-(2-aminoethyl)-4-{[9-chloro-7-(2-fluoro-6-methoxyphenyl)-5H-pyrimido[5,4-d][2]benzazepin-2-yl]amino}-N-methylbenzamide I-266: 4-(4-{[9-chloro-7-(2,6-difluorophenyl)-5H-pyrimido[5,4-d][2]benzazepin-2-yl]amino}benzoyl)piperazine-2-carboxylic acid I-267: 9-chloro-7-(2,6-difluorophenyl)-N-{4-[[3-(dimethylamino)azetidin-1-yl](imino)methyl]phenyl}-5H-pyrimido[5,4-d][2]benzazepin-2-amine I-268: 9-chloro-7-(2,6-difluorophenyl)-N-(4-{imino[3-(methylamino)pyrrolidin-1-yl]methyl}phenyl)-5H-pyrimido[5,4-d][2]benzazepin-2-amine I-269: 9-chloro-N-(4-chloro-3-{[4-(dimethylamino)piperidin-1-yl]carbonyl}phenyl)-7-(2,6-difluorophenyl)-5H-pyrimido[5,4-d][2]benzazepin-2-amine I-270: 9-chloro-7-(2,6-difluorophenyl)-N-[4-(5,5-dimethyl-4,5-dihydro-1H-imidazol-2-yl)phenyl]-5H-pyrimido[5,4-d][2]benzazepin-2-amine I-271: N-[9-chloro-7-(2,6-difluorophenyl)-5H-pyrimido[5,4-d][2]benzazepin-2-yl]-N-pyrimidin-2-ylbenzene-1,4-diamine I-272: 4-{[9-(3-aminoprop-1-yn-1-yl)-7-(2,6-difluorophenyl)-5H-pyrimido[5,4-d][2]benzazepin-2-yl]amino}benzoic acid I-273: 9-bromo-7-(2,6-difluorophenyl)-N-(3-methoxyphenyl)-5H-pyrimido[5,4-d][2]benzazepin-2-amine I-274: 4-{[9-bromo-7-(2,6-difluorophenyl)-5H-pyrimido[5,4-d][2]benzazepin-2-yl]amino}benzoic acid I-275: 7-(2,6-difluorophenyl)-N-(3-methoxyphenyl)-9-(3-pyrrolidin-1-ylprop-1-yn-1-yl)-5H-pyrimido[5,4-d][2]benzazepin-2-amine I-276: 9-(3-aminoprop-1-yn-1-yl)-7-(2,6-difluorophenyl)-N-(3-methoxyphenyl)-5H-pyrimido[5,4-d][2]benzazepin-2-amine I-277: 4-({9-chloro-7-[2-(trifluoromethyl)phenyl]-5H-pyrimido[5,4-d][2]benzazepin-2-yl}amino)benzoic acid I-278: N-{4-[(3-aminoazetidin-1-yl)carbonyl]phenyl}-9-chloro-7-(2,6-difluorophenyl)-5H-pyrimido[5,4-d][2]benzazepin-2-amine I-279: 4-[(9-chloro-7-pyridin-2-yl-5H-pyrimido[5,4-d][2]benzazepin-2-yl)amino]benzoic acid I-280: N-(4-{[9-chloro-7-(2,6-difluorophenyl)-5H-pyrimido[5,4-d][2]benzazepin-2-yl]amino}phenyl)-4-methylpiperazine-1-carboxamide I-281: 9-chloro-N-(4-chloro-3-{[3-(methylamino)pyrrolidin-1-yl]carbonyl}phenyl)-7-(2,6-difluorophenyl)-5H-pyrimido[5,4-d][2]benzazepin-2-amine I-282: 9-chloro-N-(4-chloro-3-{[4-(methylamino)piperidin-1-yl]carbonyl}phenyl)-7-(2,6-difluorophenyl)-5H-pyrimido[5,4-d][2]benzazepin-2-amine I-283: 2-chloro-5-{[9-chloro-7-(2,6-difluorophenyl)-5H-pyrimido[5,4-d][2]benzazepin-2-yl]amino}-N-methyl-N-[2-(methylamino)ethyl]benzamide I-284: N-{4-[(3-aminopyrrolidin-1-yl)(imino)methyl]phenyl}-9-chloro-7-(2,6-difluorophenyl)-5H-pyrimido[5,4-d][2]benzazepin-2-amine I-285: 2-(4-{[9-chloro-7-(2,6-difluorophenyl)-5H-pyrimido[5,4-d][2]benzazepin-2-yl]amino}phenyl)-1,4,5,6-tetrahydropyrimidin-5-ol I-286: N-{4-[(3-aminoazetidin-1-yl)carbonyl]phenyl}-9-chloro-7-(2-fluoro-6-methoxyphenyl)-5H-pyrimido[5,4-d][2]benzazepin-2-amine I-287: N-{4-[(4-aminopiperidin-1-yl)carbonyl]phenyl}-9-chloro-7-[2-(trifluoromethyl)phenyl]-5H-pyrimido[5,4-d][2]benzazepin-2-amine I-288: 9-chloro-N-(4-{[4-(methylamino)piperidin-1-yl]carbonyl}phenyl)-7-[2-(trifluoromethyl)phenyl]-5H-pyrimido[5,4-d][2]benzazepin-2-amine I-289: N-{4-[(3-aminopyrrolidin-1-yl)carbonyl]phenyl}-9-chloro-7-[2-(trifluoromethyl)phenyl]-5H-pyrimido[5,4-d][2]benzazepin-2-amine I-290: 9-chloro-N-(4-{[3-(methylamino)pyrrolidin-1-yl]carbonyl}phenyl)-7-[2-(trifluoromethyl)phenyl]-5H-pyrimido[5,4-d][2]benzazepin-2-amine I-291: 9-chloro-N-(4-chloro-3-{[3-(methylamino)azetidin-1-yl]carbonyl}phenyl)-7-(2,6-difluorophenyl)-5H-pyrimido[5,4-d][2]benzazepin-2-amine I-292: N-{3-[(4-aminopiperidin-1-yl)carbonyl]-4-chlorophenyl}-9-chloro-7-(2,6-difluorophenyl)-5H-pyrimido[5,4-d][2]benzazepin-2-amine I-293: 9-chloro-7-(2,6-difluorophenyl)-N-(4-{[3-(dimethylamino)piperidin-1-yl]carbonyl}phenyl)-5H-pyrimido[5,4-d][2]benzazepin-2-amine I-294: methyl 4-amino-1-(4-{[9-chloro-7-(2,6-difluorophenyl)-5H-pyrimido[5,4-d][2]benzazepin-2-yl]amino}benzoyl)piperidine-4-carboxylate I-295: 4-amino-1-(4-{[9-chloro-7-(2,6-difluorophenyl)-5H-pyrimido[5,4-d][2]benzazepin-2-yl]amino}benzoyl)piperidine-4-carboxylic acid I-296: N-{4-[(3-aminoazetidin-1-yl)carbonyl]phenyl}-9-chloro-7-[2-(trifluoromethyl)phenyl]-5H-pyrimido[5,4-d][2]benzazepin-2-amine I-297: 9-chloro-N-(4-{[3-(methylamino)azetidin-1-yl]carbonyl}phenyl)-7-[2-(trifluoromethyl)phenyl]-5H-pyrimido[5,4-d][2]benzazepin-2-amine I-298: N-{4-[(4-aminopiperidin-1-yl)carbonyl]phenyl}-9-chloro-7-pyridin-2-yl-5H-pyrimido[5,4-d][2]benzazepin-2-amine I-299: N-{4-[(3-aminopyrrolidin-1-yl)carbonyl]phenyl}-9-chloro-7-pyridin-2-yl-5H-pyrimido[5,4-d][2]benzazepin-2-amine I-300: ethyl 2-amino-4-[(4-{[9-chloro-7-(2,6-difluorophenyl)-5H-pyrimido[5,4-d][2]benzazepin-2-yl]amino}benzoyl)amino]butanoate I-301: 4-{[9-chloro-7-(3-fluoropyridin-2-yl)-5H-pyrimido[5,4-d][2]benzazepin-2-yl]amino}benzoic acid I-302: 9-{[3-(dimethylamino)azetidin-1-yl]carbonyl}-7-(2-fluorophenyl)-N-(3-methoxyphenyl)-5H-pyrimido[5,4-d][2]benzazepin-2-amine I-303: 7-(2-fluorophenyl)-2-[(3-methoxyphenyl)amino]-N-methyl-N-[3-(methylamino)propyl]-5H-pyrimido[5,4-d][2]benzazepine-9-carboxamide I-304: N-{4-[(4-aminopiperidin-1-yl)carbonyl]phenyl}-9-chloro-7-(3-fluoropyridin-2-yl)-5H-pyrimido[5,4-d][2]benzazepin-2-amine I-305: N-{4-[(3-aminopyrrolidin-1-yl)carbonyl]phenyl}-9-chloro-7-(3-fluoropyridin-2-yl)-5H-pyrimido[5,4-d][2]benzazepin-2-amine I-306: 2-(4-{[9-chloro-7-(2,6-difluorophenyl)-5H-pyrimido[5,4-d][2]benzazepin-2-yl]amino}phenyl)-4,5-dihydro-1H-imidazole-5-carboxylic acid I-307: N-(4-{[9-chloro-7-(2,6-difluorophenyl)-5H-pyrimido[5,4-d][2]benzazepin-2-yl]amino}phenyl)-2-(dimethylamino)acetamide I-308: 2-amino-N-(4-{[9-chloro-7-(2,6-difluorophenyl)-5H-pyrimido[5,4-d][2]benzazepin-2-yl]amino}phenyl)-2-methylpropanamide I-309: ethyl (2R)-4-amino-2-[(4-{[9-chloro-7-(2,6-difluorophenyl)-5H-pyrimido[5,4-d][2]benzazepin-2-yl]amino}benzoyl)amino]butanoate I-310: 4-(4-{[9-chloro-7-(2,6-difluorophenyl)-5H-pyrimido[5,4-d][2]benzazepin-2-yl]amino}benzoyl)-N-methylpiperazine-2-carboxamide I-311: 7-(2-fluorophenyl)-2-[(3-methoxyphenyl)amino]-N-(3-morpholin-4-ylpropyl)-5H-pyrimido[5,4-d][2]benzazepine-9-carboxamide I-312: 9-[(3,5-dimethylpiperazin-1-yl)carbonyl]-7-(2-fluorophenyl)-N-(3-methoxyphenyl)-5H-pyrimido[5,4-d][2]benzazepin-2-amine I-313: 9-chloro-N-(3-chloro-4-{[4-(dimethylamino)piperidin-1-yl]carbonyl}phenyl)-7-(2,6-difluorophenyl)-5H-pyrimido[5,4-d][2]benzazepin-2-amine I-314: ethyl 2-(4-{[9-chloro-7-(2,6-difluorophenyl)-5H-pyrimido[5,4-d][2]benzazepin-2-yl]amino}phenyl)-4,5-dihydro-1H-imidazole-5-carboxylate I-315: 9-chloro-N-(4-{[3-(methylamino)pyrrolidin-1-yl]carbonyl}phenyl)-7-pyridin-2-yl-5H-pyrimido[5,4-d][2]benzazepin-2-amine I-316: 9-chloro-N-(4-{[4-(methylamino)piperidin-1-yl]carbonyl}phenyl)-7-pyridin-2-yl-5H-pyrimido[5,4-d][2]benzazepin-2-amine I-317: 4-(4-{[9-chloro-7-(2,6-difluorophenyl)-5H-pyrimido[5,4-d][2]benzazepin-2-yl]amino}benzoyl)piperazine-2-carboxamide I-318: N-{4-[(3-aminopyrrolidin-1-yl)carbonyl]-3-chlorophenyl}-9-chloro-7-(2,6-difluorophenyl)-5H-pyrimido[5,4-d][2]benzazepin-2-amine I-319: N-(4-{[9-chloro-7-(2,6-difluorophenyl)-5H-pyrimido[5,4-d][2]benzazepin-2-yl]amino}phenyl)piperidine-4-carboxamide I-320: 4-{[9-chloro-7-(2-fluoro-6-{methyl[2-(methylamino)ethyl]amino}phenyl)-5H-pyrimido[5,4-d][2]benzazepin-2-yl]amino}benzoic acid I-321: 9-chloro-7-(2,4-difluorophenyl)-N-{4-[(3,5-dimethylpiperazin-1-yl)carbonyl]phenyl}-5H-pyrimido[5,4-d][2]benzazepin-2-amine I-322: 9-chloro-7-(2,4-dimethoxyphenyl)-N-{4-[(3,5-dimethylpiperazin-1-yl)carbonyl]phenyl}-5H-pyrimido[5,4-d][2]benzazepin-2-amine I-323: 9-chloro-7-(2-chloro-6-fluorophenyl)-N-{4-[(3-methylpiperazin-1-yl)carbonyl]phenyl}-5H-pyrimido[5,4-d][2]benzazepin-2-amine I-324: 9-chloro-7-(2-chloro-6-fluorophenyl)-N-{4-[(3,5-dimethylpiperazin-1-yl)carbonyl]phenyl}-5H-pyrimido[5,4-d][2]benzazepin-2-amine I-325: 9-chloro-7-(2-chloro-6-fluorophenyl)-N-(4-{[4-(methylamino)piperidin-1-yl]carbonyl}phenyl)-5H-pyrimido[5,4-d][2]benzazepin-2-amine I-326: 9-chloro-7-(2-chloro-6-fluorophenyl)-N-(4-{[3-(methylamino)piperidin-1-yl]carbonyl}phenyl)-5H-pyrimido[5,4-d][2]benzazepin-2-amine I-327: 9-chloro-7-(2-chloro-6-fluorophenyl)-N-(4-{[3-(methylamino)pyrrolidin-1-yl]carbonyl}phenyl)-5H-pyrimido[5,4-d][2]benzazepin-2-amine I-328: 9-chloro-N-(3,4-dimethoxyphenyl)-7-{2-[(dimethylamino)methyl]phenyl}-5H-pyrimido[5,4-d][2]benzazepin-2-amine I-329: 9-chloro-7-(2-methoxyphenyl)-N-{4-[(3-methylpiperazin-1-yl)carbonyl]phenyl}-5H-pyrimido[5,4-d][2]benzazepin-2-amine I-330: 9-chloro-N-{4-[(3,5-dimethylpiperazin-1-yl)carbonyl]phenyl}-7-(2-methoxyphenyl)-5H-pyrimido[5,4-d][2]benzazepin-2-amine I-331: 9-chloro-7-(2-methoxyphenyl)-N-(4-{[4-(methylamino)piperidin-1-yl]carbonyl}phenyl)-5H-pyrimido[5,4-d][2]benzazepin-2-amine I-332: 9-chloro-7-(2-methoxyphenyl)-N-(4-{[3-(methylamino)pyrrolidin-1-yl]carbonyl}phenyl)-5H-pyrimido[5,4-d][2]benzazepin-2-amine I-333: 9-chloro-7-(2-methoxyphenyl)-N-(4-{[3-(methylamino)piperidin-1-yl]carbonyl}phenyl)-5H-pyrimido[5,4-d][2]benzazepin-2-amine I-334: 4-{[9-chloro-7-(2,6-difluorophenyl)-5H-pyrimido[5,4-d][2]benzazepin-2-yl]amino}-N-methylbenzamide I-335: 4-{[9-chloro-7-(2-fluoro-6-{methyl[3-(methylamino)propyl]amino}phenyl)-5H-pyrimido[5,4-d][2]benzazepin-2-yl]amino}benzoic acid I-336: 4-{[9-chloro-7-(2-fluoro-6-{methyl[3-(methylamino)propyl]amino}phenyl)-5H-pyrimido[5,4-d][2]benzazepin-2-yl]amino}-N-methylbenzamide I-337: 1-(4-{[9-chloro-7-(2,6-difluorophenyl)-5H-pyrimido[5,4-d][2]benzazepin-2-yl]amino}phenyl)ethanone I-338: N-[3-(3-aminoprop-1-yn-1-yl)phenyl]-9-chloro-7-(2,6-difluorophenyl)-5H-pyrimido[5,4-d][2]benzazepin-2-amine I-339: 4-[(9-chloro-7-{2-fluoro-6-[(2-hydroxyethyl)amino]phenyl}-5H-pyrimido[5,4-d][2]benzazepin-2-yl)amino]-N-methylbenzamide I-340: 4-[(7-{2-[(2-aminoethyl)amino]-6-fluorophenyl}-9-chloro-5H-pyrimido[5,4-d][2]benzazepin-2-yl)amino]-N-methylbenzamide I-341: 4-amino-1-(4-{[9-chloro-7-(2,6-difluorophenyl)-5H-pyrimido[5,4-d][2]benzazepin-2-yl]amino}benzoyl)-N-methylpiperidine-4-carboxamide I-342: 4-[(9-chloro-7-{2-[4-(dimethylamino)piperidin-1-yl]-6-fluorophenyl}-5H-pyrimido[5,4-d][2]benzazepin-2-yl)amino]-N-methylbenzamide I-343: 9-chloro-7-(2,6-difluorophenyl)-N-{3-[3-(dimethylamino)prop-1-yn-1-yl]phenyl}-5H-pyrimido[5,4-d][2]benzazepin-2-amine I-344: 9-chloro-7-(2,6-difluorophenyl)-N-(3-iodophenyl)-5H-pyrimido[5,4-d][2]benzazepin-2-amine I-345: 4-{[9-chloro-7-(2-{[2-(dimethylamino)ethyl]amino}-6-fluorophenyl)-5H-pyrimido[5,4-d][2]benzazepin-2-yl]amino}-N-methylbenzamide I-346: 4-[(9-chloro-7-{2-[[2-(dimethylamino)ethyl](methyl)amino]-6-fluorophenyl}-5H-pyrimido[5,4-d][2]benzazepin-2-yl)amino]-N-methylbenzamide I-347: 4-{[9-chloro-7-(2-fluoro-6-{methyl[2-(methylamino)ethyl]amino}phenyl)-5H-pyrimido[5,4-d][2]benzazepin-2-yl]amino}-N-methylbenzamide I-348: 4-({7-[2-(4-aminopiperidin-1-yl)-6-fluorophenyl]-9-chloro-5H-pyrimido[5,4-d][2]benzazepin-2-yl}amino)-N-methylbenzamide I-349: 7-(2-fluorophenyl)-2-[(3-methoxyphenyl)amino]-N-methyl-N-[2-(methylamino)ethyl]-5H-pyrimido[5,4-d][2]benzazepine-9-carboxamide I-350: 4-amino-1-(4-{[9-chloro-7-(2,6-difluorophenyl)-5H-pyrimido[5,4-d][2]benzazepin-2-yl]amino}benzoyl)piperidine-4-carboxamide I-351: 9-chloro-7-(2-chloro-6-fluorophenyl)-N-(4-{[3-(methylamino)azetidin-1-yl]carbonyl}phenyl)-5H-pyrimido[5,4-d][2]benzazepin-2-amine I-352: 9-chloro-7-(2,6-difluorophenyl)-N-(4-methyl-1,3-thiazol-2-yl)-5H-pyrimido[5,4-d][2]benzazepin-2-amine I-353: 7-(2,6-difluorophenyl)-2-[(3-methoxyphenyl)amino]-5H-pyrimido[5,4-d][2]benzazepine-9-carboxylic acid I-354: 4-({9-chloro-7-[2-fluoro-6-(methylamino)phenyl]-5H-pyrimido[5,4-d][2]benzazepin-2-yl}amino)-N-methylbenzamide I-355: 2-{[9-chloro-7-(2,6-difluorophenyl)-5H-pyrimido[5,4-d][2]benzazepin-2-yl]amino}-N-methyl-1,3-thiazole-4-carboxamide I-356: N-1H-benzimidazol-2-yl-9-chloro-7-(2,6-difluorophenyl)-5H-pyrimido[5,4-d][2]benzazepin-2-amine I-357: 7-(2,6-difluorophenyl)-2-[(4-methyl-1,3-thiazol-2-yl)amino]-5H-pyrimido[5,4-d][2]benzazepine-9-carboxylic acid I-358: 3-amino-1-(3-{[9-chloro-7-(2,6-difluorophenyl)-5H-pyrimido[5,4-d][2]benzazepin-2-yl]amino}phenyl)propan-1-one I-359: 1-(3-{[9-chloro-7-(2,6-difluorophenyl)-5H-pyrimido[5,4-d][2]benzazepin-2-yl]amino}phenyl)-3-(dimethylamino)propan-1-one I-360: 2-{[9-chloro-7-(2,6-difluorophenyl)-5H-pyrimido[5,4-d][2]benzazepin-2-yl]amino}-1,3-thiazole-4-carboxylic acid I-361: ethyl 2-{[9-chloro-7-(2,6-difluorophenyl)-5H-pyrimido[5,4-d][2]benzazepin-2-yl]amino}-1,3-thiazole-4-carboxylate I-362: 9-chloro-7-(2,6-difluorophenyl)-N-{4-[(3,5-dimethylpiperazin-1-yl)carbonyl]-1,3-thiazol-2-yl}-5H-pyrimido[5,4-d][2]benzazepin-2-amine I-363: ethyl 2-{[9-chloro-7-(2,6-difluorophenyl)-5H-pyrimido[5,4-d][2]benzazepin-2-yl]amino}-1,3-oxazole-5-carboxylate I-364: 2-{[9-chloro-7-(2,6-difluorophenyl)-5H-pyrimido[5,4-d][2]benzazepin-2-yl]amino}-1,3-oxazole-5-carboxylic acid I-365: 9-chloro-7-(2,6-difluorophenyl)-N-(4-{[(3R)-3-methylpiperazin-1-yl]carbonyl}-1,3-thiazol-2-yl)-5H-pyrimido[5,4-d][2]benzazepin-2-amine I-366: 9-chloro-7-(2,6-difluorophenyl)-N-(4-{[(2R)-2-methylpiperazin-1-yl]carbonyl}phenyl)-5H-pyrimido[5,4-d][2]benzazepin-2-amine I-367: 9-chloro-7-(2,6-difluorophenyl)-N-(4-{[3-(methylamino)pyrrolidin-1-yl]carbonyl}-1,3-thiazol-2-yl)-5H-pyrimido[5,4-d][2]benzazepin-2-amine I-368: 2-{[9-chloro-7-(2,6-difluorophenyl)-5H-pyrimido[5,4-d][2]benzazepin-2-yl]amino}-1,3-oxazole-4-carboxylic acid I-369: 9-chloro-7-(2,6-difluorophenyl)-N-{5-[(3,5-dimethylpiperazin-1-yl)carbonyl]-1,3-oxazol-2-yl}-5H-pyrimido[5,4-d][2]benzazepin-2-amine I-370: 9-chloro-7-(2,6-difluorophenyl)-N-(5-{[3-(methylamino)pyrrolidin-1-yl]carbonyl}-1,3-oxazol-2-yl)-5H-pyrimido[5,4-d][2]benzazepin-2-amine I-371: 4-{[9-chloro-7-(2,6-difluorophenyl)-5-methyl-5H-pyrimido[5,4-d][2]benzazepin-2-yl]amino}benzoic acid I-372: 9-chloro-7-(2,6-difluorophenyl)-N-{3-[3-(dimethylamino)propyl]phenyl}-5H-pyrimido[5,4-d][2]benzazepin-2-amine I-373: N-[3-(3-aminopropyl)phenyl]-9-chloro-7-(2,6-difluorophenyl)-5H-pyrimido[5,4-d][2]benzazepin-2-amine I-374: 9-chloro-7-(2,6-difluorophenyl)-N-{4-[(3,5-dimethylpiperazin-1-yl)carbonyl]-1,3-oxazol-2-yl}-H-pyrimido[5,4-d][2]benzazepin-2-amine I-375: 9-chloro-7-(2,6-difluorophenyl)-N-(4-{[3-(methylamino)pyrrolidin-1-yl]carbonyl}-1,3-oxazol-2-yl)-5H-pyrimido[5,4-d][2]benzazepin-2-amine I-376: 7-(2,6-difluorophenyl)-2-({4-[(3,5-dimethylpiperazin-1-yl)carbonyl]phenyl}amino)-N-methyl-5H-pyrimido[5,4-d][2]benzazepine-9-carboxamide I-377: 2-{[4-(aminocarbonyl)phenyl]amino}-7-(2,6-difluorophenyl)-5H-pyrimido[5,4-d][2]benzazepine-9-carboxylic acid I-378: 1-(4-{[9-chloro-7-(2,6-difluorophenyl)-5H-pyrimido[5,4d][2]benzazepin-2-yl]amino}benzoyl)-N-methyl-4-(methylamino)piperidine-4-carboxamide I-379: N-{4-[(3-amino-3-methylpyrrolidin-1-yl)carbonyl]phenyl}-9-chloro-7-(2,6-difluorophenyl)-5H-pyrimido[5,4-d][2]benzazepin-2-amine I-380: 9-chloro-7-(2,6-difluorophenyl)-N-(4-{[3-methyl-3-(methylamino)pyrrolidin-1-yl]carbonyl}phenyl)-5H-pyrimido[5,4-d][2]benzazepin-2-amine I-381: 1-(4-{[9-chloro-7-(2,6-difluorophenyl)-5H-pyrimido[5,4-d][2]benzazepin-2-yl]amino}benzoyl)-4-(methylamino)piperidine-4-carboxamide I-382: 9-chloro-7-(2,6-difluorophenyl)-N-{4-[(3,3,5-trimethylpiperazin-1-yl)carbonyl]phenyl}-5H-pyrimido[5,4-d][2]benzazepin-2-amine I-383: N-1-azabicyclo[2.2.2]oct-3-yl-4-{[9-chloro-7-(2,6-difluorophenyl)-5H-pyrimido[5,4-d][2]benzazepin-2-yl]amino}-N-methylbenzamide I-384: N-1-azabicyclo[2.2.2]oct-3-yl-4-{[9-chloro-7-(2,6-difluorophenyl)-5H-pyrimido[5,4-d][2]benzazepin-2-yl]amino}benzamide I-385: 4-{[9-chloro-7-(2,6-difluorophenyl)-5H-pyrimido[5,4-d][2]benzazepin-2-yl]amino}-N-hydroxybenzamide I-386: N-{4-[(aminooxy)carbonyl]phenyl}-9-chloro-7-(2,6-difluorophenyl)-5H-pyrimido[5,4-d][2]benzazepin-2-amine I-387: 4-{[9-chloro-7-(2,6-difluorophenyl)-7H-pyrimido[5,4-d][2]benzazepin-2-yl]amino}benzoic acid I-388: 4-{[9-chloro-7-(2,3-difluorophenyl)-7H-pyrimido[5,4-d][2]benzazepin-2-yl]amino}benzoic acid I-389: 3-amino-1-(4-{[9-chloro-7-(2,6-difluorophenyl)-5H-pyrimido[5,4-d][2]benzazepin-2-yl]amino}benzoyl)-N-methylpyrrolidine-3-carboxamide I-390: 3-amino-1-(2-chloro-4-{[9-chloro-7-(2,6-difluorophenyl)-5H-pyrimido[5,4-d][2]benzazepin-2-yl]amino}benzoyl)pyrrolidine-3-carboxamide I-391: 9-chloro-7-(2,6-difluorophenyl)-N-{4-[(3,3-dimethylpiperazin-1-yl)carbonyl]phenyl}-5H-pyrimido[5,4-d][2]benzazepin-2-amine I-392: 4-{[9-chloro-7-(2,6-difluorophenyl)-5H-pyrimido[5,4-d][2]benzazepin-2-yl]amino}-N-(8-methyl-8-azabicyclo[3.2.1]oct-3-yl)benzamide I-393: 9-chloro-7-(2,6-difluorophenyl)-N-(4-{[3-(dimethylamino)-3-methylpyrrolidin-1-yl]carbonyl}phenyl)-5H-pyrimido[5,4-d][2]benzazepin-2-amine I-394: 9-chloro-7-(2,6-difluorophenyl)-N-(3-methyl-1H-pyrazol-5-yl)-5H-pyrimido[5,4-d][2]benzazepin-2-amine I-395: 2-chloro-4-{[9-chloro-7-(2,6-difluorophenyl)-5H-pyrimido[5,4-d][2]benzazepin-2-yl]amino}benzoic acid I-396: 4-amino-1-(2-chloro-4-{[9-chloro-7-(2,6-difluorophenyl)-5H-pyrimido[5,4-d][2]benzazepin-2-yl]amino}benzoyl)-N-methylpiperidine-4-carboxamide I-397: 4-amino-1-(2-chloro-4-{[9-chloro-7-(2,6-difluorophenyl)-5H-pyrimido[5,4-d][2]benzazepin-2-yl]amino}benzoyl)-N,N-dimethylpiperidine-4-carboxamide I-398: 4-[(9-methoxy-7-oxo-6,7-dihydro-5H-pyrimido[5,4-d][2]benzazepin-2-yl)amino]benzoic acid I-399: 2-({4-[(3,5-dimethylpiperazin-1-yl)carbonyl]phenyl}amino)-9-methoxy-5,6-dihydro-7H-pyrimido[5,4-d][2]benzazepin-7-one I-400: 9-methoxy-2-[(4-{[3-(methylamino)pyrrolidin-1-yl]carbonyl}phenyl)amino]-5,6-dihydro-7H-pyrimido[5,4-d][2]benzazepin-7-one I-401: 4-[(8-methyl-7-oxo-5,6,7,8-tetrahydropyrimido[5,4-c]pyrrolo[3,2-e]azepin-2-yl)amino]benzoic acid I-402: 2-({4-[(3,5-dimethylpiperazin-1-yl)carbonyl]phenyl}amino)-8-methyl-5,8-dihydropyrimido[5,4-c]pyrrolo[3,2-e]azepin-7(6H)-one I-403: 2-[(3-methoxyphenyl)amino]-8-methyl-5,8-dihydropyrimido[5,4-c]pyrrolo[3,2-e]azepin-7(6H)-one I-404: 9-chloro-2-[(3,4-dimethoxyphenyl)amino]-5,6-dihydro-7H-pyrimido[5,4-d][2]benzazepin-7-one I-405: 4-{[4-amino-9-chloro-7-(2,6-difluorophenyl)-5H-pyrimido[5,4-d][2]benzazepin-2-yl]amino}benzoic acid I-406: 9-chloro-N-(3-chloro-4-{[4-(methylamino)piperidin-1-yl]carbonyl}phenyl)-7-(2,6-difluorophenyl)-5H-pyrimido[5,4-d][2]benzazepin-2-amine I-407: 9-chloro-N-(3-chloro-4-{[4-(methylamino)piperidin-1-yl]carbonyl}phenyl)-7-(2-fluoro-6-methoxyphenyl)-5H-pyrimido[5,4-d][2]benzazepin-2-amine I-408: 4-{[9-chloro-7-(2-fluoro-6-hydroxyphenyl)-5H-pyrimido[5,4-d][2]benzazepin-2-yl]amino}benzoic acid I-409: 9-chloro-N-[4-(1,7-diazaspiro[4.4]non-7-ylcarbonyl)phenyl]-7-(2,6-difluorophenyl)-5H-pyrimido[5,4-d][2]benzazepin-2-amine I-410: 9-chloro-7-(2,6-difluorophenyl)-N-(4-{[2-(methylamino)-7-azabicyclo[2.2.1]hept-7-yl]carbonyl}phenyl)-5H-pyrimido[5,4-d][2]benzazepin-2-amine I-411: 1-(4-{[9-chloro-7-(2,6-difluorophenyl)-5H-pyrimido[5,4-d][2]benzazepin-2-yl]amino}benzoyl)-N-methyl-3-(methylamino)pyrrolidine-3-carboxamide I-412: 1-(4-{[9-chloro-7-(2,6-difluorophenyl)-5H-pyrimido[5,4-d][2]benzazepin-2-yl]amino}benzoyl)-3-(methylamino)pyrrolidine-3-carboxamide I-413: 1-(2-chloro-4-{[9-chloro-7-(2,6-difluorophenyl)-5H-pyrimido[5,4-d][2]benzazepin-2-yl]amino}benzoyl)-N-methyl-3-(methylamino)piperidine-3-carboxamide I-414: 9-chloro-7-(2,6-difluorophenyl)-N-(4-{[3-methyl-3-(methylamino)piperidin-1-yl]carbonyl}phenyl)-5H-pyrimido[5,4-d][2]benzazepin-2-amine I-415: 9-chloro-7-(2-fluoro-6-methoxyphenyl)-N-(4-{[3-methyl-3-(methylamino)piperidin-1-yl]carbonyl}phenyl)-5H-pyrimido[5,4-d][2]benzazepin-2-amine I-416: {2-Chloro-4-[9-chloro-7-(2-fluoro-6-methoxy-phenyl)-5H-benzo[c]pyrimido[4,5-e]azepin-2-ylamino]-phenyl}-(3-methyl-3-methylamino-piperidin-1-yl)-methanone I-417: 9-chloro-7-(2,6-difluorophenyl)-N-(4-{[4-methyl-4-(methylamino)piperidin-1-yl]carbonyl}phenyl)-5H-pyrimido[5,4-d][2]benzazepin-2-amine I-418: 9-chloro-7-(2,6-difluorophenyl)-N-(4-{[4-(dimethylamino)-4-methylpiperidin-1-yl]carbonyl}phenyl)-5H-pyrimido[5,4-d][2]benzazepin-2-amine I-419: N-{4-[(4-amino-4-methylpiperidin-1-yl)carbonyl]phenyl}-9-chloro-7-(2,6-difluorophenyl)-5H-pyrimido[5,4-d][2]benzazepin-2-amine I-420: 9-chloro-N-(3-chloro-4-{[4-methyl-4-(methylamino)piperidin-1-yl]carbonyl}phenyl)-7-(2,6-difluorophenyl)-5H-pyrimido[5,4-d][2]benzazepin-2-amine I-421: 9-chloro-7-(2-fluoro-6-methoxyphenyl)-N-(4-{[4-methyl-4-(methylamino)piperidin-1-yl]carbonyl}phenyl)-5H-pyrimido[5,4-d][2]benzazepin-2-amine I-422: 2-Chloro-4-[9-chloro-7-(2-fluoro-6-methoxy-phenyl)-5H-benzo[c]pyrimido[4,5-e]azepin-2-ylamino]-phenyl}-(4-methyl-4-methylamino-piperidin-1-yl)-methanone I-423: 9-chloro-7-(2-fluoro-6-methoxyphenyl)-N-(3-fluoro-4-{[4-methyl-4-(methylamino)piperidin-1-yl]carbonyl}phenyl)-5H-pyrimido[5,4-d][2]benzazepin-2-amine I-424: 9-chloro-N-{3-chloro-4-[(3,3,5,5-tetramethylpiperazin-1-yl)carbonyl]phenyl}-7-(2-fluoro-6-methoxyphenyl)-5H-pyrimido[5,4-d][2]benzazepin-2-amine I-425: N-1-azabicyclo[2.2.2]oct-3-yl-4-{[9-chloro-7-(2,6-difluorophenyl)-5H-pyrimido[5,4-d][2]benzazepin-2-yl]amino}-2-fluoro-N-methylbenzamide I-426: N-1-azabicyclo[2.2.2]oct-3-yl-4-{[9-chloro-7-(2-fluoro-6-methoxyphenyl)-5H-pyrimido[5,4-d][2]benzazepin-2-yl]amino}-N-methylbenzamide I-427: N-8-azabicyclo[3.2.1]oct-3-yl-4-{[9-chloro-7-(2,6-difluorophenyl)-5H-pyrimido[5,4-d][2]benzazepin-2-yl]amino}-N-methylbenzamide I-428: 9-chloro-7-(2,6-difluorophenyl)-N-(4-{[3-(methylamino)-8-azabicyclo[3.2.1]oct-8-yl]carbonyl}phenyl)-5H-pyrimido[5,4-d][2]benzazepin-2-amine I-429: 9-chloro-7-(2-fluoro-6-methoxyphenyl)-N-(4-{[3-(methylamino)-8-azabicyclo[3.2.1]oct-8-yl]carbonyl}phenyl)-5H-pyrimido[5,4-d][2]benzazepin-2-amine I-430: 4-{[7-(2,6-difluorophenyl)-9-methyl-5H-pyrimido[5,4-c]thieno[2,3-e]azepin-2-yl]amino}benzoic acid I-431: 7-(2,6-difluorophenyl)-N-{4-[(3,3,5,5-tetramethyl-piperazin-1-yl)carbonyl]phenyl}-5H-pyrimido[5,4-c]thieno[2,3-e]azepin-2-amine I-432: N-{4-[(3-amino-3-methylpyrrolidin-1-yl)carbonyl]phenyl}-7-(2,6-difluorophenyl)-10-methyl-5,10-dihydropyrimido[5,4-c]pyrrolo[2,3-e]azepin-2-amine I-433: 7-(2,6-difluorophenyl)-9-methyl-N-(4-{[3-(methylamino)pyrrolidin-1-yl]carbonyl}phenyl)-5H-furo[2,3-c]pyrimido[4,5-e]azepin-2-amine I-434: 4-(2,6-difluorophenyl)-2-methyl-N-(4-{[3-methyl-3-(methylamino)pyrrolidin-1-yl]carbonyl}phenyl)-6H-pyrimido[5,4-c][1,3]thiazolo[4,5-e]azepin-9-amine I-435: N-{4-[(3-amino-3-methylpyrrolidin-1-yl)carbonyl]phenyl}-7-(2-fluoro-6-methoxyphenyl)-5,9-dihydropyrimido[5,4-c]pyrrolo[3,4-e]azepin-2-amine I-436: 4-{[4-(2,6-difluorophenyl)-1-methy-1,6-dihydropyrazolo[4,3-c]pyrimido[4,5-e]azepin-9-yl]amino}benzoic acid I-437: 1-{4-[4-(2,6-Difluoro-phenyl)-2-methyl-6H-3-thia-5,8,10-triaza-benzo[e]azulen-9-ylamino]-benzoyl}-4-dimethylamino-piperidine-4-carboxylic acid methylamide I-438: 4-(4-{[7-(2,6-difluorophenyl)-5H-furo[3,2-c]pyrimido[4,5-e]azepin-2-yl]amino}benzoyl)-N-methylpiperazine-2-carboxamide I-439: 4-(4-{[4-(2,6-difluorophenyl)-6H-isoxazolo[4,5-c]pyrimido[4,5-e]azepin-9-yl]amino}benzoyl)-N-methyl-piperazine-2-carboxamide I-440: 4-(2,6-difluorophenyl)-9-[(4-{[3-methyl-3-(methylamino)pyrrolidin-1-yl]carbonyl}phenyl)amino]-3,6-dihydroimidazo[4,5-c]pyrimido[4,5-e]azepin-2(1H)-one I-441: 2-amino-N-(3-{[7-(2,6-difluorophenyl)-8,10-dimethyl-5H-pyrimido[5,4-c]thieno[3,4-e]azepin-2-yl]amino}phenyl)-N,2-dimethylpropanamide I-442: 9-chloro-7-(2,6-difluorophenyl)-N-{3-[(2,2,6,6-tetramethylpiperidin-4-yl)oxy]phenyl}-5H-pyrimido[5,4-d][2]benzazepin-2-amine I-443: 4-(4-{[9-chloro-7-(2,6-difluorophenyl)-5H-pyrimido[5,4-d][2]benzazepin-2-yl]amino}phenyl)-N-methyl-1-(methylamino)cyclohexanecarboxamide I-444: 7-(3-{[7-(2-fluoro-6-methoxyphenyl)-9-methoxy-5H-pyrimido[5,4-d][2]benzazepin-2-yl]amino}phenyl)-1,7-diazaspiro[4.4]nonan-6-one I-445: 9-chloro-N-[4-(3,8-diazabicyclo[3.2.1]oct-3-ylcarbonyl)phenyl]-7-(2,6-difluorophenyl)-5H-pyrimido[5,4-d][2]benzazepin-2-amine I-446: 1-(3-{[9-chloro-7-(2,6-difluorophenyl)-5H-pyrimido[5,4-d][2]benzazepin-2-yl]amino}phenyl)-3,5,5-trimethylpiperazin-2-one I-447: 9-chloro-N-[4-(2,6-dimethylpiperidin-4-yl)phenyl]-7-(2-fluoro-6-methoxyphenyl)-5H-pyrimido[5,4-d][2]benzazepin-2-amine I-448: N-[4-(1-amino-1-methylethyl)phenyl]-9-chloro-7-(2,6-difluorophenyl)-5H-pyrimido[5,4-d][2]benzazepin-2-amine I-449: N-[4-(2,5-diazaspiro[3.4]oct-2-ylcarbonyl)phenyl]-7-(2,6-difluorophenyl)-10-methyl-5H-isothiazolo[5,4-c]pyrimido[4,5-e]azepin-2-amine I-450: 4-(2,6-difluorophenyl)-1-methyl-9-[(4-{[4-methyl-4-(methylamino)piperidin-1-yl]carbonyl}phenyl)amino]-1,6-dihydro-2H-pyrimido[5,4-c][1,3]thiazolo[4,5-e]azepin-2-one I-451: 4-(2,6-difluorophenyl)-N-[4-(1H-imidazol-2-yl)phenyl]-1-methyl-1,6-dihydroimidazo[4,5-c]pyrimido[4,5-e]azepin-9-amine I-452: 4-{[7-(2,6-difluorophenyl)-5H-[1]benzofuro[2,3-c]pyrimido[4,5-e]azepin-2-yl]amino}benzoic acid I-453: 7-(2-fluorophenyl)-N-{4-[(3,3,5,5-tetramethylpiperazin-1-yl)carbonyl]phenyl}-8,9,10,11-tetrahydro-5H-pyrido[4',3':4,5]thieno[3,2-c]pyrimido[4,5-e]azepin-2-amine I-454: 9-bromo-7-(2-fluorophenyl)-N-(4-{[3-(methylamino)pyrrolidin-1-yl]carbonyl}phenyl)-5,8-dihydropyrimido[5,4-c]pyrrolo[3,2-e]azepin-2-amine I-455: 7-(2-fluorophenyl)-N-(3-methyl-1H-indazol-6-yl)-5,12-dihydropyrimido[4',5':5,6]azepino[4,3-b]indol-2-amine I-456: 1-(4-{[7-(2,6-difluorophenyl)-9,10-dimethyl-5,8-dihydropyrimido[5,4-c]pyrrolo[3,2-e]azepin-2-yl]amino}benzoyl)-3-(methylamino)pyrrolidine-3-carboxamide I-457: {3-[9-Chloro-7-(2-fluoro-6-methoxy-phenyl)-5H-benzo[c]pyrimido-[4,5-e]azepin-2-yl amino]-phenyl}-(4-methyl-piperazin-1-yl)-methanone I-458: [9-Chloro-7-(2,6-difluoro-phenyl)-5H-benzo[c]pyrimido[4,5-e]azepin-2-yl]-(2-methylaminomethyl-benzothiazol-6-yl)-amine I-459: 4-[9-Chloro-7-(2-isopropoxy-phenyl)-5H-benzo[c]pyrimido[4,5-e]azepin-2-ylamino]-benzoic acid I-460: 4-[9-Chloro-7-(2-fluoro-6-isopropoxy-phenyl)-5H-benzo[c]pyrimido[4,5-e]azepin-2-ylamino]-benzoic acid I-461: 4-[9-Chloro-7-(2-ethoxy-phenyl)-5H-benzo[c]pyrimido-[4,5-e]azepin-2-ylamino]-benzoic acid I-462: 4-[9-Chloro-7-(2-ethoxy-6-fluoro-phenyl)-5H-benzo[c]pyrimido-[4,5-e]azepin-2-ylamino]-benzoic acid I-463: 4-[9-Chloro-7-(2-fluoro-6-methyl-phenyl)-5H-benzo[c]pyrimido-[4,5-e]azepin-2-ylamino]-benzoic acid I-464: 4-[9-Chloro-7-(2-trifluoromethoxy-phenyl)-5H-benzo[c]pyrimido-[4,5-e]azepin-2-ylamino]-benzoic acid I-465: 4-[9-Chloro-7-(2-fluoro-6-trifluoromethoxy-phenyl)-5H-benzo[c]pyrimido[4,5-e]azepin-2-ylamino]-benzoic acid I-466: 4-[9-Chloro-7-(3-fluoro-2-trifluoromethoxy-phenyl)-5H-benzo[c]pyrimido[4,5-e]azepin-2-ylamino]-benzoic acid I-467: 4-[9-Chloro-7-(2,3-dimethoxy-phenyl)-5H-benzo[c]pyrimido-[4,5-e]azepin-2-ylamino]-benzoic acid I-468: 4-[9-Chloro-7-(2-isobutyl-phenyl)-5H-benzo[c]pyrimido[4,5-e]azepin-2-ylamino]-benzoic acid I-469: 4-(7-Benzofuran-2-yl-9-chloro-5H-benzo[c]pyrimido[4,5-e]azepin-2-ylamino)-benzoic acid I-470: 4-[9-Chloro-7-(1-methyl-1H-pyrrol-2-yl)-5H-benzo[c]pyrimido-[4,5-e]azepin-2-ylamino]-benzoic acid I-471: 4-[9-Chloro-7-(1-methyl-1H-imidazol-2-yl)-5H-benzo[c]pyrimido-[4,5-e]azepin-2-ylamino]-benzoic acid I-472: 4-(9-Chloro-7-thiophen-2-yl-5H-benzo[c]pyrimido[4,5-e]azepin-2-ylamino)-benzoic acid I-473: 4-[9-Chloro-7-(2H-pyrazol-3-yl)-5H-benzo[c]pyrimido[4,5-e]azepin-2-ylamino]-benzoic acid I-474: 4-[9-Chloro-7-(2-ethynyl-phenyl)-5H-benzo[c]pyrimido[4,5-e]azepin-2-ylamino]-benzoic acid I-475: 4-[7-(2-Aminomethyl-phenyl)-9-chloro-5H-benzo[c]pyrimido-[4,5-e]azepin-2-ylamino]-benzoic acid I-476: 4-[9-Chloro-7-(5-fluoro-2-methoxy-phenyl)-5H-benzo[c]pyrimido-[4,5-e]azepin-2-ylamino]-benzoic acid I-477: 4-[9-Chloro-7-(3-methoxy-pyridin-2-yl)-5H-benzo[c]pyrimido-[4,5-e]azepin-2-ylamino]-benzoic acid I-478: 4-[8-Fluoro-7-(2-fluoro-phenyl)-5H-benzo[c]pyrimido[4,5-e]azepin-2-ylamino]-benzoic acid I-479: 4-[8-Chloro-7-(2-fluoro-phenyl)-5H-benzo[c]pyrimido[4,5-e]azepin-2-ylamino]-benzoic acid I-480: 4-[11-Fluoro-7-(2-fluoro-phenyl)-5H-benzo[c]pyrimido[4,5-e]azepin-2-ylamino]-benzoic acid I-481: 4-[11-Chloro-7-(2-fluoro-phenyl)-5H-benzo[c]pyrimido[4,5-e]azepin-2-ylamino]-benzoic acid I-482: 6-[9-Chloro-7-(2-fluoro-phenyl)-5H-benzo[c]pyrimido[4,5-e]azepin-2-ylamino]-pyridazine-3-carboxylic acid I-483: 2-[9-Chloro-7-(2-fluoro-phenyl)-5H-benzo[c]pyrimido[4,5-e]azepin-2-ylamino]-1H-imidazole-4-carboxylic acid I-484: 4-[9-Chloro-7-(2-fluoro-phenyl)-4-methyl-5H-benzo[c]pyrimido-[4,5-e]azepin-2-ylamino]-benzoic acid I-485: 4-[4-Aminomethyl-9-chloro-7-(2-fluoro-phenyl)-5H-benzo[c]pyrimido[4,5-e]azepin-2-ylamino]-benzoic acid I-486: 4-(9-Aminomethyl-7-phenyl-5H-benzo[c]pyrimido[4,5-e]azepin-2-ylamino)-benzoic acid I-487: 9-Chloro-7-(2-fluorophenyl)-N-{4-[(2-methylpiperazin-1-yl)carbonyl]phenyl}-5H-pyrimido[5,4-d][2]benzazepin-2-amine I-488: 4-{[9-Chloro-7-(2-fluorophenyl)-5H-pyrimido[5,4-d][2]benzazepin-2-yl]amino}-N-[{3-[(dimethylamino)methyl]azetidin-1-yl}(imino)methyl]benzamide I-489: 4-{[9-Chloro-7-(2-fluorophenyl)-5H-pyrimido[5,4-d][2]benzazepin-2-yl]amino}-N-[imino(piperazin-1-yl)methyl]benzamide I-490: 4-{[9-Chloro-7-(2-fluorophenyl)-5H-pyrimido[5,4-d][2]benzazepin-2-yl]amino}-N-[imino(3-methylpiperazin-1-yl)methyl]benzamide I-491: 4-{[9-Chloro-7-(2-fluorophenyl)-5H-pyrimido[5,4-d][2]benzazepin-2-yl]amino}-N-[[3-(dimethylamino)pyrrolidin-1-yl](imino)methyl]benzamide I-492: 4-{[9-Chloro-7-(2-fluorophenyl)-5H-pyrimido[5,4-d][2]benzazepin-2-yl]amino}-N-[imino(4-methylpiperazin-1-yl)methyl]benzamide I-493: 4-{[9-Chloro-7-(2-fluorophenyl)-5H-pyrimido[5,4-d][2]benzazepin-2-yl]amino}-N-[(3,5-dimethylpiperazin-1-yl)(imino)methyl]benzamide I-494: 1-[[(4-{[9-Chloro-7-(2-fluorophenyl)-5H-pyrimido[5,4-d][2]benzazepin-2-yl]amino}benzoyl)amino](imino)methyl]pyrrolidine-3-carboxamide I-495: 1-[[(4-{[9-Chloro-7-(2-fluorophenyl)-5H-pyrimido[5,4-d][2]benzazepin-2-yl]amino}benzoyl)amino](imino)methyl]piperidine-3-carboxamide I-496: 4-{[9-Chloro-7-(2-fluorophenyl)-5H-pyrimido[5,4-d][2]benzazepin-2-yl]amino}-N-[{4-[(cyclopropylcarbonyl)amino]piperidin-1-yl}(imino)methyl]benzamide I-497: 4-{[9-Chloro-7-(2-fluorophenyl)-5H-pyrimido[5,4-d][2]benzazepin-2-yl]amino}-N-[(dimethylamino)(imino)methyl]benzamide I-498: N-[[(4-{[9-Chloro-7-(2-fluorophenyl)-5H-pyrimido[5,4-d][2]benzazepin-2-yl]amino}phenyl)amino](imino)methyl]cyclopropanecarboxamide I-499: N-[[(4-{[9-Chloro-7-(2-fluorophenyl)-5H-pyrimido[5,4-d][2]benzazepin-2-yl]amino}phenyl)amino](imino)methyl]-3-(dimethylamino)cyclopentanecarboxamide I-500: 4-({9-Chloro-7-[2-fluoro-6-(trifluoromethyl)phenyl]-5H-pyrimido-[5,4-d][2]benzazepin-2-yl}amino)benzoic acid I-501: 4-{[9-Chloro-7-(2,6-dichlorophenyl)-5H-pyrimido[5,4-d][2]benzazepin-2-yl]amino}benzoic acid I-502: 4-{[9-Chloro-7-(2-fluoro-6-methylphenyl)-5H-pyrimido-[5,4-d][2]benzazepin-2-yl]amino}benzoic acid I-503: 4-{[7-(2-Bromo-6-chlorophenyl)-9-chloro-5H-pyrimido-[5,4-d][2]benzazepin-2-yl]amino}benzoic acid I-504: 9-Chloro-7-(2,6-difluorophenyl)-N-{4-[(3,5-dimethylpiperazin-1-yl)carbonyl]-3-fluorophenyl}-5H-pyrimido[5,4-d][2]benzazepin-2-amine I-505: 4-{[9-Chloro-7-(2,6-difluorophenyl)-5H-pyrimido[5,4-d][2]benzazepin-2-yl]amino}-N-[(3,5-dimethylpiperazin-1-yl)(imino)methyl]-N-methylbenzamide I-506: 4-{[9-Chloro-7-(2,6-difluorophenyl)-5H-pyrimido[5,4-d][2]benzazepin-2-yl]amino}-N-[[3-(dimethylamino)azetidin-1-yl](imino)methyl]-N-methylbenzamide I-507: 3-{[9-Chloro-7-(2,6-difluorophenyl)-5H-pyrimido[5,4-d][2]benzazepin-2-yl]amino}-N-[(3,5-dimethylpiperazin-1-yl)(imino)methyl]benzamide I-508: 3-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide I-509: 9-Chloro-7-(2,6-difluorophenyl)-N-{3-[(3,5-dimethylpiperazin-1-yl)carbonyl]-4-fluorophenyl}-5H-pyrimido[5,4-d][2]benzazepin-2-amine I-510: N-[[(4-{[9-Chloro-7-(2,6-difluorophenyl)-5H-pyrimido-[5,4-d][2]benzazepin-2-yl]amino}phenyl)amino](imino)methyl]-3-(dimethylamino)cyclopentanecarboxamide I-511: N-[[(4-{[9-Chloro-7-(2,6-difluorophenyl)-5H-pyrimido-[5,4-d][2]benzazepin-2-yl]amino}-2-fluorophenyl)amino](imino)methyl]-3-(dimethylamino)cyclopentanecarboxamide I-512: N-[[(5-{[9-Chloro-7-(2,6-difluorophenyl)-5H-pyrimido-[5,4-d][2]benzazepin-2-yl]amino}-2-fluorophenyl)amino](imino)methyl]-3-(dimethylamino)cyclopentanecarboxamide I-513: N-(4-{[9-Chloro-7-(2,6-difluorophenyl)-5H-pyrimido-[5,4-d][2]benzazepin-2-yl]amino}phenyl)-3,5-dimethylpiperazine-1-carboximidamide I-514: 4-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]-N-methylbenzamide I-515: N-(3-{[9-Chloro-7-(2,6-difluorophenyl)-5<i>H</i>-pyrimido-[5,4-d][2]benzazepin-2-yl]amino}phenyl)-3,5-dimethylpiperazine-1-carboximidamide I-516: N-(3-{[9-Chloro-7-(2,6-difluorophenyl)-5H-pyrimido-[5,4-d][2]benzazepin-2-yl]amino}phenyl)-N,3,5-trimethylpiperazine-1-carboximidamide I-517: 3-{[9-Chloro-7-(2,6-difluorophenyl)-5H-pyrimido[5,4-d][2]benzazepin-2-yl]amino}-N-[[3-(dimethylamino)azetidin-1-yl](imino)methyl]benzamide I-518: N-(5-{[9-Chloro-7-(2,6-difluorophenyl)-5H-pyrimido-[5,4-d][2]benzazepin-2-yl]amino}-2-fluorophenyl)-N,3,5-trimethylpiperazine-1-carboximidamide I-519: N-[[(3-{[9-Chloro-7-(2,6-difluorophenyl)-5H-pyrimido-[5,4-d][2]benzazepin-2-yl]amino}phenyl)amino](imino)methyl]-3-(dimethylamino)cyclopentanecarboxamide I-520: 9-Chloro-7-(2,6-difluorophenyl)-N-{3-[(3,5-dimethylpiperazin-1-yl)(imino)methyl]phenyl}-5H-pyrimido[5,4-d][2]benzazepin-2-amine I-521: N-(4-{[9-Chloro-7-(2,6-difluorophenyl)-5H-pyrimido-[5,4-d][2]benzazepin-2-yl]amino}phenyl)-N,3,5-trimethylpiperazine-1-carboximidamide I-522: N-(4-{[9-Chloro-7-(2,6-difluorophenyl)-5H-pyrimido-[5,4-d][2]benzazepin-2-yl]amino}-2-fluorophenyl)-3,5-dimethylpiperazine-1-carboximidamide I-523: 9-Chloro-7-(2,6-difluorophenyl)-N-{4-[(3,5-dimethylpiperazin-1-yl)(imino)methyl]-3-fluorophenyl}-5H-pyrimido[5,4-d][2]benzazepin-2-amine I-524: 5-{[9-Chloro-7-(2,6-difluorophenyl)-5H-pyrimido[5,4-d][2]benzazepin-2-yl]amino}-2-(2,6-dimethylpiperidin-4-yl)-1H-isoindole-1,3(2H)-dione I-525: N-[2-(Aminomethyl)-1H-benzimidazol-6-yl]-9-chloro-7-(2-fluorophenyl)-5H-pyrimido[5,4-d][2]benzazepin-2-amine I-526: 9-Chloro-7-(2-fluorophenyl)-N-{2-[(methylamino)methyl]-1H-benzimidazol-6-yl}-5H-pyrimido[5,4-d][2]benzazepin-2-amine I-527: 9-Chloro-N-{2-[(dimethylamino)methyl]-1H-benzimidazol-6-yl}-7-(2-fluorophenyl)-5H-pyrimido[5,4-d][2]benzazepin-2-amine I-528: 9-Chloro-7-(2-fluorophenyl)-N-{2-[(methylamino)methyl]-1,3-benzothiazol-6-yl}-5H-pyrimido[5,4-d][2]benzazepin-2-amine I-529: 9-Chloro-7-(2,6-difluorophenyl)-N-{2-[(methylamino)methyl]-1H-benzimidazol-6-yl}-5H-pyrimido[5,4-d][2]benzazepin-2-amine I-530: 9-Chloro-7-(2,6-difluorophenyl)-N-{2-[(methylamino)methyl]-1,3-benzoxazol-6-yl}-5H-pyrimido[5,4-d][2]benzazepin-2-amine I-531: 9-Chloro-7-(2-fluorophenyl)-N-{2-[(methylamino)methyl]-1,3-benzoxazol-6-yl}-5H-pyrimido[5,4-d][2]benzazepin-2-amine I-532: 9-Chloro-7-(2,6-difluorophenyl)-N-{3-[(3,5-dimethylpiperazin-1-yl)(imino)methyl]-4-fluorophenyl}-5H-pyrimido[5,4-d][2]benzazepin-2-amine I-533: 9-Chloro-7-(2,6-difluorophenyl)-N-{2-[(methylamino)methyl]-1,3-benzothiazol-6-yl}-5H-pyrimido[5,4-d][2]benzazepin-2-amine I-534: {3-[9-Chloro-7-(2,6-difluorophenyl)-5H-benzo[c]pyrimido[4,5-e]azepin-2-ylamino]-phenyl}-(4-methyl-piperazin-1-yl)-methanone I-535: 3-[9-Chloro-7-(2,6-difluoro-phenyl)-5H-benzo[c]pyrimido[4,5-e]azepin-2-ylamino]-N-methyl-N-(4-methylpentyl)-benzamide In one embodiment, the invention relates to a compound selected from the group consisting of:

I-52: 4-[9-Chloro-7-(2-fluoro-phenyl)-5H-benzo[c]pyrimido[4,5-e]azepin-2-ylamino]-benzoic acid I-135: 4-[9-Chloro-7-(2,6-difluoro-phenyl)-5H-benzo[c]pyrimido[4,5-e]azepin-2-ylamino]-benzoic acid I-174: 4-{[9-Chloro-7-(2-chloro-6-fluorophenyl)-5H-pyrimido-[5,4-d][2]benzazepin-2-yl]amino}benzoic acid I-175: 9-Chloro-7-(2,6-difluorophenyl)-N-{4-[(3,5-dimethylpiperazin-1-yl)carbonyl]phenyl}-5H-pyrimido[5,4-d][2]benzazepin-2-amine I-177: 9-Chloro-N-{4-[(3,5-dimethylpiperazin-1-yl)carbonyl]phenyl}-7-(2-fluoro-6-methoxyphenyl)-5H-pyrimido[5,4-d][2]benzazepin-2-amine I-179: 9-Chloro-N-(4-{[3-(dimethylamino)azetidin-1-yl]carbonyl}phenyl)-7-(2-fluoro-6-methoxyphenyl)-5H-pyrimido[5,4-d][2]benzazepin-2-amine I-183: {4-[9-Chloro-7-(2,6-difluoro-phenyl)-5H-benzo[c]pyrimido[4,5-e]azepin-2-ylamino]-phenyl}-(4-dimethylamino-piperidin-1-yl)-methanone I-190: 4-[9-Chloro-7-(2-fluoro-6-methoxy-phenyl)-5H-benzo[c]pyrimido[4,5-e]azepin-2-ylamino]-benzoic acid I-191: {4-[9-Chloro-7-(2,6-difluoro-phenyl)-5H-benzo[c]pyrimido[4,5-e]azepin-2-ylamino]-phenyl}-(3(S)-methyl-piperazin-1-yl)-methanone I-196: (3-Amino-pyrrolidin-1-yl)-{4-[9-chloro-7-(2,6-difluoro-phenyl)-5H-benzo[c]pyrimido[4,5-e]azepin-2-ylamino]-phenyl}-methanone I-197: {4-[9-Chloro-7-(2,6-difluoro-phenyl)-5H-benzo[c]pyrimido[4,5-e]azepin-2-ylamino]-phenyl}-(3-methylamino-pyrrolidin-1-yl)-methanone I-199: {4-[9-Chloro-7-(2-fluoro-6-methoxy-phenyl)-5H-benzo[c]pyrimido[4,5-e]azepin-2-ylamino]-phenyl}-(3-methylamino-pyrrolidin-1-yl)-methanone I-220: 9-chloro-7-(2,6-difluorophenyl)-N-(4-{[4-(methylamino)piperidin-1-yl]carbonyl}phenyl)-5H-pyrimido[5,4-d][2]benzazepin-2-amine I-232: 9-chloro-7-(2-fluoro-6-methoxyphenyl)-N-{4-[(3-methylpiperazin-1-yl)carbonyl]phenyl}-5H-pyrimido[5,4-d][2]benzazepin-2-amine I-234: 9-chloro-7-(2,6-difluorophenyl)-N-(4-{[3-(methylamino)azetidin-1-yl]carbonyl}phenyl)-5H-pyrimido[5,4-d][2]benzazepin-2-amine I-235: 9-chloro-7-(2-fluoro-6-methoxyphenyl)-N-(4-{[3-(methylamino)azetidin-1-yl]carbonyl}phenyl)-5H-pyrimido[5,4-d][2]benzazepin-2-amine I-240: N-{4-[(3-aminopyrrolidin-1-yl)carbonyl]phenyl}-9-chloro-7-(2-fluoro-6-methoxyphenyl)-5H-pyrimido[5,4-d][2]benzazepin-2-amine I-241: N-{4-[(4-aminopiperidin-1-yl)carbonyl]phenyl}-9-chloro-7-(2-fluoro-6-methoxyphenyl)-5H-pyrimido[5,4-d][2]benzazepin-2-amine I-242: 9-chloro-7-(2-fluoro-6-methoxyphenyl)-N-(4-{[4-(methylamino)piperidin-1-yl]carbonyl}phenyl)-5H-pyrimido[5,4-d][2]benzazepin-2-amine I-263: 9-chloro-7-(2-fluoro-6-methoxyphenyl)-N-(4-{[3-(methylamino)piperidin-1-yl]carbonyl}phenyl)-5H-pyrimido[5,4-d][2]benzazepin-2-amine I-286: N-{4-[(3-aminoazetidin-1-yl)carbonyl]phenyl}-9-chloro-7-(2-fluoro-6-methoxyphenyl)-5H-pyrimido[5,4-d][2]benzazepin-2-amine I-293: 9-chloro-7-(2,6-difluorophenyl)-N-(4-{[3-(dimethylamino)piperidin-1-yl]carbonyl}phenyl)-5H-pyrimido[5,4-d][2]benzazepin-2-amine I-310: 4-(4-{[9-chloro-7-(2,6-difluorophenyl)-5H-pyrimido[5,4-d][2]benzazepin-2-yl]amino}benzoyl)-N-methylpiperazine-2-carboxamide I-318: N-{4-[(3-aminopyrrolidin-1-yl)carbonyl]-3-chlorophenyl}-9-chloro-7-(2,6-difluorophenyl)-5H-pyrimido[5,4-d][2]benzazepin-2-amine I-326: 9-chloro-7-(2-chloro-6-fluorophenyl)-N-(4-{[3-(methylamino)piperidin-1-yl]carbonyl}phenyl)-5H-pyrimido[5,4-d][2]benzazepin-2-amine I-341: 4-amino-1-(4-{[9-chloro-7-(2,6-difluorophenyl)-5H-pyrimido[5,4-d][2]benzazepin-2-yl]amino}benzoyl)-N-methylpiperidine-4-carboxamide I-383: N-1-azabicyclo[2.2.2]oct-3-yl-4-{[9-chloro-7-(2,6-difluorophenyl)-5H-pyrimido[5,4-d][2]benzazepin-2-yl]amino}-N-methylbenzamide I-380: 9-chloro-7-(2,6-difluorophenyl)-N-(4-{[3-methyl-3-(methylamino)pyrrolidin-1-yl]carbonyl}phenyl)-5H-pyrimido[5,4-d][2]benzazepin-2-amine I-396: 4-amino-1-(2-chloro-4-{[9-chloro-7-(2,6-difluorophenyl)-5H-pyrimido[5,4-d][2]benzazepin-2-yl]amino}benzoyl)-N-methylpiperidine-4-carboxamide can be prepared by a route analogous to that outlined in Scheme 1, by appropriate selection of the ketone starting material in Method G.

Methods for the synthesis of dimethylaminomethylene-benzo[c]azepin-5-ones of the formula v (see Scheme 1) have been described in U.S. Pat. Nos. 3,947,585, 4,022,801 and 4,028,381. Methods for the conversion of compounds of formula v to pyrimido[5,4-d][2]benzazepines lacking a Ring C substituent also are known and have been described, e.g., in U.S. Pat. Nos. 4,318,854 and 4,547,581. Compounds of the present invention (formula IIa), which include Ring C, can be prepared by the reaction of compounds of formula v with aryl or heteroaryl guanidines, as illustrated in Scheme 1.

Scheme 1: General route for the synthesis of N-Aryl-(7-phenyl-5H-benzo[c]-pyrimido[4,5-e]azepin-2-yl)-amines

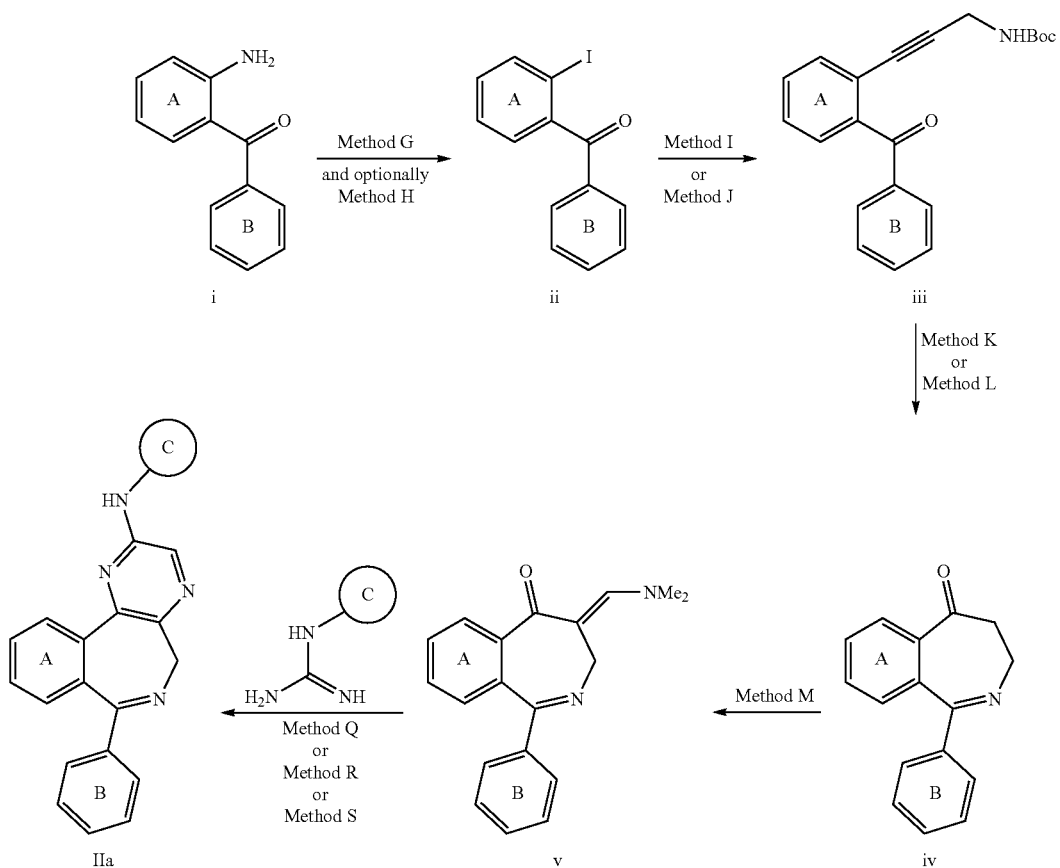

The compounds of the present invention can be prepared by methods known to one of ordinary skill in the art and/or by reference to the synthetic routes set forth in Schemes 1, 2, and 3 below. One of ordinary skill in the art will recognize that variations in reaction conditions, including variations in solvent, reagents, catalysts, and reaction temperature, may be possible for each of the reactions described below. Alternate synthetic routes also are possible.

Scheme 1 depicts a general synthetic route for preparation of compounds of formula (I) wherein each of rings A and B is an optionally substituted phenyl ring. One of ordinary skill in the art will appreciate that certain compounds of formula (I) wherein one or both of rings A and B is other than phenyl Methods for the synthesis of amino-substituted diaryl ketones of formula (i) are known, and exemplary synthetic procedures are described in the Examples. Conversion of (i) to the iodo-substituted diaryl ketone of formula (ii) can be accomplished by diazotization of the amine and iodide displacement, as exemplified in Method G. Compound (iii) can be prepared from (ii) by cross-coupling of the aryl iodide with a protected propargyl amine, according to Method I. In Scheme 1, an iodo-substituted diaryl ketone is coupled with N-Boc-propargylamine, but those of ordinary skill in the art will recognize that other halogen-substituted diaryl ketones and other protected propargylamines may be used. Additionally, a variety of catalysts, bases, solvents and tempera- Scheme 2: General route for the synthesis of compounds of formula (A-1).

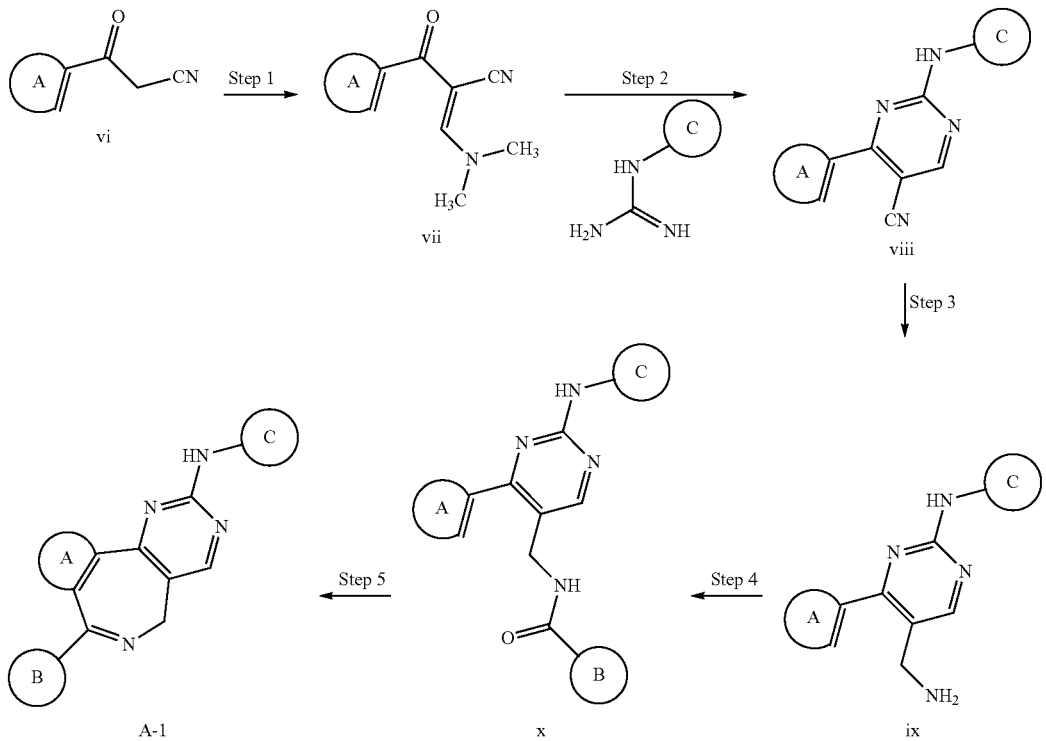

ration of (iii) may alternatively be accomplished by Method J, in which the Weinreb amide of a 2-iodobenzoic acid is coupled with N-Boc-propargylamine, followed by a lithiated Ring B.

Stepwise conversion of (iii) to (iv) can be effected by sequential treatment with mercury (II) sulfate, HCl/dioxane, and N,N-diisopropylethylamine, according to Method K. Alternatively, (iii) can be converted to (iv) by sequential treatment with aqueous HCl/dioxane and sodium carbonate, according to Method L. Those of ordinary skill in the art will recognize that aryl alkynes can be hydrated with a variety of other strong acids, such as trifluoroacetic acid and sulfuric acid. Additionally, a variety of basic conditions can promote the azepine imine bond formation.

Treatment of (iv) with N,N-dimethylformamide dimethyl acetal in various solvents and at various temperatures affords (v). Example 11 illustrates the conversion of (iv) to (v) in toluene at 80° C. The conversion of (v) to the pyrimido compound (IIa) is accomplished by treatment with an aryl or heteroaryl guanidine. The reaction may be performed by submitting a reaction mixture containing (v), an aryl or heteroaryl guanidine, and N,N-diisopropylethylamine in DMF to microwave irradiation, according to Method Q. Alternatively, the latter reaction may be performed in the presence of potassium carbonate in refluxing ethanol, according to Method R.

In some embodiments, preparation of (IIa) may alternatively be accomplished by Method S, in which (v) is first treated with guanidine hydrochloride to form a 5H-benzo[c]pyrimido[4,5-e]azepin-2-yl amine. Conversion of the amine to the corresponding iodide, followed by cross-coupling with a heteroaryl amine then affords compound (IIa), in which Ring C is heteroaryl.

Scheme 2 depicts a general synthetic route for preparation of compounds of formula (A-1) wherein Ring A is an optionally substituted 5- or 6-membered aryl, heteroaryl, or heterocyclyl ring, Ring B is an optionally substituted aryl, heterocyclyl, cycloaliphatic, or heteroaryl ring, and Ring C is a substituted or unsubstituted aryl, heteroaryl, heterocyclyl, or cycloaliphatic ring.

Methods for the synthesis of heterocyclic-substituted β-ketonitriles of formula (vi) are known and described in the literature e.g., Katritzky et al, JOC (2003), 68(12), 4932-4934 and Bergman et al, Synthesis (2004), 16, 2760-2765. Treatment of compounds (vi) with N,N-dimethylformamide dimethyl acetal in various solvents and at various temperatures affords intermediate enaminone (vii). Methods for the synthesis of intermediate enaminones of formula (vii) have been further described in PCT Int. Appl. WO 00/78731.

The preparation of cyanopyrimidine (viii) may be accomplished by treatment of enaminone (vii) with a mono-substituted guanidine, as shown in Step 2. The reaction may be performed by refluxing a reaction mixture containing (vii) and a guanidine in ethanol in the presence of potassium carbonate. Methods for the synthesis of intermediate pyrimidines of formula (viii) have been further described in PCT Int. Appl. WO 00/78731.

As shown in Step 3, compound (viii) may be reduced to amine (ix) by hydrogenation in the presence of a metal catalyst, for example Raney nickel, as described by Price et al, J. Am. Chem. Soc. 68:766-9 (1946). Alternatively, the reduction may be carried out with a reducing agent such as LiAlH$_4$ as described by Thurkauf et al, Bioorg. & Med. Chem. Letters 13(17):2921-2924, (2003).

Conversion of amine (ix) to amide (x) can be accomplished by reaction of (ix) with an acid chloride in the presence of a base, or alternatively, with a carboxylic acid in the presence of a coupling reagent. Amide (x) may then be converted to the desired compound of formula (A-1) by heating with a cyclodehydration reagent such as polyphosphoric acid, phosphorus pentoxide/methanesulfonic acid, phosphorus oxychloride, or phosphorus oxychloride/tin(IV) chloride.

synthesis of intermediate amides of formula (xiii) have been further described in the literature, e.g., Portevin et al, *Tetrahedron Letters*, 44(52):9263-9265 (2003) and El-Naggar et al, *J. Indian Chem. Soc.*, 59(6):783-6 (1982).

The preparation of acid (xiv) may be accomplished by treatment of ester (xiii) with a dilute aqueous solution of an alkali-metal hydroxide, e.g., sodium or lithium hydroxide. Examples of this transformation have been described by Scheme 3: Alternative route for the synthesis of compounds of formula (A-1)

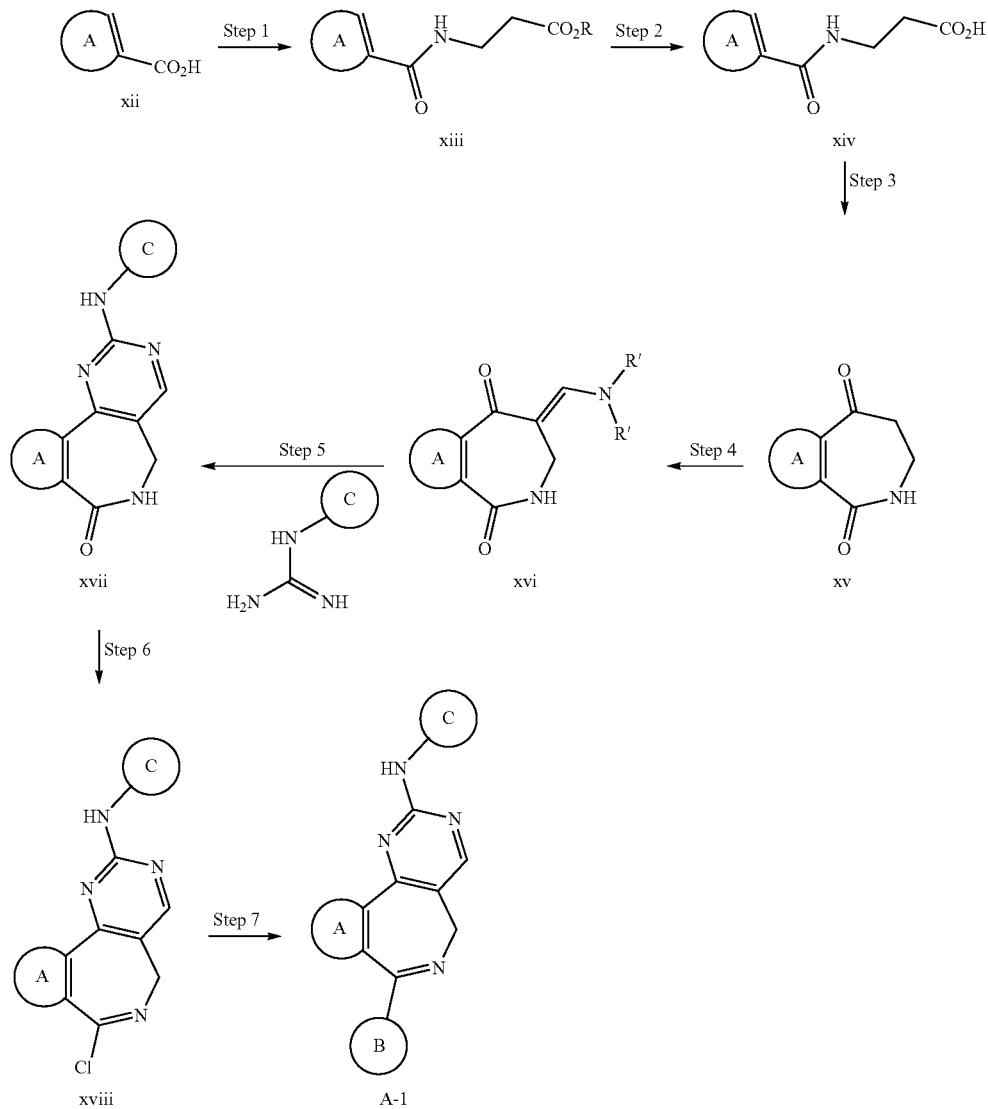

Scheme 3 depicts another general synthetic route for preparation of compounds of formula (A-1) wherein Ring A is an optionally substituted 5- or 6-membered aryl, heteroaryl, or heterocyclyl ring, Ring B is an optionally substituted aryl, heterocyclyl, cycloaliphatic, or heteroaryl ring, and Ring C is a substituted or unsubstituted aryl, heteroaryl, heterocyclyl, or cycloaliphatic ring.

Methods for the synthesis of heterocyclic-substituted carboxylic acids of formula (xii) are well-known and are widely described in the literature. Condensation of compound (xii) with a β-alanine ester affords amide (xiii). Methods for the Portevin et al, *Tetrahedron Letters*, 44(52):9263-9265 (2003)

Compound (xiv) may be cyclized to azepinedione (xv) by treatment with a cyclodehydration reagent, for example polyphosphoric acid (PPA), as described by Annoura et al, *Tetrahedron Letters* 36(3):413-16 (1995).

The preparation of enaminones (xvi) may be accomplished by treatment of compounds (xv) with N,N-dimethylformamide dimethyl acetal. The reaction may be performed in various solvents and at various temperatures.

The preparation of pyrimidinoazepinone (xvii) may be accomplished by treatment of enaminone (xvi) with a monosubstituted guanidine. The reaction may be performed by refluxing a reaction mixture containing (xvi) and a guanidine in an alcoholic solvent in the presence of potassium carbonate.

Conversion of pyrimidinoazepinone (xvii) to imidoyl chloride (xviii) may be accomplished by reaction of (xvii) with a chlorinating reagent, typically $POCl_3$ or $SOCl_2$. Compound (xviii) may then be cross-coupled with an organoboronic acid using palladium catalysis to yield azepine (xi), following the method of Nadin et al, *J. Org. Chem.*, 68(7), 2844-2852 (2003).

The compounds of this invention are inhibitors of Aurora kinase. The compounds can be assayed in vitro or in vivo for their ability to bind to and/or inhibit an Aurora kinase. In vitro assays include assays to determine inhibition of the ability of an Aurora kinase to phosphorylate a substrate protein or peptide. Alternate in vitro assays quantitate the ability of the compound to bind to an Aurora kinase. Inhibitor binding may be measured by radiolabelling the inhibitor prior to binding, isolating the inhibitor/Aurora kinase complex and determining the amount of radiolabel bound. Alternatively, inhibitor binding may be determined by running a competition experiment in which new inhibitors are incubated with Aurora kinase bound to a known radioligand. The compounds also can be assayed for their ability to affect cellular or physiological functions mediated by Aurora kinase activity. Assays for each of these activities are described in the Examples and/or are known in the art.

In another aspect, therefore, the invention provides a method for inhibiting Aurora kinase activity in a cell, comprising contacting a cell in which inhibition of Aurora kinase is desired with an Aurora kinase inhibitor of formula (I). In some embodiments, the Aurora kinase inhibitor interacts with and reduces the activity of all enzymes of the Aurora kinase family in the cell. In some other embodiments, the Aurora kinase inhibitor interacts with and reduces the activity of fewer than all Aurora kinase enzymes in the cell. In certain preferred embodiments, the Aurora kinase inhibitor selectively inhibits one Aurora kinase enzyme in the cell.

Preferably, the method according to this aspect of the invention causes an inhibition of cell proliferation of the contacted cells. The phrase "inhibiting cell proliferation" is used to denote an ability of an inhibitor of Aurora kinase to inhibit cell number or cell growth in contacted cells as compared to cells not contacted with the inhibitor. An assessment of cell proliferation can be made by counting cells using a cell counter or by an assay of cell viability, e.g., an MTT, XTT, or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, an inhibitor of Aurora kinase that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I) as defined above, or a pharmaceutically acceptable salt thereof, and a pharmaceutically acceptable carrier.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy*, 20*th Ed.*, ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth. For example, compounds of formula (V), wherein Ring C is substituted with —$CO_2H$ may be formulated as the corresponding sodium salts.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to an Aurora kinase-mediated disorder. As used herein, the term "Aurora kinase-mediated disorder" includes any disorder, disease or condition which is caused or characterized by an increase in Aurora kinase expression or activity, or which requires Aurora kinase activity. The term "Aurora kinase-mediated disorder" also includes any disorder, disease or condition in which inhibition of Aurora kinase activity is beneficial. Aurora kinase-mediated disorders include proliferative disorders. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer.

Preferably, the composition is formulated for administration to a patient having or at risk of developing or experiencing a recurrence of an Aurora kinase-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. Preferably, such other therapeutic agent is one normally administered to patients with the disease or condition being treated.

By "therapeutically effective amount" is meant an amount sufficient to cause a detectable decrease in Aurora kinase activity or the severity of an Aurora kinase-mediated disorder. The amount of Aurora kinase inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having or at risk of developing or experiencing a recurrence of an Aurora kinase-mediated disorder. The method comprises the step of administering to the patient a compound or pharmaceutical composition according to the invention. The compounds and pharmaceutical compositions of the invention can be used to achieve a beneficial therapeutic or prophylactic effect, for example, in a patient with a proliferative disorder, as discussed above. The compounds and pharmaceutical compositions of the invention are particularly useful for the treatment of cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideblasts (RARS), (refractory anemia with excess blasts (RAEB), and RAEB in transformation (RAEB-T); and myeloproliferative syndromes.

In some embodiments, the compound or composition of the invention is used to treat a cancer in which the activity of an Aurora kinase is amplified. In some embodiments, the compound or composition of the invention is used to treat a patient having or at risk of developing or experiencing a recurrence in a cancer selected from the group consisting of colorectal cancer, ovarian cancer, breast cancer, gastric cancer, prostate cancer, and pancreatic cancer. In certain embodiments, the cancer is selected from the group consisting of breast cancer, colorectal cancer, and pancreatic cancer.

In some embodiments, the Aurora kinase inhibitor of the invention is administered in conjunction with another therapeutic agent. The other therapeutic agent may also inhibit Aurora kinase or may operate by a different mechanism. In some embodiments, the other therapeutic agent is one that is normally administered to patients with the disease or condition being treated. The Aurora kinase inhibitor of the invention may be administered with the other therapeutic agent in a single dosage form or as a separate dosage form. When administered as a separate dosage form, the other therapeutic agent may be administered prior to, at the same time as, or following administration of the Aurora kinase inhibitor of the invention.

In some embodiments, the Aurora kinase inhibitor of the invention is administered in conjunction with a therapeutic agent selected from the group consisting of cytotoxic agents, radiotherapy, and immunotherapy. Non-limiting examples of cytotoxic agents suitable for use in combination with the Aurora kinase inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs, including, e.g., CC-5013 and CC-4047; protein tyrosine kinase inhibitors, including, e.g., imatinib mesylate and gefitinib; antibodies, including, e.g., trastuzumab, rituximab, cetuximab, and bevacizumab; mitoxantrone; dexamethasone; prednisone; and temozolomide.

In order that this invention be more fully understood, the following preparative and testing examples are set forth. These examples illustrate how to make or test specific compounds, and are not to be construed as limiting the scope of the invention in any way.

EXAMPLES

Definitions
AcOH acetic acid
ATP adenosine triphosphate
BSA bovine serum albumin
Boc tert-butoxycarbonyl
DMF N,N-dimethylformamide
DTT dithiothreitol
EDTA ethylenediaminetetraacetic acid
EtOAc ethyl acetate
Et$_2$O diethyl ether
MeOH methanol
MTT methylthiazoletetrazolium
XTT 2,3-bis(2-methoxy-4-nitro-5-sulfophenyl)-2H-tetrazolium-5-carboxanilide inner salt
WST (4-[3-(4-iodophenyl)-2-(4-nitrophenyl)-2H-5-tetrazolio]-1,3-benzene disulfonate sodium salt
PKA cAMP-dependent protein kinase
PPA polyphosphoric acid
TBTU O-Benzotriazol-1-yl-N,N,N',N'-tetramethyluronium tetrafluoroborate
THF tetrahydrofuran
h hours
min minutes
m/z mass to charge
MS mass spectrum
HRMS high resolution mass spectrum Example 1

Method a for the Synthesis of Compounds of Formula (i) (See Scheme 1)

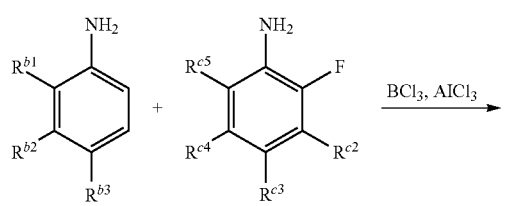

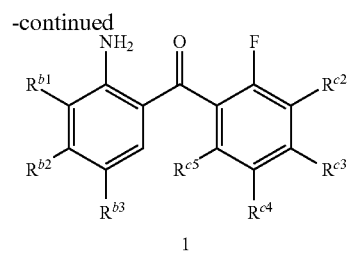

(2-Amino-4-methoxy-phenyl)-(2-fluoro-phenyl)-methanone (1h)

3-Anisidine (1.0 g, 8.0 mmol) was added dropwise to a stirred solution of BCl$_3$ (1M in CH$_2$Cl$_2$, 8.8 mL, 8.8 mmol) in anhydrous CH$_2$Cl$_2$ (20 mL) at 0° C. AlCl$_3$ (1.15 g, 8.8 mmol) was added in one portion followed by 2-fluorobenzonitrile (1.6 mL, 16.0 mmol). The mixture was refluxed for 16 h and then cooled to 0° C. HCl (2N, 30 mL) was added and the mixture was heated to 80° C. and stirred vigorously for 30 min. Upon cooling to room temperature, the mixture was extracted with CH$_2$Cl$_2$ (3×50 mL). The combined organic portions were washed with brine, dried over MgSO$_4$, filtered and evaporated in vacuo. The resulting brown oil was purified by column chromatography (silica gel, Hexanes:EtOAc, 4:1) to provide 1 h (1.1 g, 56%), MS m/z=246 (M+H).

(2-Amino-3-methyl-phenyl)-(2-fluoro-phenyl)-methanone (1b)

In a manner similar to that described above for compound 1h, o-tolylamine and 2-fluorobenzonitrile were converted to 1b (20% yield) MS m/z=230 (M+H).

(2-Amino-4-fluoro-phenyl)-(2-fluoro-phenyl)-methanone (1c)

In a manner similar to that described above for compound 1h, 3-fluoro-phenylamine and 2-fluorobenzonitrile were converted to 1c (25% yield) MS m/z=234 (M+H).

(2-Amino-4-bromo-phenyl)-(2-fluoro-phenyl)-methanone (1e)

In a manner similar to that described above for compound 1h, 3-bromo-phenylamine and 2-fluorobenzonitrile were converted to 1e (15% yield) MS m/z=294/296 (M+H).

(2-Amino-4-methyl-phenyl)-(2-fluoro-phenyl)-methanone (1g)

In a manner similar to that described above for compound 1h, m-tolylamine and 2-fluorobenzonitrile were converted to 1g (44% yield) MS m/z=230 (M+H).

(2-Amino-4,5-dichloro-phenyl)-(2-fluoro-phenyl)-methanone (1ad)

In a manner similar to that described above for compound 1h, 3,4-dichloroaniline and 2-fluorobenzonitrile were converted to 1ad (17% yield) MS m/z=284 (M+H).

(2-Amino-5-isopropyl-phenyl)-(2-fluoro-phenyl)-methanone (1ag)

In a manner similar to that described above for compound 1h, 4-isopropylaniline and 2-fluorobenzonitrile were converted to 1ag (22% yield) MS m/z=258 (M+H).

Example 2

Method B for the Synthesis of Compounds of Formula (i)

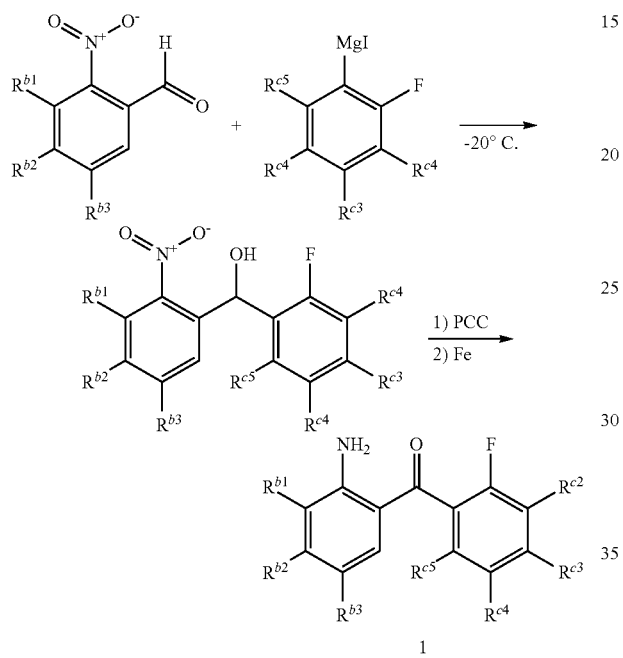

(2-Amino-5-methyl-phenyl)-(2-fluoro-phenyl)-methanone (1af)

2-Iodofluorobenzene (2.0 mL, 17 mmol) was dissolved in anhydrous THF (20 mL) under an argon atmosphere and cooled to −20° C. A solution of isopropyl magnesium chloride (8.5 mL, 17.0 mmol) was slowly added, and the solution was stirred for 20 min. 2-Nitro-5-methylbenzaldehyde (2.7 g, 16.5 mmol) in THF (20 mL) was then added, and the mixture was stirred for 20 min at −20° C. and then quenched with saturated aqueous NH₄Cl. The mixture was partitioned between EtOAc (100 mL) and H₂O (100 mL). The organic portion was collected, dried over MgSO₄, filtered and evaporated in vacuo. This material was dissolved in anhydrous CH₂Cl₂ (80 mL). Silica gel (20.3 g) and pyridinium chlorochromate (5.4 g, 25 mmol) were then added and the suspension was stirred at room temperature for 3 h. The mixture was then filtered through silica gel. The filtrate was concentrated in vacuo and the resulting residue was purified by column chromatography (silica gel, hexanes:EtOAc, 3:2) to provide the 2-nitro-benzophenone (3.7 g, 14 mmol). The benzophenone was dissolved in glacial acetic acid (50 mL), MeOH (50 mL) and deionized H₂O (10 mL). Iron powder (<10 micron, 1.0 g) was added with vigorous stirring and the suspension heated to 60° C. After 20 min, additional iron powder (2.0 g) was added and the mixture was stirred at 60° C. for 3 h. After cooling, silica gel (12.5 g) was added and the volatile components were removed in vacuo. The resulting powder was suspended in EtOAc (100 mL) and carefully treated with 1N NaOH until basic to litmus. The suspension was filtered and the organic portion was separated, washed with brine, dried over MgSO₄, filtered and evaporated in vacuo. The resulting residue was purified by column chromatography (silica gel, hexanes:EtOAc, 1:3) to provide 1af (3.1 g, 94%) MS m/z=230 (M+H).

(2-Amino-4-trifluoromethyl-phenyl)-(2-fluoro-phenyl)-methanone (1f)

In a manner similar to that described above for compound 1af, 2-nitro-4-trifluoromethyl-benzaldehyde was converted to 1f (46% yield) MS m/z=230 (M+H).

(2-Amino-5-fluoro-phenyl)-(2-fluoro-phenyl)-methanone (1f)

In a manner similar to that described above for compound 1af, 5-Fluoro-2-nitro-benzaldehyde was converted to 1j (60% yield) MS m/z=234 (M+H).

(2-Amino-5-methoxy-phenyl)-(2-fluoro-phenyl)-methanone (1ah)

In a manner similar to that described above for compound 1af, 5-methoxy-2-nitro-benzaldehyde was converted to 1ah (62% yield) MS m/z=246 (M+H).

Example 3

Method C for the Synthesis of Compounds of the Formula (i)

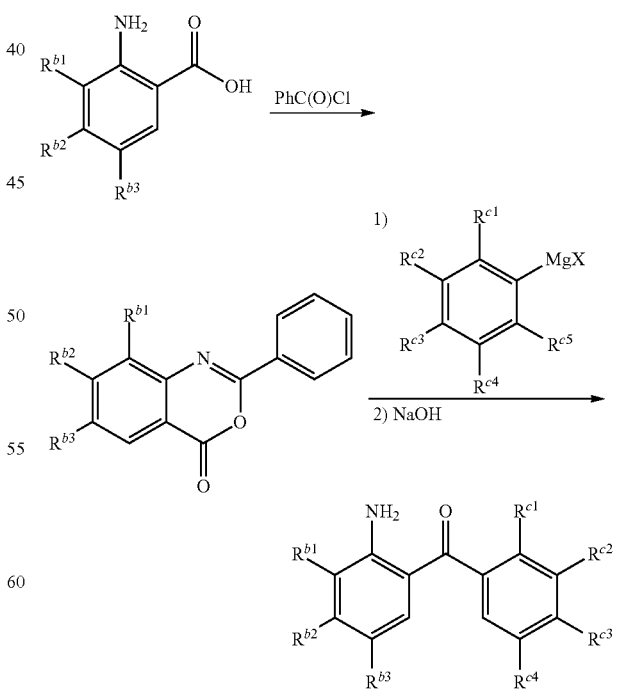

(2-Amino-5-chloro-phenyl)-(2-methyl-phenyl)-methanone (1m)

Benzoyl chloride (5.3 mL, 45 mmol) was added dropwise to a suspension of $Na_2CO_3$ (3.8 g, 36 mmol) and 2-amino-5-chloro-benzoic acid (3.1 g, 18 mmol) in THF (60 mL). The mixture was allowed to stir for 16 h and then $H_2O$ (200 mL) was added. The resulting precipitate was collected by filtration, washed with $MeOH/H_2O$ (1/1, 100 mL) and then dried in vacuo to provide 6-chloro-2-phenyl-benzo[d][1,3]oxazin-4-one (4.3 g, 92%). To a suspension of the benzoxazinone (5.0 g, 19 mmol) in $CH_2Cl_2$ (100 mL) at −78° C. was added o-tolylmagnesium chloride (2 M in THF, 48 mmol) dropwise. The mixture was allowed to warm to −30° C. and stir for 1 h. 1N HCl (100 mL) was then added. The organic phase was collected and the aqueous phase was washed with $CH_2Cl_2$ (2×50 mL). The combined organic portions were washed with 0.1N NaOH (2×50 mL), dried over $MgSO_4$, filtered and concentrated in vacuo to provide N-[4-chloro-2-(2-methyl-benzoyl)-phenyl]-benzamide (6.3 g, 93%). The acylated amino-benzophenone (3.5 g, 10 mmol) was dissolved in MeOH (50 mL) containing KOH (3 M, 30 mmol) and was refluxed for 16 h. The solution was then cooled to room temperature and diluted with $H_2O$ (50 mL) and EtOAc (100 mL). The organic phase was collected, washed with $H_2O$ (3×50 mL), dried over $MgSO_4$, filtered and evaporated to dryness in vacuo to provide 1m (2.4 g, 98%) MS m/z=246 (M+H).

(2-Amino-5-chloro-phenyl)-(2-methoxy-phenyl)-methanone (1n)

In a manner similar to that described above for compound 1m, 6-chloro-2-phenyl-benzo[d][1,3]oxazin-4-one was converted to 1n (84% yield) MS m/z=262 (M+H).

(2-Amino-5-chloro-phenyl)-(2-dimethylaminomethyl-phenyl)-methanone (1q)

To a solution of N-[4-chloro-2-(2-methyl-benzoyl)-phenyl]-benzamide (5.1 g, 14.6 mmol) and N-bromosuccinimide (2.85 g, 16 mmol) in $CCl_4$ (150 mL) was added 2,2'-azobisisobutylnitrile (0.2 g, 1.5 mmol). The solution was refluxed for 4 h. The solution was then cooled to room temperature, diluted with $CH_2Cl_2$ (150 mL) and washed with $H_2O$ (3×50 mL). The organic portion was dried over $Na_2SO_4$ and evaporated to dryness in vacuo to provide N-[2-(2-bromomethyl-benzoyl)-4-chloro-phenyl]-benzamide (4.6 g, 74%). A solution of the benzamide (2.3 g, 5.4 mmol) in $CH_2Cl_2$ (50 mL) was saturated with dimethylamine, stirred for 16 h and evaporated to dryness in vacuo. The resulting residue was dissolved in MeOH (50 mL) and KOH (0.9 g, 16 mmol) in $H_2O$ (5 mL) was added. The solution was refluxed for 24 h. The solution was concentrated in vacuo and then diluted with EtOAc (150 mL) and $H_2O$ (50 mL). The organic portion was washed with $H_2O$ (3×50 mL), dried over $Na_2SO_4$ and purified by column chromatography (silica gel, 18:80:2 $MeOH:CH_2Cl_2:NHOH$) to provide 1q (0.9 g, 53% yield) MS m/z=289 (M+H).

(2-Amino-5-chloro-phenyl)-(3-fluoro-phenyl)-methanone (1r)

In a manner similar to that described above for compound 1m, 6-chloro-2-phenyl-benzo[d][1,3]oxazin-4-one was converted to 1r (36% yield) MS m/z=250 (M+H).

(2-Amino-5-chloro-phenyl)-(3-methoxy-phenyl)-methanone (1s)

In a manner similar to that described above for compound 1m, 6-chloro-2-phenyl-benzo[d][1,3]oxazin-4-one was converted to 1s (64% yield) MS m/z=262 (M+H).

(2-Amino-5-chloro-phenyl)-(2,4-dimethoxy-phenyl)-methanone (1x)

In a manner similar to that described above for compound 1m, 6-chloro-2-phenyl-benzo[d][1,3]oxazin-4-one was converted to 1x (63% yield) MS m/z=292 (M+H).

(2-Amino-5-chloro-phenyl)-(2,5-dimethoxy-phenyl)-methanone (1z)

In a manner similar to that described above for compound 1m, 6-chloro-2-phenyl-benzo[d][1,3]oxazin-4-one was converted to 1z (62% yield) MS m/z=292 (M+H).

Example 4

Method D for the Synthesis of Compounds of the Formula (i)

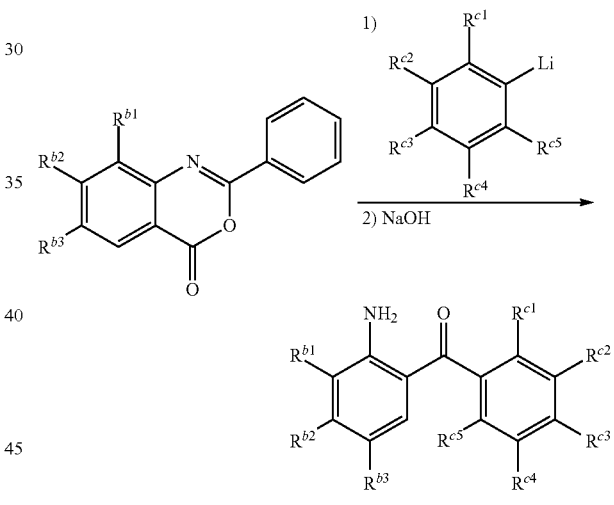

(2-Amino-5-chloro-phenyl)-(2-fluoro-6-methoxy-phenyl)-methanone (1ac)

To a solution of 1-fluoro-3-methoxy-benzene (19.6 g, 155 mmol) in THF (180 mL), at −78° C., was added dropwise 2.5 M n-butyllithium in hexanes (62 mL, 155 mmol). The solution was stirred at −78° C. for 3 h and then added to a suspension of 6-chloro-2-phenyl-benzo[d][1,3]oxazin-4-one (38.8 g, 150 mmol) in THF (280 mL) at −20° C. The mixture was allowed to gradually warm until the solution became homogenous. 1N HCl (150 mL) followed by EtOAc (250 mL) were then added and the solution allowed to warm to room temperature. The organic portion was collected and washed with $H_2O$ (250 mL), saturated $NaHCO_3$ (2×250 mL) and $H_2O$ (250 mL). The organic portion was then dried over $Na_2SO_4$ and evaporated to dryness, in vacuo, to provide the N-[4-Chloro-2-(2-fluoro-6-methoxy-benzoyl)-phenyl]-benzamide as an orange solid (42.7 g). To a solution of N-[4-Chloro-2-(2-fluoro-6-methoxy-benzoyl)-phenyl]-benzamide (42.7 g, 110 mmol) in MeOH (540 mL) was added KOH (56.4 g, 1 mole) in H$_2$O (100 mL). The solution was allowed to reflux for 16 h. The solution was then allowed to cool to room temperature and the resulting precipitate removed by filtration. The filtrate was concentrated in vacuo, diluted with EtOAc (250 mL) and washed with H$_2$O (3×100 mL). The organic portion was then dried over Na$_2$SO$_4$, concentrated in vacuo and then purified by column chromatography (silica gel, 0 to 15% EtOAc/hexanes) to provide 1ac (19.6 g, 47%) MS m/z=280 (M+H).

Example 5

Method E for the Synthesis of Compounds of the Formula (i)

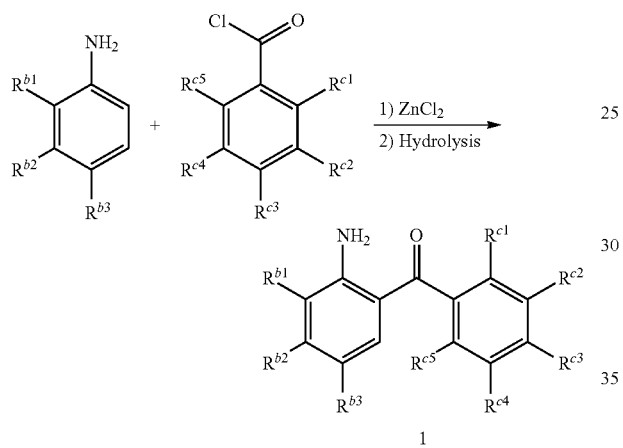

(2-Amino-5-chloro-phenyl)-(4-fluoro-phenyl)-methanone (1t)

To p-fluorobenzoyl chloride (49.7 g, 314 mmol), heated to 120° C., was added p-chloroaniline (17.8 g, 139 mmol) over 10 min. The mixture was then heated to 180° C. and ZnCl$_2$ (23.8 g, 174 mmol) was added over 10 min. The resulting mixture was heated at 205° C. for 2 h. After cooling to 120° C., 3N HCl (125 mL) was added cautiously and the mixture was maintained at 120° C. for 1 h. The hot aqueous portion was then decanted and the remaining residue was washed with hot 3N HCl (2×125 mL). The residue was poured onto ice and extracted with CH$_2$Cl$_2$ (3×100 mL). The combined organic portions were washed with 3N HCl (2×50 mL), 5N NaOH (2×50 mL) and H$_2$O (3×50 mL) and were then dried over MgSO$_4$, filtered and concentrated in vacuo to provide 15 g (29%) of the N-[4-chloro-2-(4-fluoro-benzoyl)-phenyl]-4-fluoro-benzamide as a dark yellow powder. To a flask containing the acylated amino-benzophenone (6.7 g, 18 mmol) was added 1:1 conc. HCl:AcOH (700 mL) and the resulting mixture was heated to 105° C. and stirred for 16 h. The mixture was cooled to room temperature and concentrated in vacuo. The residue was poured onto ice and extracted with CH$_2$Cl$_2$ (3×100 mL). The combined organic portions were washed with 5N NaOH (2×50 mL) and H$_2$O (3×50 mL) and then dried over MgSO$_4$, filtered and evaporated in vacuo. The resulting residue was purified by column chromatography (silica gel, 5 to 25% EtOAc/hexanes) and recrystallized from hexanes to provide 1t (3.4 g, 76%) MS m/z=250 (M+H).

(2-Amino-5-chloro-phenyl)-(4-methoxy-phenyl)-methanone (1u)

To a solution of N-[4-chloro-2-(4-fluoro-benzoyl)-phenyl]-4-fluoro-benzamide (6.0 g, 16 mmol), prepared as described above for compound 1s, in MeOH (400 mL) was added 5N NaOH (50 mL) and the resulting solution was allowed to reflux for 16 h. The solution was cooled to room temperature and concentrated in vacuo. The aqueous portion was extracted with CH$_2$Cl$_2$ (2×100 mL). The combined organic portions were washed with H$_2$O (3×50 mL), dried over MgSO$_4$, filtered and evaporated in vacuo. The resulting residue was purified by column chromatography (silica gel, 5 to 25% EtOAc/hexanes) and recrystallized from MeOH to provide 1u (3.5 g, 83%) as a light yellow powder MS m/z=262 (M+H).

(2-Amino-5-methyl-phenyl)-(2,6-difluoro-phenyl)-methanone (1aj)

In a manner similar to that described above for compound 1t, p-toluidine and 2,6-difluorobenzoyl chloride were converted to 1aj (16% yield) MS m/z=248 (M+H).

Example 6

Method F for the Synthesis of Compounds of Formula (i)

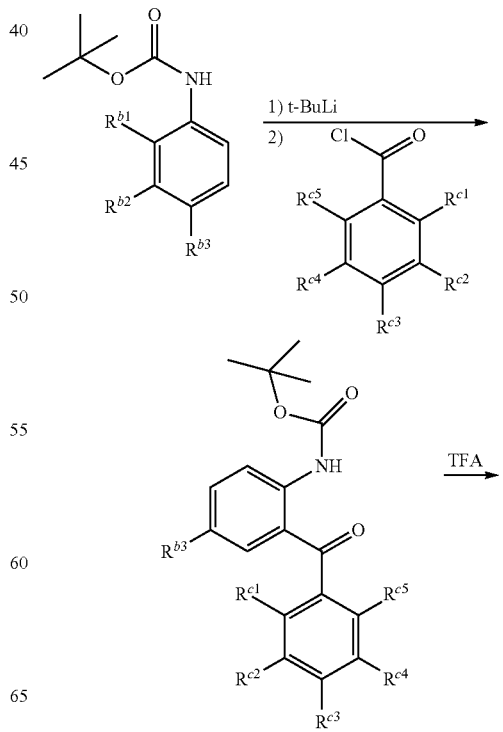

-continued

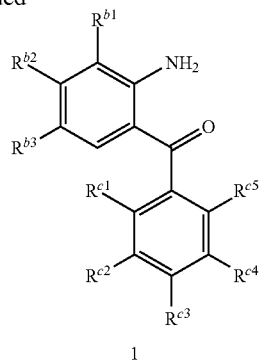

1

(2-Amino-5-chloro-phenyl)-(2,6-difluoro-phenyl)-methanone (1aj)

4-Chloro-N-Boc-aniline (3.4 g, 15 mmol) was dissolved in dry inhibitor-free THF (40 mL) under argon and cooled to −78° C. t-BuLi (1.7 M in pentane, 20 mL, 34 mmol) was cooled in a dry ice/acetone bath and added to the Boc-aniline solution, via a cannula, over 20 min. The yellow solution was stirred at −78° C. for 30 min, warmed to −30° C. for an additional 2.5 h, and then cooled to −78° C. 2,6-Difluorobenzoyl chloride (2.8 g, 16 mmol) was dissolved in dry THF (30 mL) and cooled to −78° C. under argon. The o-lithiated aniline was added, via a cannula, to the acid chloride solution over 30 min. The solution was stirred for an additional 20 min before quenching with 1N HCl (50 mL). The solution was diluted with EtOAc and the organic portion was separated, dried over $MgSO_4$ and concentrated to dryness in vacuo. The resulting orange oil was purified by column chromatography (silica gel, Hexanes:EtOAc 4:1) to provide the Boc protected amino-benzophenone (3.3 g, 60%). The N-Boc-aminobenzophenone was dissolved in dry $CH_2Cl_2$ (50 mL) and trifluoroacetic acid (50 mL) was added. After stirring for 1 h, the solution was evaporated to dryness in vacuo. The resulting residue was dissolved in EtOAc (100 mL) and water (100 mL) containing $NaHCO_3$. The organic portion was washed with a saturated aqueous $NaHCO_3$ solution, dried over $MgSO_4$, and concentrated to dryness in vacuo to provide, quantitatively, 1aa MS m/z=268 (M+H).

(2-Amino-5-chloro-phenyl)-(2,3-difluoro-phenyl)-methanone (1v)

In a manner similar to that described above for compound 1aa, 4-Chloro-N-Boc-aniline and 2,3-difluoro-benzoyl chloride were converted to 1v (14% yield) MS m/z=268 (M+H).

(2-Amino-5-chloro-phenyl)-(2,4-difluoro-phenyl)-methanone (1w)

In a manner similar to that described above for compound 1aa, 4-Chloro-N-Boc-aniline and 2,4-difluoro-benzoyl chloride were converted to 1w (20% yield) MS m/z=268 (M+H).

(2-Amino-5-chloro-phenyl)-(2,5-difluoro-phenyl)-methanone (1y)

In a manner similar to that described above for compound 1aa, 4-Chloro-N-Boc-aniline and 2,4-difluoro-benzoyl chloride were converted to 1y (10% yield) MS m/z=268 (M+H).

(2-Amino-5-chloro-phenyl)-(2-chloro-6-fluoro-phenyl)-methanone (1ab)

In a manner similar to that described above for compound 1aa, 4-Chloro-N-Boc-aniline and 2-chloro-6-fluoro-benzoyl chloride were converted to 1ab (42% yield) MS m/z=284 (M+H).

(2-amino-5-chlorophenyl)-(2-(trifluoromethyl)phenyl)methanone (1o)

In a manner similar to that described above for compound 1aa, 4-Chloro-N-Boc-aniline and 2-(trifluoromethyl)benzoyl chloride were converted to 1o (% yield) MS m/z=(M+H).

Example 7

Method G and Method H for the Synthesis of Compounds of Formula ii (See Scheme 1)

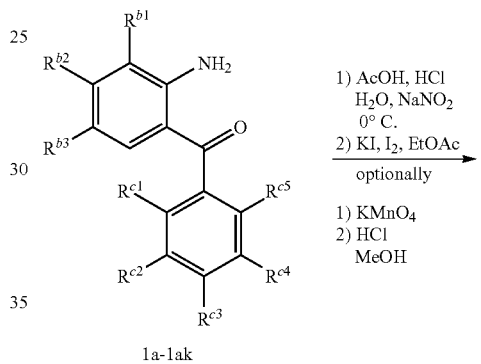

1a-1ak

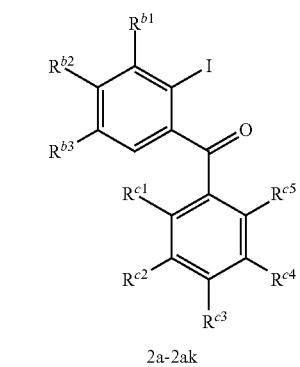

2a-2ak (5-Chloro-2-iodo-phenyl)-(2,6-difluoro-phenyl)-methanone (2aa)

Method G:
(2-Amino-5-chloro-phenyl)-(2,6-difluoro-phenyl)-methanone (1aa) (2.6 g, 9.7 mmol) was dissolved in acetic acid (10 mL) and concentrated HCl (4 mL) and the solution was cooled to 0° C. A solution of $NaNO_2$ (0.7 g, 10.7 mmol) in $H_2O$ (6 mL) was added dropwise so as to maintain a temperature of between 0-5° C. Following this addition, the reaction mixture was stirred at 0° C. for 30 min. Cold EtOAc (20 mL) was added dropwise and the solution was stirred for 20 min. Iodine (1.5 g, 5.8 mmol) and potassium iodide (1.9 g, 11.6 mmol) in $H_2O$ (10 mL) were added dropwise and the mixture was warmed to room temperature and stirred for 1 h. The reaction mixture was diluted with EtOAc (200 mL) and washed with saturated aqueous sodium thiosulfate (4×100 mL). The combined aqueous portions were extracted with EtOAc (3×50 mL). The combined organic portions were then washed with a saturated aqueous NaHCO$_3$ solution (3×50 mL), H$_2$O (2×50 mL), dried over Na$_2$SO$_4$, filtered and evaporated in vacuo to afford 2aa (3.3 g, 90%) as a light yellow solid.

4-(2-Fluoro-benzoyl)-3-iodo-benzoic acid methyl ester (2i)

Method H:
To a solution of 2g (1 g, 3 mmol) in t-butanol (25 mL) and H$_2$O (25 mL) was added KMnO$_4$ (3.8 g, 24 mmol). The solution was refluxed for 18 h. THF (50 mL) was added and the solution was refluxed for 30 min, cooled to room temperature and filtered. The filtrate was concentrated in vacuo, diluted with MeOH (20 mL) and acidified with concentrated HCl. The solution was diluted with H$_2$O (10 mL) and the resulting precipitate was collected to provide 4-(2-fluoro-benzoyl)-3-iodo-benzoic acid (1 g, 92%) as a white solid. The 4-(2-fluoro-benzoyl)-3-iodo-benzoic acid (0.5 g, 1.4 mmol) in MeOH (6 mL) containing concentrated HCl (100 μL) was submitted to microwave irradiation (300 W) for 30 min at 140° C. The resulting precipitate was collected to provide 2i (0.4 g, 79%) as a white solid MS m/z=385 (M+H).

2-(5-Chloro-2-iodo-benzoyl)-benzoic acid methyl ester (2p)

In a manner similar to that described above for compound 2i, 2m was converted to 2p (81% yield) MS m/z=401 (M+H).

3-(2-fluorobenzoyl)-4-iodobenzoic acid methyl ester (2ai)

In a manner similar to that described above for compound 2i, 2af was converted to 2ai (60% yield) MS m/z=385 (M+H).

3-(2,6-difluorobenzoyl)-4-iodobenzoic acid methyl ester (2ak)

In a manner similar to that described above for compound 2i, 2aj was converted to 2ak (58% yield) MS m/z=403 (M+H).

The illustrative compounds of the formula 2, set forth in Table 4 below, were prepared in a similar manner to that illustrated by Method G or Method H, as described above for compounds 2aa and 2i.

TABLE 4

Illustrative Examples of Compounds of Formulae 1-5

| | Substituent | | | | | | | | Mass Spectra (M + H) | | | |
|---|---|---|---|---|---|---|---|---|---|---|---|---|
| 1-5 | $R^{b1}$ | $R^{b2}$ | $R^{b3}$ | $R^{c1}$ | $R^{c2}$ | $R^{c3}$ | $R^{c4}$ | $R^{c5}$ | 2 | 3 | 4 | 5 |
| a | H | H | H | H | H | H | H | H | 309 | 336 | 236 | 291 |
| b | Me | H | H | F | H | H | H | H | 341 | 368 | 268 | 323 |
| c | H | F | H | F | H | H | H | H | 345 | 372 | 272 | 327 |
| d | H | Cl | H | F | H | H | H | H | 361 | 388 | 288 | 343 |
| e | H | Br | H | F | H | H | H | H | 405/407 | 432/434 | 332/334 | 387/389 |
| f | H | CF$_3$ | H | F | H | H | H | H | 395 | 422 | 322 | 377 |
| g | H | Me | H | F | H | H | H | H | 341 | 368 | 268 | 323 |
| h | H | OMe | H | F | H | H | H | H | 357 | 384 | 284 | 339 |
| i | H | CO$_2$Me | H | F | H | H | H | H | 385 | 412 | 312 | 367 |
| j | H | H | F | F | H | H | H | H | 345 | 372 | 272 | 327 |
| k | H | H | Cl | F | H | H | H | H | 361 | 388 | 288 | 343 |
| l | H | H | Cl | Cl | H | H | H | H | 377 | 404 | 304 | 359 |
| m | H | H | Cl | Me | H | H | H | H | 357 | 384 | 284 | 339 |
| n | H | H | Cl | OMe | H | H | H | H | 373 | 400 | 300 | 355 |
| o | H | H | Cl | CF$_3$ | H | H | H | H | 411 | 438 | 338 | 393 |
| p | H | H | Cl | CO$_2$Me | H | H | H | H | 401 | 428 | 328 | 383 |
| q | H | H | Cl | CH$_2$N(Me)$_2$ | H | H | H | H | 400 | 427 | 327 | 382 |
| r | H | H | Cl | H | F | H | H | H | 361 | 388 | 288 | 343 |
| s | H | H | Cl | H | OMe | H | H | H | 373 | 400 | 300 | 355 |
| t | H | H | Cl | H | H | F | H | H | 361 | 388 | 288 | 343 |
| u | H | H | Cl | H | H | OMe | H | H | 373 | 400 | 300 | 355 |
| v | H | H | Cl | F | F | H | H | H | — | 406 | 306 | 361 |
| w | H | H | Cl | F | H | F | H | H | — | 406 | 306 | 361 |
| x | H | H | Cl | OMe | H | OMe | H | H | 403 | 430 | 330 | 385 |
| y | H | H | Cl | F | H | H | F | H | — | 406 | 306 | 361 |
| z | H | H | Cl | OMe | H | H | OMe | H | 403 | 430 | 330 | 385 |
| aa | H | H | Cl | F | H | H | H | F | — | 406 | 306 | 361 |
| ab | H | H | Cl | F | H | H | Cl | — | — | 422 | 322 | 377 |
| ac | H | H | Cl | F | H | H | OMe | — | — | 418 | 318 | 373 |
| ad | H | Cl | Cl | F | H | H | H | H | 395 | 422 | 322 | 377 |
| ae | H | H | H | F | H | H | H | H | — | 354 | 254 | 309 |
| af | H | H | Me | F | H | H | H | H | 341 | 368 | 268 | 323 |
| ag | H | H | iPr | F | H | H | H | H | 369 | — | — | — |
| ah | H | H | OMe | F | H | H | H | H | 357 | 384 | 284 | 339 |
| ai | H | H | CO$_2$Me | F | H | H | H | H | 385 | 412 | 312 | 367 |
| aj | H | H | CH$_3$ | F | H | H | H | F | 359 | — | — | — |
| ak | H | H | CO$_2$Me | F | H | H | H | F | 403 | 430 | 330 | 385 |
| al | H | H | Cl | — (pyridyl) | H | H | H | H | — | 371 | 271 | 326 |

TABLE 4-continued

Illustrative Examples of Compounds of Formulae 1-5

| 1-5 | Substituent | | | | | | | | Mass Spectra (M + H) | | | |
|---|---|---|---|---|---|---|---|---|---|---|---|---|
| | $R^{b1}$ | $R^{b2}$ | $R^{b3}$ | $R^{c1}$ | $R^{c2}$ | $R^{c3}$ | $R^{c4}$ | $R^{c5}$ | 2 | 3 | 4 | 5 |
| am | H | H | Cl | — (pyridyl) | H | H | H | F | — | 389 | 289 | 344 |

Example 8

Method I for the Synthesis of Compounds of Formula iii (See Scheme 1)

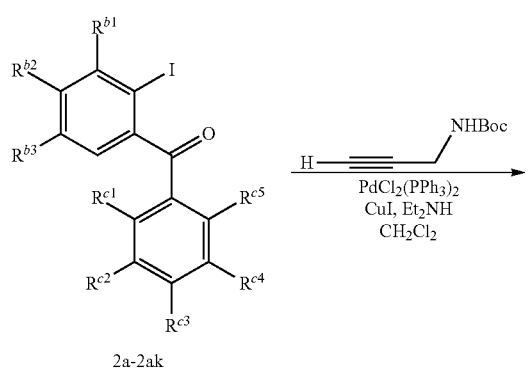

2a-2ak

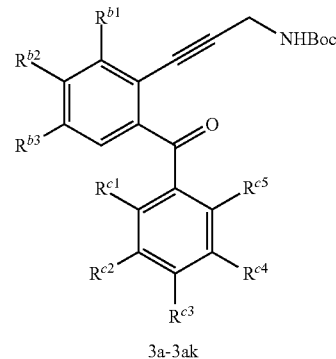

3a-3ak

{3-[4-Chloro-2-(2,6-difluoro-benzoyl)-phenyl]-prop-2-ynyl}-carbamic acid tert-butyl ester (3aa)

(5-Chloro-2-iodo-phenyl)-(2,6-difluoro-phenyl)-methanone (2aa) (5.5 g, 14.5 mmol), prop-2-ynyl-carbamic acid tert-butyl ester (2.5 g, 16 mmol), PdCl₂(PPh₃)₂ (0.6 g, 0.9 mmol) and Cu(I)I (0.2 g, 0.9 mmol) were suspended in anhydrous CH₂Cl₂ (50 mL) and the mixture was sparged with nitrogen for 30 min. Diethylamine (8 mL) was added and the solution was stirred at room temperature for 16 h. The solution was concentrated in vacuo and the resulting residue purified by column chromatography (silica gel, 0 to 15% EtOAc/hexanes) to afford 3aa (3.6 g, 61%) as a white solid, MS m/z=406 (M+H).

The illustrative compounds of the formula 3, set forth in Table 4, were prepared in a similar manner to that illustrated by Method I, as described above for compounds 3aa.

Example 9

Method J for the Synthesis of Compounds of Formula iii (See Scheme 1)

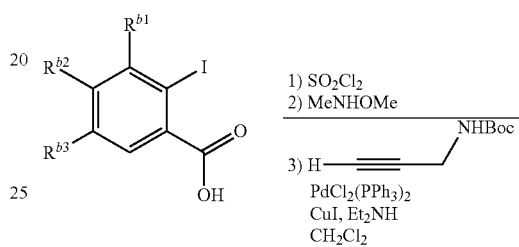

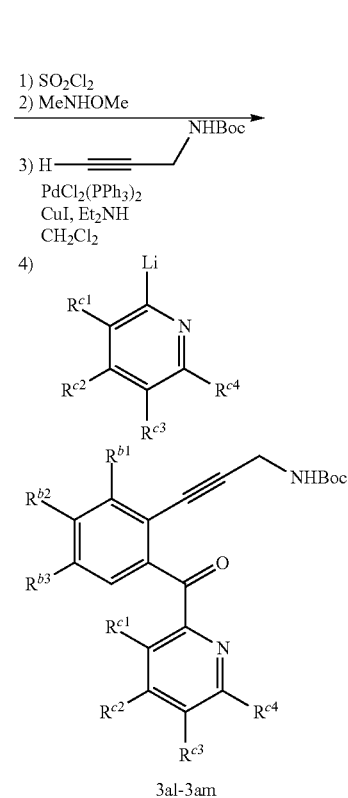

3al-3am tert-Butyl 3-(4-chloro-2-picolinoylphenyl)prop-2-ynylcarbamate (3al)

5-Chloro-2-iodobenzoic acid (2.8 g, 10 mmol) was taken up in dry methylene chloride (80 mL) and DMF (50 µL, cat.) followed by thionyl chloride (2.4 g, 20 mmol) were added. The mixture was stirred at reflux for 12 h, cooled to room temperature and evaporated in vacuo. The residue was azeotroped with toluene (2×10 mL) and used without further purification. The 5-chloro-2-iodobenzoyl chloride (10 mmol) was taken up in dry methylene chloride (50 mL) and N, O-dimethylhydroxylamine hydrochloride (1.1 g, 11 mmol) was added. The mixture was cooled to 0° C., and pyridine (2.4 g, 30 mmol) was added. The mixture was allowed to warm to room temperature, stir for 12 h, and was then quenched with saturated brine (20 mL). The organic phase was separated and the water phase was extracted with methylene chloride (2×10 mL). The combined organic extracts were dried with anhydrous MgSO$_4$, filtered and evaporated in vacuo. The residue was purified using flash chromatography on silica gel (50 g) using methylene chloride as eluent to provide 5-chloro-2-iodo-N-methoxy-N-methylbenzamide (3.1 g, 95%) MS m/z=326 (M+H).

The Weinreb amide (3.1 g, 9.5 mmol) and prop-2-ynylcarbamic acid tert-butyl ester (2.9 g, 19 mmol) were coupled according to method H to provide 3-(4-chloro-2-(methoxy(methyl)carbamoyl)phenyl)prop-2-ynylcarbamic acid tert-butyl ester (2.7 g, 80%), MS m/z=353 (M+H). To this product, dissolved in dry THF (40 mL) and cooled to −78° C., was added lithiated pyridine, prepared from 2-bromopyridine (4.2 g, 26.6 mmol) and n-butyllithium (14.3 mL of 1.6 M solution in hexanes, 22.8 mmol) in dry THF (40 mL) under argon atmosphere at −78° C. The resulting mixture was gradually warmed to −40° C. over 1 h and then quenched with brine (20 mL). After warming to room temperature, the mixture was extracted with ethyl acetate (3×20 mL). The organic extracts were dried with MgSO$_4$, filtered and evaporated. The residue was purified using flash chromatography on silica gel (100 g) using methylene chloride to 10% ethyl acetate in methylene chloride as eluent to give 3al (2.14 g, 76%): MS m/z=371 (M+H).

tert-Butyl 3-(4-chloro-2-(3-fluoropicolinoyl)phenyl)prop-2-ynlylcarbamate (3am)

In a manner similar to that described above for compound 3al, 3-(4-chloro-2-(methoxy(methyl)carbamoyl)phenyl)prop-2-ynylcarbamic acid tert-butyl ester and 2-bromo-3-fluoropyridine were converted to 3am (45% yield): MS m/z=389 (M+H).

The illustrative compounds of the formula 3, set forth in Table 4, were prepared in a similar manner to that illustrated by Method J, as described above for compounds 3al and 3am.

Example 10

Method K and Method L for the Synthesis of Compounds of Formula iv (See Scheme 1)

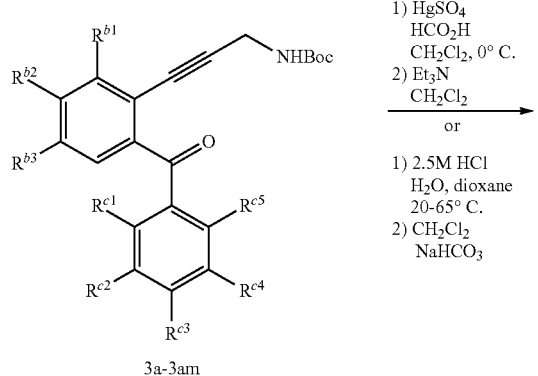

3a-3am

1) HgSO$_4$
HCO$_2$H
CH$_2$Cl$_2$, 0° C.
2) Et$_3$N
CH$_2$Cl$_2$
or
1) 2.5M HCl
H$_2$O, dioxane
20-65° C.
2) CH$_2$Cl$_2$
NaHCO$_3$

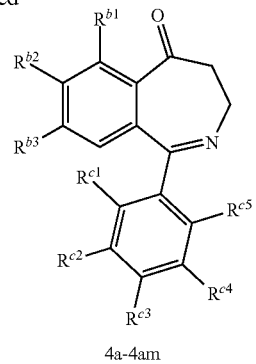

4a-4am

8-Chloro-1-(2-fluoro-phenyl)-3,4-dihydro-benzo[c]azepin-5-one (4k)

Method K:

A solution of {3-[4-chloro-2-(2-fluoro-benzoyl)-phenyl]-prop-2-ynyl}-carbamic acid tert-butyl ester (9.2 g, 23 mmol) in CH$_2$Cl$_2$ (100 mL) containing formic acid (9.18 mL) was cooled to 0° C. Mercury(II) sulphate (2.1 g, 7.1 mmol) was added and the reaction stirred for 2 h at 0° C. The mixture was diluted with H$_2$O (20 mL) and NH$_4$OH (20 mL). The organic phase was collected and the aqueous phase was extracted with EtOAc (3×100 mL). The combined organic portions were washed with H$_2$O, dried over MgSO$_4$, filtered and the solvents evaporated in vacuo to afford [3-[4-chloro-2-(2-fluorobenzoyl)-phenyl]-3-oxopropyl]-carbamic acid tert-butyl ester 8.9 g (95%) as a brown solid. This material (8.9 g, 22 mmol) was dissolved in HCl (4N in dioxane, 185 mL) and stirred at room temperature for 30 min. The solution was then evaporated in vacuo. The residue was dissolved in CH$_2$Cl$_2$ (250 mL) and diisopropylethylamine amine (18 mL) was added. The solution was stirred at room temperature for 2 h. The solution was evaporated in vacuo and the residue purified by column chromatography (silica gel, 10 to 50% EtOAc/hexanes) to provide 4k (2.9 g, 46%) as a brown solid MS m/z=288 (M+H).

8-Chloro-1-(2,6-difluoro-phenyl)-3,4-dihydro-benzo[c]azepin-5-one (4aa)

Method L:

A solution of {3-[4-chloro-2-(2,6-difluoro-benzoyl)-phenyl]-prop-2-ynyl}-carbamic acid tert-butyl ester (5.6 g, 15 mmol) was dissolved in dioxane (200 mL). 5N HCl (aq) (200 mL) was added and the solution was stirred at room temperature for 14 h and then at 60° C. for 2 h. The solution was diluted with CH$_2$Cl$_2$ (200 mL) and Na$_2$CO$_3$ was added until the solution pH was basic to litmus. The mixture was allowed to stir for 2 h. The organic portion was separated and the aqueous portion was extracted with CH$_2$Cl$_2$ (2×100 mL). The combined organic portions were washed with H$_2$O (3×50 mL), dried over Na$_2$SO$_4$, filtered and evaporated in vacuo to provide 4aa (4.2 g, 100%) MS m/z=306 (M+H).

The illustrative compounds of formula 4, set forth in Table 4, were prepared in a similar manner to that illustrated by Method K and Method L, as described above for compounds 4k and 4aa.

Example 11

Method M for the Synthesis of Compounds of the Formula v (See Scheme 1)

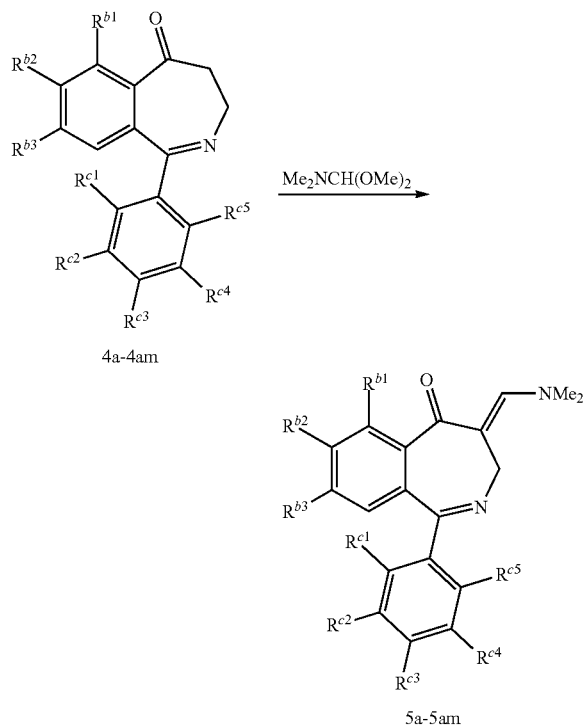

8-Chloro-4-dimethylaminomethylene-1-(2,6-difluoro-phenyl)-3,4-dihydro-benzo[c]azepin-5-one (5aa)

8-Chloro-1-(2,6-difluoro-phenyl)-3,4-dihydro-benzo[c]azepin-5-one (4aa) (4.2 g, 15 mmol) was dissolved in toluene (100 mL) and N,N-dimethylformamide dimethyl acetal (19 mL) and heated at 80° C. for 2 h. The solution was evaporated in vacuo and the resulting residue was purified by column chromatography (silica gel, 0 to 75% EtOAc/hexanes) to afford 5aa (2.6 g, 78%) as a pale brown solid MS m/z=361 (M+H).

The illustrative compounds of formula 5, set forth in Table 4, were prepared in a similar manner to that illustrated by Method M, as described above for 5aa.

Example 12

Preparation of Aryl or Heteroaryl Guanidines by Methods N, O or P

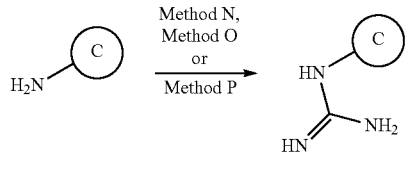

Method N:

To a vigorously stirred solution of 3,4-dimethoxyaniline (15.3 g, 0.1 mol) in EtOH (60 mL) at 0° C. was added nitric acid (69%, 9.0 mL, 0.1 mol) dropwise. A solution of cyanamide (4.6 g, 0.1 mol) in $H_2O$ (8.5 mL) was added and the solution was heated at reflux for 3 h. The mixture was then diluted with EtOH (50 mL), chilled to 4° C. and the resulting golden needles were collected and dried in vacuo to provide N-(3,4-dimethoxy-phenyl)-guanidine as the nitric acid salt (14.7 g, 57%) MS m/z=196 (M+H).

N-Pyridin-3-yl-guanidine

Method O:

To a mixture of 3-aminopyridine (1.0 g, 10.6 mmol), 1,3-bis(tert-butoxycarbonyl)-2-methyl-2-thiopseudourea (4.0 g, 13.8 mmol) and $Et_3N$ (15 mL) in $CH_2Cl_2$ (100 mL) was added mercuric chloride (4.0 g, 14.8 mmol). The resulting mixture was stirred under a nitrogen atmosphere at room temperature for 16 h, during which time a dense white precipitate formed. The mixture was filtered through Celite®, and washed with $Et_2O$. The combined filtrates were evaporated to dryness in vacuo and the resulting white solid purified by column chromatography (silica gel, 15% EtOAc/hexanes) to yield the bis-Boc protected guanidine (3.1 g, 88%). To a solution of this material (3.1 g, 9.3 mmol) in MeOH (2 mL) was added HCl (4N in dioxane, 60 mmol). The resulting solution was refluxed for 16 h, cooled to room temperature and triturated with $Et_2O$ to provide the N-pyridin-3-yl-guanidine as the hydrochloride salt (1.2 g, 74%) MS m/z=173 (M+H).

t-Butyl Guanidinobenzoate, HCl Salt

Method P:

To a solution of t-butyl 4-aminobenzoate (2.0 g, 10.3 mmol) in $CH_2Cl_2$ (20 mL) was added 1,3-bis(benzyloxycarbonyl)-2-methyl-2-thiopseudourea (5.6 g, 15.5 mmol), $Et_3N$ (5.0 mL, 36 mmol), and mercuric chloride (3.37 g, 12.4 mmol). The reaction mixture was stirred overnight at room temperature. The reaction mixture was filtered through Celite®, and the filtrates were concentrated in vacuo and purified by column chromatography (1:1 $CH_2Cl_2$/hexanes to 100% $CH_2Cl_2$, and then 10% EtOAc/$CH_2Cl_2$) to provide tert-butyl 4-(2,3-bis(benzyloxycarbonyl)guanidino)benzoate (3.9 g, 75%). To a pressure bottle was charged 20% palladium hydroxide on carbon (2 g) followed by a solution of t-butyl 4-(2,3bis(benzyloxycarbonyl)guanidine)benzoate (3.9 g, 7.7 mmol) in EtOAc (80 mL). The mixture was stirred under hydrogen at 50 psi at room temperature overnight. The solution was filtered through Celite® and the filtrate evaporated in vacuo to provide t-butyl guanidinobenzoate (1.8 g, 100%). To the guanidine (855 mg, 3.6 mmol) in EtOAc (50 mL) was add 2M HCl in $Et_2O$ (1.9 mL, 3.8 mM). The solution was concentrated and the precipitate was collected by filtration, washed with $Et_2O$ and dried in vacuo to yield (840 mg, 85%) of the HCl salt.

Example 13

Method Q, Method R and Method S for the Synthesis of Compounds of Formula (I)

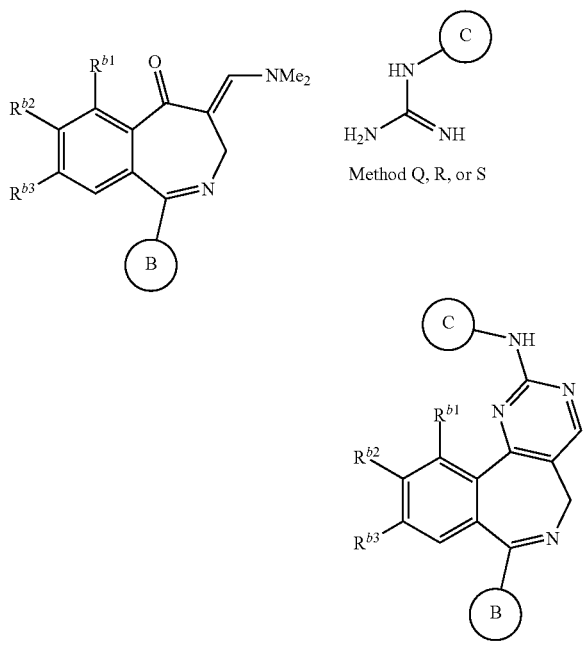

Method Q, R, or S

4-[9-Chloro-7-(2-fluoro-phenyl)-5H-benzo[c]pyrimido[4,5-e]azepin-2-ylamino]-benzoic acid (I-52)

Method Q:

A solution of 8-chloro-4-dimethylaminomethylene-1-(2-fluoro-phenyl)-3,4-dihydro-benzo[c]azepin-5-one (5k) (0.22 g, 0.64 mmol), 4-guanidino-benzoic acid hydrochloride (0.15 g, 0.70 mmol) and diisopropylethylamine (i-Pr$_2$EtN) (0.23 mL, 1.32 mmol) in DMF (2.5 mL) was submitted to microwave irradiation (300 W) for 300 sec at 250° C. The mixture was cooled and then poured into H$_2$O (100 mL). While stirring, 1N HCl was added dropwise to pH=3 followed by EtOAc (50 mL). The resulting precipitate was collected by filtration and dried under vacuum to yield I-52 as a tan solid (0.13 g, 47%).

4-[9-Chloro-7-(2,6-difluoro-phenyl)-5H-benzo[c]pyrimido[4,5-e]azepin-2-ylamino]-benzoic acid (I-135)

Method R:

8-Chloro-4-dimethylaminomethylene-1-(2,6-difluoro-phenyl)-3,4-dihydro-benzo[c]azepin-5-one (5aa) (2.6 g, 7.1 mmol), 4-guanidino-benzoic acid hydrochloride (1.7 g, 7.8 mmol) and K$_2$CO$_3$.1.5H$_2$O (2.6 g, 15.6 mmol) in EtOH (50 mL) were refluxed for 14 h. The mixture was cooled and then poured into H$_2$O (400 mL). While stirring, 1N HCl was added dropwise to pH=3. EtOAc (400 mL) was then added and the organic portion was washed with H$_2$O (2×100 mL), dried over Na$_2$SO$_4$ and concentrated to dryness in vacuo. The residue was suspended in CH$_2$Cl$_2$ and filtered. The solids were dissolved in EtOAc, filtered through silica gel, concentrated to dryness in vacuo and dried under vacuum to yield I-135 as a white solid (1.4 g, 42%).

4-[9-Chloro-7-(2,6-difluoro-phenyl)-5H-benzo[c]pyrimido[4,5-e]azepin-2-ylamino]-benzoic acid (I-135) (1.5 g, 2.95 mol) was added to a solution of ethanol (8.86 mL) and water (1.2 mL), and the mixture was heated to 50° C. An aqueous NaOH solution (0.02458 g/mL) was added to a target solution pH of 11.6. Additional water was added to a total of 4.26 mL/g of free acid. The resultant slurry was heated to 70° C. and rapidly filtered, maintaining a solution temperature of 65-70° C. Warm ethanol (9.15 mL, 7.21 g) was added, and the solution cooled to 65° C. Seed crystals of the sodium salt of I-135 (7.1 mg, 0.014 mol) were added as a slurry in 10% (wt) solution of 75:25 ethanol: water. The mixture was maintained at 65° C. for one hour, and then was cooled to 35° C. at a rate of 12° C./hour. At 35° C., a second addition of ethanol (4.72 g, 5.98 mL) was performed. The mixture was cooled to 0° C. at a rate of 12° C./hour, and then held at 0° C. for one hour. The resultant thick slurry was filtered, and the wet filter cake was rinsed with cold ethanol (5.52 g, 7 mL) to afford a 72% yield of the sodium salt of I-135, as a hydrate.

2-[9-Chloro-7-(2,6-difluoro-phenyl)-5H-benzo[c]pyrimido[4,5-e]azepin-2-ylamino]-oxazole-5-carboxylic acid (I-364)

Method S:

8-Chloro-4-dimethylaminomethylene-1-(2,6-difluoro-phenyl)-3,4-dihydrobenzo[c]azepin-5-one (5aa) (3.6 g, 10 mmol), guanidine hydrochloride (1.06 g, 11 mmol), potassium carbonate (4.6 g, 33 mmol), and ethanol (100 mL) were combined in a 100-mL round-bottomed flask and stirred at reflux for 3 hours. The reaction mixture was poured into 500 mL water with stirring. The mixture was extracted with ethyl acetate (4×200 mL). The organic extracts were combined, washed with saline, dried (Na$_2$SO$_4$), filtered, and evaporated to leave a brown solid. The solid was stirred with diethyl ether, filtered, washed with ether, then dried in vacuo to provide 9-chloro-7-(2,6-difluoro-phenyl)-5H-benzo[c]pyrimido[4,5-e]azepin-2-yl amine (3.16 g, 89%) as a light brown solid MS m/z=357 (M+H). The amine (2.0 g, 5.6 mmol), diiodomethane (7.7 g, 28.6 mmol), copper (I) iodide (1.1 g, 5.6 mmol), dry tetrahydrofuran (40 mL), and isoamyl nitrite (2.0 g, 16.8 mmol) were combined in a round-bottomed flask and stirred at reflux for 1 hour. The dark purple solution was cooled to room temperature and then transferred to a separatory funnel containing 1N HCl (250 mL) and ethyl acetate (150 mL). The organic layer was separated and the aqueous layer was extracted with ethyl acetate (100 mL). The organic extracts were combined, washed with ammonium hydroxide (3%), saturated ammonium chloride, and saturated saline, and then dried (Na$_2$SO$_4$), filtered, and concentrated to leave a dark oil. Purification by column chromatography (silica gel, CH$_2$Cl$_2$ to 10% ethyl acetate in CH$_2$Cl$_2$) afforded 9-Chloro-7-(2,6-difluoro-phenyl)-2-iodo-5H-benzo[c]pyrimido[4,5-e]azepine as a pale yellow solid (1.3 g, 50%) MS m/z=468 (M+H).

A mixture of 9-Chloro-7-(2,6-difluoro-phenyl)-2-iodo-5H-benzo[c]pyrimido[4,5-e]azepine (200 mg, 0.43 mmol), ethyl 2-aminooxazole-5-carboxylate (81.2 mg, 0.52 mmol), tris(dibenzylideneacetone)dipalladium(0) (Pd$_2$(dba)$_3$) (935 mg, 0.034 mmol), Xantphos (30 mg, 0.052 mmol), powdered K$_3$PO$_4$ (183 mg, 0.86 mmol), and degassed toluene were submitted to microwave irradiation (300 W) for 20 minutes at 145° C. The mixture was cooled to room temperature and then evaporated to leave a brown solid which was purified by column chromatography (silica gel, CH$_2$Cl$_2$ to 50% diethyl ether in CH$_2$Cl$_2$) to yield 2-[9-Chloro-7-(2,6-difluoro-phenyl)-5H-benzo[c]pyrimido[4,5-e]azepin-2-ylamino]-oxazole-5-carboxylic acid ethyl ester as a yellow powder (103 mg, 48%) MS m/z=496 (M+H). 2-[9-Chloro-7-(2,6-difluoro-phenyl)-5H-benzo[c]pyrimido[4,5-e]azepin-2-ylamino]-oxazole-5-carboxylic acid ethyl ester (91 mg, 0.18 mmol), methanol (1 mL), tetrahydrofuran (3 mL), and 1N LiOH (3.7 mL, 3.7 mmol) were stirred at room temperature for 3 hours. Water (50 mL) was added with stirring, and the resulting clear yellow solution was acidified by slowly adding 1N HCl. A yellow precipitate formed. Diethyl ether (10 mL) was added and the precipitate was collected by filtration, washed with water, diethyl ether and then dried in vacuo to yield I-364 as a yellow powder (78 mg, 93% yield) MS m/z=468 (M+H).

Example 14

Method T for the Synthesis of Compounds of Formula (I)

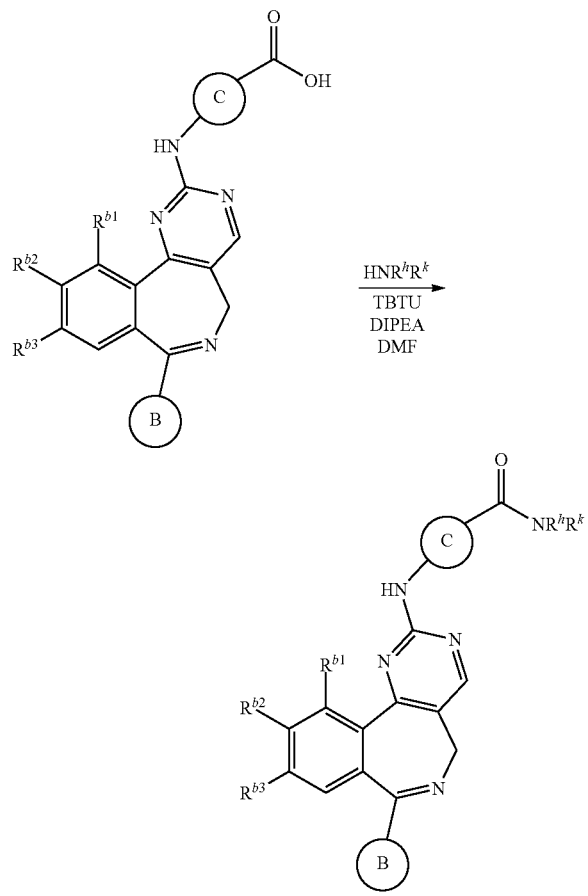

{4-[9-Chloro-7-(2-fluoro-phenyl)-5H-benzo[c]pyrimido[4,5-e]azepin-2-ylamino]-phenyl}-(4-methyl-piperazin-1-yl)-methanone (I-9)

1-Methyl-piperazine (0.03 mL, 0.3 mmole) was added to a solution of I-52 (0.1 g, 0.2 mmole), TBTU (0.08 g, 0.2 mmole) and Et$_3$N (0.06 mL, 0.4 mmole) in DMF (5 mL). The solution was allowed to stir for 30 min and then diluted with 0.1N NaOH (50 mL) and EtOAc (50 mL). The organic portion was separated, dried over Na$_2$SO$_4$ and concentrated in vacuo. The resulting residue was purified by column chromatography (Silica Gel, CH$_2$Cl$_2$:MeOH:NH$_4$OH, 94:5:1) to yield I-9 (0.07 g, 47%).

Example 15

Method U for the Synthesis of Compounds of Formula (I)

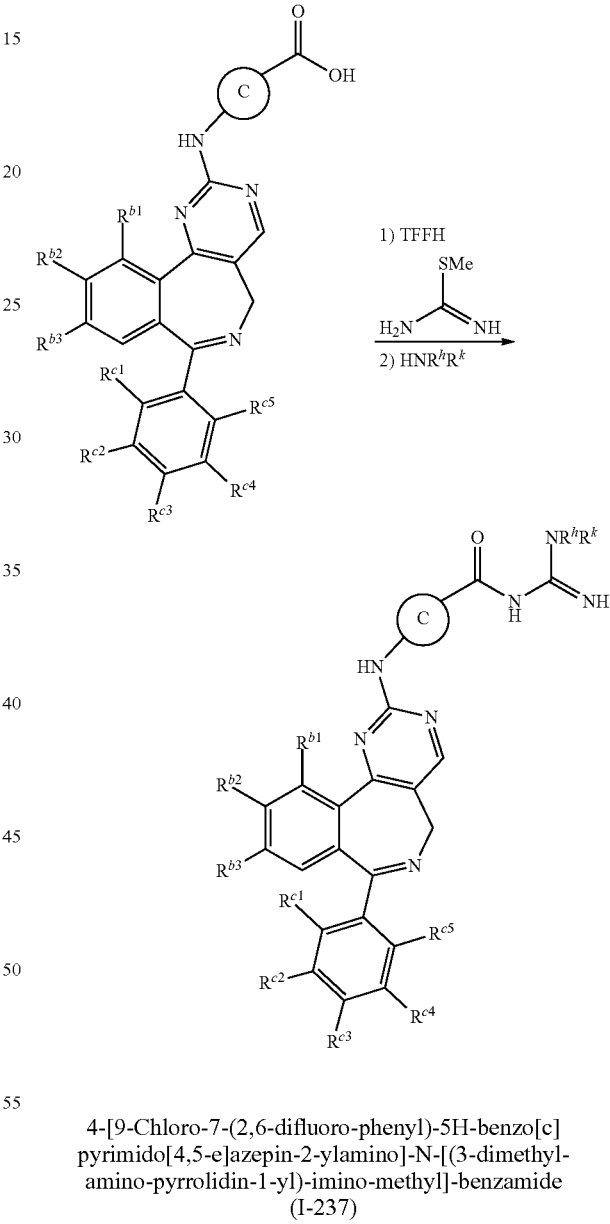

4-[9-Chloro-7-(2,6-difluoro-phenyl)-5H-benzo[c]pyrimido[4,5-e]azepin-2-ylamino]-N-[(3-dimethyl-amino-pyrrolidin-1-yl)-imino-methyl]-benzamide (I-237)

A mixture of I-135 (4.8 g, 10 mmol) and DMF (100 mL) was stirred and fluoro-N,N,N',N'-tetramethylformamidinium hexafluorophosphate (2.9 g, 11 mmol) was added in one portion, followed by diisopropylethylamine (3.9 g, 30 mmol). The mixture was stirred at room temperature for 10 minutes. 2-Methyl-2-thiopseudourea sulfate (3.2 g, 11 mmol) was then added as a solid and the reaction mixture was stirred at room temperature overnight. The reaction was quenched into saline (500 mL) and the off-white precipitate was collected by filtration, washed with water, and dried in vacuo to yield 1-{4-[9-chloro-7-(2,6-difluoro-phenyl)-5H-benzo[c]pyrimido[4,5-e]azepin-2-ylamino]-benzoyl}-2-methyl-isothiourea as a pale yellow solid (5.81 g, 100%) MS m/z=549 (M+H).

A solution of the benzoyl-methylisothiourea (250 mg, 0.5 mmol), 3-dimethylaminopyrrolidine (58 mg, 0.5 mmol), triethylamine (50 mg, 0.5 mmol), and toluene (10 mL) was stirred at reflux for 8 hours. The volatiles were then removed in vacuo and the brown residue was purified by column chromatography (silica gel, 1% 7N $NH_3$ in MeOH/$CH_2Cl_2$ to 5% $NH_3$ in MeOH/$CH_2Cl_2$) to yield 1-237 as a yellow solid (154 mg, 54%) MS m/z=615 (M+H).

Example 16

Method V for the Synthesis of Compounds of Formula (I)

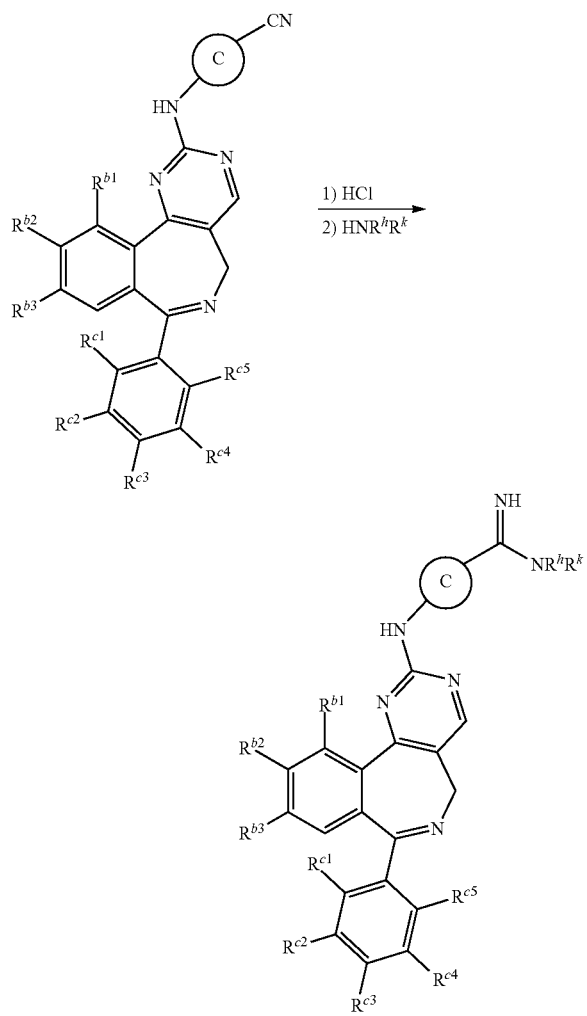

[9-Chloro-7-(2,6-difluoro-phenyl)-5H-benzo[c]pyrimido[4,5-e]azepin-2-yl]-{4-[(3,5-dimethyl-piperazin-1-yl)-imino-methyl]-phenyl}-amine (I-251)

Anhydrous HCl gas was added to a stirred suspension of I-236 (1.9 g, 4.4 mmol) in absolute ethanol (75 mL) at 0° C. until a homogeneous solution resulted. The solution was allowed to warm to room temperature and sit for three days. Diethyl ether (100 mL) was added and the resulting precipitate collected by filtration, washed with diethyl ether, and dried in vacuo to yield 4-[9-chloro-7-(2,6-difluoro-phenyl)-5H-benzo[c]pyrimido[4,5-e]azepin-2-ylamino]-benzimidic acid ethyl ester HCl salt as a bright yellow powder (2.4 g, 94%) MS m/z=504 (M+H).

A mixture of the ethyl benzimidate (100 mg, 0.17 mmol), 2,6-dimethylpiperazine (200 mg, 8.8 mmol), and absolute ethanol (1 mL) was submitted to microwave irradiation (300 W) for 7.5 minutes at 120° C. The reaction solution was cooled to room temperature and slowly poured into a stirring saline solution (10 mL). The resulting precipitate was collected and purified by column chromatography (silica gel, 0.25% $NH_4OH$/2% MeOH/97.75% $CH_2Cl_2$ to 2.5% $NH_4OH$/20% MeOH/77.5% $CH_2Cl_2$) to yield I-251 as a pale yellow solid (30 mg, 30%).

Example 17

Method W for the Synthesis of Compounds of Formula (I)

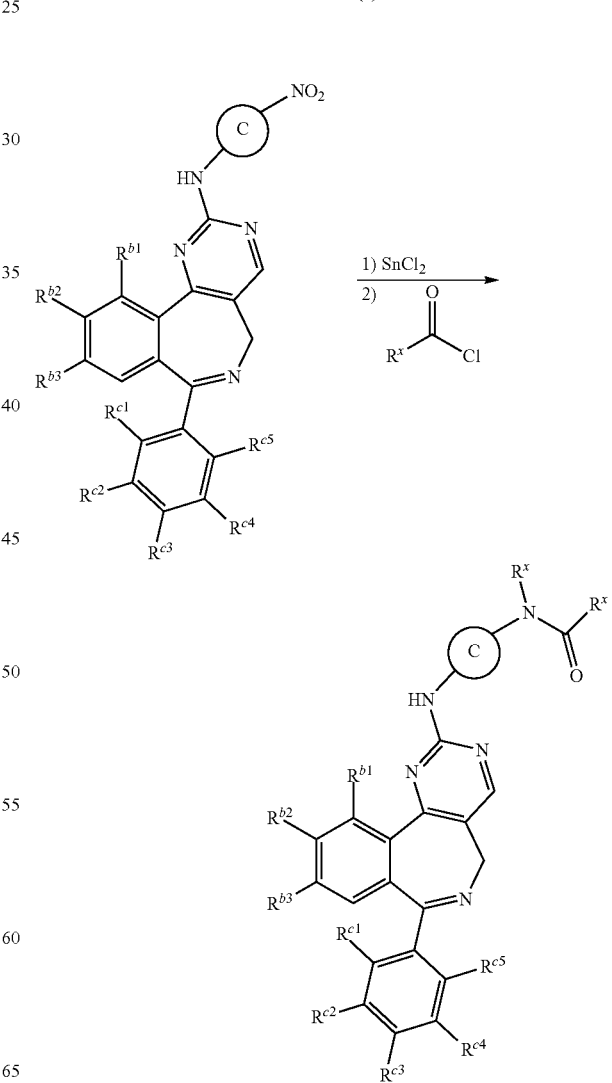

4-Methyl-piperazine-1-carboxylic acid {4-[9-chloro-7-(2,6-difluoro-phenyl)-5H-benzo[c]pyrimido[4,5-e]azepin-2-ylamino]-phenyl}-amide (I-280)

A mixture of [9-chloro-7-(2,6-difluoro-phenyl)-5H-benzo[c]pyrimido[4,5-e]azepin-2-yl]-(4-nitro-phenyl)-amine (I-212, 500 mg, 1.05 mmol), stannous chloride dihydrate (1.42 g, 6.3 mmol) and ethyl acetate (15 mL) was refluxed for 28 hours, then cooled to room temperature and allowed to sit overnight. The mustard-yellow reaction mixture was poured onto ~50 g cracked ice with stirring, and sat. NaHCO$_3$ solution was added to adjust the pH to 8. The mixture was extracted with ethyl acetate (3×100 mL). The extracts were combined, dried (Na$_2$SO$_4$), filtered and evaporated in vacuo to provide N-[9-chloro-7-(2,6-difluoro-phenyl)-5H-benzo[c]pyrimido[4,5-e]azepin-2-yl]-benzene-1,4-diamine as an orange/yellow solid (500 mg, 100%) MS m/z=448 (M+H). A solution of this product (50 mg, 0.1 mmol), 4-methylpiperazine-1-carbonylchloride (89 mg, 0.6 mmol), diisopropylethylamine (142 mg, 1.1 mmol), in dioxane (0.5 mL) was submitted to microwave irradiation (300 W) for 60 minutes at 160° C. The reaction solution was cooled to room temperature and slowly poured into a stirring saline solution (10 mL). The resulting precipitate was collected by filtration, washed with water and purified by RP-HPLC (C$_{18}$, 0 to 100% CH$_3$CN in 0.1% aqueous HCO$_2$H) to yield I-280 as a pale yellow solid (6 mg, 10%) MS m/z=574 (M+H).

Example 18

Method X for the Synthesis of Compounds of Formula (I)

4-(7-{2-[(2-aminoethyl)amino]-6-fluoropheny}-9-chloro-5H-pyrimido[5,4-d][2]benzazepin-2-yl)amino]-N-methylbenzamide (I-340)

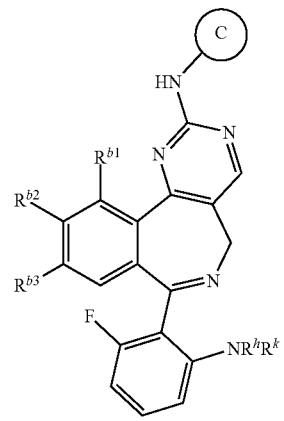

A solution of I-334 (49 mg, 0.1 mmol) in ethylene diamine (200 μL) was submitted to microwave irradiation (300 W) for 20 minutes at 140° C. The reaction solution was cooled to room temperature and slowly poured into a stirring saline solution (10 mL). The resulting precipitate was collected by filtration, washed with water and purified by column chromatography (silica gel, 1% NH$_4$OH/2% MeOH/97% CH$_2$Cl$_2$ to 2.5% NH$_4$OH/20% MeOH/77.5% CH$_2$Cl$_2$) to yield I-340 as a pale yellow solid (46 mg, 87%) MS m/z=530 (M+H).

Certain exemplary compounds of the invention were prepared by methods Q through X, employing procedures analogous to those described above for I-52, I-135, I-236, I-237, I-280, and I-340. HRMS data were collected on a Sciex Qstar® time of flight mass spectrometer coupled to an Agilent HPLC. Experimentally determined (M+H)$^+$ for certain exemplary compounds are presented in Table 5, and were within 10 ppm error of calculated (M+H)$^+$.

Example 19

Method Y for the Synthesis of Compounds of the Formula (I)

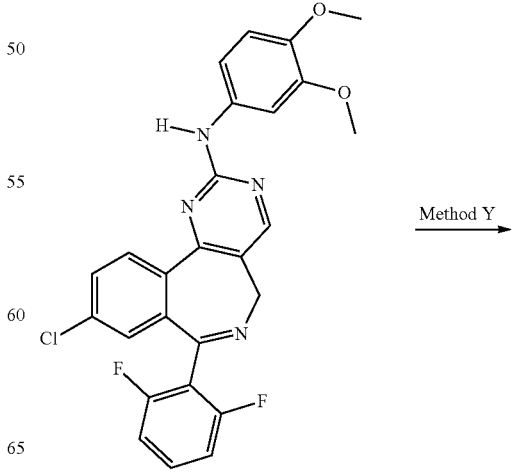

-continued

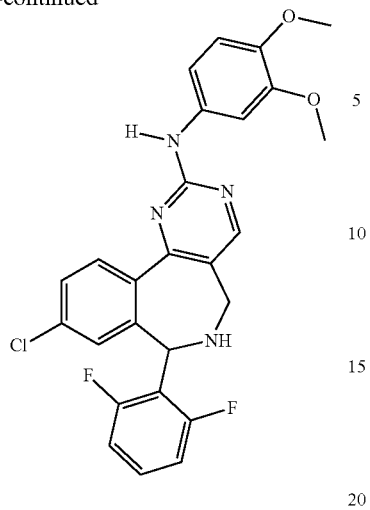

[9-Chloro-7-(2-fluoro-phenyl)-6,7-dihydro-5H-benzo[c]pyrimido[4,5-e]azepin-2-yl]-(3,4-dimethoxy-phenyl)-amine (1-72)

[9-Chloro-7-(2-fluoro-phenyl)-5H-benzo[c]pyrimido[4,5-e]azepin-2-yl]-(3,4-dimethoxy-phenyl)-amine (I-71, 49 mg, 0.10 mmol) was dissolved in dichloromethane (1.8 mL). Acetic acid (0.43 mL) was added and the solution was stirred and cooled to 0° C. Zinc dust (20 mg, 0.31 mmol) was then added and the mixture was stirred at 0° C. for 1 hour and then allowed to warm to room temperature and stir for 4 hours. Additional zinc dust (10 mg, 0.15 mmol) and acetic acid (0.22 mL) was added and the mixture was stirred at room temperature for 20 hours. The reaction mixture was diluted with dichloromethane. The organic layer was separated and washed with 1N NaOH, brine and then dried over magnesium sulfate, filtered and concentrated in vacuo. The yellow powder was purified by column chromatography (silica gel, ethyl acetate) to afford [9-Chloro-7-(2-fluoro-phenyl)-6,7-dihydro-5H-benzo[c]pyrimido[4,5-e]azepin-2-yl]-(3,4-dimethoxy-phenyl)-amine (1-72) as an orange solid (32 mg, 65%): MS m/z=477.

Example 20

Method Z for the Synthesis of Compounds of the Formula (I)

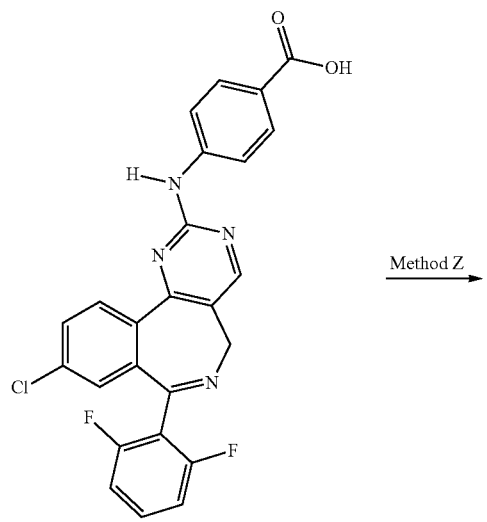

4-[9-Chloro-7-(2,6-difluoro-phenyl)-7H-benzo[c]pyrimido[4,5-e]azepin-2-ylamino]-benzoic acid (I-387). To a solution of I-135 (1.0 g, 2.1 mmol) in THF (20 mL) was added potassium tert-butoxide (1M in THF, 21 mmol). The solution was allowed to stir for 1 hr and then the pH was adjusted to 3 with 1N HCl. The solution was then diluted with water (100 mL) and extracted with EtOAc (3×50 mL). The organic portion was dried ($Na_2SO_4$), concentrated in vacuo and the resulting brown oil purified by RP-HPLC (C18, 0 to 100% $CH_3CN$ in water containing 0.1% formic acid) to provide, after lyophilization, I-387 (0.3 g, 30%).

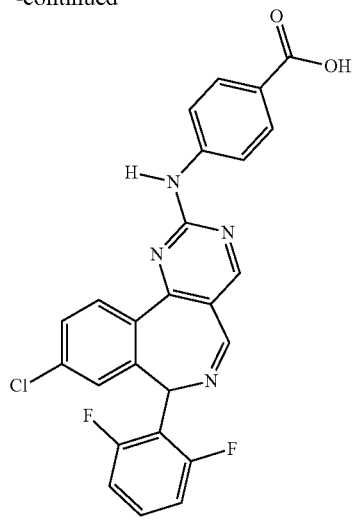

TABLE 5

High Resolution Mass Spectra of Exemplary Compounds of Formula (A)

| Compound | HRMS |
|---|---|
| I-1: | 515.1739 |
| I-2: | 515.1775 |
| I-3: | 529.1881 |
| I-4: | 529.1889 |
| I-5: | 543.2054 |
| I-6: | 543.2066 |
| I-7: | 557.2233 |
| I-8: | 527.1769 |
| I-9: | 541.1910 |
| I-10: | 557.1613 |
| I-11: | 537.2175 |
| I-12: | 553.2114 |
| I-13: | 541.1881 |
| I-14: | 521.2463 |
| I-15: | 555.2072 |
| I-16: | 541.1897 |
| I-17: | 541.1908 |
| I-18: | 569.2207 |
| I-19: | 598.2473 |
| I-20: | 614.2190 |
| I-21: | 594.2742 |
| I-22: | 610.2708 |
| I-23: | 598.2503 |
| I-24: | 578.3039 |
| I-25: | 612.2655 |
| I-26: | 528.1619 |
| I-27: | 546.1722 |
| I-28: | 544.1313 |
| I-29: | 571.2018 |
| I-30: | 587.1709 |
| I-31: | 567.2256 |
| I-32: | 597.2367 |
| I-33: | 571.2046 |

TABLE 5-continued

High Resolution Mass Spectra of Exemplary Compounds of Formula (A)

| Compound | HRMS |
|---|---|
| I-34: | 603.1674 |
| I-35: | 432.0783 |
| I-36: | 483.0332 |
| I-37: | 445.1213 |
| I-38: | 459.1367 |
| I-39: | 445.1213 |
| I-40: | 445.1215 |
| I-41: | 449.0731 |
| I-42: | 465.0443 |
| I-43: | 449.0728 |
| I-44: | 449.0727 |
| I-45: | 447.0789 |
| I-46: | 500.1630 |
| I-47: | 513.1947 |
| I-48: | 506.1558 |
| I-49: | 440.1073 |
| I-50: | 460.0966 |
| I-51: | 425.1431 |
| I-52: | 459.1014 |
| I-53: | 475.0752 |
| I-54: | 455.1261 |
| I-55: | 471.1210 |
| I-56: | 459.1027 |
| I-57: | 443.1332 |
| I-58: | 439.1550 |
| I-59: | 443.1286 |
| I-60: | 459.1016 |
| I-61: | 503.0516 |
| I-62: | 455.1496 |
| I-63: | 474.0871 |
| I-64: | 474.0879 |
| I-65: | 489.0889 |
| I-66: | 488.1034 |
| I-67: | 495.0690 |
| I-68: | 494.0832 |
| I-69: | 591.0810 |
| I-70: | 547.0605 |
| I-71: | 475.1339 |
| I-72: | 477.1491 |
| I-73: | 491.1031 |
| I-74: | 471.1579 |
| I-75: | 455.1873 |
| I-76: | 483.2202 |
| I-77: | 459.1602 |
| I-78: | 519.0851 |
| I-79: | 509.1604 |
| I-80: | 455.1873 |
| I-81: | 471.1830 |
| I-82: | 455.1872 |
| I-83: | 473.1168 |
| I-84: | 463.1152 |
| I-85: | 475.1000 |
| I-86: | 491.0677 |
| I-87: | 483.0331 |
| I-88: | 491.1035 |
| I-89: | 443.1442 |
| I-90: | 477.093 |
| I-91: | 477.0928 |
| I-92: | 551.2557 |
| I-93: | 501.1302 |
| I-94: | 542.2212 |
| I-95: | 477.0929 |
| I-96: | 477.0931 |
| I-97: | 541.1928 |
| I-98: | 555.2058 |
| I-99: | 555.208 |
| I-100: | 501.134 |
| I-101: | 541.1905 |
| I-102: | 527.1755 |
| I-103: | 491.1094 |
| I-104: | 477.1084 |
| I-105: | 495.0789 |
| I-106: | 508.105 |
| I-107: | 486.1508 |
| I-108: | 574.1296 |
| I-109: | 489.1484 |
| I-110: | 555.2063 |
| I-111: | 556.1545 |
| I-112: | 541.1925 |
| I-113: | 483.1249 |
| I-114: | 472.1352 |
| I-115: | 477.0961 |
| I-116: | 529.1913 |
| I-117: | 530.1387 |
| I-118: | 585.217 |
| I-119: | 489.1156 |
| I-120: | 473.1179 |
| I-121: | 460.0964 |
| I-122: | 607.1699 |
| I-123: | 493.0631 |
| I-124: | 473.1161 |
| I-128: | 569.221 |
| I-129: | 515.1759 |
| I-130: | 529.1927 |
| I-131: | 529.1929 |
| I-132: | 485.1637 |
| I-134: | 493.0633 |
| I-135: | 477.0955 |
| I-136: | 477.0929 |
| I-137: | 455.1529 |
| I-138: | 471.1842 |
| I-139: | 509.0987 |
| I-140: | 493.0648 |
| I-141: | 489.1129 |
| I-142: | 501.1594 |
| I-143: | 441.1137 |
| I-144: | 535.0517 |
| I-145: | 554.2076 |
| I-146: | 459.1021 |
| I-147: | 552.1697 |
| I-148: | 551.2548 |
| I-150: | 563.1742 |
| I-151: | 563.175 |
| I-152: | 457.1424 |
| I-153: | 439.1575 |
| I-154: | 441.1735 |
| I-155: | 471.1229 |
| I-156: | 471.1243 |
| I-157: | 598.2497 |
| I-158: | 571.2015 |
| I-159: | 541.1905 |
| I-160: | 577.1898 |
| I-161: | 563.1744 |
| I-162: | 459.1019 |
| I-163: | 541.1911 |
| I-164: | 604.2055 |
| I-165: | 654.2409 |
| I-166: | 621.1838 |
| I-167: | 661.2162 |
| I-168: | 599.2003 |
| I-169: | 647.1998 |
| I-170: | 626.2448 |
| I-171: | 624.2685 |
| I-172: | 577.1576 |
| I-173: | 605.2002 |
| I-174: | 493.0656 |
| I-175: | 573.1983 |
| I-176: | 573.1986 |
| I-177: | 585.2192 |
| I-178: | 585.2203 |
| I-179: | 571.2037 |
| I-180: | 559.1851 |
| I-181: | 652.2994 |
| I-182: | 638.2822 |
| I-183: | 587.2117 |
| I-184: | 559.1845 |
| I-185: | 575.2131 |
| I-186: | 599.2348 |
| I-187: | 654.3136 |
| I-188: | 638.2832 |

TABLE 5-continued

High Resolution Mass Spectra of Exemplary Compounds of Formula (A)

| Compound | HRMS |
| --- | --- |
| I-189: | 640.2628 |
| I-190: | 489.1142 |
| I-191: | 559.1845 |
| I-192: | 513.1625 |
| I-193: | 555.2103 |
| I-194: | 559.1843 |
| I-195: | 545.1683 |
| I-196: | 545.1693 |
| I-197: | 559.1814 |
| I-198: | 561.2004 |
| I-199: | 571.2047 |
| I-200: | 465.1514 |
| I-201: | 647.2340 |
| I-202: | 518.1331 |
| I-203: | 477.0943 |
| I-204: | 559.1814 |
| I-205: | 587.2156 |
| I-206: | 573.2001 |
| I-207: | 503.1197 |
| I-208: | 640.2953 |
| I-209: | 626.2832 |
| I-210: | 612.2649 |
| I-211: | 638.2782 |
| I-212: | 478.0905 |
| I-213: | 658.2264 |
| I-214: | 575.1556 |
| I-215: | 607.1598 |
| I-216: | 593.1427 |
| I-217: | 448.1154 |
| I-218: | 525.0715 |
| I-219: | 589.1588 |
| I-220: | 573.1994 |
| I-221: | 559.1807 |
| I-222: | 573.1989 |
| I-223: | 629.2331 |
| I-224: | 587.1893 |
| I-225: | 587.2358 |
| I-226: | 587.2364 |
| I-227: | 571.2031 |
| I-228: | 585.2198 |
| I-229: | 599.2352 |
| I-230: | 527.1765 |
| I-231: | 585.2195 |
| I-232: | 571.2033 |
| I-233: | 571.2028 |
| I-234: | 545.1676 |
| I-235: | 557.1849 |
| I-236: | 458.0994 |
| I-237: | 615.2217 |
| I-238: | 615.2214 |
| I-239: | 559.1851 |
| I-240: | 557.1880 |
| I-241: | 571.2035 |
| I-242: | 585.2169 |
| I-243: | 557.1893 |
| I-244: | 586.2295 |
| I-245: | 490.1365 |
| I-246: | 547.1831 |
| I-247: | 561.2004 |
| I-248: | 603.1714 |
| I-249: | 469.1317 |
| I-250: | 572.2137 |
| I-251: | 572.2140 |
| I-252: | 533.1689 |
| I-253: | 573.1966 |
| I-254: | 559.2009 |
| I-255: | 573.2187 |
| I-256: | 455.1499 |
| I-257: | 547.1803 |
| I-258: | 511.0542 |
| I-259: | 601.2042 |
| I-260: | 547.1813 |
| I-261: | 573.2173 |
| I-262: | 571.2009 |
| I-263: | 585.2164 |
| I-264: | 559.2041 |
| I-265: | 545.1858 |
| I-266: | 589.1555 |
| I-267: | 558.1969 |
| I-268: | 558.1982 |
| I-269: | 621.1760 |
| I-270: | 529.1733 |
| I-271: | 526.1345 |
| I-272: | 496.1588 |
| I-273: | 507.0622 |
| I-274: | 521.0448 |
| I-275: | 536.2267 |
| I-276: | 482.1776 |
| I-277: | 509.0967 |
| I-278: | 531.1524 |
| I-279: | 442.1091 |
| I-280: | 574.1943 |
| I-281: | 593.1419 |
| I-282: | 607.1584 |
| I-283: | 581.1453 |
| I-284: | 544.1826 |
| I-285: | 531.1529 |
| I-286: | 543.1704 |
| I-287: | 591.1867 |
| I-288: | 605.2016 |
| I-289: | 577.1710 |
| I-290: | 591.1900 |
| I-291: | 579.1263 |
| I-292: | 593.1439 |
| I-293: | 587.2139 |
| I-294: | 617.1853 |
| I-295: | 603.1746 |
| I-296: | 563.1593 |
| I-297: | 577.1714 |
| I-298: | 524.1949 |
| I-299: | 510.1813 |
| I-300: | 605.1879 |
| I-301: | 460.0978 |
| I-302: | 537.2438 |
| I-303: | 539.2562 |
| I-304: | 542.1863 |
| I-305: | 528.1737 |
| I-306: | 545.1308 |
| I-307: | 533.1642 |
| I-308: | 533.1680 |
| I-309: | 605.1894 |
| I-310: | 602.1863 |
| I-311: | 581.2652 |
| I-312: | 551.2576 |
| I-313: | 621.1731 |
| I-314: | 573.1610 |
| I-315: | 524.1979 |
| I-316: | 538.2110 |
| I-317: | 588.1727 |
| I-318: | 579.1300 |
| I-319: | 559.1850 |
| I-320: | 545.1876 |
| I-321: | 573.1971 |
| I-322: | 597.2403 |
| I-323: | 575.1523 |
| I-324: | 589.1704 |
| I-325: | 589.1678 |
| I-326: | 589.1680 |
| I-327: | 575.1517 |
| I-328: | 514.1995 |
| I-329: | 553.2092 |
| I-330: | 567.2287 |
| I-331: | 567.2301 |
| I-332: | 553.2124 |
| I-333: | 567.2288 |
| I-334: | 490.1270 |
| I-335: | 559.2007 |
| I-336: | 572.2352 |
| I-337: | 475.1144 |
| I-338: | 486.1287 |

TABLE 5-continued

High Resolution Mass Spectra of Exemplary Compounds of Formula (A)

| Compound | HRMS |
|---|---|
| I-339: | 531.1727 |
| I-340: | 530.1895 |
| I-341: | 616.2019 |
| I-342: | 598.2501 |
| I-343: | 514.1631 |
| I-344: | 558.9984 |
| I-345: | 558.2185 |
| I-346: | 572.2341 |
| I-347: | 558.2203 |
| I-348: | 570.2169 |
| I-349: | 525.2404 |
| I-350: | 602.1911 |
| I-351: | 561.1395 |
| I-352: | 454.0727 |
| I-353: | 473.1430 |
| I-354: | 501.1626 |
| I-355: | 497.0780 |
| I-356: | 473.1106 |
| I-357: | 464.1012 |
| I-358: | 504.1412 |
| I-359: | 532.1712 |
| I-360: | 484.0467 |
| I-361: | 512.0783 |
| I-362: | 580.1487 |
| I-363: | 496.0996 |
| I-364: | 468.0686 |
| I-365: | 566.1355 |
| I-366: | 559.1852 |
| I-367: | 566.1333 |
| I-368: | 468.0684 |
| I-369: | 564.1728 |
| I-370: | 550.1549 |
| I-371: | 491.1096 |
| I-372: | 518.1921 |
| I-373: | 490.1603 |
| I-374: | 564.1736 |
| I-375: | 550.1579 |
| I-376: | 596.2613 |
| I-377: | 486.1401 |
| I-378: | 630.2207 |
| I-379: | 559.1829 |
| I-380: | 573.1978 |
| I-381: | 616.2039 |
| I-382: | 587.2132 |
| I-383: | 599.2158 |
| I-384: | 585.1999 |
| I-385: | 492.106 |
| I-386: | 492.1055 |
| I-387: | 477.095 |
| I-388: | 477.0948 |
| I-389: | 602.1900 |
| I-390: | 588.1738 |
| I-301: | 573.1996 |
| I-392: | 599.2152 |
| I-393: | 587.2156 |
| I-394: | 437.1107 |
| I-395: | 511.0564 |
| I-396: | 650.1655 |
| I-397: | 664.1835 |

Example 21

Expression and Purification of Aurora Kinase Enzymes

Aurora A Enzyme Expression and Purification

Recombinant mouse Aurora A with an amino-terminus hexahistidine tag (His-Aurora A) was expressed using a standard baculovirus vector and insect cell expression system (Bac-to-Bac®, Invitrogen).

Soluble, recombinant mouse Aurora A was purified from insect cells using Ni-NTA agarose (Qiagen) as described by the manufacturer and further purified over an S75 size exclusion column (Amersham Pharmacia Biotech).

Aurora B Enzyme Expression and Purification

Recombinant mouse Aurora B with an amino-terminus hexahistidine tag (His-Aurora B) was expressed using a standard baculovirus vector and insect cell expression system (Bac-to-Bac®, Invitrogen).

Soluble, recombinant mouse Aurora B was purified from insect cells using Ni-NTA agarose (Qiagen) as described by the manufacturer.

Example 22

Aurora Kinase Enzyme Assays

Aurora A DELFIA® Kinase Assay

The mouse Aurora A enzymatic reaction totaled 25 µL and contained 25 mM Tris-HCl (pH 8.5), 2.5 mM $MgCl_2$, 0.05% Surfact-AMPS-20, 5 mM Sodium Fluoride, 5 mM DTT, 250 µM ATP, 10 µM peptide substrate (Biotin-β-Ala-QTRRK-STGGKAPR-$NH_2$), and 500 µM recombinant murine Aurora A enzyme. The enzymatic reaction mixture, with and without Aurora inhibitors, was incubated for 15 minutes at room temperature before termination with 100 µL of stop buffer (1% BSA, 0.05% Surfact-AMPS-20, and 100 mM EDTA). A total of 100 µL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 µL of antibody reaction mixture containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 µL of Enhancement Solution (Perkin Elmer). Quantification of europium was done using a Wallac™ EnVision (Perkin Elmer).

Compounds I-1 to I-12, I-14 to I-32, I-34, I-37, I-39, I-45, I-52 to I-55, I-57 to I-59, I-63 to I-69, I-73 to I-75, I-80, I-85, I-86, I-91, I-93 to I-96, I-98 to I-103, I-109, I-111 to I-113, I-117, I-118, I-120, I-126, I-128 to I-131, II-134 to I-138, I-142, I-145, I-147 to I-151, I-157, I-160 to I-163, I-165, I-166, I-168 to I-171, II-173 to I-199, I-202 to I-211, I-213 to I-217, I-219 to I-235, I-237 to I-301, I-304 to I-310, I-313 to I-327, I-329 to I-335, I-337 to I-341, I-343, I-350 to I-355, I-357 to I-360, and I-362 to I-376 exhibited $IC_{50}$ values less than or equal to 1.0 µM in this assay.

Compounds I-1 to I-12, I-14 to I-22, II-24 to I-32, II-52 to I-55, I-57, I-58, I-63, I-65 to I-67, I-69, I-73, I-86, I-93, I-98 to I-100, I-102, I-103, I-111 to I-113, I-117, I-128, 1-130, I-135, I-145, I-147, I-148, I-160, I-161, I-163, I-171, I-174 to I-199, I-204 to I-206, I-208 to I-211, I-213 to I-217, I-219 to I-229, I-231 to I-235, I-237 to I-244, I-246 to I-257, I-259 to I-270, I-272, I-274, I-277, I-278, I-280 to I-301, I-304 to I-310, I-313 to I-319, I-321, 1-323 to I-327, I-329 to I-334, I-337, I-338, I-341, I-343, I-350, I-351, I-353, I-355, I-357, I-359, I-362, I-365 to I-368, and I-371 to I-376 exhibited $IC_{50}$ values less than or equal to 100 nM in this assay.

Aurora B DELFIA® Kinase Assay

The mouse Aurora B enzymatic reaction totaling 25 µL contained 25 mM Tris-HCl (pH 8.5), 2.5 mM $MgCl_2$, 0.025% Surfact-AMPS-20 (Pierce), 1% Glycerol, 1 mM DTT, 1 mM ATP, 3 µM peptide substrate (Biotin-β-Ala-QTRRKSTGGKAPR-$NH_2$), and 20 nM recombinant murine Aurora B enzyme. The enzymatic reaction mixture, with or without Aurora inhibitors, was incubated for 3 hours at room temperature before termination with 100 µL of stop buffer (1% BSA, 0.05% Surfact-AMPS-20, and 100 mM EDTA). A total of 100 µL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 μL of antibody reaction mix containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 μL of Enhancement Solution (Perkin Elmer). Quantification of europium was done using a Wallac™ EnVision (Perkin Elmer).

Example 23

Cellular Assay

Aurora Phosphorylation Assays

Inhibition of Aurora A or Aurora B activity in whole cell systems can be assessed by determination of decreased phosphorylation of Aurora substrates. For example, determining decreased phosphorylation of histone H3 on Serine 10, an Aurora B substrate can be used to measure inhibition of Aurora B activity in a whole cell system. Alternatively, any known Aurora B substrate can be used in similar assay methods to assess inhibition of Aurora B activity. Similarly, Aurora A inhibition can be determined using analogous methods and known Aurora A substrates for detection.

In a specific example, HeLa cells were seeded in a 96-well cell culture plate ($10 \times 10^3$ cells/well) and incubated overnight at 37° C. Cells were incubated with Aurora inhibitors for 1 hour at 37° C., fixed with 4% paraformaldehyde for 10 minutes and then permeabilized with 0.5% TritonX-100 in PBS. Cells were incubated with mouse anti-pHisH3 (1:120, Cell Signaling Technologies) and rabbit anti-mitotic marker (1:120, Millennium Pharmaceuticals Inc.) antibodies for 1 hour at room temperature. After washing with PBS the cells were stained with anti-rabbit IgG Alexa 488 (1:180, Molecular Probes) and anti-mouse IgG Alexa 594 (1:180) for 1 hour at room temperature. DNA was then stained with Hoechst solution (2 g/ml). The percentage of pHisH3 and anti-mitotic positive cells were quantified using Discovery I and Meta-Morph (Universal Imaging Corp.). Aurora B inhibition was determined by calculating the decrease of pHisH3 positive cells.

Anti-Proliferation Assays

HCT-116 (1000) or other tumor cells in 100 μL of appropriate cell culture medium (McCoy's 5A for HCT-116, Invitrogen) supplemented with 10% fetal bovine serum (Invitrogen) was seeded in wells of a 96-well cell culture plate and incubated overnight at 37° C. Aurora inhibitors were added to the wells and the plates were incubated for 96 hours at 37° C. MTT or WST reagent (10 μL, Roche) was added to each well and incubated for 4 hours at 37° C. as described by the manufacturer. For MTT the metabolized dye was solubilzed overnight according to manufacturer's instructions (Roche). The optical density for each well was read at 595 nm (primary) and 690 nm (reference) for the MTT and 450 nm for the WST using a spectrophotometer (Molecular Devices). For the MTT the reference optical density values were subtracted from the values of the primary wavelength. Percent inhibition was calculated using the values from a DMSO control set to 100%.

Example 24

In Vivo Assays

In Vivo Tumor Efficacy Model

HCT-116 ($1 \times 10^6$) or other tumor cells in 100 μL of phosphate buffered saline were aseptically injected into the subcutaneous space in the right dorsal flank of female CD-1 nude mice (age 5-8 weeks, Charles River) using a 23-ga needle. Beginning at day 7 after inoculation tumors were measured twice weekly using a vernier caliper. Tumor volumes were calculated using standard procedures (0.5× (length×width$^2$)). When the tumors reached a volume of approximately 200 mm$^3$ mice were injected i.v. in the tail vein with Aurora inhibitors (100 μL) at various doses and schedules. All control groups received vehicle alone. Tumor size and body weight was measure twice a week and the study was terminated when the control tumors reached approximately 2000 mm$^3$.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A process for preparing a compound of formula (A-1):

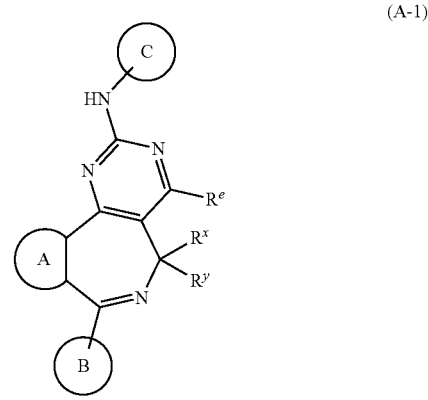

(A-1)

or a pharmaceutically acceptable salt thereof;
wherein:
Ring A is a substituted or unsubstituted 5- or 6-membered aryl, heteroaryl, cycloaliphatic, or heterocyclyl ring;
Ring B is a substituted or unsubstituted aryl, heteroaryl, cycloaliphatic, or heterocyclyl ring;
Ring C is a substituted or unsubstituted aryl, heteroaryl, heterocyclyl, or cycloaliphatic ring;
$R^e$ is hydrogen, —OR$^5$, —N(R$^4$)$_2$, —SR$^5$, or a C$_{1-3}$ aliphatic optionally substituted with R$^3$ or R$^7$;
each of R$^x$ and R$^y$ independently is hydrogen, fluoro, or an optionally substituted C$_{1-6}$ aliphatic; or R$^x$ and R$^y$, taken together with the carbon atom to which they are attached, form an optionally substituted 3- to 6-membered cycloaliphatic ring;
each R$^3$ independently is selected from the group consisting of halo, —OH, —O(C$_{1-3}$ alkyl), —CN, —N(R$^4$)$_2$, —C(O)(C$_{1-3}$ alkyl), —CO$_2$H, —CO$_2$(C$_{1-3}$ alkyl), —C(O)NH$_2$, and —C(O)NH(C$_{1-3}$ alkyl);

each R$^4$ independently is hydrogen or an optionally substituted aliphatic, aryl, heteroaryl, or heterocyclyl group; or two R$^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;

each R$^5$ independently is hydrogen or an optionally substituted aliphatic, aryl, heteroaryl, or heterocyclyl group; and each R$^7$ independently is an optionally substituted aryl, heterocyclyl, or heteroaryl group;

said process comprising step (e) of:

heating a compound of formula (x):

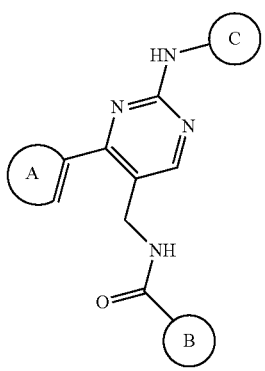

(x)

with a cyclodehydration reagent to afford the compound of formula (A-1).

2. The process of claim 1, wherein the compound of formula (A-1) is a compound of formula (Va):

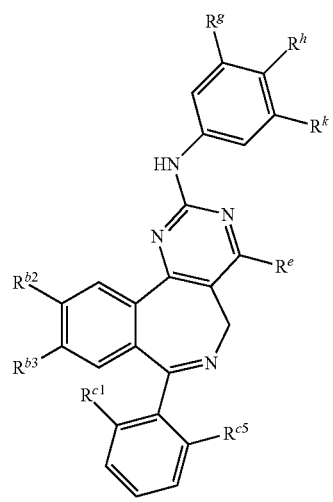

(Va)

wherein:

R$^e$ is hydrogen;

each of R$^{b2}$ and R$^{b3}$ independently is selected from the group consisting of hydrogen, halo, C$_{1-3}$ aliphatic, C$_{1-3}$ fluoroaliphatic, and —OR$^5$, where R$^5$ is hydrogen or C$_{1-3}$ aliphatic; and each of R$^{c1}$ and R$^{c5}$ independently is selected from the group consisting of hydrogen, halo, C$_{1-3}$ aliphatic, C$_{1-3}$ fluoroaliphatic, and —OR$^5$, where R$^5$ is hydrogen or C$_{1-3}$ aliphatic;

R$^g$ is selected from the group consisting of hydrogen, C$_{1-6}$ aliphatic, and R$^{2d}$; and each of R$^h$ and R$^k$ independently is hydrogen or R$^d$.

3. The process of claim 2, wherein each of R$^g$, R$^h$, and R$^k$ independently is selected from the group consisting of hydrogen, C$_{1-3}$ aliphatic, halo, —OR$^5$, —CO$_2$R$^5$, —C(O)N(R$^4$)$_2$, —SO$_2$N(R$^4$)$_2$, —C(=NR$^4$)N(R$^4$)$_2$, —C(O)N(R$^4$)C(=NR$^4$)—N(R$^4$)$_2$, —N(R$^4$)C(=NR$^4$)—N(R$^4$)—C(O)R$^5$, and —N(R$^4$)C(O)R$^5$.

4. The process of claim 2, wherein R$^g$ is hydrogen, and at least one of R$^h$ and R$^k$ is selected from the group consisting of —CO$_2$R$^5$, —C(O)N(R$^4$)$_2$, —C(=NR$^4$)N(R$^4$)$_2$, —C(O)N(R$^4$)C(=NR$^4$)—N(R$^4$)$_2$, —N(R$^4$)C(=NR$^4$)—N(R$^4$)—C(O)R$^5$, and —N(R$^4$)C(O)R$^5$.

5. The process of claim 1, further comprising step (d), prior to step (e), of treating a compound of formula (ix):

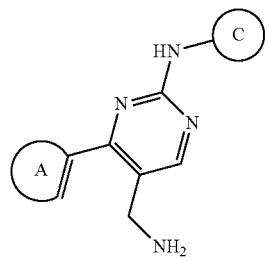

(ix)

with (i) an acid chloride in the presence of a base; or (ii) a carboxylic acid in the presence of a coupling reagent to afford the compound of formula (x).

6. The process of claim 5, further comprising step (c), prior to (d), of reducing a compound of formula (viii):

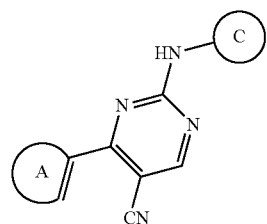

(viii)

(i) by hydrogenation in the presence of a metal catalyst; or (ii) with a reducing agent to afford the compound of formula (ix).

7. The process of claim 6, further comprising the step (b), prior to step (c), of treating a compound of formula (vii) with a mono-substituted guanidine of formula (xix):

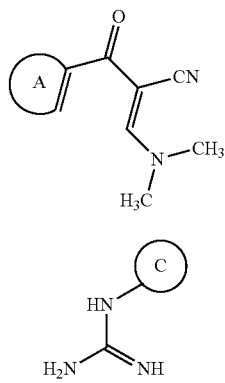

to afford the compound of formula (viii).

8. The process of claim 7, further comprising the step (a), prior to step (b), of providing a compound of formula (vi):

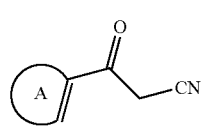

and treating the compound of formula (vi) with N,N-dimethylformamide dimethyl acetal to prepare the compound of formula (vii) for use in step (b).

9. A process for preparing a compound of formula (A-1):

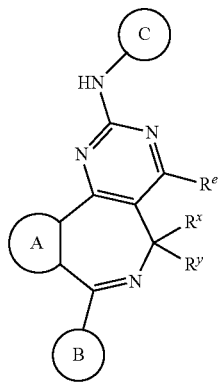

or a pharmaceutically acceptable salt thereof;
wherein:
Ring A is a substituted or unsubstituted 5- or 6-membered aryl, heteroaryl, cycloaliphatic, or heterocyclyl ring;
Ring B is a substituted or unsubstituted aryl, heteroaryl, cycloaliphatic, or heterocyclyl ring;
Ring C is a substituted or unsubstituted aryl, heteroaryl, heterocyclyl, or cycloaliphatic ring;
$R^e$ is hydrogen, —$OR^5$, —$N(R^4)_2$, —$SR^5$, or a $C_{1-3}$ aliphatic optionally substituted with $R^3$ or $R^7$;
each of $R^x$ and $R^y$ independently is hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring;

each $R^3$ independently is selected from the group consisting of halo, —OH, —O($C_{1-3}$ alkyl), —CN, —$N(R^4)_2$, —C(O)($C_{1-3}$ alkyl), —$CO_2H$, —$CO_2(C_{1-3}$ alkyl), —C(O)$NH_2$, and —C(O)NH($C_{1-3}$ alkyl);

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group; and each $R^7$ independently is an optionally substituted aryl, heterocyclyl, or heteroaryl group;

said process comprising step (g) of cross-coupling a compound of formula (xviii):

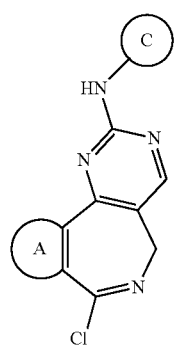

with an organoboronic acid using palladium catalysis to afford the compound of formula (A-1).

10. The process of claim 9, further comprising step (f), prior to step (g), of treating a compound of formula (xvii):

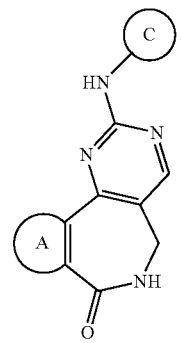

with a chlorinating reagent to afford the compound of formula (xviii).

11. The process of claim 10, further comprising step (e), prior to step (f), of treating a compound of formula (xvi) with a mono-substituted guanidine of formula (xix):

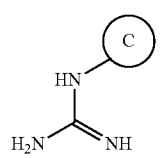

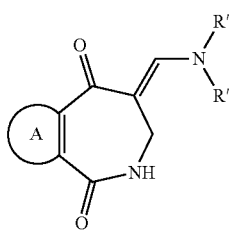

xvi

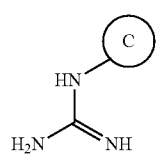

xix to afford the compound of formula (xvii).

12. The process of claim 11, further comprising step (d), prior to step (e), of treating a compound of formula (xv):

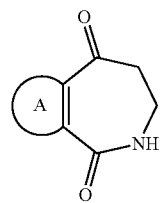

xv with N,N-dimethylformamide dimethyl acetal to afford the compound of formula (xvi).

13. The process of claim 12, further comprising step (c), prior to step (d), of treating a compound of formula (xiv):

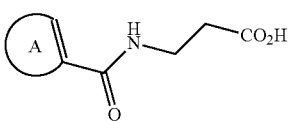

xiv with a cyclodehydration reagent to afford the compound of formula (xv).

14. The process of claim 13, further comprising step (b), prior to step (c), of treating a compound of formula (xiii):

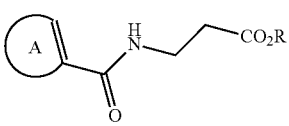

xiii with a dilute aqueous solution of an alkali-metal hydroxide to afford the compound of formula (xiv).

15. The process of claim 14, further comprising step (a), prior to step (b), of providing a compound of formula (xii)

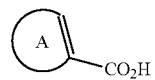

xii and condensing the compound of formula (xii) with a β-alanine ester to prepare the compound of formula (xiii).

16. The process of claim 9, wherein the compound of formula (A-1) is a compound of formula (Va):

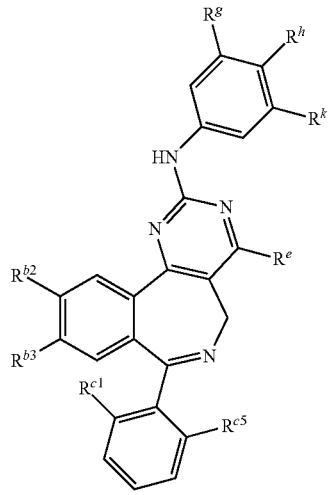

(Va)

wherein:
$R^e$ is hydrogen;
each of $R^{b2}$ and $R^{b3}$ independently is selected from the group consisting of hydrogen, halo, $C_{1-3}$ aliphatic, $C_{1-3}$ fluoroaliphatic, and —$OR^5$, where $R^5$ is hydrogen or $C_{1-3}$ aliphatic; and
each of $R^{c1}$ and $R^{c5}$ independently is selected from the group consisting of hydrogen, halo, $C_{1-3}$ aliphatic, $C_{1-3}$ fluoroaliphatic, and —$OR^5$, where $R^5$ is hydrogen or $C_{1-3}$ aliphatic;
$R^g$ is selected from the group consisting of hydrogen, $C_{1-6}$ aliphatic, and $R^{2d}$; and
each of $R^h$ and $R^k$ independently is hydrogen or $R^d$.

17. The process of claim 16, wherein each of $R^g$, $R^h$, and $R^k$ independently is selected from the group consisting of hydrogen, $C_{1-3}$ aliphatic, halo, —$OR^5$, —$CO_2R^5$, —$C(O)N(R^4)_2$, —$SO_2N(R^4)_2$, —$C(=NR^4)N(R^4)_2$, —$C(O)N(R^4)C(=NR^4)$—$N(R^4)_2$, —$N(R^4)C(=NR^4)$—$N(R^4)$—$C(O)R^5$, and —$N(R^4)C(O)R^5$.

18. The process of claim 16, wherein $R^g$ is hydrogen, and at least one of $R^h$ and $R^k$ is selected from the group consisting of —$CO_2R^5$, —$C(O)N(R^4)_2$, —$C(=NR^4)N(R^4)_2$, —$C(O)N(R^4)C(=NR^4)$—$N(R^4)_2$, —$N(R^4)C(=NR^4)$—$N(R^4)$—$C(O)R^5$, and —$N(R^4)C(O)R^5$.

* * * * *